(12) United States Patent
Lohmann et al.

(10) Patent No.: US 8,178,540 B2
(45) Date of Patent: May 15, 2012

(54) PYRIMIDYLMETHYL-SULFONAMIDE COMPOUNDS

(75) Inventors: Jan Klaas Lohmann, Ludwigshafen (DE); Wassilios Grammenos, Ludwigshafen (DE); Michael Puhl, Lampertheim (DE); Jochen Dietz, Mannheim (DE); Bernd Müller, Frankenthal (DE); Joachim Rheinheimer, Ludwigshafen (DE); Jens Renner, Bad Dürkheim (DE); Marianna Vrettou, Mannheim (DE); Sarah Ulmschneider, Bad Dürkheim (DE); Thomas Grote, Wachenheim (DE)

(73) Assignee: BASF SE, Ludwigshafen (DE)

( * ) Notice: Subject to any disclaimer, the term of this patent is extended or adjusted under 35 U.S.C. 154(b) by 263 days.

(21) Appl. No.: 12/515,138

(22) PCT Filed: Nov. 21, 2007

(86) PCT No.: PCT/EP2007/062630
§ 371 (c)(1),
(2), (4) Date: May 15, 2009

(87) PCT Pub. No.: WO2008/062011
PCT Pub. Date: May 29, 2008

(65) Prior Publication Data
US 2010/0069243 A1  Mar. 18, 2010

(30) Foreign Application Priority Data
Nov. 22, 2006 (EP) ..................... 06124589

(51) Int. Cl.
*C07D 239/20* (2006.01)
*C07D 239/22* (2006.01)
*C07D 403/12* (2006.01)
*A01N 43/54* (2006.01)

(52) U.S. Cl. ........ 514/256; 514/269; 514/275; 544/242; 544/316; 544/330; 544/331

(58) Field of Classification Search ................. 544/242, 544/316, 330, 331; 514/256, 269, 275
See application file for complete search history.

(56) References Cited

U.S. PATENT DOCUMENTS

| | | |
|---|---|---|
| 2006/0293314 A1 | 12/2006 | Grammenos et al. |
| 2008/0161187 A1 | 7/2008 | Grammenos et al. |
| 2010/0069243 A1 | 3/2010 | Lohmann et al. |
| 2010/0077512 A1 | 3/2010 | Lohmann et al. |
| 2010/0249077 A1 | 9/2010 | Grammenos et al. |

FOREIGN PATENT DOCUMENTS

| | | |
|---|---|---|
| CA | 2 537 486 | 4/2005 |
| EP | 1 224 158 | 7/2002 |
| JP | 5294945 | 11/1993 |
| JP | 2002-145778 | * 5/2002 |
| WO | WO 2005/033081 | 4/2005 |
| WO | WO 2006/097488 | 9/2006 |
| WO | WO 2006/097489 | 9/2006 |
| WO | WO 2007/104726 | 9/2007 |
| WO | WO 2008/022937 | 2/2008 |
| WO | WO 2008/062012 | 5/2008 |
| WO | WO 2009/101078 | 2/2009 |
| WO | WO 2009/071448 | 6/2009 |
| WO | WO 2009/101082 | 8/2009 |

OTHER PUBLICATIONS

Fukumoto et al., CAPLUS Abstract 136:232313 (2002).*
JP 2002-145778 A published May 2002 (Claim + Detailed Description Machine Translation obtained on Oct. 30, 2011).*
International Search Report for International Application No. PCT/EP2007/062630; International Filing Date: Nov. 21, 2007; Date of Completion: Feb. 15, 2008; Date of Mailing: Feb. 28, 2008.
International Preliminary Report on Patentability International Application No. PCT/EP2007/062630; International Filing Date: Nov. 21, 2007; Date of Submission: Oct. 19, 2008; Date of Completion: Feb. 26, 2009.
Cowden, Cameron J. , "Use of N-Protected Amino Acids in the Minisci Radical Alkylation", Organic Letters, 2003, p. 4497-4499, vol. 5, No. 23.

* cited by examiner

*Primary Examiner* — Deepak Rao
(74) *Attorney, Agent, or Firm* — Brinks Hofer Gilson & Lione

(57) ABSTRACT

The present invention relates to novel pyrimidylmethyl-sulfonamide compounds and to their N-oxides, their agriculturally acceptable salts and their veterinarily acceptable salts and also to agricultural compositions comprising at least one such compound as active component, and also to their use for controlling harmful fungi. The present invention also relates to a method for controlling arthropod pests.

10 Claims, No Drawings

PYRIMIDYLMETHYL-SULFONAMIDE COMPOUNDS

This application is a National Stage application of International Application No. PCT/EP2007/062630 filed Nov. 21, 2007, the entire contents of which is hereby incorporated herein by reference. This application also claims the benefit under 35 U.S.C. §119 of European Patent Application No. 06124589.0, filed Nov. 22, 2006, the entire contents of which is hereby incorporated herein by reference.

The present invention relates to novel pyrimidylmethyl-sulfonamide compounds and the N-oxides, and salts thereof and their use for combating arthropod pests and/or phytopathogenic harmful fungi, and also to compositions comprising, as active component, at least one such compound. The present invention also relates to a method for controlling arthropod pests.

WO 2005/033081 describes 4-pyridylmethyl sulphonamide compounds which are active against plant pathogenic fungi. With respect to their fungicidal activity, some of said 4-pyridylmethyl sulphonylamide are unsatisfactory, or they have unwanted properties such as low crop plant compatibility.

WO 2006/097489 (PCT/EP/2006/060753) describes various 4-pyridylmethylamides of biphenylsulphonic acid, wherein the biphenyl moiety may carry substituents at the phenyl ring of the biphenyl moiety at the sulfonamide group. The compounds are used for combating arthropodal pests and for protecting materials against infestation and/or destruction by said pests.

WO 2006/097488 (PCT/EP/2006/060752) inter alia describes arthropodal quinolone compounds of the formula (A),

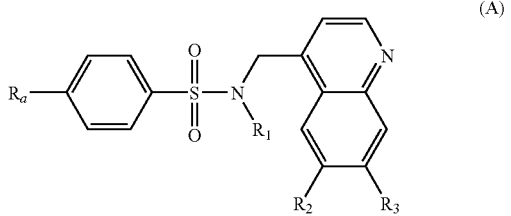

wherein $R_2$ and $R_3$ are both hydrogen, halogen, methoxy or trifluoromethoxy, $R_1$ is hydrogen or methyl and $R_1$ is selected from phenyl which may be unsubstituted or may carry one substituent selected from chloro, $C_1$-$C_4$-alkyl, methoxy, trifluoromethoxy or phenyl.

WO 2007/104726 (corresponds to U.S. 60/782,429) describes specific quinoline methylsulfonamides carrying a biphenyl moiety at the sulfonamide group wherein the phenylene moiety of biphenyl is unsubstituted.

PCT/EP2007/058348 (corresponds to EP 06119331.4) describes thiophene-sulfonic acid picolyl amide compounds and their use for combating arthropod pests. Said compounds have also a fungicidal activity.

Based on this, there is ongoing need to provide compounds which are useful for combating harmful arthropods such as insects and arachnids and/or harmful fungi.

This object is, surprisingly, achieved by pyrimidylmethyl-sulfonamide compounds of the general formula (I) described below

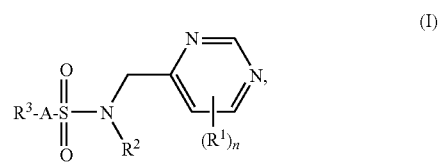

where:
n is zero, one, two or three;
$R^1$ is halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, amino, $C_1$-$C_4$-alkylamino, di($C_1$-$C_4$-alkyl)amino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_8$-cycloalkyl or $C_1$-$C_4$-alkyl-$C_3$-$C_8$-cycloalkyl; and/or
one radical $R^1$ that is bound to a carbon atom adjacent to a nitrogen atom of the pyrimidine ring may form together with said carbon atom and nitrogen atom a fused five-membered aromatic heterocycle, which may contain one or two further nitrogen atoms as ring members; or
two radicals $R^1$ that are bound to adjacent carbon atoms of the pyrimidine ring may form together with said carbon atoms a fused benzene ring, a fused saturated or partially unsaturated 5-, 6-, or 7-membered carbocycle or a fused 5-, 6-, or 7-membered heterocycle containing one, two or three heteroatoms selected from the group consisting of 2 nitrogen, 1 oxygen and 1 sulfur atoms as ring members, it being possible for the fused ring to carry one or two radicals selected from the group consisting of halogen, $C_1$-$C_4$-alkyl, halomethyl, $C_1$-$C_4$-alkoxy or halomethoxy;
$R^2$ is hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylamino, di($C_1$-$C_4$-alkyl)amino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_3$-$C_8$-cycloalkyl, alkyl-$C_3$-$C_8$-cycloalkyl or benzyl wherein the phenyl moiety of benzyl is unsubstituted or carries 1, 2, 3, 4, or 5 substituents selected from the group consisting of cyano, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl;
A is phenylene, 5- or 6-membered heteroarenediyl, where heteroarenediyl contains one, two, three or four heteroatoms selected from the group consisting of 1, 2, 3 or 4 nitrogen atoms, 1 oxygen atom and 1 sulfur atom, as ring members, and where phenylene and heteroarenediyl for their part are unsubstituted or carry 1, 2, 3 or 4 substituents $R^4$, each selected from the group consisting of cyano, halogen, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, ($C_1$-$C_4$-alkoxy)carbonyl and di($C_1$-$C_4$-alkyl)aminocarbonyl, or
A is $C_1$-$C_8$-alkanediyl, $C_1$-$C_8$-haloalkanediyl, $C_2$-$C_8$-alkenediyl, $C_2$-$C_8$-haloalkenediyl, $C_2$-$C_8$-alkynediyl, or $C_2$-$C_8$-haloalkynediyl, wherein the six last-mentioned radicals are unsubstituted or carry one, two or three substituents $R^{AA}$, each selected from the group consisting of cyano, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl;
$R^3$ is hydrogen, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino, di($C_1$-$C_4$-alkyl)amino, ($C_1$-$C_4$-alkyl)carbonyl, ($C_1$-$C_4$- alkoxy)iminomethyl, acryloyl(vinylcarbonyl), $C_3$-$C_8$-cycloalkyl, $C_1$-$C_4$-alkyl-$C_3$-$C_8$-cycloalkyl, or $C_5$-$C_8$-cycloalkenyl,

- phenyl, benzyl, phenoxy, phenylthio, a 5- or 6-membered heteroaryl radical, wherein the heteroaryl ring has 1, 2, 3 or 4 heteroatoms selected from the group consisting of 1, 2, 3 or 4 nitrogen atoms, 1 oxygen atom and 1 sulfur atom, as ring members, it being possible for the heteroaryl ring and the phenyl ring of phenyl, benzyl, phenoxy and phenylthio to be unsubstituted or substituted by one, two or three substituents $R^B$, each selected from the group consisting of cyano, nitro, amino, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl, di($C_1$-$C_4$-alkyl)aminocarbonyl, $C_1$-$C_4$-alkylthio, $C_1$-$C_4$-alkylsulfinyl and $C_1$-$C_4$-alkylsulfonyl; or
- a 5- or 6-membered heteroaryloxy radical or a 5- or 6-membered heteroarylthio radical, wherein the heteroaryl ring in the two aforementioned radicals has 1, 2, 3 or 4 heteroatoms selected from the group consisting of 1, 2, 3, or 4 nitrogen atoms, 1 oxygen atom and 1 sulfur atom, as ring members, it being possible for said heteroaromatic ring to carry one, two or three substituents $R^B$;
- or if A is phenylene or 5- or 6-membered heteroarenediyl, the radical $R^3$ together with a radical $R^4$ may form together with the carbon atoms to which they are bound a fused benzene ring, wherein the fused benzene ring may be unsubstituted or may carry 1, 2 or 3 substituents selected, independently from one another, from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl, or
- if A is phenylene or 5- or 6-membered heteroarenediyl, the radical $R^3$ can also be $C_1$-$C_4$-alkyl, $C_2$-$C_4$-alkenyl or $C_2$-$C_4$-alkynyl;

the N-oxides, and the salts of the compounds of the formula (I).

Accordingly, the present invention relates to pyrimidylmethyl-sulfonamide compounds of the general formula (I) and the N-oxides and salts thereof. Moreover, the invention relates to a process for preparing these compounds.

The compounds of the present invention are useful for combating phytopathogenic harmful fungi. Therefore the present invention also relates to the use of pyrimidylmethyl-sulfonamide compounds of the general formula (I), their N-oxides and salts for combating phytopathogenic harmful fungi.

The present invention furthermore relates to a method for the treatment of phytopathogenic harmful fungi, which process comprises treating the fungi or the materials, plants, the soil or seeds to be protected against fungal attack, with an effective amount of at least one compound of the formula (I) or an or an N-oxide or an agriculturally acceptable salt thereof.

The compounds of the present invention are also useful for combating arthropod pests, especially insects and arachnids. Therefore the present invention also relates to the use of compounds of the general formula (I) and their N-oxides and salts for combating arthropod pests. The present invention furthermore relates to a method for combating arthropod pests, which comprises contacting said pests, their habitat, breeding ground, food supply, plant, seed, soil, area, material or environment in which the arthropod pests are growing or may grow, or the materials, plants, seeds, soils, surfaces or spaces to be protected from an attack of or infestation by said pests, with a pesticidally effective amount of at least one compound of the formula (I), or a N-oxide or an agriculturally acceptable salt thereof or with a composition comprising at least one compound of the formula (I), and/or a N-oxide or a salt thereof. Furthermore, the present invention relates to a method of protecting growing plants from attack or infestation by arthropod pests, which comprises contacting a crop with a pesticidally effective amount of at least one compound of the formula (I) or a N-oxide or an agriculturally acceptable salt thereof.

Furthermore, the present invention relates to a method for protecting seeds from infestation by arthropodal pests and of the seedlings' roots and shoots from infestation by arthropod pests, which comprises contacting the seed or of the seedlings' roots and shoots with a pesticidally effective amount of at least one compound of the formula (I), or an N-oxide or an agriculturally acceptable salt thereof.

The present invention also relates to a method for protecting non-living materials from attack or infestation by arthropod pests, which comprises contacting the non-living material with a pesticidally effective amount of at least one compound of the formula (I), or an N-oxide or an agriculturally acceptable salt thereof.

The present invention also relates to seeds comprising a compound of the formula (I), or an N-oxide or an agriculturally acceptable salt thereof, in an amount of from 0.1 g to 10 kg per 100 kg of seed.

Depending on the substitution pattern, the compounds of the formula (I) and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

The compounds of the formula (I) can be present in different crystal modifications whose biological activity may differ. They also form part of the subject matter of the present invention.

Agriculturally useful salts of the compounds (I) encompass especially the salts of those cations or the acid addition salts of those acids whose cations and anions, respectively, have no adverse effect on the pesticidal action of the compounds (I). Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula (I) with an acid of the corresponding anion, preferably of hydrochloric acid, hydrobromic acid, sulfuric acid, phosphoric acid or nitric acid.

Veterinarily acceptable salts of the compounds of formula (I) encompass especially the salts of those cations or the acid addition salts which are known and accepted in the art for the formation of salts for veterinary use. Suitable acid addition salts, e.g. formed by compounds of formula (I) containing a basic nitrogen atom, e.g. an amino group, include salts with inorganic acids, for example hydrochlorides, sulphates, phosphates, and nitrates and salts of organic acids for example acetic acid, maleic acid, dimaleic acid, fumaric acid, difumaric acid, methane sulfenic acid, methane sulfonic acid, and succinic acid.

In the definitions of the variables given above, collective terms are used which are generally representative for the substituents in question. The term $C_n$—$C_m$ indicates the number of carbon atoms possible in each case in the substituent or substituent moiety in question.

The term "halogen" refers to fluorine, chlorine, bromine and iodine.

The term "$C_1$-$C_4$-alkyl" refers to a straight-chained or branched saturated hydrocarbon group having 1 to 4 carbon atoms, for example methyl, ethyl, propyl, 1-methylethyl, butyl, 1-methylpropyl, 2-methylpropyl, and 1,1-dimethylethyl.

The term "$C_1$-$C_4$-haloalkyl" refers to a straight-chained or branched alkyl group having 1 to 4 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, and the like.

The term "$C_1$-$C_4$-alkoxy" refers to a straight-chain or branched alkyl group having 1 to 4 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_4$-haloalkoxy" refers to a $C_1$-$C_4$-alkoxy radical as defined above which is partly or fully substituted by fluorine, chlorine, bromine and/or iodine, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro-ethoxy, $OC_2F_5$, 2-fluoropropoxy, 3-fluoropropoxy, 2,2-difluoropropoxy, 2,3-difluoro-propoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above).

Accordingly, the term "$C_1$-$C_4$-alkylthio" as used herein refers to straight-chain or branched alkyl groups having 1 to 4 carbon atoms (as defined above) bonded through a sulfur atom, at any position in the alkyl group, for example methylthio, ethylthio, propylthio, isopropylthio, and n-butylthio.

The term "$C_1$-$C_4$-alkylsulfinyl" refers to straight-chain or branched alkyl group having 1 to 4 carbon atoms (as defined above) bonded through a —S(=O) moiety, at any position in the alkyl group, for example methylsulfinyl and the like.

The term "$C_1$-$C_4$-haloalkylsulfinyl" refers to straight-chain or branched haloalkyl group having 1 to 4 carbon atoms (as defined above) bonded through a —S(=O) moiety, at any position in the alkyl group.

The term "$C_1$-$C_4$-alkylsulfonyl" refers to straight-chain or branched alkyl group having 1 to 4 carbon atoms (as defined above) bonded through a —S(=O)$_2$ moiety, at any position in the alkyl group, for example methylsulfonyl.

The term "$C_1$-$C_4$-haloalkylsulfonyl" refers to straight-chain or branched haloalkyl group having 1 to 4 carbon atoms (as defined above) bonded through a —S(=O)$_2$ moiety, at any position in the alkyl group.

The term "alkylamino" refers to an amino radical carrying one $C_1$-$C_4$-alkyl group (as defined above) as substituent, for example methylamino, ethylamino, propylamino, 1-methylethylamino, butylamino, 1-methylpropylamino, 2-methylpropylamino, 1,1-dimethylethylamino and the like.

The term "di($C_1$-$C_4$-alkyl)amino" refers to an amino radical carrying two identical or different $C_1$-$C_4$-alkyl groups (as defined above) as substituents, for example dimethylamino, diethylamino, di-n-propylamino, diisopropylamino, N-ethyl-N-methylamino, N-(n-propyl)-N-methylamino, N-(isopropyl)-N-methylamino, N-(n-butyl)-N-methylamino, N-(n-pentyl)-N-methylamino, N-(2-butyl)-N-methylamino, N-(isobutyl)-N-methylamino, and the like.

The term "$C_1$-$C_4$-alkoxycarbonyl" refers to a $C_1$-$C_4$-alkoxy radical as defined above which is attached via a carbonyl group.

The term "di($C_1$-$C_4$-alkyl)aminocarbonyl" refers to a di($C_1$-$C_4$)alkylamino radical as defined above which is attached via a carbonyl group.

The terms "phenoxy" and "phenylthio", respectively, refer to a phenyl radical which is attached via an oxygen and sulfur atom, respectively.

The term "$C_2$-$C_4$-alkenyl" refers to a branched or unbranched unsaturated hydrocarbon radical having 2 to 4 carbon atoms and a double bond in any position, such as ethenyl, 1-propenyl, 2-propenyl(allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_4$-haloalkenyl" refers to an unsaturated straight-chain or branched hydrocarbon radical having from 2 to 4 carbon atoms and one double bond in any position (as defined above), where some or all of the hydrogen atoms in these groups may be replaced by halogen atoms as specified above, in particular fluorine, chlorine and bromine.

The term "$C_2$-$C_4$-alkynyl" refers to a branched or unbranched unsaturated hydrocarbon radical having 2 to 4 carbon atoms and containing at least one triple bond, such as ethynyl, 1-propynyl, 2-propynyl(propargyl), 1-butynyl, 2-butynyl, 3-butynyl, 1-methyl-2-propynyl.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkenyl" refers to monocyclic monounsaturated hydrocarbon radicals having from 3 to 8, preferably from 5 to 6, carbon ring members, such as cyclopenten-1-yl, cyclopenten-3-yl, cyclohexen-1-yl, cyclohexen-3-yl, cyclohexen-4-yl and the like The term "$C_1$-$C_4$-alkyl-$C_3$-$C_8$-cycloalkyl" refers to a cycloalkyl radical having 3 to 8 carbon atoms (as defined above), wherein one hydrogen atom of the cycloalkyl radical is replaced by a $C_1$-$C_4$-alkyl group (as defined above).

The term "five- or six-membered heterocycle" which contains one, two, three or four heteroatoms from the group consisting of O, N and S, is to be understood as meaning both saturated, partially unsaturated and aromatic heterocycles having 5 or 6 ring atoms, including:

- 5- or 6-membered heterocyclyl which contains one, two or three nitrogen atoms and/or one oxygen or sulfur atom or one or two oxygen and/or sulfur atoms, and which is saturated or partially unsaturated, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl and 2-piperazinyl;
- 5-membered aromatic heterocyclyl(heteroaryl) which contains one, two, three or four nitrogen atoms or one, two or three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-thienyl, 3-thienyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl and 1,3,4-triazol-2-yl;
- 6-membered heteroaryl which contains one, two, three or four nitrogen atoms: 6-membered heteroaryl groups which, in addition to carbon atoms, may contain one, two, three or four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

Fused 5- or 6-membered carbocycle means a hydrocarbon ring which shares two adjacent carbon atoms with another ring, examples being cyclopentane, cyclopentene, cyclohexane, cyclohexene and benzene. Examples for 5- or 6-membered heterocycles which contain a contain a fused 5 or 6 membered carbocyclic ring as mentioned above are indolyl, indolinyl, isoindolinyl, benzpyrazolyl, benzimidazolyl, benzotriazolyl, quinolinyl, 1,2,3,4-tetrahydroquinolinyl, isoquinolinyl, phthalazinyl, quinazinyl, quinazolinyl, cinnolinyl, benzofuranyl, benzo-thiophenyl, benzopyranyl, dihydrobenzopyranyl, benzothiopyranyl, 1,3-benzodioxolyl, benzoxazolyl, benzthiazolyl, benzisoxazolyl and 1,4-benzodioxanyl.

The term "5-, 6- or 7-membered carbocycle" comprises monocyclic nonaromatic saturated or partially unsaturated carbocyclic rings having 5, 6 or 7 ring members. Examples for non-aromatic rings include cyclopentyl, cyclopentenyl, cyclopentadienyl, cyclohexyl, cyclohexenyl, cyclohexadienyl, cycloheptyl, cycloheptenyl, cycloheptadienyl and the like.

The term "$C_1$-$C_8$-alkanediyl" refers to a divalent, branched, or straight-chain saturated hydrocarbon radical having 1 to 8 carbon atoms, derived by the removal of one hydrogen atom from each of two different carbon atoms of a parent $C_1$-$C_8$-alkane, or by the removal of two hydrogen atoms from a single carbon atom of a parent $C_1$-$C_8$-alkane, for example, methanediyl, ethan-1,1-diyl, ethan-1,2-diyl, propan-1,1-diyl, propan-1,2-diyl, propan-2,2-diyl, propan-1,3-diyl, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, and the like.

The term "$C_1$-$C_8$-haloalkanediyl" refers to a divalent, branched, or straight-chain saturated hydrocarbon group having 1 to 8 carbon atoms, as defined above, wherein some or all of the hydrogen atoms in these groups may be replaced by halogen atoms as mentioned above.

The term "$C_2$-$C_8$-alkenediyl" refers to a divalent, branched, or straight-chain unsaturated hydrocarbon group having 2 to 8 carbon atoms, derived by the removal of one hydrogen atom from each of two different carbon atoms of a parent $C_2$-$C_8$-alkene, or by the removal of two hydrogen atoms from a single carbon atom of a parent $C_2$-$C_8$-alkene, for example, ethen-1,2-diyl, ethen-1,1-diyl, prop-1-en-1,1-diyl, prop-2-en-1,2-diyl, prop-1-en-1,3-diyl, propen-3,3-diyl, propen-2,2-diyl, but-2-en-1,4-diyl and the like.

The term "$C_2$-$C_8$-haloalkenediyl" refers to a divalent, branched, or straight-chain unsaturated hydrocarbon group having 2 to 8 carbon atoms, as defined above, wherein some or all of the hydrogen atoms in these groups may be replaced by halogen atoms as mentioned above.

The term "$C_2$-$C_8$-alkynediyl" refers to a divalent, branched, or straight-chain unsaturated hydrocarbon radical having 2 to 8 carbon atoms, derived by the removal of one hydrogen atom from each of two different carbon atoms of a parent $C_2$-$C_8$-alkyne, or by the removal of two hydrogen atoms from a single carbon atom of a parent $C_2$-$C_8$-alkyne, for example, prop-2-yn-1,1-diyl, prop-2-yn-1,3-diyl, prop-1-yn-1,3-diyl, but-1-yn-1,3-diyl, but-1-yn-1,4-diyl, but-2-yn-1,4-diyl and the like.

The term "$C_2$-$C_8$-haloalkynediyl" refers to a divalent, branched, or straight-chain unsaturated hydrocarbon radical having 2 to 8 carbon, as defined above, wherein some or all of the hydrogen atoms in these groups may be replaced by halogen atoms as mentioned above.

The term "phenylene" refers to 1,2-phenylene (o-phenylene), 1,3-phenylene (m-phenylene) and 1,4-phenylene (p-phenylene).

The term "5- or 6-membered heteroarenediyl" refers to a divalent radical derived from aromatic heterocycles having 5 or 6 ring atoms, as defined above, aromatic heterocycles having two points of attachment. Examples of heteroarenediyl radicals are, for example, divalent radicals derived from pyridine, pyrimidine, pyridazine, 1,2,3-triazine, 1,2,4-triazine, 1,2,3,4-tetrazine, furan, thiophene, pyrrole, thiazole, thiadiazole, pyrazole, imidazole, triazole, tetrazole, oxazole, isoxazole, isothiazole, oxadiazole and the like. The aforementioned groups can be C-attached or N-attached where such is possible. For example, a group derived from pyrrole, imidazole or pyrazole can be N-attached or C-attached.

The term "if A is phenylene or 5- or 6-membered heteroarenediyl, the radical $R^3$ together with a radical $R^A$ may form together with the carbon atoms to which they are bound a fused benzene ring" refers to a bicyclic ring system, wherein phenylene and heteroarenediyl, respectively, carry a fused-on benzene ring. Examples of fused bicyclic rings include naphthalene, benzo[b]furan, benzo[b]thiophene, benzimidazole, benzoxazole, benzthiazole, indole, quinoline and the like. The fused-on benzene ring can be unsubstituted or substituted by 1, 2, 3 radicals substituents selected, independently from one another, from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl. In addition, the phenylene moiety and the heteroarenediyl moiety of the bicyclic ring systems can be unsubstituted or substituted with 1, 2 or 3 substituents $R^4$.

The term "one radical $R^1$ that is bound to a carbon atom adjacent to a nitrogen atom of the pyrimidine ring may form together with said carbon atom and nitrogen atom a fused five-membered aromatic heterocycle, which may contain one, two or three further nitrogen atoms as ring members" refers in particular to a radical of the formula (B)

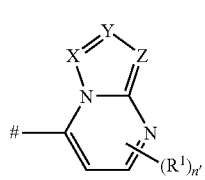

(B)

in which # denotes the point of attachment to the skeleton of the remaining molecule, X, Y and Z are, independently of one another, selected from CH and nitrogen, $R^1$ is as defined above and n' is 0 or 1.

As regards the pesticidal activity of the compounds of the formula (I), preference is given to those compounds of the formula (I), wherein the variables n, $R^1$, $R^2$, $R^3$, and A have independently of each other or more preferably in combination the following meanings.

Preference is given to compounds of the formula (I), in which A is phenylene or heteroarenediyl, as defined above, which both may be unsubstituted or may carry one, two or three substituents $R^4$.

Particular preference is given to compounds of the formula (I), in which A is phenylene, which is unsubstituted or substituted by one, two or three substituents $R^4$, with 1,3-phenylene or 1,4-phenylene being more preferred. Most preference is given to compounds of the formula (I), in which A is 1,4-phenylene, which may be unsubstituted or substituted by one, two or three substituents $R^4$, especially preferably A is 1,4-phenylene, which is unsubstituted.

Likewise, particular preference is given to compounds of the formula (I), in which A is heteroarenediyl selected from the group consisting of pyridinediyl, pyrimidinediyl, pyridazinediyl, pyrazinediyl, furandiyl, thiophenediyl, pyrrolediyl, thiazolediyl, pyrazolediyl, imidazolediyl, triazolediyl, tetrazolediyl, triazine, oxazolediyl, isoxazolediyl, isothiazolediyl, thiadiazolediyl, and oxadiazole, and where the 18 last-mentioned radicals are unsubstituted or carry one, two or three substituents $R^4$. If one point of attachment is located on a nitrogen atom of the heteroarenediyl radical, said nitrogen atom is attached either to the sulfur atom of the sulfonamide group or to $R^3$, with the point of attachment to $R^3$ being more preferred.

Examples of heteroarenediyl radicals A are pyridin-2,3-diyl, pyridin-2,4-diyl, pyridin-2,5-diyl, pyridin-2,6-diyl, pyridin-3,5-diyl, pyrimidin-2,4-diyl, pyrimidin-2,5-diyl, pyrimidin-4,6-diyl, pyridazin-3,6-diyl, pyridazin-3,5-diyl, pyrazin-2,6-diyl, pyrazin-2,5-diyl, 1,2,3-triazin-4,5-diyl, 1,2,3-triazin-4,6-diyl, 1,2,4-triazin-3,6-diyl, 1,2,4-triazin-3,5-diyl 1,3,5-triazin-2,4-diyl, furan-2,5-diyl, furan-2,4-diyl, furan-3,5-diyl, thiophen-2,5-diyl, thiophen-2,4-diyl, thiophen-3,5-diyl, pyrrol-2,4-diyl, pyrrol-2,5-diyl, [1H]-pyrrol-1,3-diyl, thiazol-2,4-diyl, thiazol-2,5-diyl, pyrrol-2,4-diyl, pyrazol-3,5-diyl, [1H]-pyrazol-1,3-diyl, [1H]-pyrazol-1,4-diyl, imidazol-2,4-diyl, imidazol-2,5-diyl, [1H]imidazol-1,4-diyl, [1H]-1,2,3-triazol-4,5-diyl, [1H]-1,2,3-triazol-1,5-diyl, [1H]-1,2,3-triazol-1,4-diyl, [1H]-1,2,4-triazol-3,5-diyl, [1H]-1,2,4-triazol-1,3-diyl, [1H]-1,2,3-triazol-1,5-diyl, [1H]-1,2,3,4-tetrazol-4,5-diyl, 2,4-oxazoldiyl, 2,5-oxazoldiyl, 4,5-oxazoldiyl, isoxazol-3,4-diyl, isoxazol-3,5-diyl, isoxazol-4,5-diyl, isothiazol-3,4-diyl, isothiazol-3,5-diyl, isothiazol-4,5-diyl, 1,2,3-oxadiazol-4,5-diyl, 1,2,4-oxadiazol-3,5-diyl, 1,3,4-oxadiazol-2,5-diyl, 1,2,5-oxadiazol-3,4-diyl, 1,2,3-thiadiazol-4,5-diyl, 1,2,4-thiadiazol-3,5-diyl, 1,3,4-thiadiazol-2,5-diyl and 1,2,5-thiadiazol-3,4-diyl, and each of which is optionally substituted by one, two or three substituents $R^4$.

Amongst compounds of the formula (I), in which A is heteroarenediyl, particular preference is given to those, in which A is thiophenediyl, thiazolediyl, oxazolediyl, pyrazolediyl or pyridinediyl, where each of the aforementioned five radicals are unsubstituted or carry one, two or three substituents $R^4$.

Amongst compounds of the formula (I), in which A is heteroarenediyl, most preference is given to those, in which A is selected from the group consisting of thiophene-2,5-diyl, thiophene-2,4-diyl, thiophene-3,5-diyl, thiazole-2,5-diyl, thiazole-2,4-diyl, oxazole-2,5-diyl, oxazole-2,4-diyl, pyrazole-3,5-diyl, pyrazole-1,3-diyl, pyrazole-1,4-diyl, pyridine-2,5-diyl, pyridine-2,6-diyl, pyridine-2,4-diyl, pyridine-3,5-diyl, wherein heteroarenediyl is unsubstituted or carries one, two or three substituents $R^4$.

Particularly preferred embodiments of the invention relate to compounds of the formula (I), in which A is one of the radicals A-1 to A-30

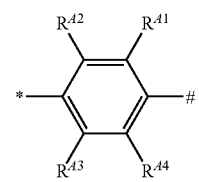

A-1

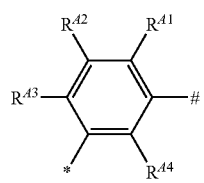

A-2

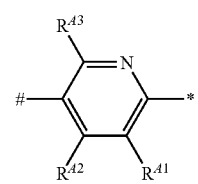

A-3

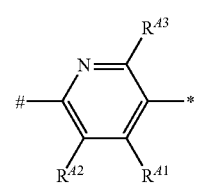

A-4

-continued
| | |
|---|---|
| 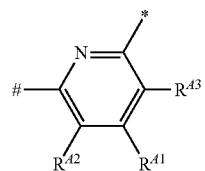 | A-5 |
| 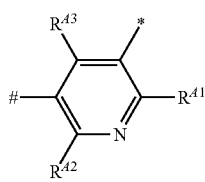 | A-6 |
| 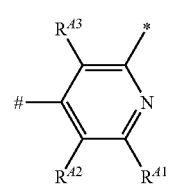 | A-7 |
| 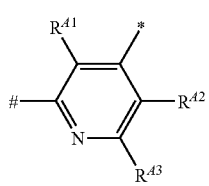 | A-8 |
| 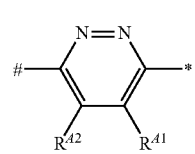 | A-9 |
| 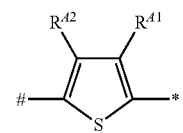 | A-10 |
| 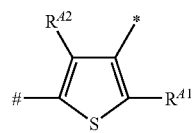 | A-11 |
| 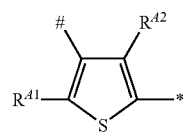 | A-12 |
| 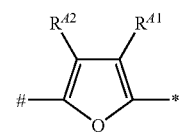 | A-13 |
| 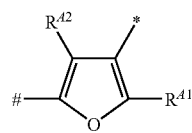 | A-14 |
-continued
| | |
|---|---|
| 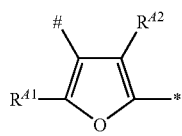 | A-15 |
| 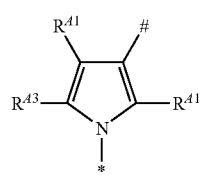 | A-16 |
| 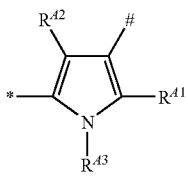 | A-17 |
| 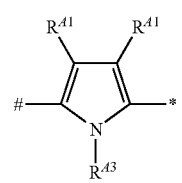 | A-18 |
| 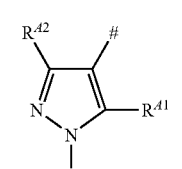 | A-19 |
| 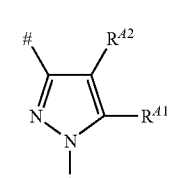 | A-20 |
| 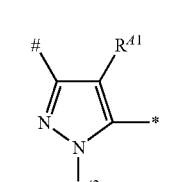 | A-21 |
| 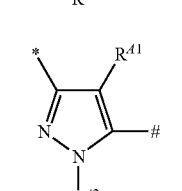 | A-22 |
| 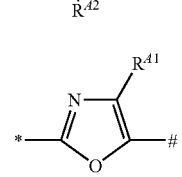 | A-23 |

-continued

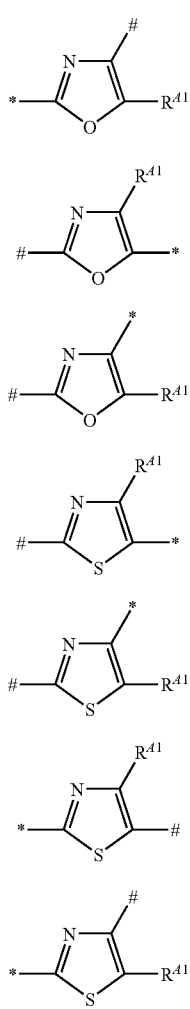

in which
# indicates the point of attachment to the sulfur atom of the sulfonamide group;
* indicates the point of attachment to $R^3$; and
$R^{A1}$, $R^{A2}$, $R^{A3}$ and $R^{A4}$ are each independently hydrogen or have one of the definitions specified for $R^A$, especially those being preferred.

If $R^A$ is present, preferred substituents $R^A$ are selected, independently of one another, from halogen, such as fluorine or chlorine, $C_1$-$C_4$-alkyl, such as methyl or ethyl, $C_1$-$C_4$-alkoxy, such as methoxy, $C_1$-$C_4$-haloalkoxy such as $C_1$-$C_2$-fluoroalkoxy, $C_1$-$C_4$-haloalkyl such as $C_1$-$C_2$-fluoroalkyl and cyano.

A further preferred embodiment of the invention relates to compounds of the formula (I) in which A is $C_2$-$C_4$-alkenediyl, $C_2$-$C_4$-haloalkenediyl, $C_2$-$C_4$-alkynediyl or $C_2$-$C_4$-haloalkynediyl, and where the four last-mentioned radicals are unsubstituted or carry one, two, or three substituents $R^{AA}$. Preferred substituents $R^{AA}$ are selected from $C_1$-$C_4$-alkoxy and $C_1$-$C_4$-haloalkoxy. $R^{AA}$ is in particular $C_1$-$C_2$-alkoxy, such as methoxy, or $C_1$-$C_2$-fluoroalkoxy, such as trifluoromethoxy. Among these, particular preference is given to compounds of the formula (I), in which A is ethen-1,2-diyl or ethyn-1,2-diyl, which may be unsubstituted or carry 1 substituent $R^{AA}$ as defined above.

Preferred are compounds of the formula (I), wherein $R^3$ is phenyl or phenoxy, where the two last-mentioned radicals are unsubstituted or carry one, two, or three substituents $R^B$. Preferred substituents $R^B$ are halogen, in particular fluorine or chlorine, $C_1$-$C_2$-alkyl such as methyl or ethyl, $C_1$-$C_2$-fluoroalkyl such as trifluoromethyl, $C_1$-$C_2$-alkoxy such as methoxy, $C_1$-$C_2$-fluoroalkoxy, in particular $C_1$-$C_2$-fluoroalkoxy, such as trifluoromethoxy, $C_1$-$C_2$-alkoxycarbonyl such as methoxycarbony, ($C_1$-$C_2$-alkoxy)carbonyl, in particular methoxycarbony, or di($C_1$-$C_2$-alkyl)aminocarbonyl, such as dimethylaminocarbonyl. Especially preferred radicals $R^B$ are each independently selected from fluorine and chlorine.

Very particular preference is given to compounds of the formula (I) in which $R^3$ is phenyl, which is substituted by at least one substituent $R^B$. In this case, especially preferably, at least one of the radicals $R^B$ is arranged in the para-position relative to the bonding site of phenyl to the A-moiety. In this embodiment, preferred substituents $R^B$ are halogen, in particular fluorine or chlorine, $C_1$-$C_2$-alkyl such as methyl or ethyl, $C_1$-$C_2$-fluoroalkyl such as trifluoromethyl, $C_1$-$C_2$-alkoxy such as methoxy, $C_1$-$C_2$-fluoroalkoxy, in particular $C_1$-$C_2$-fluoroalkoxy, such as trifluoromethoxy, $C_1$-$C_2$-alkoxycarbonyl such as methoxycarbony, ($C_1$-$C_2$-alkoxy)carbonyl, in particular methoxycarbony, or di($C_1$-$C_2$-alkyl)aminocarbonyl, such as dimethylaminocarbonyl. Especially preferred radicals $R^B$ are each independently selected from fluorine and chlorine.

Likewise, most preferred are compounds of the formula (I), in which $R^3$ is phenoxy, which is substituted by one substituent $R^B$, with chlorine and fluorine being most preferred substituents $R^B$. Likewise, most preferred are compounds of the formula (I) in which $R^3$ is phenoxy, which is substituted with two, different or same substituents $R^B$. In this embodiment, preferred substituents $R^B$ are halogen, in particular fluorine or chlorine, $C_1$-$C_2$-alkyl such as methyl or ethyl, $C_1$-$C_2$-fluoroalkyl such as trifluoromethyl, $C_1$-$C_2$-alkoxy such as methoxy, $C_1$-$C_2$-fluoroalkoxy, in particular $C_1$-$C_2$-fluoroalkoxy, such as trifluoromethoxy, $C_1$-$C_2$-alkoxycarbonyl such as methoxycarbony, ($C_1$-$C_2$-alkoxy)carbonyl, in particular methoxycarbony, or di($C_1$-$C_2$-alkyl)aminocarbonyl, such as dimethylaminocarbonyl, with fluorine or chlorine being most preferred. In this embodiment, especially preferably at least one of the radicals $R^B$ is located in the para-position relative to the bonding site of phenoxy to the A-moiety.

Preference is likewise given to compounds of the formula (I) in which $R^3$-A are together $C_2$-$C_8$-alkenyl or $C_2$-$C_8$-alkynyl, where said alkenyl or said alkynyl are unsubstituted or substituted by $R^{AA}$, preferably by 1, 2, 3 or 4 substituents $R^{AA}$. Preferred substituents $R^{AA}$ are selected from halogen, $C_1$-$C_4$-alkoxy and $C_1$-$C_4$-haloalkoxy. $R^{AA}$ is in particular halogen, especially fluorine and chlorine, $C_1$-$C_2$-alkoxy, such as methoxy, or $C_1$-$C_2$-fluoroalkoxy, such as trifluoromethoxy. Among these, particular preference is given to compounds of the formula (I), in which $R^3$-A are together $C_2$-$C_4$-alkenyl or $C_2$-$C_4$-alkynyl, which may be unsubstituted or substituted as defined above.

Particular preference is given to those compounds of the formula (I), in which the variables $R^3$ and A have in combination the following meanings:
$R^3$ is phenyl, which is unsubstituted or substituted by at least one substituent $R^B$, preferably one or two. If $R^B$ is present, especially preferably, one of the radicals $R^B$ is arranged in the para-position relative to the bonding site of phenyl to the A-moiety. Preferred substituents $R^B$ are halogen, in particular fluorine or chlorine, $C_1$-$C_2$-alkyl such as methyl or ethyl, $C_1$-$C_2$-fluoroalkyl such as trifluoromethyl, $C_1$-$C_2$-alkoxy such as methoxy, $C_1$-$C_2$-fluoroalkoxy, in particular $C_1$-$C_2$-fluoroalkoxy, such as trifluoromethoxy, $C_1$-$C_2$-alkoxycarbonyl such as methoxycarbony, ($C_1$-$C_2$-alkoxy)

carbonyl, in particular methoxycarbony, or di($C_1$-$C_2$-alkyl)aminocarbonyl, such as dimethylaminocarbonyl. Especially preferred radicals $R^B$ are each independently selected from fluorine and chlorine; and A is phenylene, which is unsubstituted or substituted by one, two or three substituents $R^A$, in particular 1,3-phenylene or 1,4-phenylene, especially preferably 1,4-phenylene. With particular preference A is 1,4-phenylene, which is unsubstituted. If $R^A$ is present, preferred substituents $R^A$ are selected, independently of one another, from halogen, such as fluorine or chlorine, cyano, $C_1$-$C_4$-alkyl, such as methyl or ethyl, $C_1$-$C_4$-alkoxy, such as methoxy, $C_1$-$C_4$-haloalkoxy such as $C_1$-$C_2$-fluoroalkoxy, and $C_1$-$C_4$-haloalkyl such as $C_1$-$C_2$-fluoroalkyl.

Particular preference is likewise given to those compounds of the formula (I), in which the variables $R^3$ and A have in combination the following meanings:

$R^3$ is phenyl, which is unsubstituted or substituted by at least one substituent $R^B$, preferably one or two. If $R^B$ is present, especially preferably, one of the radicals $R^B$ is arranged in the para-position relative to the bonding site of phenyl to the A-moiety. Preferred substituents $R^B$ are halogen, in particular fluorine or chlorine, $C_1$-$C_2$-alkyl such as methyl or ethyl, $C_1$-$C_2$-fluoroalkyl such as trifluoromethyl, $C_1$-$C_2$-alkoxy such as methoxy, $C_1$-$C_2$-fluoroalkoxy, in particular $C_1$-$C_2$-fluoroalkoxy, such as trifluoromethoxy, $C_1$-$C_2$-alkoxycarbonyl such as methoxycarbony, ($C_1$-$C_2$-alkoxy)carbonyl, in particular methoxycarbony, or di($C_1$-$C_2$-alkyl)aminocarbonyl, such as dimethylaminocarbonyl. Especially preferred radicals $R^B$ are each independently selected from fluorine and chlorine; and A is heteroarenediyl, which is unsubstituted or carries one, two or three substituents $R^A$. If $R^A$ is present, preferred substituents $R^A$ are selected, independently of one another, from halogen, such as fluorine or chlorine, cyano, $C_1$-$C_4$-alkyl, such as methyl or ethyl, $C_1$-$C_4$-alkoxy, such as methoxy, $C_1$-$C_4$-haloalkoxy such as $C_1$-$C_2$-fluoroalkoxy, and $C_1$-$C_4$-haloalkyl such as $C_1$-$C_2$-fluoroalkyl. More preferably heteroarenediyl is selected from the group consisting of thiophene-2,5-diyl, thiophene-2,4-diyl, furan-2,5-diyl, furan-2,4-diyl, pyrrol-2,4-diyl, pyrrol-2,5-diyl, [1H]-pyrrol-1,3-diyl, thiazole-2,5-diyl, thiazole-2,4-diyl, oxazole-2,5-diyl, oxazole-2,4-diyl, pyrazole-3,5-diyl, pyrazole-1,3-diyl, pyrazole-1,4-diyl, pyridine-2,5-diyl, pyridine-2,6-diyl, pyridine-2,4-diyl, pyridine-3,5-diyl and pyridazine-3,6-diyl, wherein heteroarenediyl is unsubstituted or carries one, two or three substituents $R^A$, especially one of the radicals A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29 or A-30 as defined above.

Particular preference is likewise given to those compounds of the formula (I), in which the variables $R^3$ and A have in combination the following meanings:

$R^3$ is phenoxy, which is unsubstituted;
is phenoxy, which is substituted by one substituent $R^B$, with chlorine and fluorine being most preferred substituents $R^B$, or
is phenoxy, which is substituted by two, different or same substituents $R^B$. In this embodiment, preferred substituents $R^B$ are halogen, in particular fluorine or chlorine, $C_1$-$C_2$-alkyl such as methyl or ethyl, $C_1$-$C_2$-fluoroalkyl such as trifluoromethyl, $C_1$-$C_2$-alkoxy such as methoxy, $C_1$-$C_2$-fluoroalkoxy, in particular $C_1$-$C_2$-fluoroalkoxy, such as trifluoromethoxy, $C_1$-$C_2$-alkoxycarbonyl such as methoxycarbony, ($C_1$-$C_2$-alkoxy)carbonyl, in particular methoxycarbony, or di($C_1$-$C_2$-alkyl)aminocarbonyl, such as dimethylaminocarbonyl, with fluorine or chlorine being most preferred. If $R^B$ is present, especially preferably one of the radicals $R^B$ is arranged in the para-position relative to the bonding site of phenoxy to the A-moiety; and A is phenylene, which is unsubstituted or substituted by one, two or three substituents $R^A$, in particular 1,3-phenylene or 1,4-phenylene, especially preferably 1,4-phenylene. With particular preference A is 1,4-phenylene, which is unsubstituted. If $R^A$ is present, preferred substituents $R^A$ are selected, independently of one another, from halogen, such as fluorine or chlorine, cyano, $C_1$-$C_4$-alkyl, such as methyl or ethyl, $C_1$-$C_4$-alkoxy, such as methoxy, $C_1$-$C_4$-haloalkoxy such as $C_1$-$C_2$-fluoroalkoxy, and $C_1$-$C_4$-haloalkyl such as $C_1$-$C_2$-fluoroalkyl.

Particular preference is likewise given to those compounds of the formula (I), in which the variables $R^3$ and A have in combination the following meanings:

$R^3$ is phenoxy, which is unsubstituted,
is phenoxy, which is substituted by one substituent $R^B$, with chlorine and fluorine being most preferred substituents $R^B$, or
is phenoxy, which is substituted with two, different or same substituents $R^B$. In this embodiment, preferred substituents $R^B$ are halogen, in particular fluorine or chlorine, $C_1$-$C_2$-alkyl such as methyl or ethyl, $C_1$-$C_2$-fluoroalkyl such as trifluoromethyl, $C_1$-$C_2$-alkoxy such as methoxy, $C_1$-$C_2$-fluoroalkoxy, in particular $C_1$-$C_2$-fluoroalkoxy, such as trifluoromethoxy, $C_1$-$C_2$-alkoxycarbonyl such as methoxycarbony, ($C_1$-$C_2$-alkoxy)carbonyl, in particular methoxycarbony, or di($C_1$-$C_2$-alkyl)aminocarbonyl, such as dimethylaminocarbonyl, with fluorine or chlorine being most preferred. If $R^B$ is present, especially preferably one of the radicals $R^B$ is arranged in the para-position relative to the bonding site of phenoxy to the A-moiety; and A is heteroarenediyl, which is unsubstituted or carries one, two or three substituents $R^A$. If $R^A$ is present, preferred substituents $R^A$ are selected, independently of one another, from halogen, such as fluorine or chlorine, cyano, $C_1$-$C_4$-alkyl, such as methyl or ethyl, $C_1$-$C_4$-alkoxy, such as methoxy, $C_1$-$C_4$-haloalkoxy such as $C_1$-$C_2$-fluoroalkoxy, and $C_1$-$C_4$-haloalkyl such as $C_1$-$C_2$-fluoroalkyl. More preferably heteroarenediyl is selected from the group consisting of thiophene-2,5-diyl, thiophene-2,4-diyl, furan-2,5-diyl, furan-2,4-diyl, pyrrol-2,4-diyl, pyrrol-2,5-diyl, [1H]-pyrrol-1,3-diyl, thiazole-2,5-diyl, thiazole-2,4-diyl, oxazole-2,5-diyl, oxazole-2,4-diyl, pyrazole-3,5-diyl, pyrazole-1,3-diyl, pyrazole-1,4-diyl, pyridine-2,5-diyl, pyridine-2,6-diyl, pyridine-2,4-diyl, pyridine-3,5-diyl and pyridazine-3,6-diyl, wherein heteroarenediyl is unsubstituted or carries one, two or three substituents $R^A$, especially one of the radicals A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29 or A-30 as defined above.

A specific embodiment relates to compounds of the formula (I), in which A is a 5- or 6-membered heteroarenediyl, and the radical $R^3$ together with a radical $R^A$ form together with the carbon atoms to which they are bound a fused benzene ring, wherein the fused benzene ring may be unsubstituted or may carry 1, 2 or 3 substituents selected, independently from one another, from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl. In this case, preference is given to $R^3$-A being together benzo[b]furan or benzo[b]thiophene, wherein the benzene moiety of benzo[b]furan and benzo[b]thiophene is unsubstituted or carries one or two substituents. Said substituents on the benzene moiety are preferable $C_1$-$C_2$-alkyl, especially methyl, or halogen, in particular chlorine. The furan moiety of benzo[b]furan and the thiophene moiety of benzo[b]thiophene can be unsubstituted or carry one substituent preferably selected from $C_1$-$C_2$-alkyl, especially methyl, or halogen, especially chlorine.

Preference is furthermore given to compounds of the formula (I) in which $R^2$ is hydrogen, $C_1$-$C_4$-alkyl, especially methyl, ethyl, n-propyl, 1-methylethyl(isopropyl), n-butyl or 2-methylpropyl(isobutyl), $C_1$-$C_2$-fluoroalkyl, especially trifluoromethyl, $C_1$-$C_2$-alkoxy, especially methoxy, di($C_1$-$C_2$-alkyl)amino, especially dimethylamino, $C_2$-$C_3$-alkenyl, especially allyl, or $C_2$-$C_3$-alkynyl, especially propargyl. More preference is given to compounds of the formula (I) in which $R^2$ is hydrogen, methyl, ethyl, n-butyl, allyl or propargyl, hydrogen being most preferred.

$R^1$ is preferably $C_1$-$C_4$-alkyl, cyclopropyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, ($C_1$-$C_4$-alkyl)amino, di($C_1$-$C_4$-alkyl)amino, or halogen such as F, Cl and Br. Especially preferably, $R^1$ is s chlorine, bromine, fluorine, $C_1$-$C_2$-alkyl, especially methyl, $C_1$-$C_2$-alkoxy, especially methoxy, $C_1$-$C_2$-alkylthio, especially methylthio, or di($C_1$-$C_2$-alkyl)amino, especially dimethylamino. Likewise especially preferably, $R^1$ is selected from $C_1$-$C_2$-haloalkoxy, in particular difluoromethoxy or trifluoromethoxy, $C_1$-$C_2$-haloalkylthio, in particular difluoromethylthio or trifluoromethylthio, ($C_1$-$C_2$-alkyl)amino, in particular methylamino and $C_1$-$C_2$-alkylsulfonyl, in particular methylsulfonyl.

A preferred embodiment of the present invention relates to compounds of the formula (I), in which the index n is zero. These compounds are also referred to compounds (I.a).

A further preferred embodiment of the present invention relates to compounds of the formula (I), in which the index n is one. These compounds are also referred to compounds (I.b). From among these, particular preference is given to those compounds of the formula (I.b), in which $R^1$ is chlorine, bromine, fluorine, methyl, methoxy, methylthio, dimethylamino, with chlorine being most preferred. Likewise preference is given to compounds of the formula I.b, wherein $R^1$ is selected from the group consisting of methylamino, methylsulfonyl, difluoromethylthio, trifluoromethylthio, difluoromethoxy, difluoromethoxy and cyclopropyl.

A further preferred embodiment relates to compounds of the formula (I) in which n is two. These compounds are also referred to compounds (I.c). From among these, particular preference is given to those compounds of the formula (I.c), in which $R^1$ is, independently, from one another, selected from chlorine, methoxy, methyl and methylthio.

A further preferred embodiment relates to compounds of the formula (I) in which n is three. These compounds are also referred to compounds (I.d). From among these, particular preference is given to those compounds of the formula (I.d), in which $R^1$ is chlorine, methyl, methoxy, methylthio or dimethylamino, with chlorine being most preferred.

Especially preferred are the compounds of the formulae (I.a.a), (I.b.a) and (I.c.a)

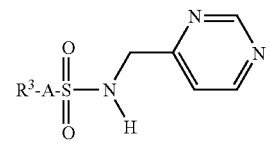

(I.a.a)

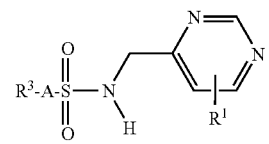

(I.b.a)

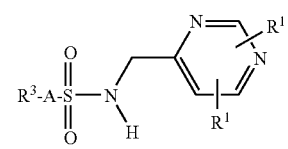

(I.c.a)

in which $R^1$, $R^3$ and A are as defined above.

A skilled person will readily understand that the preferences given for $R^3$ and A in connection with compounds of formula (I) also apply for formula (I.a.a) as defined herein.

A skilled person will readily understand that the preferences given for $R^1$, $R^3$ and A in connection with compounds of formula (I) also apply for formulae (I.b.a) and (I.c.a) as defined herein.

With respect to their use, particular preference is given to the compounds of formula (I) compiled in the tables 1 to 34 below.

Table 1: Compounds 1 to 4368

Compounds of the formula (I.a), wherein $R^2$ is hydrogen and the combination $R^3$-A for a compound corresponds in each case to one line of table A.

TABLE A

| no. | $R^3$-A- |
|---|---|
| 1. | 4-(o-CN-phenyl)-phenyl |
| 2. | 4-(m-CN-phenyl)-phenyl |
| 3. | 4-(p-CN-phenyl)-phenyl |
| 4. | 4-(o-NO$_2$-phenyl)-phenyl |
| 5. | 4-(m-NO$_2$-phenyl)-phenyl |
| 6. | 4-(p-NO$_2$-phenyl)-phenyl |
| 7. | 4-(o-F-phenyl)-phenyl |
| 8. | 4-(m-F-phenyl)-phenyl |
| 9. | 4-(p-F-phenyl)-phenyl |
| 10. | 4-(o-Cl-phenyl)-phenyl |
| 11. | 4-(m-Cl-phenyl)-phenyl |
| 12. | 4-(p-Cl-phenyl)-phenyl |
| 13. | 4-(o-Br-phenyl)-phenyl |
| 14. | 4-(m-Br-phenyl)-phenyl |
| 15. | 4-(p-Br-phenyl)-phenyl |
| 16. | 4-(o-CH$_3$-phenyl)-phenyl |
| 17. | 4-(m-CH$_3$-phenyl)-phenyl |
| 18. | 4-(p-CH$_3$-phenyl)-phenyl |
| 19. | 4-(o-CF$_3$-phenyl)-phenyl |
| 20. | 4-(m-CF$_3$-phenyl)-phenyl |
| 21. | 4-(p-CF$_3$-phenyl)-phenyl |
| 22. | 4-(o-CF$_3$-phenyl)-phenyl |
| 23. | 4-(m-CF$_3$-phenyl)-phenyl |
| 24. | 4-(p-CF$_3$-phenyl)-phenyl |
| 25. | 4-(o-OCH$_3$-phenyl)-phenyl |
| 26. | 4-(m-OCH$_3$-phenyl)-phenyl |
| 27. | 4-(p-OCH$_3$-phenyl)-phenyl |
| 28. | 4-(o-OCF$_3$-phenyl)-phenyl |
| 29. | 4-(m-OCF$_3$-phenyl)-phenyl |
| 30. | 4-(p-OCF$_3$-phenyl)-phenyl |
| 31. | 4-(o-COOCH$_3$-phenyl)-phenyl |
| 32. | 4-(m-COOCH$_3$-phenyl)-phenyl |
| 33. | 4-(p-COOCH$_3$-phenyl)-phenyl |

TABLE A-continued

| no. | R³-A- |
|---|---|
| 34. | 4-[o-N(CH₃)₂-phenyl]-phenyl |
| 35. | 4-[m-N(CH₃)₂-phenyl]-phenyl |
| 36. | 4-[p-N(CH₃)₂-phenyl]-phenyl |
| 37. | 4-(2,3-dicyanophenyl)-phenyl |
| 38. | 4-(2,4-dicyanophenyl)-phenyl |
| 39. | 4-(2,5-dicyanophenyl)-phenyl |
| 40. | 4-(2,6-dicyanophenyl)-phenyl |
| 41. | 4-(3,4-dicyanophenyl)-phenyl |
| 42. | 4-(3,5-dicyanophenyl)-phenyl |
| 43. | 4-(2,3-difluorophenyl)-phenyl |
| 44. | 4-(2,4-difluorophenyl)-phenyl |
| 45. | 4-(2,5-difluorophenyl)-phenyl |
| 46. | 4-(2,6-difluorophenyl)-phenyl |
| 47. | 4-(3,4-difluorophenyl)-phenyl |
| 48. | 4-(3,5-difluorophenyl)-phenyl |
| 49. | 4-(2,3-dichlorophenyl)-phenyl |
| 50. | 4-(2,4-dichlorophenyl)-phenyl |
| 51. | 4-(2,5-dichlorophenyl)-phenyl |
| 52. | 4-(2,6-dichlorophenyl)-phenyl |
| 53. | 4-(3,4-dichlorophenyl)-phenyl |
| 54. | 4-(3,5-dichlorophenyl)-phenyl |
| 55. | 4-(2,3-dibromophenyl)-phenyl |
| 56. | 4-(2,4-dibromophenyl)-phenyl |
| 57. | 4-(2,5-dibromophenyl)-phenyl |
| 58. | 4-(2,6-dibromophenyl)-phenyl |
| 59. | 4-(3,4-dibromophenyl)-phenyl |
| 60. | 4-(3,5-dibromophenyl)-phenyl |
| 61. | 4-(2,3-dimethylphenyl)-phenyl |
| 62. | 4-(2,4-dimethylphenyl)-phenyl |
| 63. | 4-(2,5-dimethylphenyl)-phenyl |
| 64. | 4-(2,6-dimethylphenyl)-phenyl |
| 65. | 4-(3,4-dimethylphenyl)-phenyl |
| 66. | 4-(3,5-dimethylphenyl)-phenyl |
| 67. | 4-[2,3-di(trifluoromethyl)phenyl]-phenyl |
| 68. | 4-[2,4-di(trifluoromethyl)phenyl]-phenyl |
| 69. | 4-[2,5-di(trifluoromethyl)phenyl]-phenyl |
| 70. | 4-[2,6-di(trifluoromethyl)phenyl]-phenyl |
| 71. | 4-[3,4-di(trifluoromethyl)phenyl]-phenyl |
| 72. | 4-[3,5-di(trifluoromethyl)phenyl]-phenyl |
| 73. | 4-(2,3-dimethoxyphenyl)-phenyl |
| 74. | 4-(2,4-dimethoxyphenyl)-phenyl |
| 75. | 4-(2,5-dimethoxyphenyl)-phenyl |
| 76. | 4-(2,6-dimethoxyphenyl)-phenyl |
| 77. | 4-(3,4-dimethoxyphenyl)-phenyl |
| 78. | 4-(3,5-dimethoxyphenyl)-phenyl |
| 79. | 4-(o-CN-phenoxy)-phenyl |
| 80. | 4-(m-CN-phenoxy)-phenyl |
| 81. | 4-(p-CN-phenoxy)-phenyl |
| 82. | 4-(o-NO₂-phenoxy)-phenyl |
| 83. | 4-(m-NO₂-phenoxy)-phenyl |
| 84. | 4-(p-NO₂-phenoxy)-phenyl |
| 85. | 4-(o-F-phenoxy)-phenyl |
| 86. | 4-(m-F-phenoxy)-phenyl |
| 87. | 4-(p-F-phenoxy)-phenyl |
| 88. | 4-(o-Cl-phenoxy)-phenyl |
| 89. | 4-(m-Cl-phenoxy)-phenyl |
| 90. | 4-(p-Cl-phenoxy)-phenyl |
| 91. | 4-(o-Br-phenoxy)-phenyl |
| 92. | 4-(m-Br-phenoxy)-phenyl |
| 93. | 4-(p-Br-phenoxy)-phenyl |
| 94. | 4-(o-CH₃-phenoxy)-phenyl |
| 95. | 4-(m-CH₃-phenoxy)-phenyl |
| 96. | 4-(p-CH₃-phenoxy)-phenyl |
| 97. | 4-(o-CF₃-phenoxy)-phenyl |
| 98. | 4-(m-CF₃-phenoxy)-phenyl |
| 99. | 4-(p-CF₃-phenoxy)-phenyl |
| 100. | 4-(o-CF₃-phenoxy)-phenyl |
| 101. | 4-(m-CF₃-phenoxy)-phenyl |
| 102. | 4-(p-CF₃-phenoxy)-phenyl |
| 103. | 4-(o-OCH₃-phenoxy)-phenyl |
| 104. | 4-(m-OCH₃-phenoxy)-phenyl |
| 105. | 4-(p-OCH₃-phenoxy)-phenyl |
| 106. | 4-(o-OCF₃-phenoxy)-phenyl |
| 107. | 4-(m-OCF₃-phenoxy)-phenyl |
| 108. | 4-(p-OCF₃-phenoxy)-phenyl |
| 109. | 4-(o-COOCH₃-phenoxy)-phenyl |
| 110. | 4-(m-COOCH₃-phenoxy)-phenyl |
| 111. | 4-(p-COOCH₃-phenoxy)-phenyl |
| 112. | 4-[o-N(CH₃)₂-phenoxy]-phenyl |
| 113. | 4-[m-N(CH₃)₂-phenoxy]-phenyl |
| 114. | 4-[p-N(CH₃)₂-phenoxy]-phenyl |
| 115. | 4-(2,3-dicyanophenoxy)-phenyl |
| 116. | 4-(2,4-dicyanophenoxy)-phenyl |
| 117. | 4-(2,5-dicyanophenoxy)-phenyl |
| 118. | 4-(2,6-dicyanophenoxy)-phenyl |
| 119. | 4-(3,4-dicyanophenoxy)-phenyl |
| 120. | 4-(3,5-dicyanophenoxy)-phenyl |
| 121. | 4-(2,3-difluorophenoxy)-phenyl |
| 122. | 4-(2,4-difluorophenoxy)-phenyl |
| 123. | 4-(2,5-difluorophenoxy)-phenyl |
| 124. | 4-(2,6-difluorophenoxy)-phenyl |
| 125. | 4-(3,4-difluorophenoxy)-phenyl |
| 126. | 4-(3,5-difluorophenoxy)-phenyl |
| 127. | 4-(2,3-dichlorophenoxy)-phenyl |
| 128. | 4-(2,4-dichlorophenoxy)-phenyl |
| 129. | 4-(2,5-dichlorophenoxy)-phenyl |
| 130. | 4-(2,6-dichlorophenoxy)-phenyl |
| 131. | 4-(3,4-dichlorophenoxy)-phenyl |
| 132. | 4-(3,5-dichlorophenoxy)-phenyl |
| 133. | 4-(2,3-dibromophenoxy)-phenyl |
| 134. | 4-(2,4-dibromophenoxy)-phenyl |
| 135. | 4-(2,5-dibromophenoxy)-phenyl |
| 136. | 4-(2,6-dibromophenoxy)-phenyl |
| 137. | 4-(3,4-dibromophenoxy)-phenyl |
| 138. | 4-(3,5-dibromophenoxy)-phenyl |
| 139. | 4-(2,3-dimethylphenoxy)-phenyl |
| 140. | 4-(2,4-dimethylphenoxy)-phenyl |
| 141. | 4-(2,5-dimethylphenoxy)-phenyl |
| 142. | 4-(2,6-dimethylphenoxy)-phenyl |
| 143. | 4-(3,4-dimethylphenoxy)-phenyl |
| 144. | 4-(3,5-dimethylphenoxy)-phenyl |
| 145. | 4-[2,3-di(trifluoromethyl)phenoxy]-phenyl |
| 146. | 4-[2,4-di(trifluoromethyl)phenoxy]-phenyl |
| 147. | 4-[2,5-di(trifluoromethyl)phenoxy]-phenyl |
| 148. | 4-[2,6-di(trifluoromethyl)phenoxy]-phenyl |
| 149. | 4-[3,4-di(trifluoromethyl)phenoxy]-phenyl |
| 150. | 4-[3,5-di(trifluoromethyl)phenoxy]-phenyl |
| 151. | 4-(2,3-dimethoxyphenoxy)-phenyl |
| 152. | 4-(2,4-dimethoxyphenoxy)-phenyl |
| 153. | 4-(2,5-dimethoxyphenoxy)-phenyl |
| 154. | 4-(2,6-dimethoxyphenoxy)-phenyl |
| 155. | 4-(3,4-dimethoxyphenoxy)-phenyl |
| 156. | 4-(3,5-dimethoxyphenoxy)-phenyl |
| 157. | 3-(o-CN-phenyl)-phenyl |
| 158. | 3-(m-CN-phenyl)-phenyl |
| 159. | 3-(p-CN-phenyl)-phenyl |
| 160. | 3-(o-NO₂-phenyl)-phenyl |
| 161. | 3-(m-NO₂-phenyl)-phenyl |
| 162. | 3-(p-NO₂-phenyl)-phenyl |
| 163. | 3-(o-F-phenyl)-phenyl |
| 164. | 3-(m-F-phenyl)-phenyl |
| 165. | 3-(p-F-phenyl)-phenyl |
| 166. | 3-(o-Cl-phenyl)-phenyl |
| 167. | 3-(m-Cl-phenyl)-phenyl |
| 168. | 3-(p-Cl-phenyl)-phenyl |
| 169. | 3-(o-Br-phenyl)-phenyl |
| 170. | 3-(m-Br-phenyl)-phenyl |
| 171. | 3-(p-Br-phenyl)-phenyl |
| 172. | 3-(o-CH₃-phenyl)-phenyl |
| 173. | 3-(m-CH₃-phenyl)-phenyl |
| 174. | 3-(p-CH₃-phenyl)-phenyl |
| 175. | 3-(o-CF₃-phenyl)-phenyl |
| 176. | 3-(m-CF₃-phenyl)-phenyl |
| 177. | 3-(p-CF₃-phenyl)-phenyl |

TABLE A-continued

| no. | R³-A- |
|---|---|
| 178. | 3-(o-CF₃-phenyl)-phenyl |
| 179. | 3-(m-CF₃-phenyl)-phenyl |
| 180. | 3-(p-CF₃-phenyl)-phenyl |
| 181. | 3-(o-OCH₃-phenyl)-phenyl |
| 182. | 3-(m-OCH₃-phenyl)-phenyl |
| 183. | 3-(p-OCH₃-phenyl)-phenyl |
| 184. | 3-(o-OCF₃-phenyl)-phenyl |
| 185. | 3-(m-OCF₃-phenyl)-phenyl |
| 186. | 3-(p-OCF₃-phenyl)-phenyl |
| 187. | 3-(o-COOCH₃-phenyl)-phenyl |
| 188. | 3-(m-COOCH₃-phenyl)-phenyl |
| 189. | 3-(p-COOCH₃-phenyl)-phenyl |
| 190. | 3-[o-N(CH₃)₂-phenyl]-phenyl |
| 191. | 3-[m-N(CH₃)₂-phenyl]-phenyl |
| 192. | 3-[p-N(CH₃)₂-phenyl]-phenyl |
| 193. | 3-(2,3-dicyanophenyl)-phenyl |
| 194. | 3-(2,4-dicyanophenyl)-phenyl |
| 195. | 3-(2,5-dicyanophenyl)-phenyl |
| 196. | 3-(2,6-dicyanophenyl)-phenyl |
| 197. | 3-(3,4-dicyanophenyl)-phenyl |
| 198. | 3-(3,5-dicyanophenyl)-phenyl |
| 199. | 3-(2,3-difluorophenyl)-phenyl |
| 200. | 3-(2,4-difluorophenyl)-phenyl |
| 201. | 3-(2,5-difluorophenyl)-phenyl |
| 202. | 3-(2,6-difluorophenyl)-phenyl |
| 203. | 3-(3,4-difluorophenyl)-phenyl |
| 204. | 3-(3,5-difluorophenyl)-phenyl |
| 205. | 3-(2,3-dichlorophenyl)-phenyl |
| 206. | 3-(2,4-dichlorophenyl)-phenyl |
| 207. | 3-(2,5-dichlorophenyl)-phenyl |
| 208. | 3-(2,6-dichlorophenyl)-phenyl |
| 209. | 3-(3,4-dichlorophenyl)-phenyl |
| 210. | 3-(3,5-dichlorophenyl)-phenyl |
| 211. | 3-(2,3-dibromophenyl)-phenyl |
| 212. | 3-(2,4-dibromophenyl)-phenyl |
| 213. | 3-(2,5-dibromophenyl)-phenyl |
| 214. | 3-(2,6-dibromophenyl)-phenyl |
| 215. | 3-(3,4-dibromophenyl)-phenyl |
| 216. | 3-(3,5-dibromophenyl)-phenyl |
| 217. | 3-(2,3-dimethylphenyl)-phenyl |
| 218. | 3-(2,4-dimethylphenyl)-phenyl |
| 219. | 3-(2,5-dimethylphenyl)-phenyl |
| 220. | 3-(2,6-dimethylphenyl)-phenyl |
| 221. | 3-(3,4-dimethylphenyl)-phenyl |
| 222. | 3-(3,5-dimethylphenyl)-phenyl |
| 223. | 3-[2,3-di(trifluoromethyl)phenyl]-phenyl |
| 224. | 3-[2,4-di(trifluoromethyl)phenyl]-phenyl |
| 225. | 3-[2,5-di(trifluoromethyl)phenyl]-phenyl |
| 226. | 3-[2,6-di(trifluoromethyl)phenyl]-phenyl |
| 227. | 3-[3,4-di(trifluoromethyl)phenyl]-phenyl |
| 228. | 3-[3,5-di(trifluoromethyl)phenyl]-phenyl |
| 229. | 3-(2,3-dimethoxyphenyl)-phenyl |
| 230. | 3-(2,4-dimethoxyphenyl)-phenyl |
| 231. | 3-(2,5-dimethoxyphenyl)-phenyl |
| 232. | 3-(2,6-dimethoxyphenyl)-phenyl |
| 233. | 3-(3,4-dimethoxyphenyl)-phenyl |
| 234. | 3-(3,5-dimethoxyphenyl)-phenyl |
| 235. | 3-(o-CN-phenoxy)-phenyl |
| 236. | 3-(m-CN-phenoxy)-phenyl |
| 237. | 3-(p-CN-phenoxy)-phenyl |
| 238. | 3-(o-NO₂-phenoxy)-phenyl |
| 239. | 3-(m-NO₂-phenoxy)-phenyl |
| 240. | 3-(p-NO₂-phenoxy)-phenyl |
| 241. | 3-(o-F-phenoxy)-phenyl |
| 242. | 3-(m-F-phenoxy)-phenyl |
| 243. | 3-(p-F-phenoxy)-phenyl |
| 244. | 3-(o-Cl-phenoxy)-phenyl |
| 245. | 3-(m-Cl-phenoxy)-phenyl |
| 246. | 3-(p-Cl-phenoxy)-phenyl |
| 247. | 3-(o-Br-phenoxy)-phenyl |
| 248. | 3-(m-Br-phenoxy)-phenyl |
| 249. | 3-(p-Br-phenoxy)-phenyl |
| 250. | 3-(o-CH₃-phenoxy)-phenyl |
| 251. | 3-(m-CH₃-phenoxy)-phenyl |
| 252. | 3-(p-CH₃-phenoxy)-phenyl |
| 253. | 3-(o-CF₃-phenoxy)-phenyl |
| 254. | 3-(m-CF₃-phenoxy)-phenyl |
| 255. | 3-(p-CF₃-phenoxy)-phenyl |
| 256. | 3-(o-CF₃-phenoxy)-phenyl |
| 257. | 3-(m-CF₃-phenoxy)-phenyl |
| 258. | 3-(p-CF₃-phenoxy)-phenyl |
| 259. | 3-(o-OCH₃-phenoxy)-phenyl |
| 260. | 3-(m-OCH₃-phenoxy)-phenyl |
| 261. | 3-(p-OCH₃-phenoxy)-phenyl |
| 262. | 3-(o-OCF₃-phenoxy)-phenyl |
| 263. | 3-(m-OCF₃-phenoxy)-phenyl |
| 264. | 3-(p-OCF₃-phenoxy)-phenyl |
| 265. | 3-(o-COOCH₃-phenoxy)-phenyl |
| 266. | 3-(m-COOCH₃-phenoxy)-phenyl |
| 267. | 3-(p-COOCH₃-phenoxy)-phenyl |
| 268. | 3-[o-N(CH₃)₂-phenoxy]-phenyl |
| 269. | 3-[m-N(CH₃)₂-phenoxy]-phenyl |
| 270. | 3-[p-N(CH₃)₂-phenoxy]-phenyl |
| 271. | 3-(2,3-dicyanophenoxy)-phenyl |
| 272. | 3-(2,4-dicyanophenoxy)-phenyl |
| 273. | 3-(2,5-dicyanophenoxy)-phenyl |
| 274. | 3-(2,6-dicyanophenoxy)-phenyl |
| 275. | 3-(3,4-dicyanophenoxy)-phenyl |
| 276. | 3-(3,5-dicyanophenoxy)-phenyl |
| 277. | 3-(2,3-difluorophenoxy)-phenyl |
| 278. | 3-(2,4-difluorophenoxy)-phenyl |
| 279. | 3-(2,5-difluorophenoxy)-phenyl |
| 280. | 3-(2,6-difluorophenoxy)-phenyl |
| 281. | 3-(3,4-difluorophenoxy)-phenyl |
| 282. | 3-(3,5-difluorophenoxy)-phenyl |
| 283. | 3-(2,3-dichlorophenoxy)-phenyl |
| 284. | 3-(2,4-dichlorophenoxy)-phenyl |
| 285. | 3-(2,5-dichlorophenoxy)-phenyl |
| 286. | 3-(2,6-dichlorophenoxy)-phenyl |
| 287. | 3-(3,4-dichlorophenoxy)-phenyl |
| 288. | 3-(3,5-dichlorophenoxy)-phenyl |
| 289. | 3-(2,3-dibromophenoxy)-phenyl |
| 290. | 3-(2,4-dibromophenoxy)-phenyl |
| 291. | 3-(2,5-dibromophenoxy)-phenyl |
| 292. | 3-(2,6-dibromophenoxy)-phenyl |
| 293. | 3-(3,4-dibromophenoxy)-phenyl |
| 294. | 3-(3,5-dibromophenoxy)-phenyl |
| 295. | 3-(2,3-dimethylphenoxy)-phenyl |
| 296. | 3-(2,4-dimethylphenoxy)-phenyl |
| 297. | 3-(2,5-dimethylphenoxy)-phenyl |
| 298. | 3-(2,6-dimethylphenoxy)-phenyl |
| 299. | 3-(3,4-dimethylphenoxy)-phenyl |
| 300. | 3-(3,5-dimethylphenoxy)-phenyl |
| 301. | 3-[2,3-di(trifluoromethyl)phenoxy]-phenyl |
| 302. | 3-[2,4-di(trifluoromethyl)phenoxy]-phenyl |
| 303. | 3-[2,5-di(trifluoromethyl)phenoxy]-phenyl |
| 304. | 3-[2,6-di(trifluoromethyl)phenoxy]-phenyl |
| 305. | 3-[3,4-di(trifluoromethyl)phenoxy]-phenyl |
| 306. | 3-[3,5-di(trifluoromethyl)phenoxy]-phenyl |
| 307. | 3-(2,3-dimethoxyphenoxy)-phenyl |
| 308. | 3-(2,4-dimethoxyphenoxy)-phenyl |
| 309. | 3-(2,5-dimethoxyphenoxy)-phenyl |
| 310. | 3-(2,6-dimethoxyphenoxy)-phenyl |
| 311. | 3-(3,4-dimethoxyphenoxy)-phenyl |
| 312. | 3-(3,5-dimethoxyphenoxy)-phenyl |
| 313. | 5-(o-CN-phenyl)-thien-2-yl |
| 314. | 5-(m-CN-phenyl)-thien-2-yl |
| 315. | 5-(p-CN-phenyl)-thien-2-yl |
| 316. | 5-(o-NO₂-phenyl)-thien-2-yl |
| 317. | 5-(m-NO₂-phenyl)-thien-2-yl |
| 318. | 5-(p-NO₂-phenyl)-thien-2-yl |
| 319. | 5-(o-F-phenyl)-thien-2-yl |
| 320. | 5-(m-F-phenyl)-thien-2-yl |
| 321. | 5-(p-F-phenyl)-thien-2-yl |

TABLE A-continued

| no. | R³-A- |
|---|---|
| 322. | 5-(o-Cl-phenyl)-thien-2-yl |
| 323. | 5-(m-Cl-phenyl)-thien-2-yl |
| 324. | 5-(p-Cl-phenyl)-thien-2-yl |
| 325. | 5-(o-Br-phenyl)-thien-2-yl |
| 326. | 5-(m-Br-phenyl)-thien-2-yl |
| 327. | 5-(p-Br-phenyl)-thien-2-yl |
| 328. | 5-(o-CH₃-phenyl)-thien-2-yl |
| 329. | 5-(m-CH₃-phenyl)-thien-2-yl |
| 330. | 5-(p-CH₃-phenyl)-thien-2-yl |
| 331. | 5-(o-CF₃-phenyl)-thien-2-yl |
| 332. | 5-(m-CF₃-phenyl)-thien-2-yl |
| 333. | 5-(p-CF₃-phenyl)-thien-2-yl |
| 334. | 5-(o-CF₃-phenyl)-thien-2-yl |
| 335. | 5-(m-CF₃-phenyl)-thien-2-yl |
| 336. | 5-(p-CF₃-phenyl)-thien-2-yl |
| 337. | 5-(o-OCH₃-phenyl)-thien-2-yl |
| 338. | 5-(m-OCH₃-phenyl)-thien-2-yl |
| 339. | 5-(p-OCH₃-phenyl)-thien-2-yl |
| 340. | 5-(o-OCF₃-phenyl)-thien-2-yl |
| 341. | 5-(m-OCF₃-phenyl)-thien-2-yl |
| 342. | 5-(p-OCF₃-phenyl)-thien-2-yl |
| 343. | 5-(o-COOCH₃-phenyl)-thien-2-yl |
| 344. | 5-(m-COOCH₃-phenyl)-thien-2-yl |
| 345. | 5-(p-COOCH₃-phenyl)-thien-2-yl |
| 346. | 5-[o-N(CH₃)₂-phenyl]-thien-2-yl |
| 347. | 5-[m-N(CH₃)₂-phenyl]-thien-2-yl |
| 348. | 5-[p-N(CH₃)₂-phenyl]-thien-2-yl |
| 349. | 5-(2,3-dicyanophenyl)-thien-2-yl |
| 350. | 5-(2,4-dicyanophenyl)-thien-2-yl |
| 351. | 5-(2,5-dicyanophenyl)-thien-2-yl |
| 352. | 5-(2,6-dicyanophenyl)-thien-2-yl |
| 353. | 5-(3,4-dicyanophenyl)-thien-2-yl |
| 354. | 5-(3,5-dicyanophenyl)-thien-2-yl |
| 355. | 5-(2,3-difluorophenyl)-thien-2-yl |
| 356. | 5-(2,4-difluorophenyl)-thien-2-yl |
| 357. | 5-(2,5-difluorophenyl)-thien-2-yl |
| 358. | 5-(2,6-difluorophenyl)-thien-2-yl |
| 359. | 5-(3,4-difluorophenyl)-thien-2-yl |
| 360. | 5-(3,5-difluorophenyl)-thien-2-yl |
| 361. | 5-(2,3-dichlorophenyl)-thien-2-yl |
| 362. | 5-(2,4-dichlorophenyl)-thien-2-yl |
| 363. | 5-(2,5-dichlorophenyl)-thien-2-yl |
| 364. | 5-(2,6-dichlorophenyl)-thien-2-yl |
| 365. | 5-(3,4-dichlorophenyl)-thien-2-yl |
| 366. | 5-(3,5-dichlorophenyl)-thien-2-yl |
| 367. | 5-(2,3-dibromophenyl)-thien-2-yl |
| 368. | 5-(2,4-dibromophenyl)-thien-2-yl |
| 369. | 5-(2,5-dibromophenyl)-thien-2-yl |
| 370. | 5-(2,6-dibromophenyl)-thien-2-yl |
| 371. | 5-(3,4-dibromophenyl)-thien-2-yl |
| 372. | 5-(3,5-dibromophenyl)-thien-2-yl |
| 373. | 5-(2,3-dimethylphenyl)-thien-2-yl |
| 374. | 5-(2,4-dimethylphenyl)-thien-2-yl |
| 375. | 5-(2,5-dimethylphenyl)-thien-2-yl |
| 376. | 5-(2,6-dimethylphenyl)-thien-2-yl |
| 377. | 5-(3,4-dimethylphenyl)-thien-2-yl |
| 378. | 5-(3,5-dimethylphenyl)-thien-2-yl |
| 379. | 5-[2,3-di(trifluoromethyl)phenyl]-thien-2-yl |
| 380. | 5-[2,4-di(trifluoromethyl)phenyl]-thien-2-yl |
| 381. | 5-[2,5-di(trifluoromethyl)phenyl]-thien-2-yl |
| 382. | 5-[2,6-di(trifluoromethyl)phenyl]-thien-2-yl |
| 383. | 5-[3,4-di(trifluoromethyl)phenyl]-thien-2-yl |
| 384. | 5-[3,5-di(trifluoromethyl)phenyl]-thien-2-yl |
| 385. | 5-(2,3-dimethoxyphenyl)-thien-2-yl |
| 386. | 5-(2,4-dimethoxyphenyl)-thien-2-yl |
| 387. | 5-(2,5-dimethoxyphenyl)-thien-2-yl |
| 388. | 5-(2,6-dimethoxyphenyl)-thien-2-yl |
| 389. | 5-(3,4-dimethoxyphenyl)-thien-2-yl |
| 390. | 5-(3,5-dimethoxyphenyl)-thien-2-yl |
| 391. | 5-(o-CN-phenoxy)-thien-2-yl |
| 392. | 5-(m-CN-phenoxy)-thien-2-yl |
| 393. | 5-(p-CN-phenoxy)-thien-2-yl |
| 394. | 5-(o-NO₂-phenoxy)-thien-2-yl |
| 395. | 5-(m-NO₂-phenoxy)-thien-2-yl |
| 396. | 5-(p-NO₂-phenoxy)-thien-2-yl |
| 397. | 5-(o-F-phenoxy)-thien-2-yl |
| 398. | 5-(m-F-phenoxy)-thien-2-yl |
| 399. | 5-(p-F-phenoxy)-thien-2-yl |
| 400. | 5-(o-Cl-phenoxy)-thien-2-yl |
| 401. | 5-(m-Cl-phenoxy)-thien-2-yl |
| 402. | 5-(p-Cl-phenoxy)-thien-2-yl |
| 403. | 5-(o-Br-phenoxy)-thien-2-yl |
| 404. | 5-(m-Br-phenoxy)-thien-2-yl |
| 405. | 5-(p-Br-phenoxy)-thien-2-yl |
| 406. | 5-(o-CH₃-phenoxy)-thien-2-yl |
| 407. | 5-(m-CH₃-phenoxy)-thien-2-yl |
| 408. | 5-(p-CH₃-phenoxy)-thien-2-yl |
| 409. | 5-(o-CF₃-phenoxy)-thien-2-yl |
| 410. | 5-(m-CF₃-phenoxy)-thien-2-yl |
| 411. | 5-(p-CF₃-phenoxy)-thien-2-yl |
| 412. | 5-(o-CF₃-phenoxy)-thien-2-yl |
| 413. | 5-(m-CF₃-phenoxy)-thien-2-yl |
| 414. | 5-(p-CF₃-phenoxy)-thien-2-yl |
| 415. | 5-(o-OCH₃-phenoxy)-thien-2-yl |
| 416. | 5-(m-OCH₃-phenoxy)-thien-2-yl |
| 417. | 5-(p-OCH₃-phenoxy)-thien-2-yl |
| 418. | 5-(o-OCF₃-phenoxy)-thien-2-yl |
| 419. | 5-(m-OCF₃-phenoxy)-thien-2-yl |
| 420. | 5-(p-OCF₃-phenoxy)-thien-2-yl |
| 421. | 5-(o-COOCH₃-phenoxy)-thien-2-yl |
| 422. | 5-(m-COOCH₃-phenoxy)-thien-2-yl |
| 423. | 5-(p-COOCH₃-phenoxy)-thien-2-yl |
| 424. | 5-[o-N(CH₃)₂-phenoxy]-thien-2-yl |
| 425. | 5-[m-N(CH₃)₂-phenoxy]-thien-2-yl |
| 426. | 5-[p-N(CH₃)₂-phenoxy]-thien-2-yl |
| 427. | 5-(2,3-dicyanophenoxy)-thien-2-yl |
| 428. | 5-(2,4-dicyanophenoxy)-thien-2-yl |
| 429. | 5-(2,5-dicyanophenoxy)-thien-2-yl |
| 430. | 5-(2,6-dicyanophenoxy)-thien-2-yl |
| 431. | 5-(3,4-dicyanophenoxy)-thien-2-yl |
| 432. | 5-(3,5-dicyanophenoxy)-thien-2-yl |
| 433. | 5-(2,3-difluorophenoxy)-thien-2-yl |
| 434. | 5-(2,4-difluorophenoxy)-thien-2-yl |
| 435. | 5-(2,5-difluorophenoxy)-thien-2-yl |
| 436. | 5-(2,6-difluorophenoxy)-thien-2-yl |
| 437. | 5-(3,4-difluorophenoxy)-thien-2-yl |
| 438. | 5-(3,5-difluorophenoxy)-thien-2-yl |
| 439. | 5-(2,3-dichlorophenoxy)-thien-2-yl |
| 440. | 5-(2,4-dichlorophenoxy)-thien-2-yl |
| 441. | 5-(2,5-dichlorophenoxy)-thien-2-yl |
| 442. | 5-(2,6-dichlorophenoxy)-thien-2-yl |
| 443. | 5-(3,4-dichlorophenoxy)-thien-2-yl |
| 444. | 5-(3,5-dichlorophenoxy)-thien-2-yl |
| 445. | 5-(2,3-dibromophenoxy)-thien-2-yl |
| 446. | 5-(2,4-dibromophenoxy)-thien-2-yl |

TABLE A-continued

| no. | R³-A- |
|---|---|
| 447. | 5-(2,5-dibromophenoxy)-thien-2-yl |
| 448. | 5-(2,6-dibromophenoxy)-thien-2-yl |
| 449. | 5-(3,4-dibromophenoxy)-thien-2-yl |
| 450. | 5-(3,5-dibromophenoxy)-thien-2-yl |
| 451. | 5-(2,3-dimethylphenoxy)-thien-2-yl |
| 452. | 5-(2,4-dimethylphenoxy)-thien-2-yl |
| 453. | 5-(2,5-dimethylphenoxy)-thien-2-yl |
| 454. | 5-(2,6-dimethylphenoxy)-thien-2-yl |
| 455. | 5-(3,4-dimethylphenoxy)-thien-2-yl |
| 456. | 5-(3,5-dimethylphenoxy)-thien-2-yl |
| 457. | 5-[2,3-di(trifluoromethyl)phenoxy]-thien-2-yl |
| 458. | 5-[2,4-di(trifluoromethyl)phenoxy]-thien-2-yl |
| 459. | 5-[2,5-di(trifluoromethyl)phenoxy]-thien-2-yl |
| 460. | 5-[2,6-di(trifluoromethyl)phenoxy]-thien-2-yl |
| 461. | 5-[3,4-di(trifluoromethyl)phenoxy]-thien-2-yl |
| 462. | 5-[3,5-di(trifluoromethyl)phenoxy]-thien-2-yl |
| 463. | 5-(2,3-dimethoxyphenoxy)-thien-2-yl |
| 464. | 5-(2,4-dimethoxyphenoxy)-thien-2-yl |
| 465. | 5-(2,5-dimethoxyphenoxy)-thien-2-yl |
| 466. | 5-(2,6-dimethoxyphenoxy)-thien-2-yl |
| 467. | 5-(3,4-dimethoxyphenoxy)-thien-2-yl |
| 468. | 5-(3,5-dimethoxyphenoxy)-thien-2-yl |
| 469. | 4-(o-CN-phenyl)-thien-2-yl |
| 470. | 4-(m-CN-phenyl)-thien-2-yl |
| 471. | 4-(p-CN-phenyl)-thien-2-yl |
| 472. | 4-(o-NO$_2$-phenyl)-thien-2-yl |
| 473. | 4-(m-NO$_2$-phenyl)-thien-2-yl |
| 474. | 4-(p-NO$_2$-phenyl)-thien-2-yl |
| 475. | 4-(o-F-phenyl)-thien-2-yl |
| 476. | 4-(m-F-phenyl)-thien-2-yl |
| 477. | 4-(p-F-phenyl)-thien-2-yl |
| 478. | 4-(o-Cl-phenyl)-thien-2-yl |
| 479. | 4-(m-Cl-phenyl)-thien-2-yl |
| 480. | 4-(p-Cl-phenyl)-thien-2-yl |
| 481. | 4-(o-Br-phenyl)-thien-2-yl |
| 482. | 4-(m-Br-phenyl)-thien-2-yl |
| 483. | 4-(p-Br-phenyl)-thien-2-yl |
| 484. | 4-(o-CH$_3$-phenyl)-thien-2-yl |
| 485. | 4-(m-CH$_3$-phenyl)-thien-2-yl |
| 486. | 4-(p-CH$_3$-phenyl)-thien-2-yl |
| 487. | 4-(o-CF$_3$-phenyl)-thien-2-yl |
| 488. | 4-(m-CF$_3$-phenyl)-thien-2-yl |
| 489. | 4-(p-CF$_3$-phenyl)-thien-2-yl |
| 490. | 4-(o-CF$_3$-phenyl)-thien-2-yl |
| 491. | 4-(m-CF$_3$-phenyl)-thien-2-yl |
| 492. | 4-(p-CF$_3$-phenyl)-thien-2-yl |
| 493. | 4-(o-OCH$_3$-phenyl)-thien-2-yl |
| 494. | 4-(m-OCH$_3$-phenyl)-thien-2-yl |
| 495. | 4-(p-OCH$_3$-phenyl)-thien-2-yl |
| 496. | 4-(o-OCF$_3$-phenyl)-thien-2-yl |
| 497. | 4-(m-OCF$_3$-phenyl)-thien-2-yl |
| 498. | 4-(p-OCF$_3$-phenyl)-thien-2-yl |
| 499. | 4-(o-COOCH$_3$-phenyl)-thien-2-yl |
| 500. | 4-(m-COOCH$_3$-phenyl)-thien-2-yl |
| 501. | 4-(p-COOCH$_3$-phenyl)-thien-2-yl |
| 502. | 4-[o-N(CH$_3$)$_2$-phenyl]-thien-2-yl |
| 503. | 4-[m-N(CH$_3$)$_2$-phenyl]-thien-2-yl |
| 504. | 4-[p-N(CH$_3$)$_2$-phenyl]-thien-2-yl |
| 505. | 4-(2,3-dicyanophenyl)-thien-2-yl |
| 506. | 4-(2,4-dicyanophenyl)-thien-2-yl |
| 507. | 4-(2,5-dicyanophenyl)-thien-2-yl |
| 508. | 4-(2,6-dicyanophenyl)-thien-2-yl |
| 509. | 4-(3,4-dicyanophenyl)-thien-2-yl |
| 510. | 4-(3,5-dicyanophenyl)-thien-2-yl |
| 511. | 4-(2,3-difluorophenyl)-thien-2-yl |
| 512. | 4-(2,4-difluorophenyl)-thien-2-yl |
| 513. | 4-(2,5-difluorophenyl)-thien-2-yl |
| 514. | 4-(2,6-difluorophenyl)-thien-2-yl |
| 515. | 4-(3,4-difluorophenyl)-thien-2-yl |
| 516. | 4-(3,5-difluorophenyl)-thien-2-yl |
| 517. | 4-(2,3-dichlorophenyl)-thien-2-yl |
| 518. | 4-(2,4-dichlorophenyl)-thien-2-yl |
| 519. | 4-(2,5-dichlorophenyl)-thien-2-yl |
| 520. | 4-(2,6-dichlorophenyl)-thien-2-yl |
| 521. | 4-(3,4-dichlorophenyl)-thien-2-yl |
| 522. | 4-(3,5-dichlorophenyl)-thien-2-yl |
| 523. | 4-(2,3-dibromophenyl)-thien-2-yl |
| 524. | 4-(2,4-dibromophenyl)-thien-2-yl |
| 525. | 4-(2,5-dibromophenyl)-thien-2-yl |
| 526. | 4-(2,6-dibromophenyl)-thien-2-yl |
| 527. | 4-(3,4-dibromophenyl)-thien-2-yl |
| 528. | 4-(3,5-dibromophenyl)-thien-2-yl |
| 529. | 4-(2,3-dimethylphenyl)-thien-2-yl |
| 530. | 4-(2,4-dimethylphenyl)-thien-2-yl |
| 531. | 4-(2,5-dimethylphenyl)-thien-2-yl |
| 532. | 4-(2,6-dimethylphenyl)-thien-2-yl |
| 533. | 4-(3,4-dimethylphenyl)-thien-2-yl |
| 534. | 4-(3,5-dimethylphenyl)-thien-2-yl |
| 535. | 4-[2,3-di(trifluoromethyl)phenyl]-thien-2-yl |
| 536. | 4-[2,4-di(trifluoromethyl)phenyl]-thien-2-yl |
| 537. | 4-[2,5-di(trifluoromethyl)phenyl]-thien-2-yl |
| 538. | 4-[2,6-di(trifluoromethyl)phenyl]-thien-2-yl |
| 539. | 4-[3,4-di(trifluoromethyl)phenyl]-thien-2-yl |
| 540. | 4-[3,5-di(trifluoromethyl)phenyl]-thien-2-yl |
| 541. | 4-(2,3-dimethoxyphenyl)-thien-2-yl |
| 542. | 4-(2,4-dimethoxyphenyl)-thien-2-yl |
| 543. | 4-(2,5-dimethoxyphenyl)-thien-2-yl |
| 544. | 4-(2,6-dimethoxyphenyl)-thien-2-yl |
| 545. | 4-(3,4-dimethoxyphenyl)-thien-2-yl |
| 546. | 4-(3,5-dimethoxyphenyl)-thien-2-yl |
| 547. | 4-(o-CN-phenoxy)-thien-2-yl |
| 548. | 4-(m-CN-phenoxy)-thien-2-yl |
| 549. | 4-(p-CN-phenoxy)-thien-2-yl |
| 550. | 4-(o-NO$_2$-phenoxy)-thien-2-yl |
| 551. | 4-(m-NO$_2$-phenoxy)-thien-2-yl |
| 552. | 4-(p-NO$_2$-phenoxy)-thien-2-yl |
| 553. | 4-(o-F-phenoxy)-thien-2-yl |
| 554. | 4-(m-F-phenoxy)-thien-2-yl |
| 555. | 4-(p-F-phenoxy)-thien-2-yl |
| 556. | 4-(o-Cl-phenoxy)-thien-2-yl |
| 557. | 4-(m-Cl-phenoxy)-thien-2-yl |
| 558. | 4-(p-Cl-phenoxy)-thien-2-yl |
| 559. | 4-(o-Br-phenoxy)-thien-2-yl |
| 560. | 4-(m-Br-phenoxy)-thien-2-yl |
| 561. | 4-(p-Br-phenoxy)-thien-2-yl |
| 562. | 4-(o-CH$_3$-phenoxy)-thien-2-yl |
| 563. | 4-(m-CH$_3$-phenoxy)-thien-2-yl |
| 564. | 4-(p-CH$_3$-phenoxy)-thien-2-yl |
| 565. | 4-(o-CF$_3$-phenoxy)-thien-2-yl |
| 566. | 4-(m-CF$_3$-phenoxy)-thien-2-yl |
| 567. | 4-(p-CF$_3$-phenoxy)-thien-2-yl |
| 568. | 4-(o-CF$_3$-phenoxy)-thien-2-yl |

TABLE A-continued

| no. | R³-A- |
|---|---|
| 569. | 4-(m-CF₃-phenoxy)-thien-2-yl |
| 570. | 4-(p-CF₃-phenoxy)-thien-2-yl |
| 571. | 4-(o-OCH₃-phenoxy)-thien-2-yl |
| 572. | 4-(m-OCH₃-phenoxy)-thien-2-yl |
| 573. | 4-(p-OCH₃-phenoxy)-thien-2-yl |
| 574. | 4-(o-OCF₃-phenoxy)-thien-2-yl |
| 575. | 4-(m-OCF₃-phenoxy)-thien-2-yl |
| 576. | 4-(p-OCF₃-phenoxy)-thien-2-yl |
| 577. | 4-(o-COOCH₃-phenoxy)-thien-2-yl |
| 578. | 4-(m-COOCH₃-phenoxy)-thien-2-yl |
| 579. | 4-(p-COOCH₃-phenoxy)-thien-2-yl |
| 580. | 4-[o-N(CH₃)₂-phenoxy]-thien-2-yl |
| 581. | 4-[m-N(CH₃)₂-phenoxy]-thien-2-yl |
| 582. | 4-[p-N(CH₃)₂-phenoxy]-thien-2-yl |
| 583. | 4-(2,3-dicyanophenoxy)-thien-2-yl |
| 584. | 4-(2,4-dicyanophenoxy)-thien-2-yl |
| 585. | 4-(2,5-dicyanophenoxy)-thien-2-yl |
| 586. | 4-(2,6-dicyanophenoxy)-thien-2-yl |
| 587. | 4-(3,4-dicyanophenoxy)-thien-2-yl |
| 588. | 4-(3,5-dicyanophenoxy)-thien-2-yl |
| 589. | 4-(2,3-difluorophenoxy)-thien-2-yl |
| 590. | 4-(2,4-difluorophenoxy)-thien-2-yl |
| 591. | 4-(2,5-difluorophenoxy)-thien-2-yl |
| 592. | 4-(2,6-difluorophenoxy)-thien-2-yl |
| 593. | 4-(3,4-difluorophenoxy)-thien-2-yl |
| 594. | 4-(3,5-difluorophenoxy)-thien-2-yl |
| 595. | 5-(2,3-dichlorophenoxy)-thien-2-yl |
| 596. | 4-(2,4-dichlorophenoxy)-thien-2-yl |
| 597. | 4-(2,5-dichlorophenoxy)-thien-2-yl |
| 598. | 4-(2,6-dichlorophenoxy)-thien-2-yl |
| 599. | 4-(3,4-dichlorophenoxy)-thien-2-yl |
| 600. | 4-(3,5-dichlorophenoxy)-thien-2-yl |
| 601. | 4-(2,3-dibromophenoxy)-thien-2-yl |
| 602. | 4-(2,4-dibromophenoxy)-thien-2-yl |
| 603. | 4-(2,5-dibromophenoxy)-thien-2-yl |
| 604. | 4-(2,6-dibromophenoxy)-thien-2-yl |
| 605. | 4-(3,4-dibromophenoxy)-thien-2-yl |
| 606. | 4-(3,5-dibromophenoxy)-thien-2-yl |
| 607. | 4-(2,3-dimethylphenoxy)-thien-2-yl |
| 608. | 4-(2,4-dimethylphenoxy)-thien-2-yl |
| 609. | 4-(2,5-dimethylphenoxy)-thien-2-yl |
| 610. | 4-(2,6-dimethylphenoxy)-thien-2-yl |
| 611. | 4-(3,4-dimethylphenoxy)-thien-2-yl |
| 612. | 4-(3,5-dimethylphenoxy)-thien-2-yl |
| 613. | 4-[2,3-di(trifluoromethyl)phenoxy]-thien-2-yl |
| 614. | 4-[2,4-di(trifluoromethyl)phenoxy]-thien-2-yl |
| 615. | 4-[2,5-di(trifluoromethyl)phenoxy]-thien-2-yl |
| 616. | 4-[2,6-di(trifluoromethyl)phenoxy]-thien-2-yl |
| 617. | 4-[3,4-di(trifluoromethyl)phenoxy]-thien-2-yl |
| 618. | 4-[3,5-di(trifluoromethyl)phenoxy]-thien-2-yl |
| 619. | 4-(2,3-dimethoxyphenoxy)-thien-2-yl |
| 620. | 4-(2,4-dimethoxyphenoxy)-thien-2-yl |
| 621. | 4-(2,5-dimethoxyphenoxy)-thien-2-yl |
| 622. | 4-(2,6-dimethoxyphenoxy)-thien-2-yl |
| 623. | 4-(3,4-dimethoxyphenoxy)-thien-2-yl |
| 624. | 4-(3,5-dimethoxyphenoxy)-thien-2-yl |
| 625. | 5-(o-CN-phenyl)-thien-3-yl |
| 626. | 5-(m-CN-phenyl)-thien-3-yl |
| 627. | 5-(p-CN-phenyl)-thien-3-yl |
| 628. | 5-(o-NO₂-phenyl)-thien-3-yl |
| 629. | 5-(m-NO₂-phenyl)-thien-3-yl |
| 630. | 5-(p-NO₂-phenyl)-thien-3-yl |
| 631. | 5-(o-F-phenyl)-thien-3-yl |
| 632. | 5-(m-F-phenyl)-thien-3-yl |
| 633. | 5-(p-F-phenyl)-thien-3-yl |
| 634. | 5-(o-Cl-phenyl)-thien-3-yl |
| 635. | 5-(m-Cl-phenyl)-thien-3-yl |
| 636. | 5-(p-Cl-phenyl)-thien-3-yl |
| 637. | 5-(o-Br-phenyl)-thien-3-yl |
| 638. | 5-(m-Br-phenyl)-thien-3-yl |
| 639. | 5-(p-Br-phenyl)-thien-3-yl |
| 640. | 5-(o-CH₃-phenyl)-thien-3-yl |
| 641. | 5-(m-CH₃-phenyl)-thien-3-yl |
| 642. | 5-(p-CH₃-phenyl)-thien-3-yl |
| 643. | 5-(o-CF₃-phenyl)-thien-3-yl |
| 644. | 5-(m-CF₃-phenyl)-thien-3-yl |
| 645. | 5-(p-CF₃-phenyl)-thien-3-yl |
| 646. | 5-(o-CF₃-phenyl)-thien-3-yl |
| 647. | 5-(m-CF₃-phenyl)-thien-3-yl |
| 648. | 5-(p-CF₃-phenyl)-thien-3-yl |
| 649. | 5-(o-OCH₃-phenyl)-thien-3-yl |
| 650. | 5-(m-OCH₃-phenyl)-thien-3-yl |
| 651. | 5-(p-OCH₃-phenyl)-thien-3-yl |
| 652. | 5-(o-OCF₃-phenyl)-thien-3-yl |
| 653. | 5-(m-OCF₃-phenyl)-thien-3-yl |
| 654. | 5-(p-OCF₃-phenyl)-thien-3-yl |
| 655. | 5-(o-COOCH₃-phenyl)-thien-3-yl |
| 656. | 5-(m-COOCH₃-phenyl)-thien-3-yl |
| 657. | 5-(p-COOCH₃-phenyl)-thien-3-yl |
| 658. | 5-[o-N(CH₃)₂-phenyl]-thien-3-yl |
| 659. | 5-[m-N(CH₃)₂-phenyl]-thien-3-yl |
| 660. | 5-[p-N(CH₃)₂-phenyl]-thien-3-yl |
| 661. | 5-(2,3-dicyanophenyl)-thien-3-yl |
| 662. | 5-(2,4-dicyanophenyl)-thien-3-yl |
| 663. | 5-(2,5-dicyanophenyl)-thien-3-yl |
| 664. | 5-(2,6-dicyanophenyl)-thien-3-yl |
| 665. | 5-(3,4-dicyanophenyl)-thien-3-yl |
| 666. | 5-(3,5-dicyanophenyl)-thien-3-yl |
| 667. | 5-(2,3-difluorophenyl)-thien-3-yl |
| 668. | 5-(2,4-difluorophenyl)-thien-3-yl |
| 669. | 5-(2,5-difluorophenyl)-thien-3-yl |
| 670. | 5-(2,6-difluorophenyl)-thien-3-yl |
| 671. | 5-(3,4-difluorophenyl)-thien-3-yl |
| 672. | 5-(3,5-difluorophenyl)-thien-3-yl |
| 673. | 5-(2,3-dichlorophenyl)-thien-3-yl |
| 674. | 5-(2,4-dichlorophenyl)-thien-3-yl |
| 675. | 5-(2,5-dichlorophenyl)-thien-3-yl |
| 676. | 5-(2,6-dichlorophenyl)-thien-3-yl |
| 677. | 5-(3,4-dichlorophenyl)-thien-3-yl |
| 678. | 5-(3,5-dichlorophenyl)-thien-3-yl |
| 679. | 5-(2,3-dibromophenyl)-thien-3-yl |
| 680. | 5-(2,4-dibromophenyl)-thien-3-yl |
| 681. | 5-(2,5-dibromophenyl)-thien-3-yl |
| 682. | 5-(2,6-dibromophenyl)-thien-3-yl |
| 683. | 5-(3,4-dibromophenyl)-thien-3-yl |
| 684. | 5-(3,5-dibromophenyl)-thien-3-yl |

TABLE A-continued

| no. | R³-A- |
|---|---|
| 685. | 5-(2,3-dimethylphenyl)-thien-3-yl |
| 686. | 5-(2,4-dimethylphenyl)-thien-3-yl |
| 687. | 5-(2,5-dimethylphenyl)-thien-3-yl |
| 688. | 5-(2,6-dimethylphenyl)-thien-3-yl |
| 689. | 5-(3,4-dimethylphenyl)-thien-3-yl |
| 690. | 5-(3,5-dimethylphenyl)-thien-3-yl |
| 691. | 5-[2,3-di(trifluoromethyl)phenyl]-thien-3-yl |
| 692. | 5-[2,4-di(trifluoromethyl)phenyl]-thien-3-yl |
| 693. | 5-[2,5-di(trifluoromethyl)phenyl]-thien-3-yl |
| 694. | 5-[2,6-di(trifluoromethyl)phenyl]-thien-3-yl |
| 695. | 5-[3,4-di(trifluoromethyl)phenyl]-thien-3-yl |
| 696. | 5-[3,5-di(trifluoromethyl)phenyl]-thien-3-yl |
| 697. | 5-(2,3-dimethoxyphenyl)-thien-3-yl |
| 698. | 5-(2,4-dimethoxyphenyl)-thien-3-yl |
| 699. | 5-(2,5-dimethoxyphenyl)-thien-3-yl |
| 700. | 5-(2,6-dimethoxyphenyl)-thien-3-yl |
| 701. | 5-(3,4-dimethoxyphenyl)-thien-3-yl |
| 702. | 5-(3,5-dimethoxyphenyl)-thien-3-yl |
| 703. | 5-(o-CN-phenoxy)-thien-3-yl |
| 704. | 5-(m-CN-phenoxy)-thien-3-yl |
| 705. | 5-(p-CN-phenoxy)-thien-3-yl |
| 706. | 5-(o-NO$_2$-phenoxy)-thien-3-yl |
| 707. | 5-(m-NO$_2$-phenoxy)-thien-3-yl |
| 708. | 5-(p-NO$_2$-phenoxy)-thien-3-yl |
| 709. | 5-(o-F-phenoxy)-thien-3-yl |
| 710. | 5-(m-F-phenoxy)-thien-3-yl |
| 711. | 5-(p-F-phenoxy)-thien-3-yl |
| 712. | 5-(o-Cl-phenoxy)-thien-3-yl |
| 713. | 5-(m-Cl-phenoxy)-thien-3-yl |
| 714. | 5-(p-Cl-phenoxy)-thien-3-yl |
| 715. | 5-(o-Br-phenoxy)-thien-3-yl |
| 716. | 5-(m-Br-phenoxy)-thien-3-yl |
| 717. | 5-(p-Br-phenoxy)-thien-3-yl |
| 718. | 5-(o-CH$_3$-phenoxy)-thien-3-yl |
| 719. | 5-(m-CH$_3$-phenoxy)-thien-3-yl |
| 720. | 5-(p-CH$_3$-phenoxy)-thien-3-yl |
| 721. | 5-(o-CF$_3$-phenoxy)-thien-3-yl |
| 722. | 5-(m-CF$_3$-phenoxy)-thien-3-yl |
| 723. | 5-(p-CF$_3$-phenoxy)-thien-3-yl |
| 724. | 5-(o-CF$_3$-phenoxy)-thien-3-yl |
| 725. | 5-(m-CF$_3$-phenoxy)-thien-3-yl |
| 726. | 5-(p-CF$_3$-phenoxy)-thien-3-yl |
| 727. | 5-(o-OCH$_3$-phenoxy)-thien-3-yl |
| 728. | 5-(m-OCH$_3$-phenoxy)-thien-3-yl |
| 729. | 5-(p-OCH$_3$-phenoxy)-thien-3-yl |
| 730. | 5-(o-OCF$_3$-phenoxy)-thien-3-yl |
| 731. | 5-(m-OCF$_3$-phenoxy)-thien-3-yl |
| 732. | 5-(p-OCF$_3$-phenoxy)-thien-3-yl |
| 733. | 5-(o-COOCH$_3$-phenoxy)-thien-3-yl |
| 734. | 5-(m-COOCH$_3$-phenoxy)-thien-3-yl |
| 735. | 5-(p-COOCH$_3$-phenoxy)-thien-3-yl |
| 736. | 5-[o-N(CH$_3$)$_2$-phenoxy]-thien-3-yl |
| 737. | 5-[m-N(CH$_3$)$_2$-phenoxy]-thien-3-yl |
| 738. | 5-[p-N(CH$_3$)$_2$-phenoxy]-thien-3-yl |
| 739. | 5-(2,3-dicyanophenoxy)-thien-3-yl |
| 740. | 5-(2,4-dicyanophenoxy)-thien-3-yl |
| 741. | 5-(2,5-dicyanophenoxy)-thien-3-yl |
| 742. | 5-(2,6-dicyanophenoxy)-thien-3-yl |
| 743. | 5-(3,4-dicyanophenoxy)-thien-3-yl |
| 744. | 5-(3,5-dicyanophenoxy)-thien-3-yl |
| 745. | 5-(2,3-difluorophenoxy)-thien-3-yl |
| 746. | 5-(2,4-difluorophenoxy)-thien-3-yl |
| 747. | 5-(2,5-difluorophenoxy)-thien-3-yl |
| 748. | 5-(2,6-difluorophenoxy)-thien-3-yl |
| 749. | 5-(3,4-difluorophenoxy)-thien-3-yl |
| 750. | 5-(3,5-difluorophenoxy)-thien-3-yl |
| 751. | 5-(2,3-dichlorophenoxy)-thien-3-yl |
| 752. | 5-(2,4-dichlorophenoxy)-thien-3-yl |
| 753. | 5-(2,5-dichlorophenoxy)-thien-3-yl |
| 754. | 5-(2,6-dichlorophenoxy)-thien-3-yl |
| 755. | 5-(3,4-dichlorophenoxy)-thien-3-yl |
| 756. | 5-(3,5-dichlorophenoxy)-thien-3-yl |
| 757. | 5-(2,3-dibromophenoxy)-thien-3-yl |
| 758. | 5-(2,4-dibromophenoxy)-thien-3-yl |
| 759. | 5-(2,5-dibromophenoxy)-thien-3-yl |
| 760. | 5-(2,6-dibromophenoxy)-thien-3-yl |
| 761. | 5-(3,4-dibromophenoxy)-thien-3-yl |
| 762. | 5-(3,5-dibromophenoxy)-thien-3-yl |
| 763. | 5-(2,3-dimethylphenoxy)-thien-3-yl |
| 764. | 5-(2,4-dimethylphenoxy)-thien-3-yl |
| 765. | 5-(2,5-dimethylphenoxy)-thien-3-yl |
| 766. | 5-(2,6-dimethylphenoxy)-thien-3-yl |
| 767. | 5-(3,4-dimethylphenoxy)-thien-3-yl |
| 768. | 5-(3,5-dimethylphenoxy)-thien-3-yl |
| 769. | 5-[2,3-di(trifluoromethyl)phenoxy]-thien-3-yl |
| 770. | 5-[2,4-di(trifluoromethyl)phenoxy]-thien-3-yl |
| 771. | 5-[2,5-di(trifluoromethyl)phenoxy]-thien-3-yl |
| 772. | 5-[2,6-di(trifluoromethyl)phenoxy]-thien-3-yl |
| 773. | 5-[3,4-di(trifluoromethyl)phenoxy]-thien-3-yl |
| 774. | 5-[3,5-di(trifluoromethyl)phenoxy]-thien-3-yl |
| 775. | 5-(2,3-dimethoxyphenoxy)-thien-3-yl |
| 776. | 5-(2,4-dimethoxyphenoxy)-thien-3-yl |
| 777. | 5-(2,5-dimethoxyphenoxy)-thien-3-yl |
| 778. | 5-(2,6-dimethoxyphenoxy)-thien-3-yl |
| 779. | 5-(3,4-dimethoxyphenoxy)-thien-3-yl |
| 780. | 5-(3,5-dimethoxyphenoxy)-thien-3-yl |
| 781. | 4-(o-CN-phenyl)-furan-2-yl |
| 782. | 4-(m-CN-phenyl)-furan-2-yl |
| 783. | 4-(p-CN-phenyl)-furan-2-yl |
| 784. | 4-(o-NO$_2$-phenyl)-furan-2-yl |
| 785. | 4-(m-NO$_2$-phenyl)-furan-2-yl |
| 786. | 4-(p-NO$_2$-phenyl)-furan-2-yl |
| 787. | 4-(o-F-phenyl)-furan-2-yl |
| 788. | 4-(m-F-phenyl)-furan-2-yl |

TABLE A-continued

| no. | R³-A- |
|---|---|
| 789. | 4-(p-F-phenyl)-furan-2-yl |
| 790. | 4-(o-Cl-phenyl)-furan-2-yl |
| 791. | 4-(m-Cl-phenyl)-furan-2-yl |
| 792. | 4-(p-Cl-phenyl)-furan-2-yl |
| 793. | 4-(o-Br-phenyl)-furan-2-yl |
| 794. | 4-(m-Br-phenyl)-furan-2-yl |
| 795. | 4-(p-Br-phenyl)-furan-2-yl |
| 796. | 4-(o-CH₃-phenyl)-furan-2-yl |
| 797. | 4-(m-CH₃-phenyl)-furan-2-yl |
| 798. | 4-(p-CH₃-phenyl)-furan-2-yl |
| 799. | 4-(o-CF₃-phenyl)-furan-2-yl |
| 800. | 4-(m-CF₃-phenyl)-furan-2-yl |
| 801. | 4-(p-CF₃-phenyl)-furan-2-yl |
| 802. | 4-(o-CF₃-phenyl)-furan-2-yl |
| 803. | 4-(m-CF₃-phenyl)-furan-2-yl |
| 804. | 4-(p-CF₃-phenyl)-furan-2-yl |
| 805. | 4-(o-OCH₃-phenyl)-furan-2-yl |
| 806. | 4-(m-OCH₃-phenyl)-furan-2-yl |
| 807. | 4-(p-OCH₃-phenyl)-furan-2-yl |
| 808. | 4-(o-OCF₃-phenyl)-furan-2-yl |
| 809. | 4-(m-OCF₃-phenyl)-furan-2-yl |
| 810. | 4-(p-OCF₃-phenyl)-furan-2-yl |
| 811. | 4-(o-COOCH₃-phenyl)-furan-2-yl |
| 812. | 4-(m-COOCH₃-phenyl)-furan-2-yl |
| 813. | 4-(p-COOCH₃-phenyl)-furan-2-yl |
| 814. | 4-[o-N(CH₃)₂-phenyl]-furan-2-yl |
| 815. | 4-[m-N(CH₃)₂-phenyl]-furan-2-yl |
| 816. | 4-[p-N(CH₃)₂-phenyl]-furan-2-yl |
| 817. | 4-(2,3-dicyanophenyl)-furan-2-yl |
| 818. | 4-(2,4-dicyanophenyl)-furan-2-yl |
| 819. | 4-(2,5-dicyanophenyl)-furan-2-yl |
| 820. | 4-(2,6-dicyanophenyl)-furan-2-yl |
| 821. | 4-(3,4-dicyanophenyl)-furan-2-yl |
| 822. | 4-(3,5-dicyanophenyl)-furan-2-yl |
| 823. | 4-(2,3-difluorophenyl)-furan-2-yl |
| 824. | 4-(2,4-difluorophenyl)-furan-2-yl |
| 825. | 4-(2,5-difluorophenyl)-furan-2-yl |
| 826. | 4-(2,6-difluorophenyl)-furan-2-yl |
| 827. | 4-(3,4-difluorophenyl)-furan-2-yl |
| 828. | 4-(3,5-difluorophenyl)-furan-2-yl |
| 829. | 4-(2,3-dichlorophenyl)-furan-2-yl |
| 830. | 4-(2,4-dichlorophenyl)-furan-2-yl |
| 831. | 4-(2,5-dichlorophenyl)-furan-2-yl |
| 832. | 4-(2,6-dichlorophenyl)-furan-2-yl |
| 833. | 4-(3,4-dichlorophenyl)-furan-2-yl |
| 834. | 4-(3,5-dichlorophenyl)-furan-2-yl |
| 835. | 4-(2,3-dibromophenyl)-furan-2-yl |
| 836. | 4-(2,4-dibromophenyl)-furan-2-yl |
| 837. | 4-(2,5-dibromophenyl)-furan-2-yl |
| 838. | 4-(2,6-dibromophenyl)-furan-2-yl |
| 839. | 4-(3,4-dibromophenyl)-furan-2-yl |
| 840. | 4-(3,5-dibromophenyl)-furan-2-yl |
| 841. | 4-(2,3-dimethylphenyl)-furan-2-yl |
| 842. | 4-(2,4-dimethylphenyl)-furan-2-yl |
| 843. | 4-(2,5-dimethylphenyl)-furan-2-yl |
| 844. | 4-(2,6-dimethylphenyl)-furan-2-yl |
| 845. | 4-(3,4-dimethylphenyl)-furan-2-yl |
| 846. | 4-(3,5-dimethylphenyl)-furan-2-yl |
| 847. | 4-[2,3-di(trifluoromethyl)phenyl]-furan-2-yl |
| 848. | 4-[2,4-di(trifluoromethyl)phenyl]-furan-2-yl |
| 849. | 4-[2,5-di(trifluoromethyl)phenyl]-furan-2-yl |
| 850. | 4-[2,6-di(trifluoromethyl)phenyl]-furan-2-yl |
| 851. | 4-[3,4-di(trifluoromethyl)phenyl]-furan-2-yl |
| 852. | 4-[3,5-di(trifluoromethyl)phenyl]-furan-2-yl |
| 853. | 4-(2,3-dimethoxyphenyl)-furan-2-yl |
| 854. | 4-(2,4-dimethoxyphenyl)-furan-2-yl |
| 855. | 4-(2,5-dimethoxyphenyl)-furan-2-yl |
| 856. | 4-(2,6-dimethoxyphenyl)-furan-2-yl |
| 857. | 4-(3,4-dimethoxyphenyl)-furan-2-yl |
| 858. | 4-(3,5-dimethoxyphenyl)-furan-2-yl |
| 859. | 4-(o-CN-phenoxy)-furan-2-yl |
| 860. | 4-(m-CN-phenoxy)-furan-2-yl |
| 861. | 4-(p-CN-phenoxy)-furan-2-yl |
| 862. | 4-(o-NO₂-phenoxy)-furan-2-yl |
| 863. | 4-(m-NO₂-phenoxy)-furan-2-yl |
| 864. | 4-(p-NO₂-phenoxy)-furan-2-yl |
| 865. | 4-(o-F-phenoxy)-furan-2-yl |
| 866. | 4-(m-F-phenoxy)-furan-2-yl |
| 867. | 4-(p-F-phenoxy)-furan-2-yl |
| 868. | 4-(o-Cl-phenoxy)-furan-2-yl |
| 869. | 4-(m-Cl-phenoxy)-furan-2-yl |
| 870. | 4-(p-Cl-phenoxy)-furan-2-yl |
| 871. | 4-(o-Br-phenoxy)-furan-2-yl |
| 872. | 4-(m-Br-phenoxy)-furan-2-yl |
| 873. | 4-(p-Br-phenoxy)-furan-2-yl |
| 874. | 4-(o-CH₃-phenoxy)-furan-2-yl |
| 875. | 4-(m-CH₃-phenoxy)-furan-2-yl |
| 876. | 4-(p-CH₃-phenoxy)-furan-2-yl |
| 877. | 4-(o-CF₃-phenoxy)-furan-2-yl |
| 878. | 4-(m-CF₃-phenoxy)-furan-2-yl |
| 879. | 4-(p-CF₃-phenoxy)-furan-2-yl |
| 880. | 4-(o-CF₃-phenoxy)-furan-2-yl |
| 881. | 4-(m-CF₃-phenoxy)-furan-2-yl |
| 882. | 4-(p-CF₃-phenoxy)-furan-2-yl |
| 883. | 4-(o-OCH₃-phenoxy)-furan-2-yl |
| 884. | 4-(m-OCH₃-phenoxy)-furan-2-yl |
| 885. | 4-(p-OCH₃-phenoxy)-furan-2-yl |
| 886. | 4-(o-OCF₃-phenoxy)-furan-2-yl |
| 887. | 4-(m-OCF₃-phenoxy)-furan-2-yl |
| 888. | 4-(p-OCF₃-phenoxy)-furan-2-yl |
| 889. | 4-(o-COOCH₃-phenoxy)-furan-2-yl |
| 890. | 4-(m-COOCH₃-phenoxy)-furan-2-yl |
| 891. | 4-(p-COOCH₃-phenoxy)-furan-2-yl |
| 892. | 4-[o-N(CH₃)₂-phenoxy]-furan-2-yl |
| 893. | 4-[m-N(CH₃)₂-phenoxy]-furan-2-yl |
| 894. | 4-[p-N(CH₃)₂-phenoxy]-furan-2-yl |
| 895. | 4-(2,3-dicyanophenoxy)-furan-2-yl |
| 896. | 4-(2,4-dicyanophenoxy)-furan-2-yl |
| 897. | 4-(2,5-dicyanophenoxy)-furan-2-yl |
| 898. | 4-(2,6-dicyanophenoxy)-furan-2-yl |
| 899. | 4-(3,4-dicyanophenoxy)-furan-2-yl |
| 900. | 4-(3,5-dicyanophenoxy)-furan-2-yl |
| 901. | 4-(2,3-difluorophenoxy)-furan-2-yl |
| 902. | 4-(2,4-difluorophenoxy)-furan-2-yl |
| 903. | 4-(2,5-difluorophenoxy)-furan-2-yl |
| 904. | 4-(2,6-difluorophenoxy)-furan-2-yl |
| 905. | 4-(3,4-difluorophenoxy)-furan-2-yl |
| 906. | 4-(3,5-difluorophenoxy)-furan-2-yl |
| 907. | 5-(2,3-dichlorophenoxy)-furan-2-yl |
| 908. | 4-(2,4-dichlorophenoxy)-furan-2-yl |
| 909. | 4-(2,5-dichlorophenoxy)-furan-2-yl |
| 910. | 4-(2,6-dichlorophenoxy)-furan-2-yl |
| 911. | 4-(3,4-dichlorophenoxy)-furan-2-yl |
| 912. | 4-(3,5-dichlorophenoxy)-furan-2-yl |
| 913. | 4-(2,3-dibromophenoxy)-furan-2-yl |
| 914. | 4-(2,4-dibromophenoxy)-furan-2-yl |

TABLE A-continued

| no. | R³-A- |
|---|---|
| 915. | 4-(2,5-dibromophenoxy)-furan-2-yl |
| 916. | 4-(2,6-dibromophenoxy)-furan-2-yl |
| 917. | 4-(3,4-dibromophenoxy)-furan-2-yl |
| 918. | 4-(3,5-dibromophenoxy)-furan-2-yl |
| 919. | 4-(2,3-dimethylphenoxy)-furan-2-yl |
| 920. | 4-(2,4-dimethylphenoxy)-furan-2-yl |
| 921. | 4-(2,5-dimethylphenoxy)-furan-2-yl |
| 922. | 4-(2,6-dimethylphenoxy)-furan-2-yl |
| 923. | 4-(3,4-dimethylphenoxy)-furan-2-yl |
| 924. | 4-(3,5-dimethylphenoxy)-furan-2-yl |
| 925. | 4-[2,3-di(trifluoromethyl)phenoxy]-furan-2-yl |
| 926. | 4-[2,4-di(trifluoromethyl)phenoxy]-furan-2-yl |
| 927. | 4-[2,5-di(trifluoromethyl)phenoxy]-furan-2-yl |
| 928. | 4-[2,6-di(trifluoromethyl)phenoxy]-furan-2-yl |
| 929. | 4-[3,4-di(trifluoromethyl)phenoxy]-furan-2-yl |
| 930. | 4-[3,5-di(trifluoromethyl)phenoxy]-furan-2-yl |
| 931. | 4-(2,3-dimethoxyphenoxy)-furan-2-yl |
| 932. | 4-(2,4-dimethoxyphenoxy)-furan-2-yl |
| 933. | 4-(2,5-dimethoxyphenoxy)-furan-2-yl |
| 934. | 4-(2,6-dimethoxyphenoxy)-furan-2-yl |
| 935. | 4-(3,4-dimethoxyphenoxy)-furan-2-yl |
| 936. | 4-(3,5-dimethoxyphenoxy)-furan-2-yl |
| 937. | 2-(o-CN-phenyl)-pyrid-5-yl |
| 938. | 2-(m-CN-phenyl)-pyrid-5-yl |
| 939. | 2-(p-CN-phenyl)-pyrid-5-yl |
| 940. | 2-(o-NO₂-phenyl)-pyrid-5-yl |
| 941. | 2-(m-NO₂-phenyl)-pyrid-5-yl |
| 942. | 2-(p-NO₂-phenyl)-pyrid-5-yl |
| 943. | 2-(o-F-phenyl)-pyrid-5-yl |
| 944. | 2-(m-F-phenyl)-pyrid-5-yl |
| 945. | 2-(p-F-phenyl)-pyrid-5-yl |
| 946. | 2-(o-Cl-phenyl)-pyrid-5-yl |
| 947. | 2-(m-Cl-phenyl)-pyrid-5-yl |
| 948. | 2-(p-Cl-phenyl)-pyrid-5-yl |
| 949. | 2-(o-Br-phenyl)-pyrid-5-yl |
| 950. | 2-(m-Br-phenyl)-pyrid-5-yl |
| 951. | 2-(p-Br-phenyl)-pyrid-5-yl |
| 952. | 2-(o-CH₃-phenyl)-pyrid-5-yl |
| 953. | 2-(m-CH₃-phenyl)-pyrid-5-yl |
| 954. | 2-(p-CH₃-phenyl)-pyrid-5-yl |
| 955. | 2-(o-CF₃-phenyl)-pyrid-5-yl |
| 956. | 2-(m-CF₃-phenyl)-pyrid-5-yl |
| 957. | 2-(p-CF₃-phenyl)-pyrid-5-yl |
| 958. | 2-(o-CF₃-phenyl)-pyrid-5-yl |
| 959. | 2-(m-CF₃-phenyl)-pyrid-5-yl |
| 960. | 2-(p-CF₃-phenyl)-pyrid-5-yl |
| 961. | 2-(o-OCH₃-phenyl)-pyrid-5-yl |
| 962. | 2-(m-OCH₃-phenyl)-pyrid-5-yl |
| 963. | 2-(p-OCH₃-phenyl)-pyrid-5-yl |
| 964. | 2-(o-OCF₃-phenyl)-pyrid-5-yl |
| 965. | 2-(m-OCF₃-phenyl)-pyrid-5-yl |
| 966. | 2-(p-OCF₃-phenyl)-pyrid-5-yl |
| 967. | 2-(o-COOCH₃-phenyl)-pyrid-5-yl |
| 968. | 2-(m-COOCH₃-phenyl)-pyrid-5-yl |
| 969. | 2-(p-COOCH₃-phenyl)-pyrid-5-yl |
| 970. | 2-[o-N(CH₃)₂-phenyl]-pyrid-5-yl |
| 971. | 2-[m-N(CH₃)₂-phenyl]-pyrid-5-yl |
| 972. | 2-[p-N(CH₃)₂-phenyl]-pyrid-5-yl |
| 973. | 2-(2,3-dicyanophenyl)-pyrid-5-yl |
| 974. | 2-(2,4-dicyanophenyl)-pyrid-5-yl |
| 975. | 2-(2,5-dicyanophenyl)-pyrid-5-yl |
| 976. | 2-(2,6-dicyanophenyl)-pyrid-5-yl |
| 977. | 2-(3,4-dicyanophenyl)-pyrid-5-yl |
| 978. | 2-(3,5-dicyanophenyl)-pyrid-5-yl |
| 979. | 2-(2,3-difluorophenyl)-pyrid-5-yl |
| 980. | 2-(2,4-difluorophenyl)-pyrid-5-yl |
| 981. | 2-(2,5-difluorophenyl)-pyrid-5-yl |
| 982. | 2-(2,6-difluorophenyl)-pyrid-5-yl |
| 983. | 2-(3,4-difluorophenyl)-pyrid-5-yl |
| 984. | 2-(3,5-difluorophenyl)-pyrid-5-yl |
| 985. | 2-(2,3-dichlorophenyl)-pyrid-5-yl |
| 986. | 2-(2,4-dichlorophenyl)-pyrid-5-yl |
| 987. | 2-(2,5-dichlorophenyl)-pyrid-5-yl |
| 988. | 2-(2,6-dichlorophenyl)-pyrid-5-yl |
| 989. | 2-(3,4-dichlorophenyl)-pyrid-5-yl |
| 990. | 2-(3,5-dichlorophenyl)-pyrid-5-yl |
| 991. | 2-(2,3-dibromophenyl)-pyrid-5-yl |
| 992. | 2-(2,4-dibromophenyl)-pyrid-5-yl |
| 993. | 2-(2,5-dibromophenyl)-pyrid-5-yl |
| 994. | 2-(2,6-dibromophenyl)-pyrid-5-yl |
| 995. | 2-(3,4-dibromophenyl)-pyrid-5-yl |
| 996. | 2-(3,5-dibromophenyl)-pyrid-5-yl |
| 997. | 2-(2,3-dimethylphenyl)-pyrid-5-yl |
| 998. | 2-(2,4-dimethylphenyl)-pyrid-5-yl |
| 999. | 2-(2,5-dimethylphenyl)-pyrid-5-yl |
| 1000. | 2-(2,6-dimethylphenyl)-pyrid-5-yl |
| 1001. | 2-(3,4-dimethylphenyl)-pyrid-5-yl |
| 1002. | 2-(3,5-dimethylphenyl)-pyrid-5-yl |
| 1003. | 2-[2,3-di(trifluoromethyl)phenyl]-pyrid-5-yl |
| 1004. | 2-[2,4-di(trifluoromethyl)phenyl]-pyrid-5-yl |
| 1005. | 2-[2,5-di(trifluoromethyl)phenyl]-pyrid-5-yl |
| 1006. | 2-[2,6-di(trifluoromethyl)phenyl]-pyrid-5-yl |
| 1007. | 2-[3,4-di(trifluoromethyl)phenyl]-pyrid-5-yl |
| 1008. | 2-[3,5-di(trifluoromethyl)phenyl]-pyrid-5-yl |
| 1009. | 2-(2,3-dimethoxyphenyl)-pyrid-5-yl |
| 1010. | 2-(2,4-dimethoxyphenyl)-pyrid-5-yl |
| 1011. | 2-(2,5-dimethoxyphenyl)-pyrid-5-yl |
| 1012. | 2-(2,6-dimethoxyphenyl)-pyrid-5-yl |
| 1013. | 2-(3,4-dimethoxyphenyl)-pyrid-5-yl |
| 1014. | 2-(3,5-dimethoxyphenyl)-pyrid-5-yl |
| 1015. | 2-(o-CN-phenoxy)-pyrid-5-yl |
| 1016. | 2-(m-CN-phenoxy)-pyrid-5-yl |
| 1017. | 2-(p-CN-phenoxy)-pyrid-5-yl |
| 1018. | 2-(o-NO₂-phenoxy)-pyrid-5-yl |
| 1019. | 2-(m-NO₂-phenoxy)-pyrid-5-yl |
| 1020. | 2-(p-NO₂-phenoxy)-pyrid-5-yl |
| 1021. | 2-(o-F-phenoxy)-pyrid-5-yl |
| 1022. | 2-(m-F-phenoxy)-pyrid-5-yl |
| 1023. | 2-(p-F-phenoxy)-pyrid-5-yl |
| 1024. | 2-(o-Cl-phenoxy)-pyrid-5-yl |
| 1025. | 2-(m-Cl-phenoxy)-pyrid-5-yl |
| 1026. | 2-(p-Cl-phenoxy)-pyrid-5-yl |
| 1027. | 2-(o-Br-phenoxy)-pyrid-5-yl |
| 1028. | 2-(m-Br-phenoxy)-pyrid-5-yl |
| 1029. | 2-(p-Br-phenoxy)-pyrid-5-yl |
| 1030. | 2-(o-CH₃-phenoxy)-pyrid-5-yl |
| 1031. | 2-(m-CH₃-phenoxy)-pyrid-5-yl |
| 1032. | 2-(p-CH₃-phenoxy)-pyrid-5-yl |
| 1033. | 2-(o-CF₃-phenoxy)-pyrid-5-yl |
| 1034. | 2-(m-CF₃-phenoxy)-pyrid-5-yl |
| 1035. | 2-(p-CF₃-phenoxy)-pyrid-5-yl |
| 1036. | 2-(o-CF₃-phenoxy)-pyrid-5-yl |

TABLE A-continued

| no. | R³-A- |
|---|---|
| 1037. | 2-(m-CF₃-phenoxy)-pyrid-5-yl |
| 1038. | 2-(p-CF₃-phenoxy)-pyrid-5-yl |
| 1039. | 2-(o-OCH₃-phenoxy)-pyrid-5-yl |
| 1040. | 2-(m-OCH₃-phenoxy)-pyrid-5-yl |
| 1041. | 2-(p-OCH₃-phenoxy)-pyrid-5-yl |
| 1042. | 2-(o-OCF₃-phenoxy)-pyrid-5-yl |
| 1043. | 2-(m-OCF₃-phenoxy)-pyrid-5-yl |
| 1044. | 2-(p-OCF₃-phenoxy)-pyrid-5-yl |
| 1045. | 2-(o-COOCH₃-phenoxy)-pyrid-5-yl |
| 1046. | 2-(m-COOCH₃-phenoxy)-pyrid-5-yl |
| 1047. | 2-(p-COOCH₃-phenoxy)-pyrid-5-yl |
| 1048. | 2-[o-N(CH₃)₂-phenoxy]-pyrid-5-yl |
| 1049. | 2-[m-N(CH₃)₂-phenoxy]-pyrid-5-yl |
| 1050. | 2-[p-N(CH₃)₂-phenoxy]-pyrid-5-yl |
| 1051. | 2-(2,3-dicyanophenoxy)-pyrid-5-yl |
| 1052. | 2-(2,4-dicyanophenoxy)-pyrid-5-yl |
| 1053. | 2-(2,5-dicyanophenoxy)-pyrid-5-yl |
| 1054. | 2-(2,6-dicyanophenoxy)-pyrid-5-yl |
| 1055. | 2-(3,4-dicyanophenoxy)-pyrid-5-yl |
| 1056. | 2-(3,5-dicyanophenoxy)-pyrid-5-yl |
| 1057. | 2-(2,3-difluorophenoxy)-pyrid-5-yl |
| 1058. | 2-(2,4-difluorophenoxy)-pyrid-5-yl |
| 1059. | 2-(2,5-difluorophenoxy)-pyrid-5-yl |
| 1060. | 2-(2,6-difluorophenoxy)-pyrid-5-yl |
| 1061. | 2-(3,4-difluorophenoxy)-pyrid-5-yl |
| 1062. | 2-(3,5-difluorophenoxy)-pyrid-5-yl |
| 1063. | 2-(2,3-dichlorophenoxy)-pyrid-5-yl |
| 1064. | 2-(2,4-dichlorophenoxy)-pyrid-5-yl |
| 1065. | 2-(2,5-dichlorophenoxy)-pyrid-5-yl |
| 1066. | 2-(2,6-dichlorophenoxy)-pyrid-5-yl |
| 1067. | 2-(3,4-dichlorophenoxy)-pyrid-5-yl |
| 1068. | 2-(3,5-dichlorophenoxy)-pyrid-5-yl |
| 1069. | 2-(2,3-dibromophenoxy)-pyrid-5-yl |
| 1070. | 2-(2,4-dibromophenoxy)-pyrid-5-yl |
| 1071. | 2-(2,5-dibromophenoxy)-pyrid-5-yl |
| 1072. | 2-(2,6-dibromophenoxy)-pyrid-5-yl |
| 1073. | 2-(3,4-dibromophenoxy)-pyrid-5-yl |
| 1074. | 2-(3,5-dibromophenoxy)-pyrid-5-yl |
| 1075. | 2-(2,3-dimethylphenoxy)-pyrid-5-yl |
| 1076. | 2-(2,4-dimethylphenoxy)-pyrid-5-yl |
| 1077. | 2-(2,5-dimethylphenoxy)-pyrid-5-yl |
| 1078. | 2-(2,6-dimethylphenoxy)-pyrid-5-yl |
| 1079. | 2-(3,4-dimethylphenoxy)-pyrid-5-yl |
| 1080. | 2-(3,5-dimethylphenoxy)-pyrid-5-yl |
| 1081. | 2-[2,3-di(trifluoromethyl)phenoxy]-pyrid-5-yl |
| 1082. | 2-[2,4-di(trifluoromethyl)phenoxy]-pyrid-5-yl |
| 1083. | 2-[2,5-di(trifluoromethyl)phenoxy]-pyrid-5-yl |
| 1084. | 2-[2,6-di(trifluoromethyl)phenoxy]-pyrid-5-yl |
| 1085. | 2-[3,4-di(trifluoromethyl)phenoxy]-pyrid-5-yl |
| 1086. | 2-[3,5-di(trifluoromethyl)phenoxy]-pyrid-5-yl |
| 1087. | 2-(2,3-dimethoxyphenoxy)-pyrid-5-yl |
| 1088. | 2-(2,4-dimethoxyphenoxy)-pyrid-5-yl |
| 1089. | 2-(2,5-dimethoxyphenoxy)-pyrid-5-yl |
| 1090. | 2-(2,6-dimethoxyphenoxy)-pyrid-5-yl |
| 1091. | 2-(3,4-dimethoxyphenoxy)-pyrid-5-yl |
| 1092. | 2-(3,5-dimethoxyphenoxy)-pyrid-5-yl |
| 1093. | 5-(o-CN-phenyl)-pyrid-3-yl |
| 1094. | 5-(m-CN-phenyl)-pyrid-3-yl |
| 1095. | 5-(p-CN-phenyl)-pyrid-3-yl |
| 1096. | 5-(o-NO₂-phenyl)-pyrid-3-yl |
| 1097. | 5-(m-NO₂-phenyl)-pyrid-3-yl |
| 1098. | 5-(p-NO₂-phenyl)-pyrid-3-yl |
| 1099. | 5-(o-F-phenyl)-pyrid-3-yl |
| 1100. | 5-(m-F-phenyl)-pyrid-3-yl |
| 1101. | 5-(p-F-phenyl)-pyrid-3-yl |
| 1102. | 5-(o-Cl-phenyl)-pyrid-3-yl |
| 1103. | 5-(m-Cl-phenyl)-pyrid-3-yl |
| 1104. | 5-(p-Cl-phenyl)-pyrid-3-yl |
| 1105. | 5-(o-Br-phenyl)-pyrid-3-yl |
| 1106. | 5-(m-Br-phenyl)-pyrid-3-yl |
| 1107. | 5-(p-Br-phenyl)-pyrid-3-yl |
| 1108. | 5-(o-CH₃-phenyl)-pyrid-3-yl |
| 1109. | 5-(m-CH₃-phenyl)-pyrid-3-yl |
| 1110. | 5-(p-CH₃-phenyl)-pyrid-3-yl |
| 1111. | 5-(o-CF₃-phenyl)-pyrid-3-yl |
| 1112. | 5-(m-CF₃-phenyl)-pyrid-3-yl |
| 1113. | 5-(p-CF₃-phenyl)-pyrid-3-yl |
| 1114. | 5-(o-CF₃-phenyl)-pyrid-3-yl |
| 1115. | 5-(m-CF₃-phenyl)-pyrid-3-yl |
| 1116. | 5-(p-CF₃-phenyl)-pyrid-3-yl |
| 1117. | 5-(o-OCH₃-phenyl)-pyrid-3-yl |
| 1118. | 5-(m-OCH₃-phenyl)-pyrid-3-yl |
| 1119. | 5-(p-OCH₃-phenyl)-pyrid-3-yl |
| 1120. | 5-(o-OCF₃-phenyl)-pyrid-3-yl |
| 1121. | 5-(m-OCF₃-phenyl)-pyrid-3-yl |
| 1122. | 5-(p-OCF₃-phenyl)-pyrid-3-yl |
| 1123. | 5-(o-COOCH₃-phenyl)-pyrid-3-yl |
| 1124. | 5-(m-COOCH₃-phenyl)-pyrid-3-yl |
| 1125. | 5-(p-COOCH₃-phenyl)-pyrid-3-yl |
| 1126. | 5-[o-N(CH₃)₂-phenyl]-pyrid-3-yl |
| 1127. | 5-[m-N(CH₃)₂-phenyl]-pyrid-3-yl |
| 1128. | 5-[p-N(CH₃)₂-phenyl]-pyrid-3-yl |
| 1129. | 5-(2,3-dicyanophenyl)-pyrid-3-yl |
| 1130. | 5-(2,4-dicyanophenyl)-pyrid-3-yl |
| 1131. | 5-(2,5-dicyanophenyl)-pyrid-3-yl |
| 1132. | 5-(2,6-dicyanophenyl)-pyrid-3-yl |
| 1133. | 5-(3,4-dicyanophenyl)-pyrid-3-yl |
| 1134. | 5-(3,5-dicyanophenyl)-pyrid-3-yl |
| 1135. | 5-(2,3-difluorophenyl)-pyrid-3-yl |
| 1136. | 5-(2,4-difluorophenyl)-pyrid-3-yl |
| 1137. | 5-(2,5-difluorophenyl)-pyrid-3-yl |
| 1138. | 5-(2,6-difluorophenyl)-pyrid-3-yl |
| 1139. | 5-(3,4-difluorophenyl)-pyrid-3-yl |
| 1140. | 5-(3,5-difluorophenyl)-pyrid-3-yl |
| 1141. | 5-(2,3-dichlorophenyl)-pyrid-3-yl |
| 1142. | 5-(2,4-dichlorophenyl)-pyrid-3-yl |
| 1143. | 5-(2,5-dichlorophenyl)-pyrid-3-yl |
| 1144. | 5-(2,6-dichlorophenyl)-pyrid-3-yl |
| 1145. | 5-(3,4-dichlorophenyl)-pyrid-3-yl |
| 1146. | 5-(3,5-dichlorophenyl)-pyrid-3-yl |
| 1147. | 5-(2,3-dibromophenyl)-pyrid-3-yl |
| 1148. | 5-(2,4-dibromophenyl)-pyrid-3-yl |
| 1149. | 5-(2,5-dibromophenyl)-pyrid-3-yl |
| 1150. | 5-(2,6-dibromophenyl)-pyrid-3-yl |
| 1151. | 5-(3,4-dibromophenyl)-pyrid-3-yl |
| 1152. | 5-(3,5-dibromophenyl)-pyrid-3-yl |

TABLE A-continued

| no. | R³-A- |
|---|---|
| 1153. | 5-(2,3-dimethylphenyl)-pyrid-3-yl |
| 1154. | 5-(2,4-dimethylphenyl)-pyrid-3-yl |
| 1155. | 5-(2,5-dimethylphenyl)-pyrid-3-yl |
| 1156. | 5-(2,6-dimethylphenyl)-pyrid-3-yl |
| 1157. | 5-(3,4-dimethylphenyl)-pyrid-3-yl |
| 1158. | 5-(3,5-dimethylphenyl)-pyrid-3-yl |
| 1159. | 5-[2,3-di(trifluoromethyl)phenyl]-pyrid-3-yl |
| 1160. | 5-[2,4-di(trifluoromethyl)phenyl]-pyrid-3-yl |
| 1161. | 5-[2,5-di(trifluoromethyl)phenyl]-pyrid-3-yl |
| 1162. | 5-[2,6-di(trifluoromethyl)phenyl]-pyrid-3-yl |
| 1163. | 5-[3,4-di(trifluoromethyl)phenyl]-pyrid-3-yl |
| 1164. | 5-[3,5-di(trifluoromethyl)phenyl]-pyrid-3-yl |
| 1165. | 5-(2,3-dimethoxyphenyl)-pyrid-3-yl |
| 1166. | 5-(2,4-dimethoxyphenyl)-pyrid-3-yl |
| 1167. | 5-(2,5-dimethoxyphenyl)-pyrid-3-yl |
| 1168. | 5-(2,6-dimethoxyphenyl)-pyrid-3-yl |
| 1169. | 5-(3,4-dimethoxyphenyl)-pyrid-3-yl |
| 1170. | 5-(3,5-dimethoxyphenyl)-pyrid-3-yl |
| 1171. | 5-(o-CN-phenoxy)-pyrid-3-yl |
| 1172. | 5-(m-CN-phenoxy)-pyrid-3-yl |
| 1173. | 5-(p-CN-phenoxy)-pyrid-3-yl |
| 1174. | 5-(o-$NO_2$-phenoxy)-pyrid-3-yl |
| 1175. | 5-(m-$NO_2$-phenoxy)-pyrid-3-yl |
| 1176. | 5-(p-$NO_2$-phenoxy)-pyrid-3-yl |
| 1177. | 5-(o-F-phenoxy)-pyrid-3-yl |
| 1178. | 5-(m-F-phenoxy)-pyrid-3-yl |
| 1179. | 5-(p-F-phenoxy)-pyrid-3-yl |
| 1180. | 5-(o-Cl-phenoxy)-pyrid-3-yl |
| 1181. | 5-(m-Cl-phenoxy)-pyrid-3-yl |
| 1182. | 5-(p-Cl-phenoxy)-pyrid-3-yl |
| 1183. | 5-(o-Br-phenoxy)-pyrid-3-yl |
| 1184. | 5-(m-Br-phenoxy)-pyrid-3-yl |
| 1185. | 5-(p-Br-phenoxy)-pyrid-3-yl |
| 1186. | 5-(o-$CH_3$-phenoxy)-pyrid-3-yl |
| 1187. | 5-(m-$CH_3$-phenoxy)-pyrid-3-yl |
| 1188. | 5-(p-$CH_3$-phenoxy)-pyrid-3-yl |
| 1189. | 5-(o-$CF_3$-phenoxy)-pyrid-3-yl |
| 1190. | 5-(m-$CF_3$-phenoxy)-pyrid-3-yl |
| 1191. | 5-(p-$CF_3$-phenoxy)-pyrid-3-yl |
| 1192. | 5-(o-$CF_3$-phenoxy)-pyrid-3-yl |
| 1193. | 5-(m-$CF_3$-phenoxy)-pyrid-3-yl |
| 1194. | 5-(p-$CF_3$-phenoxy)-pyrid-3-yl |
| 1195. | 5-(o-$OCH_3$-phenoxy)-pyrid-3-yl |
| 1196. | 5-(m-$OCH_3$-phenoxy)-pyrid-3-yl |
| 1197. | 5-(p-$OCH_3$-phenoxy)-pyrid-3-yl |
| 1198. | 5-(o-$OCF_3$-phenoxy)-pyrid-3-yl |
| 1199. | 5-(m-$OCF_3$-phenoxy)-pyrid-3-yl |
| 1200. | 5-(p-$OCF_3$-phenoxy)-pyrid-3-yl |
| 1201. | 5-(o-$COOCH_3$-phenoxy)-pyrid-3-yl |
| 1202. | 5-(m-$COOCH_3$-phenoxy)-pyrid-3-yl |
| 1203. | 5-(p-$COOCH_3$-phenoxy)-pyrid-3-yl |
| 1204. | 5-[o-$N(CH_3)_2$-phenoxy]-pyrid-3-yl |
| 1205. | 5-[m-$N(CH_3)_2$-phenoxy]-pyrid-3-yl |
| 1206. | 5-[p-$N(CH_3)_2$-phenoxy]-pyrid-3-yl |
| 1207. | 5-(2,3-dicyanophenoxy)-pyrid-3-yl |
| 1208. | 5-(2,4-dicyanophenoxy)-pyrid-3-yl |
| 1209. | 5-(2,5-dicyanophenoxy)-pyrid-3-yl |
| 1210. | 5-(2,6-dicyanophenoxy)-pyrid-3-yl |
| 1211. | 5-(3,4-dicyanophenoxy)-pyrid-3-yl |
| 1212. | 5-(3,5-dicyanophenoxy)-pyrid-3-yl |
| 1213. | 5-(2,3-difluorophenoxy)-pyrid-3-yl |
| 1214. | 5-(2,4-difluorophenoxy)-pyrid-3-yl |
| 1215. | 5-(2,5-difluorophenoxy)-pyrid-3-yl |
| 1216. | 5-(2,6-difluorophenoxy)-pyrid-3-yl |
| 1217. | 5-(3,4-difluorophenoxy)-pyrid-3-yl |
| 1218. | 5-(3,5-difluorophenoxy)-pyrid-3-yl |
| 1219. | 5-(2,3-dichlorophenoxy)-pyrid-3-yl |
| 1220. | 5-(2,4-dichlorophenoxy)-pyrid-3-yl |
| 1221. | 5-(2,5-dichlorophenoxy)-pyrid-3-yl |
| 1222. | 5-(2,6-dichlorophenoxy)-pyrid-3-yl |
| 1223. | 5-(3,4-dichlorophenoxy)-pyrid-3-yl |
| 1224. | 5-(3,5-dichlorophenoxy)-pyrid-3-yl |
| 1225. | 5-(2,3-dibromophenoxy)-pyrid-3-yl |
| 1226. | 5-(2,4-dibromophenoxy)-pyrid-3-yl |
| 1227. | 5-(2,5-dibromophenoxy)-pyrid-3-yl |
| 1228. | 5-(2,6-dibromophenoxy)-pyrid-3-yl |
| 1229. | 5-(3,4-dibromophenoxy)-pyrid-3-yl |
| 1230. | 5-(3,5-dibromophenoxy)-pyrid-3-yl |
| 1231. | 5-(2,3-dimethylphenoxy)-pyrid-3-yl |
| 1232. | 5-(2,4-dimethylphenoxy)-pyrid-3-yl |
| 1233. | 5-(2,5-dimethylphenoxy)-pyrid-3-yl |
| 1234. | 5-(2,6-dimethylphenoxy)-pyrid-3-yl |
| 1235. | 5-(3,4-dimethylphenoxy)-pyrid-3-yl |
| 1236. | 5-(3,5-dimethylphenoxy)-pyrid-3-yl |
| 1237. | 5-[2,3-di(trifluoromethyl)phenoxy]-pyrid-3-yl |
| 1238. | 5-[2,4-di(trifluoromethyl)phenoxy]-pyrid-3-yl |
| 1239. | 5-[2,5-di(trifluoromethyl)phenoxy]-pyrid-3-yl |
| 1240. | 5-[2,6-di(trifluoromethyl)phenoxy]-pyrid-3-yl |
| 1241. | 5-[3,4-di(trifluoromethyl)phenoxy]-pyrid-3-yl |
| 1242. | 5-[3,5-di(trifluoromethyl)phenoxy]-pyrid-3-yl |
| 1243. | 5-(2,3-dimethoxyphenoxy)-pyrid-3-yl |
| 1244. | 5-(2,4-dimethoxyphenoxy)-pyrid-3-yl |
| 1245. | 5-(2,5-dimethoxyphenoxy)-pyrid-3-yl |
| 1246. | 5-(2,6-dimethoxyphenoxy)-pyrid-3-yl |
| 1247. | 5-(3,4-dimethoxyphenoxy)-pyrid-3-yl |
| 1248. | 5-(3,5-dimethoxyphenoxy)-pyrid-3-yl |
| 1249. | 5-(o-CN-phenyl)-pyrid-2-yl |
| 1250. | 5-(m-CN-phenyl)-pyrid-2-yl |
| 1251. | 5-(p-CN-phenyl)-pyrid-2-yl |
| 1252. | 5-(o-$NO_2$-phenyl)-pyrid-2-yl |
| 1253. | 5-(m-$NO_2$-phenyl)-pyrid-2-yl |
| 1254. | 5-(p-$NO_2$-phenyl)-pyrid-2-yl |
| 1255. | 5-(o-F-phenyl)-pyrid-2-yl |
| 1256. | 5-(m-F-phenyl)-pyrid-2-yl |

TABLE A-continued

| no. | R³-A- |
|---|---|
| 1257. | 5-(p-F-phenyl)-pyrid-2-yl |
| 1258. | 5-(o-Cl-phenyl)-pyrid-2-yl |
| 1259. | 5-(m-Cl-phenyl)-pyrid-2-yl |
| 1260. | 5-(p-Cl-phenyl)-pyrid-2-yl |
| 1261. | 5-(o-Br-phenyl)-pyrid-2-yl |
| 1262. | 5-(m-Br-phenyl)-pyrid-2-yl |
| 1263. | 5-(p-Br-phenyl)-pyrid-2-yl |
| 1264. | 5-(o-CH₃-phenyl)-pyrid-2-yl |
| 1265. | 5-(m-CH₃-phenyl)-pyrid-2-yl |
| 1266. | 5-(p-CH₃-phenyl)-pyrid-2-yl |
| 1267. | 5-(o-CF₃-phenyl)-pyrid-2-yl |
| 1268. | 5-(m-CF₃-phenyl)-pyrid-2-yl |
| 1269. | 5-(p-CF₃-phenyl)-pyrid-2-yl |
| 1270. | 5-(o-CF₃-phenyl)-pyrid-2-yl |
| 1271. | 5-(m-CF₃-phenyl)-pyrid-2-yl |
| 1272. | 5-(p-CF₃-phenyl)-pyrid-2-yl |
| 1273. | 5-(o-OCH₃-phenyl)-pyrid-2-yl |
| 1274. | 5-(m-OCH₃-phenyl)-pyrid-2-yl |
| 1275. | 5-(p-OCH₃-phenyl)-pyrid-2-yl |
| 1276. | 5-(o-OCF₃-phenyl)-pyrid-2-yl |
| 1277. | 5-(m-OCF₃-phenyl)-pyrid-2-yl |
| 1278. | 5-(p-OCF₃-phenyl)-pyrid-2-yl |
| 1279. | 5-(o-COOCH₃-phenyl)-pyrid-2-yl |
| 1280. | 5-(m-COOCH₃-phenyl)-pyrid-2-yl |
| 1281. | 5-(p-COOCH₃-phenyl)-pyrid-2-yl |
| 1282. | 5-[o-N(CH₃)₂-phenyl]-pyrid-2-yl |
| 1283. | 5-[m-N(CH₃)₂-phenyl]-pyrid-2-yl |
| 1284. | 5-[p-N(CH₃)₂-phenyl]-pyrid-2-yl |
| 1285. | 5-(2,3-dicyanophenyl)-pyrid-2-yl |
| 1286. | 5-(2,4-dicyanophenyl)-pyrid-2-yl |
| 1287. | 5-(2,5-dicyanophenyl)-pyrid-2-yl |
| 1288. | 5-(2,6-dicyanophenyl)-pyrid-2-yl |
| 1289. | 5-(3,4-dicyanophenyl)-pyrid-2-yl |
| 1290. | 5-(3,5-dicyanophenyl)-pyrid-2-yl |
| 1291. | 5-(2,3-difluorophenyl)-pyrid-2-yl |
| 1292. | 5-(2,4-difluorophenyl)-pyrid-2-yl |
| 1293. | 5-(2,5-difluorophenyl)-pyrid-2-yl |
| 1294. | 5-(2,6-difluorophenyl)-pyrid-2-yl |
| 1295. | 5-(3,4-difluorophenyl)-pyrid-2-yl |
| 1296. | 5-(3,5-difluorophenyl)-pyrid-2-yl |
| 1297. | 5-(2,3-dichlorophenyl)-pyrid-2-yl |
| 1298. | 5-(2,4-dichlorophenyl)-pyrid-2-yl |
| 1299. | 5-(2,5-dichlorophenyl)-pyrid-2-yl |
| 1300. | 5-(2,6-dichlorophenyl)-pyrid-2-yl |
| 1301. | 5-(3,4-dichlorophenyl)-pyrid-2-yl |
| 1302. | 5-(3,5-dichlorophenyl)-pyrid-2-yl |
| 1303. | 5-(2,3-dibromophenyl)-pyrid-2-yl |
| 1304. | 5-(2,4-dibromophenyl)-pyrid-2-yl |
| 1305. | 5-(2,5-dibromophenyl)-pyrid-2-yl |
| 1306. | 5-(2,6-dibromophenyl)-pyrid-2-yl |
| 1307. | 5-(3,4-dibromophenyl)-pyrid-2-yl |
| 1308. | 5-(3,5-dibromophenyl)-pyrid-2-yl |
| 1309. | 5-(2,3-dimethylphenyl)-pyrid-2-yl |
| 1310. | 5-(2,4-dimethylphenyl)-pyrid-2-yl |
| 1311. | 5-(2,5-dimethylphenyl)-pyrid-2-yl |
| 1312. | 5-(2,6-dimethylphenyl)-pyrid-2-yl |
| 1313. | 5-(3,4-dimethylphenyl)-pyrid-2-yl |
| 1314. | 5-(3,5-dimethylphenyl)-pyrid-2-yl |
| 1315. | 5-[2,3-di(trifluoromethyl)phenyl]-pyrid-2-yl |
| 1316. | 5-[2,4-di(trifluoromethyl)phenyl]-pyrid-2-yl |
| 1317. | 5-[2,5-di(trifluoromethyl)phenyl]-pyrid-2-yl |
| 1318. | 5-[2,6-di(trifluoromethyl)phenyl]-pyrid-2-yl |
| 1319. | 5-[3,4-di(trifluoromethyl)phenyl]-pyrid-2-yl |
| 1320. | 5-[3,5-di(trifluoromethyl)phenyl]-pyrid-2-yl |
| 1321. | 5-(2,3-dimethoxyphenyl)-pyrid-2-yl |
| 1322. | 5-(2,4-dimethoxyphenyl)-pyrid-2-yl |
| 1323. | 5-(2,5-dimethoxyphenyl)-pyrid-2-yl |
| 1324. | 5-(2,6-dimethoxyphenyl)-pyrid-2-yl |
| 1325. | 5-(3,4-dimethoxyphenyl)-pyrid-2-yl |
| 1326. | 5-(3,5-dimethoxyphenyl)-pyrid-2-yl |
| 1327. | 5-(o-CN-phenoxy)-pyrid-2-yl |
| 1328. | 5-(m-CN-phenoxy)-pyrid-2-yl |
| 1329. | 5-(p-CN-phenoxy)-pyrid-2-yl |
| 1330. | 5-(o-NO₂-phenoxy)-pyrid-2-yl |
| 1331. | 5-(m-NO₂-phenoxy)-pyrid-2-yl |
| 1332. | 5-(p-NO₂-phenoxy)-pyrid-2-yl |
| 1333. | 5-(o-F-phenoxy)-pyrid-2-yl |
| 1334. | 5-(m-F-phenoxy)-pyrid-2-yl |
| 1335. | 5-(p-F-phenoxy)-pyrid-2-yl |
| 1336. | 5-(o-Cl-phenoxy)-pyrid-2-yl |
| 1337. | 5-(m-Cl-phenoxy)-pyrid-2-yl |
| 1338. | 5-(p-Cl-phenoxy)-pyrid-2-yl |
| 1339. | 5-(o-Br-phenoxy)-pyrid-2-yl |
| 1340. | 5-(m-Br-phenoxy)-pyrid-2-yl |
| 1341. | 5-(p-Br-phenoxy)-pyrid-2-yl |
| 1342. | 5-(o-CH₃-phenoxy)-pyrid-2-yl |
| 1343. | 5-(m-CH₃-phenoxy)-pyrid-2-yl |
| 1344. | 5-(p-CH₃-phenoxy)-pyrid-2-yl |
| 1345. | 5-(o-CF₃-phenoxy)-pyrid-2-yl |
| 1346. | 5-(m-CF₃-phenoxy)-pyrid-2-yl |
| 1347. | 5-(p-CF₃-phenoxy)-pyrid-2-yl |
| 1348. | 5-(o-CF₃-phenoxy)-pyrid-2-yl |
| 1349. | 5-(m-CF₃-phenoxy)-pyrid-2-yl |
| 1350. | 5-(p-CF₃-phenoxy)-pyrid-2-yl |
| 1351. | 5-(o-OCH₃-phenoxy)-pyrid-2-yl |
| 1352. | 5-(m-OCH₃-phenoxy)-pyrid-2-yl |
| 1353. | 5-(p-OCH₃-phenoxy)-pyrid-2-yl |
| 1354. | 5-(o-OCF₃-phenoxy)-pyrid-2-yl |
| 1355. | 5-(m-OCF₃-phenoxy)-pyrid-2-yl |
| 1356. | 5-(p-OCF₃-phenoxy)-pyrid-2-yl |
| 1357. | 5-(o-COOCH₃-phenoxy)-pyrid-2-yl |
| 1358. | 5-(m-COOCH₃-phenoxy)-pyrid-2-yl |
| 1359. | 5-(p-COOCH₃-phenoxy)-pyrid-2-yl |
| 1360. | 5-[o-N(CH₃)₂-phenoxy]-pyrid-2-yl |
| 1361. | 5-[m-N(CH₃)₂-phenoxy]-pyrid-2-yl |
| 1362. | 5-[p-N(CH₃)₂-phenoxy]-pyrid-2-yl |
| 1363. | 5-(2,3-dicyanophenoxy)-pyrid-2-yl |
| 1364. | 5-(2,4-dicyanophenoxy)-pyrid-2-yl |
| 1365. | 5-(2,5-dicyanophenoxy)-pyrid-2-yl |
| 1366. | 5-(2,6-dicyanophenoxy)-pyrid-2-yl |
| 1367. | 5-(3,4-dicyanophenoxy)-pyrid-2-yl |
| 1368. | 5-(3,5-dicyanophenoxy)-pyrid-2-yl |
| 1369. | 5-(2,3-difluorophenoxy)-pyrid-2-yl |
| 1370. | 5-(2,4-difluorophenoxy)-pyrid-2-yl |
| 1371. | 5-(2,5-difluorophenoxy)-pyrid-2-yl |
| 1372. | 5-(2,6-difluorophenoxy)-pyrid-2-yl |
| 1373. | 5-(3,4-difluorophenoxy)-pyrid-2-yl |
| 1374. | 5-(3,5-difluorophenoxy)-pyrid-2-yl |
| 1375. | 5-(2,3-dichlorophenoxy)-pyrid-2-yl |
| 1376. | 5-(2,4-dichlorophenoxy)-pyrid-2-yl |
| 1377. | 5-(2,5-dichlorophenoxy)-pyrid-2-yl |
| 1378. | 5-(2,6-dichlorophenoxy)-pyrid-2-yl |
| 1379. | 5-(3,4-dichlorophenoxy)-pyrid-2-yl |
| 1380. | 5-(3,5-dichlorophenoxy)-pyrid-2-yl |
| 1381. | 5-(2,3-dibromophenoxy)-pyrid-2-yl |
| 1382. | 5-(2,4-dibromophenoxy)-pyrid-2-yl |

TABLE A-continued

| no. | R³-A- |
|---|---|
| 1383. | 5-(2,5-dibromophenoxy)-pyrid-2-yl |
| 1384. | 5-(2,6-dibromophenoxy)-pyrid-2-yl |
| 1385. | 5-(3,4-dibromophenoxy)-pyrid-2-yl |
| 1386. | 5-(3,5-dibromophenoxy)-pyrid-2-yl |
| 1387. | 5-(2,3-dimethylphenoxy)-pyrid-2-yl |
| 1388. | 5-(2,4-dimethylphenoxy)-pyrid-2-yl |
| 1389. | 5-(2,5-dimethylphenoxy)-pyrid-2-yl |
| 1390. | 5-(2,6-dimethylphenoxy)-pyrid-2-yl |
| 1391. | 5-(3,4-dimethylphenoxy)-pyrid-2-yl |
| 1392. | 5-(3,5-dimethylphenoxy)-pyrid-2-yl |
| 1393. | 5-[2,3-di(trifluoromethyl)phenoxy]-pyrid-2-yl |
| 1394. | 5-[2,4-di(trifluoromethyl)phenoxy]-pyrid-2-yl |
| 1395. | 5-[2,5-di(trifluoromethyl)phenoxy]-pyrid-2-yl |
| 1396. | 5-[2,6-di(trifluoromethyl)phenoxy]-pyrid-2-yl |
| 1397. | 5-[3,4-di(trifluoromethyl)phenoxy]-pyrid-2-yl |
| 1398. | 5-[3,5-di(trifluoromethyl)phenoxy]-pyrid-2-yl |
| 1399. | 5-(2,3-dimethoxyphenoxy)-pyrid-2-yl |
| 1400. | 5-(2,4-dimethoxyphenoxy)-pyrid-2-yl |
| 1401. | 5-(2,5-dimethoxyphenoxy)-pyrid-2-yl |
| 1402. | 5-(2,6-dimethoxyphenoxy)-pyrid-2-yl |
| 1403. | 5-(3,4-dimethoxyphenoxy)-pyrid-2-yl |
| 1404. | 5-(3,5-dimethoxyphenoxy)-pyrid-2-yl |
| 1405. | 6-(o-CN-phenyl)-pyrid-2-yl |
| 1406. | 6-(m-CN-phenyl)-pyrid-2-yl |
| 1407. | 6-(p-CN-phenyl)-pyrid-2-yl |
| 1408. | 6-(o-NO₂-phenyl)-pyrid-2-yl |
| 1409. | 6-(m-NO₂-phenyl)-pyrid-2-yl |
| 1410. | 6-(p-NO₂-phenyl)-pyrid-2-yl |
| 1411. | 6-(o-F-phenyl)-pyrid-2-yl |
| 1412. | 6-(m-F-phenyl)-pyrid-2-yl |
| 1413. | 6-(p-F-phenyl)-pyrid-2-yl |
| 1414. | 6-(o-Cl-phenyl)-pyrid-2-yl |
| 1415. | 6-(m-Cl-phenyl)-pyrid-2-yl |
| 1416. | 6-(p-Cl-phenyl)-pyrid-2-yl |
| 1417. | 6-(o-Br-phenyl)-pyrid-2-yl |
| 1418. | 6-(m-Br-phenyl)-pyrid-2-yl |
| 1419. | 6-(p-Br-phenyl)-pyrid-2-yl |
| 1420. | 6-(o-CH₃-phenyl)-pyrid-2-yl |
| 1421. | 6-(m-CH₃-phenyl)-pyrid-2-yl |
| 1422. | 6-(p-CH₃-phenyl)-pyrid-2-yl |
| 1423. | 6-(o-CF₃-phenyl)-pyrid-2-yl |
| 1424. | 6-(m-CF₃-phenyl)-pyrid-2-yl |
| 1425. | 6-(p-CF₃-phenyl)-pyrid-2-yl |
| 1426. | 6-(o-CF₃-phenyl)-pyrid-2-yl |
| 1427. | 6-(m-CF₃-phenyl)-pyrid-2-yl |
| 1428. | 6-(p-CF₃-phenyl)-pyrid-2-yl |
| 1429. | 6-(o-OCH₃-phenyl)-pyrid-2-yl |
| 1430. | 6-(m-OCH₃-phenyl)-pyrid-2-yl |
| 1431. | 6-(p-OCH₃-phenyl)-pyrid-2-yl |
| 1432. | 6-(o-OCF₃-phenyl)-pyrid-2-yl |
| 1433. | 6-(m-OCF₃-phenyl)-pyrid-2-yl |
| 1434. | 6-(p-OCF₃-phenyl)-pyrid-2-yl |
| 1435. | 6-(o-COOCH₃-phenyl)-pyrid-2-yl |
| 1436. | 6-(m-COOCH₃-phenyl)-pyrid-2-yl |
| 1437. | 6-(p-COOCH₃-phenyl)-pyrid-2-yl |
| 1438. | 6-[o-N(CH₃)₂-phenyl]-pyrid-2-yl |
| 1439. | 6-[m-N(CH₃)₂-phenyl]-pyrid-2-yl |
| 1440. | 6-[p-N(CH₃)₂-phenyl]-pyrid-2-yl |
| 1441. | 6-(2,3-dicyanophenyl)-pyrid-2-yl |
| 1442. | 6-(2,4-dicyanophenyl)-pyrid-2-yl |
| 1443. | 6-(2,5-dicyanophenyl)-pyrid-2-yl |
| 1444. | 6-(2,6-dicyanophenyl)-pyrid-2-yl |
| 1445. | 6-(3,4-dicyanophenyl)-pyrid-2-yl |
| 1446. | 6-(3,5-dicyanophenyl)-pyrid-2-yl |
| 1447. | 6-(2,3-difluorophenyl)-pyrid-2-yl |
| 1448. | 6-(2,4-difluorophenyl)-pyrid-2-yl |
| 1449. | 6-(2,5-difluorophenyl)-pyrid-2-yl |
| 1450. | 6-(2,6-difluorophenyl)-pyrid-2-yl |
| 1451. | 6-(3,4-difluorophenyl)-pyrid-2-yl |
| 1452. | 6-(3,5-difluorophenyl)-pyrid-2-yl |
| 1453. | 6-(2,3-dichlorophenyl)-pyrid-2-yl |
| 1454. | 6-(2,4-dichlorophenyl)-pyrid-2-yl |
| 1455. | 6-(2,5-dichlorophenyl)-pyrid-2-yl |
| 1456. | 6-(2,6-dichlorophenyl)-pyrid-2-yl |
| 1457. | 6-(3,4-dichlorophenyl)-pyrid-2-yl |
| 1458. | 6-(3,5-dichlorophenyl)-pyrid-2-yl |
| 1459. | 6-(2,3-dibromophenyl)-pyrid-2-yl |
| 1460. | 6-(2,4-dibromophenyl)-pyrid-2-yl |
| 1461. | 6-(2,5-dibromophenyl)-pyrid-2-yl |
| 1462. | 6-(2,6-dibromophenyl)-pyrid-2-yl |
| 1463. | 6-(3,4-dibromophenyl)-pyrid-2-yl |
| 1464. | 6-(3,5-dibromophenyl)-pyrid-2-yl |
| 1465. | 6-(2,3-dimethylphenyl)-pyrid-2-yl |
| 1466. | 6-(2,4-dimethylphenyl)-pyrid-2-yl |
| 1467. | 6-(2,5-dimethylphenyl)-pyrid-2-yl |
| 1468. | 6-(2,6-dimethylphenyl)-pyrid-2-yl |
| 1469. | 6-(3,4-dimethylphenyl)-pyrid-2-yl |
| 1470. | 6-(3,5-dimethylphenyl)-pyrid-2-yl |
| 1471. | 6-[2,3-di(trifluoromethyl)phenyl]-pyrid-2-yl |
| 1472. | 6-[2,4-di(trifluoromethyl)phenyl]-pyrid-2-yl |
| 1473. | 6-[2,5-di(trifluoromethyl)phenyl]-pyrid-2-yl |
| 1474. | 6-[2,6-di(trifluoromethyl)phenyl]-pyrid-2-yl |
| 1475. | 6-[3,4-di(trifluoromethyl)phenyl]-pyrid-2-yl |
| 1476. | 6-[3,5-di(trifluoromethyl)phenyl]-pyrid-2-yl |
| 1477. | 6-(2,3-dimethoxyphenyl)-pyrid-2-yl |
| 1478. | 6-(2,4-dimethoxyphenyl)-pyrid-2-yl |
| 1479. | 6-(2,5-dimethoxyphenyl)-pyrid-2-yl |
| 1480. | 6-(2,6-dimethoxyphenyl)-pyrid-2-yl |
| 1481. | 6-(3,4-dimethoxyphenyl)-pyrid-2-yl |
| 1482. | 6-(3,5-dimethoxyphenyl)-pyrid-2-yl |
| 1483. | 6-(o-CN-phenoxy)-pyrid-2-yl |
| 1484. | 6-(m-CN-phenoxy)-pyrid-2-yl |
| 1485. | 6-(p-CN-phenoxy)-pyrid-2-yl |
| 1486. | 6-(o-NO₂-phenoxy)-pyrid-2-yl |
| 1487. | 6-(m-NO₂-phenoxy)-pyrid-2-yl |
| 1488. | 6-(p-NO₂-phenoxy)-pyrid-2-yl |
| 1489. | 6-(o-F-phenoxy)-pyrid-2-yl |
| 1490. | 6-(m-F-phenoxy)-pyrid-2-yl |
| 1491. | 6-(p-F-phenoxy)-pyrid-2-yl |
| 1492. | 6-(o-Cl-phenoxy)-pyrid-2-yl |
| 1493. | 6-(m-Cl-phenoxy)-pyrid-2-yl |
| 1494. | 6-(p-Cl-phenoxy)-pyrid-2-yl |
| 1495. | 6-(o-Br-phenoxy)-pyrid-2-yl |
| 1496. | 6-(m-Br-phenoxy)-pyrid-2-yl |
| 1497. | 6-(p-Br-phenoxy)-pyrid-2-yl |
| 1498. | 6-(o-CH₃-phenoxy)-pyrid-2-yl |
| 1499. | 6-(m-CH₃-phenoxy)-pyrid-2-yl |
| 1500. | 6-(p-CH₃-phenoxy)-pyrid-2-yl |
| 1501. | 6-(o-CF₃-phenoxy)-pyrid-2-yl |
| 1502. | 6-(m-CF₃-phenoxy)-pyrid-2-yl |
| 1503. | 6-(p-CF₃-phenoxy)-pyrid-2-yl |

TABLE A-continued

| no. | R³-A- |
|---|---|
| 1504. | 6-(o-CF₃-phenoxy)-pyrid-2-yl |
| 1505. | 6-(m-CF₃-phenoxy)-pyrid-2-yl |
| 1506. | 6-(p-CF₃-phenoxy)-pyrid-2-yl |
| 1507. | 6-(o-OCH₃-phenoxy)-pyrid-2-yl |
| 1508. | 6-(m-OCH₃-phenoxy)-pyrid-2-yl |
| 1509. | 6-(p-OCH₃-phenoxy)-pyrid-2-yl |
| 1510. | 6-(o-OCF₃-phenoxy)-pyrid-2-yl |
| 1511. | 6-(m-OCF₃-phenoxy)-pyrid-2-yl |
| 1512. | 6-(p-OCF₃-phenoxy)-pyrid-2-yl |
| 1513. | 6-(o-COOCH₃-phenoxy)-pyrid-2-yl |
| 1514. | 6-(m-COOCH₃-phenoxy)-pyrid-2-yl |
| 1515. | 6-(p-COOCH₃-phenoxy)-pyrid-2-yl |
| 1516. | 6-[o-N(CH₃)₂-phenoxy]-pyrid-2-yl |
| 1517. | 6-[m-N(CH₃)₂-phenoxy]-pyrid-2-yl |
| 1518. | 6-[p-N(CH₃)₂-phenoxy]-pyrid-2-yl |
| 1519. | 6-(2,3-dicyanophenoxy)-pyrid-2-yl |
| 1520. | 6-(2,4-dicyanophenoxy)-pyrid-2-yl |
| 1521. | 6-(2,5-dicyanophenoxy)-pyrid-2-yl |
| 1522. | 6-(2,6-dicyanophenoxy)-pyrid-2-yl |
| 1523. | 6-(3,4-dicyanophenoxy)-pyrid-2-yl |
| 1524. | 6-(3,5-dicyanophenoxy)-pyrid-2-yl |
| 1525. | 6-(2,3-difluorophenoxy)-pyrid-2-yl |
| 1526. | 6-(2,4-difluorophenoxy)-pyrid-2-yl |
| 1527. | 6-(2,5-difluorophenoxy)-pyrid-2-yl |
| 1528. | 6-(2,6-difluorophenoxy)-pyrid-2-yl |
| 1529. | 6-(3,4-difluorophenoxy)-pyrid-2-yl |
| 1530. | 6-(3,5-difluorophenoxy)-pyrid-2-yl |
| 1531. | 6-(2,3-dichlorophenoxy)-pyrid-2-yl |
| 1532. | 6-(2,4-dichlorophenoxy)-pyrid-2-yl |
| 1533. | 6-(2,5-dichlorophenoxy)-pyrid-2-yl |
| 1534. | 6-(2,6-dichlorophenoxy)-pyrid-2-yl |
| 1535. | 6-(3,4-dichlorophenoxy)-pyrid-2-yl |
| 1536. | 6-(3,5-dichlorophenoxy)-pyrid-2-yl |
| 1537. | 6-(2,3-dibromophenoxy)-pyrid-2-yl |
| 1538. | 6-(2,4-dibromophenoxy)-pyrid-2-yl |
| 1539. | 6-(2,5-dibromophenoxy)-pyrid-2-yl |
| 1540. | 6-(2,6-dibromophenoxy)-pyrid-2-yl |
| 1541. | 6-(3,4-dibromophenoxy)-pyrid-2-yl |
| 1542. | 6-(3,5-dibromophenoxy)-pyrid-2-yl |
| 1543. | 6-(2,3-dimethylphenoxy)-pyrid-2-yl |
| 1544. | 6-(2,4-dimethylphenoxy)-pyrid-2-yl |
| 1545. | 6-(2,5-dimethylphenoxy)-pyrid-2-yl |
| 1546. | 6-(2,6-dimethylphenoxy)-pyrid-2-yl |
| 1547. | 6-(3,4-dimethylphenoxy)-pyrid-2-yl |
| 1548. | 6-(3,5-dimethylphenoxy)-pyrid-2-yl |
| 1549. | 6-[2,3-di(trifluoromethyl)phenoxy]-pyrid-2-yl |
| 1550. | 6-[2,4-di(trifluoromethyl)phenoxy]-pyrid-2-yl |
| 1551. | 6-[2,5-di(trifluoromethyl)phenoxy]-pyrid-2-yl |
| 1552. | 6-[2,6-di(trifluoromethyl)phenoxy]-pyrid-2-yl |
| 1553. | 6-[3,4-di(trifluoromethyl)phenoxy]-pyrid-2-yl |
| 1554. | 6-[3,5-di(trifluoromethyl)phenoxy]-pyrid-2-yl |
| 1555. | 6-(2,3-dimethoxyphenoxy)-pyrid-2-yl |
| 1556. | 6-(2,4-dimethoxyphenoxy)-pyrid-2-yl |
| 1557. | 6-(2,5-dimethoxyphenoxy)-pyrid-2-yl |
| 1558. | 6-(2,6-dimethoxyphenoxy)-pyrid-2-yl |
| 1559. | 6-(3,4-dimethoxyphenoxy)-pyrid-2-yl |
| 1560. | 6-(3,5-dimethoxyphenoxy)-pyrid-2-yl |
| 1561. | 4-(o-CN-phenyl)-pyrid-2-yl |
| 1562. | 4-(m-CN-phenyl)-pyrid-2-yl |
| 1563. | 4-(p-CN-phenyl)-pyrid-2-yl |
| 1564. | 4-(o-NO₂-phenyl)-pyrid-2-yl |
| 1565. | 4-(m-NO₂-phenyl)-pyrid-2-yl |
| 1566. | 4-(p-NO₂-phenyl)-pyrid-2-yl |
| 1567. | 4-(o-F-phenyl)-pyrid-2-yl |
| 1568. | 4-(m-F-phenyl)-pyrid-2-yl |
| 1569. | 4-(p-F-phenyl)-pyrid-2-yl |
| 1570. | 4-(o-Cl-phenyl)-pyrid-2-yl |
| 1571. | 4-(m-Cl-phenyl)-pyrid-2-yl |
| 1572. | 4-(p-Cl-phenyl)-pyrid-2-yl |
| 1573. | 4-(o-Br-phenyl)-pyrid-2-yl |
| 1574. | 4-(m-Br-phenyl)-pyrid-2-yl |
| 1575. | 4-(p-Br-phenyl)-pyrid-2-yl |
| 1576. | 4-(o-CH₃-phenyl)-pyrid-2-yl |
| 1577. | 4-(m-CH₃-phenyl)-pyrid-2-yl |
| 1578. | 4-(p-CH₃-phenyl)-pyrid-2-yl |
| 1579. | 4-(o-CF₃-phenyl)-pyrid-2-yl |
| 1580. | 4-(m-CF₃-phenyl)-pyrid-2-yl |
| 1581. | 4-(p-CF₃-phenyl)-pyrid-2-yl |
| 1582. | 4-(o-CF₃-phenyl)-pyrid-2-yl |
| 1583. | 4-(m-CF₃-phenyl)-pyrid-2-yl |
| 1584. | 4-(p-CF₃-phenyl)-pyrid-2-yl |
| 1585. | 4-(o-OCH₃-phenyl)-pyrid-2-yl |
| 1586. | 4-(m-OCH₃-phenyl)-pyrid-2-yl |
| 1587. | 4-(p-OCH₃-phenyl)-pyrid-2-yl |
| 1588. | 4-(o-OCF₃-phenyl)-pyrid-2-yl |
| 1589. | 4-(m-OCF₃-phenyl)-pyrid-2-yl |
| 1590. | 4-(p-OCF₃-phenyl)-pyrid-2-yl |
| 1591. | 4-(o-COOCH₃-phenyl)-pyrid-2-yl |
| 1592. | 4-(m-COOCH₃-phenyl)-pyrid-2-yl |
| 1593. | 4-(p-COOCH₃-phenyl)-pyrid-2-yl |
| 1594. | 4-[o-N(CH₃)₂-phenyl]-pyrid-2-yl |
| 1595. | 4-[m-N(CH₃)₂-phenyl]-pyrid-2-yl |
| 1596. | 4-[p-N(CH₃)₂-phenyl]-pyrid-2-yl |
| 1597. | 4-(2,3-dicyanophenyl)-pyrid-2-yl |
| 1598. | 4-(2,4-dicyanophenyl)-pyrid-2-yl |
| 1599. | 4-(2,5-dicyanophenyl)-pyrid-2-yl |
| 1600. | 4-(2,6-dicyanophenyl)-pyrid-2-yl |
| 1601. | 4-(3,4-dicyanophenyl)-pyrid-2-yl |
| 1602. | 4-(3,5-dicyanophenyl)-pyrid-2-yl |
| 1603. | 4-(2,3-difluorophenyl)-pyrid-2-yl |
| 1604. | 4-(2,4-difluorophenyl)-pyrid-2-yl |
| 1605. | 4-(2,5-difluorophenyl)-pyrid-2-yl |
| 1606. | 4-(2,6-difluorophenyl)-pyrid-2-yl |
| 1607. | 4-(3,4-difluorophenyl)-pyrid-2-yl |
| 1608. | 4-(3,5-difluorophenyl)-pyrid-2-yl |
| 1609. | 4-(2,3-dichlorophenyl)-pyrid-2-yl |
| 1610. | 4-(2,4-dichlorophenyl)-pyrid-2-yl |
| 1611. | 4-(2,5-dichlorophenyl)-pyrid-2-yl |
| 1612. | 4-(2,6-dichlorophenyl)-pyrid-2-yl |
| 1613. | 4-(3,4-dichlorophenyl)-pyrid-2-yl |
| 1614. | 4-(3,5-dichlorophenyl)-pyrid-2-yl |
| 1615. | 4-(2,3-dibromophenyl)-pyrid-2-yl |
| 1616. | 4-(2,4-dibromophenyl)-pyrid-2-yl |
| 1617. | 4-(2,5-dibromophenyl)-pyrid-2-yl |
| 1618. | 4-(2,6-dibromophenyl)-pyrid-2-yl |
| 1619. | 4-(3,4-dibromophenyl)-pyrid-2-yl |
| 1620. | 4-(3,5-dibromophenyl)-pyrid-2-yl |

TABLE A-continued

| no. | R³-A- |
|---|---|
| 1621. | 4-(2,3-dimethylphenyl)-pyrid-2-yl |
| 1622. | 4-(2,4-dimethylphenyl)-pyrid-2-yl |
| 1623. | 4-(2,5-dimethylphenyl)-pyrid-2-yl |
| 1624. | 4-(2,6-dimethylphenyl)-pyrid-2-yl |
| 1625. | 4-(3,4-dimethylphenyl)-pyrid-2-yl |
| 1626. | 4-(3,5-dimethylphenyl)-pyrid-2-yl |
| 1627. | 4-[2,3-di(trifluoromethyl)phenyl]-pyrid-2-yl |
| 1628. | 4-[2,4-di(trifluoromethyl)phenyl]-pyrid-2-yl |
| 1629. | 4-[2,5-di(trifluoromethyl)phenyl]-pyrid-2-yl |
| 1630. | 4-[2,6-di(trifluoromethyl)phenyl]-pyrid-2-yl |
| 1631. | 4-[3,4-di(trifluoromethyl)phenyl]-pyrid-2-yl |
| 1632. | 4-[3,5-di(trifluoromethyl)phenyl]-pyrid-2-yl |
| 1633. | 4-(2,3-dimethoxyphenyl)-pyrid-2-yl |
| 1634. | 4-(2,4-dimethoxyphenyl)-pyrid-2-yl |
| 1635. | 4-(2,5-dimethoxyphenyl)-pyrid-2-yl |
| 1636. | 4-(2,6-dimethoxyphenyl)-pyrid-2-yl |
| 1637. | 4-(3,4-dimethoxyphenyl)-pyrid-2-yl |
| 1638. | 4-(3,5-dimethoxyphenyl)-pyrid-2-yl |
| 1639. | 4-(o-CN-phenoxy)-pyrid-2-yl |
| 1640. | 4-(m-CN-phenoxy)-pyrid-2-yl |
| 1641. | 4-(p-CN-phenoxy)-pyrid-2-yl |
| 1642. | 4-(o-NO₂-phenoxy)-pyrid-2-yl |
| 1643. | 4-(m-NO₂-phenoxy)-pyrid-2-yl |
| 1644. | 4-(p-NO₂-phenoxy)-pyrid-2-yl |
| 1645. | 4-(o-F-phenoxy)-pyrid-2-yl |
| 1646. | 4-(m-F-phenoxy)-pyrid-2-yl |
| 1647. | 4-(p-F-phenoxy)-pyrid-2-yl |
| 1648. | 4-(o-Cl-phenoxy)-pyrid-2-yl |
| 1649. | 4-(m-Cl-phenoxy)-pyrid-2-yl |
| 1650. | 4-(p-Cl-phenoxy)-pyrid-2-yl |
| 1651. | 4-(o-Br-phenoxy)-pyrid-2-yl |
| 1652. | 4-(m-Br-phenoxy)-pyrid-2-yl |
| 1653. | 4-(p-Br-phenoxy)-pyrid-2-yl |
| 1654. | 4-(o-CH₃-phenoxy)-pyrid-2-yl |
| 1655. | 4-(m-CH₃-phenoxy)-pyrid-2-yl |
| 1656. | 4-(p-CH₃-phenoxy)-pyrid-2-yl |
| 1657. | 4-(o-CF₃-phenoxy)-pyrid-2-yl |
| 1658. | 4-(m-CF₃-phenoxy)-pyrid-2-yl |
| 1659. | 4-(p-CF₃-phenoxy)-pyrid-2-yl |
| 1660. | 4-(o-CF₃-phenoxy)-pyrid-2-yl |
| 1661. | 4-(m-CF₃-phenoxy)-pyrid-2-yl |
| 1662. | 4-(p-CF₃-phenoxy)-pyrid-2-yl |
| 1663. | 4-(o-OCH₃-phenoxy)-pyrid-2-yl |
| 1664. | 4-(m-OCH₃-phenoxy)-pyrid-2-yl |
| 1665. | 4-(p-OCH₃-phenoxy)-pyrid-2-yl |
| 1666. | 4-(o-OCF₃-phenoxy)-pyrid-2-yl |
| 1667. | 4-(m-OCF₃-phenoxy)-pyrid-2-yl |
| 1668. | 4-(p-OCF₃-phenoxy)-pyrid-2-yl |
| 1669. | 4-(o-COOCH₃-phenoxy)-pyrid-2-yl |
| 1670. | 4-(m-COOCH₃-phenoxy)-pyrid-2-yl |
| 1671. | 4-(p-COOCH₃-phenoxy)-pyrid-2-yl |
| 1672. | 4-[o-N(CH₃)₂-phenoxy]-pyrid-2-yl |
| 1673. | 4-[m-N(CH₃)₂-phenoxy]-pyrid-2-yl |
| 1674. | 4-[p-N(CH₃)₂-phenoxy]-pyrid-2-yl |
| 1675. | 4-(2,3-dicyanophenoxy)-pyrid-2-yl |
| 1676. | 4-(2,4-dicyanophenoxy)-pyrid-2-yl |
| 1677. | 4-(2,5-dicyanophenoxy)-pyrid-2-yl |
| 1678. | 4-(2,6-dicyanophenoxy)-pyrid-2-yl |
| 1679. | 4-(3,4-dicyanophenoxy)-pyrid-2-yl |
| 1680. | 4-(3,5-dicyanophenoxy)-pyrid-2-yl |
| 1681. | 4-(2,3-difluorophenoxy)-pyrid-2-yl |
| 1682. | 4-(2,4-difluorophenoxy)-pyrid-2-yl |
| 1683. | 4-(2,5-difluorophenoxy)-pyrid-2-yl |
| 1684. | 4-(2,6-difluorophenoxy)-pyrid-2-yl |
| 1685. | 4-(3,4-difluorophenoxy)-pyrid-2-yl |
| 1686. | 4-(3,5-difluorophenoxy)-pyrid-2-yl |
| 1687. | 4-(2,3-dichlorophenoxy)-pyrid-2-yl |
| 1688. | 4-(2,4-dichlorophenoxy)-pyrid-2-yl |
| 1689. | 4-(2,5-dichlorophenoxy)-pyrid-2-yl |
| 1690. | 4-(2,6-dichlorophenoxy)-pyrid-2-yl |
| 1691. | 4-(3,4-dichlorophenoxy)-pyrid-2-yl |
| 1692. | 4-(3,5-dichlorophenoxy)-pyrid-2-yl |
| 1693. | 4-(2,3-dibromophenoxy)-pyrid-2-yl |
| 1694. | 4-(2,4-dibromophenoxy)-pyrid-2-yl |
| 1695. | 4-(2,5-dibromophenoxy)-pyrid-2-yl |
| 1696. | 4-(2,6-dibromophenoxy)-pyrid-2-yl |
| 1697. | 4-(3,4-dibromophenoxy)-pyrid-2-yl |
| 1698. | 4-(3,5-dibromophenoxy)-pyrid-2-yl |
| 1699. | 4-(2,3-dimethylphenoxy)-pyrid-2-yl |
| 1700. | 4-(2,4-dimethylphenoxy)-pyrid-2-yl |
| 1701. | 4-(2,5-dimethylphenoxy)-pyrid-2-yl |
| 1702. | 4-(2,6-dimethylphenoxy)-pyrid-2-yl |
| 1703. | 4-(3,4-dimethylphenoxy)-pyrid-2-yl |
| 1704. | 4-(3,5-dimethylphenoxy)-pyrid-2-yl |
| 1705. | 4-[2,3-di(trifluoromethyl)phenoxy]-pyrid-2-yl |
| 1706. | 4-[2,4-di(trifluoromethyl)phenoxy]-pyrid-2-yl |
| 1707. | 4-[2,5-di(trifluoromethyl)phenoxy]-pyrid-2-yl |
| 1708. | 4-[2,6-di(trifluoromethyl)phenoxy]-pyrid-2-yl |
| 1709. | 4-[3,4-di(trifluoromethyl)phenoxy]-pyrid-2-yl |
| 1710. | 4-[3,5-di(trifluoromethyl)phenoxy]-pyrid-2-yl |
| 1711. | 4-(2,3-dimethoxyphenoxy)-pyrid-2-yl |
| 1712. | 4-(2,4-dimethoxyphenoxy)-pyrid-2-yl |
| 1713. | 4-(2,5-dimethoxyphenoxy)-pyrid-2-yl |
| 1714. | 4-(2,6-dimethoxyphenoxy)-pyrid-2-yl |
| 1715. | 4-(3,4-dimethoxyphenoxy)-pyrid-2-yl |
| 1716. | 4-(3,5-dimethoxyphenoxy)-pyrid-2-yl |
| 1717. | 6-(o-CN-phenyl)-pyrid-4-yl |
| 1718. | 6-(m-CN-phenyl)-pyrid-4-yl |
| 1719. | 6-(p-CN-phenyl)-pyrid-4-yl |
| 1720. | 6-(o-NO₂-phenyl)-pyrid-4-yl |
| 1721. | 6-(m-NO₂-phenyl)-pyrid-4-yl |
| 1722. | 6-(p-NO₂-phenyl)-pyrid-4-yl |
| 1723. | 6-(o-F-phenyl)-pyrid-4-yl |
| 1724. | 6-(m-F-phenyl)-pyrid-4-yl |

TABLE A-continued

| no. | R³-A- |
|---|---|
| 1725. | 6-(p-F-phenyl)-pyrid-4-yl |
| 1726. | 6-(o-Cl-phenyl)-pyrid-4-yl |
| 1727. | 6-(m-Cl-phenyl)-pyrid-4-yl |
| 1728. | 6-(p-Cl-phenyl)-pyrid-4-yl |
| 1729. | 6-(o-Br-phenyl)-pyrid-4-yl |
| 1730. | 6-(m-Br-phenyl)-pyrid-4-yl |
| 1731. | 6-(p-Br-phenyl)-pyrid-4-yl |
| 1732. | 6-(o-CH₃-phenyl)-pyrid-4-yl |
| 1733. | 6-(m-CH₃-phenyl)-pyrid-4-yl |
| 1734. | 6-(p-CH₃-phenyl)-pyrid-4-yl |
| 1735. | 6-(o-CF₃-phenyl)-pyrid-4-yl |
| 1736. | 6-(m-CF₃-phenyl)-pyrid-4-yl |
| 1737. | 6-(p-CF₃-phenyl)-pyrid-4-yl |
| 1738. | 6-(o-CF₃-phenyl)-pyrid-4-yl |
| 1739. | 6-(m-CF₃-phenyl)-pyrid-4-yl |
| 1740. | 6-(p-CF₃-phenyl)-pyrid-4-yl |
| 1741. | 6-(o-OCH₃-phenyl)-pyrid-4-yl |
| 1742. | 6-(m-OCH₃-phenyl)-pyrid-4-yl |
| 1743. | 6-(p-OCH₃-phenyl)-pyrid-4-yl |
| 1744. | 6-(o-OCF₃-phenyl)-pyrid-4-yl |
| 1745. | 6-(m-OCF₃-phenyl)-pyrid-4-yl |
| 1746. | 6-(p-OCF₃-phenyl)-pyrid-4-yl |
| 1747. | 6-(o-COOCH₃-phenyl)-pyrid-4-yl |
| 1748. | 6-(m-COOCH₃-phenyl)-pyrid-4-yl |
| 1749. | 6-(p-COOCH₃-phenyl)-pyrid-4-yl |
| 1750. | 6-[o-N(CH₃)₂-phenyl]-pyrid-4-yl |
| 1751. | 6-[m-N(CH₃)₂-pyrid-4-yl |
| 1752. | 6-[p-N(CH₃)₂-phenyl]-pyrid-4-yl |
| 1753. | 6-(2,3-dicyanophenyl)-pyrid-4-yl |
| 1754. | 6-(2,4-dicyanophenyl)-pyrid-4-yl |
| 1755. | 6-(2,5-dicyanophenyl)-pyrid-4-yl |
| 1756. | 6-(2,6-dicyanophenyl)-pyrid-4-yl |
| 1757. | 6-(3,4-dicyanophenyl)-pyrid-4-yl |
| 1758. | 6-(3,5-dicyanophenyl)-pyrid-4-yl |
| 1759. | 6-(2,3-difluorophenyl)-pyrid-4-yl |
| 1760. | 6-(2,4-difluorophenyl)-pyrid-4-yl |
| 1761. | 6-(2,5-difluorophenyl)-pyrid-4-yl |
| 1762. | 6-(2,6-difluorophenyl)-pyrid-4-yl |
| 1763. | 6-(3,4-difluorophenyl)-pyrid-4-yl |
| 1764. | 6-(3,5-difluorophenyl)-pyrid-4-yl |
| 1765. | 6-(2,3-dichlorophenyl)-pyrid-4-yl |
| 1766. | 6-(2,4-dichlorophenyl)-pyrid-4-yl |
| 1767. | 6-(2,5-dichlorophenyl)-pyrid-4-yl |
| 1768. | 6-(2,6-dichlorophenyl)-pyrid-4-yl |
| 1769. | 6-(3,4-dichlorophenyl)-pyrid-4-yl |
| 1770. | 6-(3,5-dichlorophenyl)-pyrid-4-yl |
| 1771. | 6-(2,3-dibromophenyl)-pyrid-4-yl |
| 1772. | 6-(2,4-dibromophenyl)-pyrid-4-yl |
| 1773. | 6-(2,5-dibromophenyl)-pyrid-4-yl |
| 1774. | 6-(2,6-dibromophenyl)-pyrid-4-yl |
| 1775. | 6-(3,4-dibromophenyl)-pyrid-4-yl |
| 1776. | 6-(3,5-dibromophenyl)-pyrid-4-yl |
| 1777. | 6-(2,3-dimethylphenyl)-pyrid-4-yl |
| 1778. | 6-(2,4-dimethylphenyl)-pyrid-4-yl |
| 1779. | 6-(2,5-dimethylphenyl)-pyrid-4-yl |
| 1780. | 6-(2,6-dimethylphenyl)-pyrid-4-yl |
| 1781. | 6-(3,4-dimethylphenyl)-pyrid-4-yl |
| 1782. | 6-(3,5-dimethylphenyl)-pyrid-4-yl |
| 1783. | 6-[2,3-di(trifluoromethyl)phenyl]-pyrid-4-yl |
| 1784. | 6-[2,4-di(trifluoromethyl)phenyl]-pyrid-4-yl |
| 1785. | 6-[2,5-di(trifluoromethyl)phenyl]-pyrid-4-yl |
| 1786. | 6-[2,6-di(trifluoromethyl)phenyl]-pyrid-4-yl |
| 1787. | 6-[3,4-di(trifluoromethyl)phenyl]-pyrid-4-yl |
| 1788. | 6-[3,5-di(trifluoromethyl)phenyl]-pyrid-4-yl |
| 1789. | 6-(2,3-dimethoxyphenyl)-pyrid-4-yl |
| 1790. | 6-(2,4-dimethoxyphenyl)-pyrid-4-yl |
| 1791. | 6-(2,5-dimethoxyphenyl)-pyrid-4-yl |
| 1792. | 6-(2,6-dimethoxyphenyl)-pyrid-4-yl |
| 1793. | 6-(3,4-dimethoxyphenyl)-pyrid-4-yl |
| 1794. | 6-(3,5-dimethoxyphenyl)-pyrid-4-yl |
| 1795. | 6-(o-CN-phenoxy)-pyrid-4-yl |
| 1796. | 6-(m-CN-phenoxy)-pyrid-4-yl |
| 1797. | 6-(p-CN-phenoxy)-pyrid-4-yl |
| 1798. | 6-(o-NO₂-phenoxy)-pyrid-4-yl |
| 1799. | 6-(m-NO₂-phenoxy)-pyrid-4-yl |
| 1800. | 6-(p-NO₂-phenoxy)-pyrid-4-yl |
| 1801. | 6-(o-F-phenoxy)-pyrid-4-yl |
| 1802. | 6-(m-F-phenoxy)-pyrid-4-yl |
| 1803. | 6-(p-F-phenoxy)-pyrid-4-yl |
| 1804. | 6-(o-Cl-phenoxy)-pyrid-4-yl |
| 1805. | 6-(m-Cl-phenoxy)-pyrid-4-yl |
| 1806. | 6-(p-Cl-phenoxy)-pyrid-4-yl |
| 1807. | 6-(o-Br-phenoxy)-pyrid-4-yl |
| 1808. | 6-(m-Br-phenoxy)-pyrid-4-yl |
| 1809. | 6-(p-Br-phenoxy)-pyrid-4-yl |
| 1810. | 6-(o-CH₃-phenoxy)-pyrid-4-yl |
| 1811. | 6-(m-CH₃-phenoxy)-pyrid-4-yl |
| 1812. | 6-(p-CH₃-phenoxy)-pyrid-4-yl |
| 1813. | 6-(o-CF₃-phenoxy)-pyrid-4-yl |
| 1814. | 6-(m-CF₃-phenoxy)-pyrid-4-yl |
| 1815. | 6-(p-CF₃-phenoxy)-pyrid-4-yl |
| 1816. | 6-(o-CF₃-phenoxy)-pyrid-4-yl |
| 1817. | 6-(m-CF₃-phenoxy)-pyrid-4-yl |
| 1818. | 6-(p-CF₃-phenoxy)-pyrid-4-yl |
| 1819. | 6-(o-OCH₃-phenoxy)-pyrid-4-yl |
| 1820. | 6-(m-OCH₃-phenoxy)-pyrid-4-yl |
| 1821. | 6-(p-OCH₃-phenoxy)-pyrid-4-yl |
| 1822. | 6-(o-OCF₃-phenoxy)-pyrid-4-yl |
| 1823. | 6-(m-OCF₃-phenoxy)-pyrid-4-yl |
| 1824. | 6-(p-OCF₃-phenoxy)-pyrid-4-yl |
| 1825. | 6-(o-COOCH₃-phenoxy)-pyrid-4-yl |
| 1826. | 6-(m-COOCH₃-phenoxy)-pyrid-4-yl |
| 1827. | 6-(p-COOCH₃-phenoxy)-pyrid-4-yl |
| 1828. | 6-[o-N(CH₃)₂-phenoxy]-pyrid-4-yl |
| 1829. | 6-[m-N(CH₃)₂-phenoxy]-pyrid-4-yl |
| 1830. | 6-[p-N(CH₃)₂-phenoxy]-pyrid-4-yl |
| 1831. | 6-(2,3-dicyanophenoxy)-pyrid-4-yl |
| 1832. | 6-(2,4-dicyanophenoxy)-pyrid-4-yl |
| 1833. | 6-(2,5-dicyanophenoxy)-pyrid-4-yl |
| 1834. | 6-(2,6-dicyanophenoxy)-pyrid-4-yl |
| 1835. | 6-(3,4-dicyanophenoxy)-pyrid-4-yl |
| 1836. | 6-(3,5-dicyanophenoxy)-pyrid-4-yl |
| 1837. | 6-(2,3-difluorophenoxy)-pyrid-4-yl |
| 1838. | 6-(2,4-difluorophenoxy)-pyrid-4-yl |
| 1839. | 6-(2,5-difluorophenoxy)-pyrid-4-yl |
| 1840. | 6-(2,6-difluorophenoxy)-pyrid-4-yl |
| 1841. | 6-(3,4-difluorophenoxy)-pyrid-4-yl |
| 1842. | 6-(3,5-difluorophenoxy)-pyrid-4-yl |
| 1843. | 6-(2,3-dichlorophenoxy)-pyrid-4-yl |
| 1844. | 6-(2,4-dichlorophenoxy)-pyrid-4-yl |
| 1845. | 6-(2,5-dichlorophenoxy)-pyrid-4-yl |
| 1846. | 6-(2,6-dichlorophenoxy)-pyrid-4-yl |
| 1847. | 6-(3,4-dichlorophenoxy)-pyrid-4-yl |
| 1848. | 6-(3,5-dichlorophenoxy)-pyrid-4-yl |
| 1849. | 6-(2,3-dibromophenoxy)-pyrid-4-yl |
| 1850. | 6-(2,4-dibromophenoxy)-pyrid-4-yl |

TABLE A-continued

| no. | R³-A- |
|---|---|
| 1851. | 6-(2,5-dibromophenoxy)-pyrid-4-yl |
| 1852. | 6-(2,6-dibromophenoxy)-pyrid-4-yl |
| 1853. | 6-(3,4-dibromophenoxy)-pyrid-4-yl |
| 1854. | 6-(3,5-dibromophenoxy)-pyrid-4-yl |
| 1855. | 6-(2,3-dimethylphenoxy)-pyrid-4-yl |
| 1856. | 6-(2,4-dimethylphenoxy)-pyrid-4-yl |
| 1857. | 6-(2,5-dimethylphenoxy)-pyrid-4-yl |
| 1858. | 6-(2,6-dimethylphenoxy)-pyrid-4-yl |
| 1859. | 6-(3,4-dimethylphenoxy)-pyrid-4-yl |
| 1860. | 6-(3,5-dimethylphenoxy)-pyrid-4-yl |
| 1861. | 6-[2,3-di(trifluoromethyl)phenoxy]-pyrid-4-yl |
| 1862. | 6-[2,4-di(trifluoromethyl)phenoxy]-pyrid-4-yl |
| 1863. | 6-[2,5-di(trifluoromethyl)phenoxy]-pyrid-4-yl |
| 1864. | 6-[2,6-di(trifluoromethyl)phenoxy]-pyrid-4-yl |
| 1865. | 6-[3,4-di(trifluoromethyl)phenoxy]-pyrid-4-yl |
| 1866. | 6-[3,5-di(trifluoromethyl)phenoxy]-pyrid-4-yl |
| 1867. | 6-(2,3-dimethoxyphenoxy)-pyrid-4-yl |
| 1868. | 6-(2,4-dimethoxyphenoxy)-pyrid-4-yl |
| 1869. | 6-(2,5-dimethoxyphenoxy)-pyrid-4-yl |
| 1870. | 6-(2,6-dimethoxyphenoxy)-pyrid-4-yl |
| 1871. | 6-(3,4-dimethoxyphenoxy)-pyrid-4-yl |
| 1872. | 6-(3,5-dimethoxyphenoxy)-pyrid-4-yl |
| 1873. | 6-(o-CN-phenyl)-pyridazine-3-yl |
| 1874. | 6-(m-CN-phenyl)-pyridazine-3-yl |
| 1875. | 6-(p-CN-phenyl)-pyridazine-3-yl |
| 1876. | 6-(o-NO₂-phenyl)-pyridazine-3-yl |
| 1877. | 6-(m-NO₂-phenyl)-pyridazine-3-yl |
| 1878. | 6-(p-NO₂-phenyl)-pyridazine-3-yl |
| 1879. | 6-(o-F-phenyl)-pyridazine-3-yl |
| 1880. | 6-(m-F-phenyl)-pyridazine-3-yl |
| 1881. | 6-(p-F-phenyl)-pyridazine-3-yl |
| 1882. | 6-(o-Cl-phenyl)-pyridazine-3-yl |
| 1883. | 6-(m-Cl-phenyl)-pyridazine-3-yl |
| 1884. | 6-(p-Cl-phenyl)-pyridazine-3-yl |
| 1885. | 6-(o-Br-phenyl)-pyridazine-3-yl |
| 1886. | 6-(m-Br-phenyl)-pyridazine-3-yl |
| 1887. | 6-(p-Br-phenyl)-pyridazine-3-yl |
| 1888. | 6-(o-CH₃-phenyl)-pyridazine-3-yl |
| 1889. | 6-(m-CH₃-phenyl)-pyridazine-3-yl |
| 1890. | 6-(p-CH₃-phenyl)-pyridazine-3-yl |
| 1891. | 6-(o-CF₃-phenyl)-pyridazine-3-yl |
| 1892. | 6-(m-CF₃-phenyl)-pyridazine-3-yl |
| 1893. | 6-(p-CF₃-phenyl)-pyridazine-3-yl |
| 1894. | 6-(o-CF₃-phenyl)-pyridazine-3-yl |
| 1895. | 6-(m-CF₃-phenyl)-pyridazine-3-yl |
| 1896. | 6-(p-CF₃-phenyl)-pyridazine-3-yl |
| 1897. | 6-(o-OCH₃-phenyl)-pyridazine-3-yl |
| 1898. | 6-(m-OCH₃-phenyl)-pyridazine-3-yl |
| 1899. | 6-(p-OCH₃-phenyl)-pyridazine-3-yl |
| 1900. | 6-(o-OCF₃-phenyl)-pyridazine-3-yl |
| 1901. | 6-(m-OCF₃-phenyl)-pyridazine-3-yl |
| 1902. | 6-(p-OCF₃-phenyl)-pyridazine-3-yl |
| 1903. | 6-(o-COOCH₃-phenyl)-pyridazine-3-yl |
| 1904. | 6-(m-COOCH₃-phenyl)-pyridazine-3-yl |
| 1905. | 6-(p-COOCH₃-phenyl)-pyridazine-3-yl |
| 1906. | 6-[o-N(CH₃)₂-phenyl]-pyridazine-3-yl |
| 1907. | 6-[m-N(CH₃)₂-phenyl]-pyridazine-3-yl |
| 1908. | 6-[p-N(CH₃)₂-phenyl]-pyridazine-3-yl |
| 1909. | 6-(2,3-dicyanophenyl)-pyridazine-3-yl |
| 1910. | 6-(2,4-dicyanophenyl)-pyridazine-3-yl |
| 1911. | 6-(2,5-dicyanophenyl)-pyridazine-3-yl |
| 1912. | 6-(2,6-dicyanophenyl)-pyridazine-3-yl |
| 1913. | 6-(3,4-dicyanophenyl)-pyridazine-3-yl |
| 1914. | 6-(3,5-dicyanophenyl)-pyridazine-3-yl |
| 1915. | 6-(2,3-difluorophenyl)-pyridazine-3-yl |
| 1916. | 6-(2,4-difluorophenyl)-pyridazine-3-yl |
| 1917. | 6-(2,5-difluorophenyl)-pyridazine-3-yl |
| 1918. | 6-(2,6-difluorophenyl)-pyridazine-3-yl |
| 1919. | 6-(3,4-difluorophenyl)-pyridazine-3-yl |
| 1920. | 6-(3,5-difluorophenyl)-pyridazine-3-yl |
| 1921. | 6-(2,3-dichlorophenyl)-pyridazine-3-yl |
| 1922. | 6-(2,4-dichlorophenyl)-pyridazine-3-yl |
| 1923. | 6-(2,5-dichlorophenyl)-pyridazine-3-yl |
| 1924. | 6-(2,6-dichlorophenyl)-pyridazine-3-yl |
| 1925. | 6-(3,4-dichlorophenyl)-pyridazine-3-yl |
| 1926. | 6-(3,5-dichlorophenyl)-pyridazine-3-yl |
| 1927. | 6-(2,3-dibromophenyl)-pyridazine-3-yl |
| 1928. | 6-(2,4-dibromophenyl)-pyridazine-3-yl |
| 1929. | 6-(2,5-dibromophenyl)-pyridazine-3-yl |
| 1930. | 6-(2,6-dibromophenyl)-pyridazine-3-yl |
| 1931. | 6-(3,4-dibromophenyl)-pyridazine-3-yl |
| 1932. | 6-(3,5-dibromophenyl)-pyridazine-3-yl |
| 1933. | 6-(2,3-dimethylphenyl)-pyridazine-3-yl |
| 1934. | 6-(2,4-dimethylphenyl)-pyridazine-3-yl |
| 1935. | 6-(2,5-dimethylphenyl)-pyridazine-3-yl |
| 1936. | 6-(2,6-dimethylphenyl)-pyridazine-3-yl |
| 1937. | 6-(3,4-dimethylphenyl)-pyridazine-3-yl |
| 1938. | 6-(3,5-dimethylphenyl)-pyridazine-3-yl |
| 1939. | 6-[2,3-di(trifluoromethyl)phenyl]-pyridazine-3-yl |
| 1940. | 6-[2,4-di(trifluoromethyl)phenyl]-pyridazine-3-yl |

TABLE A-continued

| no. | R³-A- |
|---|---|
| 1941. | 6-[2,5-di(trifluoromethyl)phenyl]-pyridazine-3-yl |
| 1942. | 6-[2,6-di(trifluoromethyl)phenyl]-pyridazine-3-yl |
| 1943. | 6-[3,4-di(trifluoromethyl)phenyl]-pyridazine-3-yl |
| 1944. | 6-[3,5-di(trifluoromethyl)phenyl]-pyridazine-3-yl |
| 1945. | 6-(2,3-dimethoxyphenyl)-pyridazine-3-yl |
| 1946. | 6-(2,4-dimethoxyphenyl)-pyridazine-3-yl |
| 1947. | 6-(2,5-dimethoxyphenyl)-pyridazine-3-yl |
| 1948. | 6-(2,6-dimethoxyphenyl)-pyridazine-3-yl |
| 1949. | 6-(3,4-dimethoxyphenyl)-pyridazine-3-yl |
| 1950. | 6-(3,5-dimethoxyphenyl)-pyridazine-3-yl |
| 1951. | 6-(o-CN-phenoxy)-pyridazine-3-yl |
| 1952. | 6-(m-CN-phenoxy)-pyridazine-3-yl |
| 1953. | 6-(p-CN-phenoxy)-pyridazine-3-yl |
| 1954. | 6-(o-NO$_2$-phenoxy)-pyridazine-3-yl |
| 1955. | 6-(m-NO$_2$-phenoxy)-pyridazine-3-yl |
| 1956. | 6-(p-NO$_2$-phenoxy)-pyridazine-3-yl |
| 1957. | 6-(o-F-phenoxy)-pyridazine-3-yl |
| 1958. | 6-(m-F-phenoxy)-pyridazine-3-yl |
| 1959. | 6-(p-F-phenoxy)-pyridazine-3-yl |
| 1960. | 6-(o-Cl-phenoxy)-pyridazine-3-yl |
| 1961. | 6-(m-Cl-phenoxy)-pyridazine-3-yl |
| 1962. | 6-(p-Cl-phenoxy)-pyridazine-3-yl |
| 1963. | 6-(o-Br-phenoxy)-pyridazine-3-yl |
| 1964. | 6-(m-Br-phenoxy)-pyridazine-3-yl |
| 1965. | 6-(p-Br-phenoxy)-pyridazine-3-yl |
| 1966. | 6-(o-CH$_3$-phenoxy)-pyridazine-3-yl |
| 1967. | 6-(m-CH$_3$-phenoxy)-pyridazine-3-yl |
| 1968. | 6-(p-CH$_3$-phenoxy)-pyridazine-3-yl |
| 1969. | 6-(o-CF$_3$-phenoxy)-pyridazine-3-yl |
| 1970. | 6-(m-CF$_3$-phenoxy)-pyridazine-3-yl |
| 1971. | 6-(p-CF$_3$-phenoxy)-pyridazine-3-yl |
| 1972. | 6-(o-CF$_3$-phenoxy)-pyridazine-3-yl |
| 1973. | 6-(m-CF$_3$-phenoxy)-pyridazine-3-yl |
| 1974. | 6-(p-CF$_3$-phenoxy)-pyridazine-3-yl |
| 1975. | 6-(o-OCH$_3$-phenoxy)-pyridazine-3-yl |
| 1976. | 6-(m-OCH$_3$-phenoxy)-pyridazine-3-yl |
| 1977. | 6-(p-OCH$_3$-phenoxy)-pyridazine-3-yl |
| 1978. | 6-(o-OCF$_3$-phenoxy)-pyridazine-3-yl |
| 1979. | 6-(m-OCF$_3$-phenoxy)-pyridazine-3-yl |
| 1980. | 6-(p-OCF$_3$-phenoxy)-pyridazine-3-yl |
| 1981. | 6-(o-COOCH$_3$-phenoxy)-pyridazine-3-yl |
| 1982. | 6-(m-COOCH$_3$-phenoxy)-pyridazine-3-yl |
| 1983. | 6-(p-COOCH$_3$-phenoxy)-pyridazine-3-yl |
| 1984. | 6-[o-N(CH$_3$)$_2$-phenoxy]-pyridazine-3-yl |
| 1985. | 6-[m-N(CH$_3$)$_2$-phenoxy]-pyridazine-3-yl |
| 1986. | 6-[p-N(CH$_3$)$_2$-phenoxy]-pyridazine-3-yl |
| 1987. | 6-(2,3-dicyanophenoxy)-pyridazine-3-yl |
| 1988. | 6-(2,4-dicyanophenoxy)-pyridazine-3-yl |
| 1989. | 6-(2,5-dicyanophenoxy)-pyridazine-3-yl |
| 1990. | 6-(2,6-dicyanophenoxy)-pyridazine-3-yl |
| 1991. | 6-(3,4-dicyanophenoxy)-pyridazine-3-yl |
| 1992. | 6-(3,5-dicyanophenoxy)-pyridazine-3-yl |
| 1993. | 6-(2,3-difluorophenoxy)-pyridazine-3-yl |
| 1994. | 6-(2,4-difluorophenoxy)-pyridazine-3-yl |
| 1995. | 6-(2,5-difluorophenoxy)-pyridazine-3-yl |
| 1996. | 6-(2,6-difluorophenoxy)-pyridazine-3-yl |
| 1997. | 6-(3,4-difluorophenoxy)-pyridazine-3-yl |
| 1998. | 6-(3,5-difluorophenoxy)-pyridazine-3-yl |
| 1999. | 6-(2,3-dichlorophenoxy)-pyridazine-3-yl |
| 2000. | 6-(2,4-dichlorophenoxy)-pyridazine-3-yl |
| 2001. | 6-(2,5-dichlorophenoxy)-pyridazine-3-yl |
| 2002. | 6-(2,6-dichlorophenoxy)-pyridazine-3-yl |
| 2003. | 6-(3,4-dichlorophenoxy)-pyridazine-3-yl |
| 2004. | 6-(3,5-dichlorophenoxy)-pyridazine-3-yl |
| 2005. | 6-(2,3-dibromophenoxy)-pyridazine-3-yl |
| 2006. | 6-(2,4-dibromophenoxy)-pyridazine-3-yl |
| 2007. | 6-(2,5-dibromophenoxy)-pyridazine-3-yl |
| 2008. | 6-(2,6-dibromophenoxy)-pyridazine-3-yl |
| 2009. | 6-(3,4-dibromophenoxy)-pyridazine-3-yl |
| 2010. | 6-(3,5-dibromophenoxy)-pyridazine-3-yl |
| 2011. | 6-(2,3-dimethylphenoxy)-pyridazine-3-yl |
| 2012. | 6-(2,4-dimethylphenoxy)-pyridazine-3-yl |
| 2013. | 6-(2,5-dimethylphenoxy)-pyridazine-3-yl |
| 2014. | 6-(2,6-dimethylphenoxy)-pyridazine-3-yl |
| 2015. | 6-(3,4-dimethylphenoxy)-pyridazine-3-yl |
| 2016. | 6-(3,5-dimethylphenoxy)-pyridazine-3-yl |
| 2017. | 6-[2,3-di(trifluoromethyl)phenoxy]-pyridazine-3-yl |
| 2018. | 6-[2,4-di(trifluoromethyl)phenoxy]-pyridazine-3-yl |
| 2019. | 6-[2,5-di(trifluoromethyl)phenoxy]-pyridazine-3-yl |
| 2020. | 6-[2,6-di(trifluoromethyl)phenoxy]-pyridazine-3-yl |
| 2021. | 6-[3,4-di(trifluoromethyl)phenoxy]-pyridazine-3-yl |
| 2022. | 6-[3,5-di(trifluoromethyl)phenoxy]-pyridazine-3-yl |
| 2023. | 6-(2,3-dimethoxyphenoxy)-pyridazine-3-yl |

TABLE A-continued

| no. | R³-A- |
|---|---|
| 2024. | 6-(2,4-dimethoxyphenoxy)-pyridazine-3-yl |
| 2025. | 6-(2,5-dimethoxyphenoxy)-pyridazine-3-yl |
| 2026. | 6-(2,6-dimethoxyphenoxy)-pyridazine-3-yl |
| 2027. | 6-(3,4-dimethoxyphenoxy)-pyridazine-3-yl |
| 2028. | 6-(3,5-dimethoxyphenoxy)-pyridazine-3-yl |
| 2029. | 4-(o-CN-phenyl)-oxazol-2-yl |
| 2030. | 4-(m-CN-phenyl)-oxazol-2-yl |
| 2031. | 4-(p-CN-phenyl)-oxazol-2-yl |
| 2032. | 4-(o-NO₂-phenyl)-oxazol-2-yl |
| 2033. | 4-(m-NO₂-phenyl)-oxazol-2-yl |
| 2034. | 4-(p-NO₂-phenyl)-oxazol-2-yl |
| 2035. | 4-(o-F-phenyl)-oxazol-2-yl |
| 2036. | 4-(m-F-phenyl)-oxazol-2-yl |
| 2037. | 4-(p-F-phenyl)-oxazol-2-yl |
| 2038. | 4-(o-Cl-phenyl)-oxazol-2-yl |
| 2039. | 4-(m-Cl-phenyl)-oxazol-2-yl |
| 2040. | 4-(p-Cl-phenyl)-oxazol-2-yl |
| 2041. | 4-(o-Br-phenyl)-oxazol-2-yl |
| 2042. | 4-(m-Br-phenyl)-oxazol-2-yl |
| 2043. | 4-(p-Br-phenyl)-oxazol-2-yl |
| 2044. | 4-(o-CH₃-phenyl)-oxazol-2-yl |
| 2045. | 4-(m-CH₃-phenyl)-oxazol-2-yl |
| 2046. | 4-(p-CH₃-phenyl)-oxazol-2-yl |
| 2047. | 4-(o-CF₃-phenyl)-oxazol-2-yl |
| 2048. | 4-(m-CF₃-phenyl)-oxazol-2-yl |
| 2049. | 4-(p-CF₃-phenyl)-oxazol-2-yl |
| 2050. | 4-(o-CF₃-phenyl)-oxazol-2-yl |
| 2051. | 4-(m-CF₃-phenyl)-oxazol-2-yl |
| 2052. | 4-(p-CF₃-phenyl)-oxazol-2-yl |
| 2053. | 4-(o-OCH₃-phenyl)-oxazol-2-yl |
| 2054. | 4-(m-OCH₃-phenyl)-oxazol-2-yl |
| 2055. | 4-(p-OCH₃-phenyl)-oxazol-2-yl |
| 2056. | 4-(o-OCF₃-phenyl)-oxazol-2-yl |
| 2057. | 4-(m-OCF₃-phenyl)-oxazol-2-yl |
| 2058. | 4-(p-OCF₃-phenyl)-oxazol-2-yl |
| 2059. | 4-(o-COOCH₃-phenyl)-oxazol-2-yl |
| 2060. | 4-(m-COOCH₃-phenyl)-oxazol-2-yl |
| 2061. | 4-(p-COOCH₃-phenyl)-oxazol-2-yl |
| 2062. | 4-[o-N(CH₃)₂-phenyl]-oxazol-2-yl |
| 2063. | 4-[m-N(CH₃)₂-phenyl]-oxazol-2-yl |
| 2064. | 4-[p-N(CH₃)₂-phenyl]-oxazol-2-yl |
| 2065. | 4-(2,3-dicyanophenyl)-oxazol-2-yl |
| 2066. | 4-(2,4-dicyanophenyl)-oxazol-2-yl |
| 2067. | 4-(2,5-dicyanophenyl)-oxazol-2-yl |
| 2068. | 4-(2,6-dicyanophenyl)-oxazol-2-yl |
| 2069. | 4-(3,4-dicyanophenyl)-oxazol-2-yl |
| 2070. | 4-(3,5-dicyanophenyl)-oxazol-2-yl |
| 2071. | 4-(2,3-difluorophenyl)-oxazol-2-yl |
| 2072. | 4-(2,4-difluorophenyl)-oxazol-2-yl |
| 2073. | 4-(2,5-difluorophenyl)-oxazol-2-yl |
| 2074. | 4-(2,6-difluorophenyl)-oxazol-2-yl |
| 2075. | 4-(3,4-difluorophenyl)-oxazol-2-yl |
| 2076. | 4-(3,5-difluorophenyl)-oxazol-2-yl |
| 2077. | 4-(2,3-dichlorophenyl)-oxazol-2-yl |
| 2078. | 4-(2,4-dichlorophenyl)-oxazol-2-yl |
| 2079. | 4-(2,5-dichlorophenyl)-oxazol-2-yl |
| 2080. | 4-(2,6-dichlorophenyl)-oxazol-2-yl |
| 2081. | 4-(3,4-dichlorophenyl)-oxazol-2-yl |
| 2082. | 4-(3,5-dichlorophenyl)-oxazol-2-yl |
| 2083. | 4-(2,3-dibromophenyl)-oxazol-2-yl |
| 2084. | 4-(2,4-dibromophenyl)-oxazol-2-yl |
| 2085. | 4-(2,5-dibromophenyl)-oxazol-2-yl |
| 2086. | 4-(2,6-dibromophenyl)-oxazol-2-yl |
| 2087. | 4-(3,4-dibromophenyl)-oxazol-2-yl |
| 2088. | 4-(3,5-dibromophenyl)-oxazol-2-yl |
| 2089. | 4-(2,3-dimethylphenyl)-oxazol-2-yl |
| 2090. | 4-(2,4-dimethylphenyl)-oxazol-2-yl |
| 2091. | 4-(2,5-dimethylphenyl)-oxazol-2-yl |
| 2092. | 4-(2,6-dimethylphenyl)-oxazol-2-yl |
| 2093. | 4-(3,4-dimethylphenyl)-oxazol-2-yl |
| 2094. | 4-(3,5-dimethylphenyl)-oxazol-2-yl |
| 2095. | 4-[2,3-di(trifluoromethyl)phenyl]-oxazol-2-yl |
| 2096. | 4-[2,4-di(trifluoromethyl)phenyl]-oxazol-2-yl |
| 2097. | 4-[2,5-di(trifluoromethyl)phenyl]-oxazol-2-yl |
| 2098. | 4-[2,6-di(trifluoromethyl)phenyl]-oxazol-2-yl |
| 2099. | 4-[3,4-di(trifluoromethyl)phenyl]-oxazol-2-yl |
| 2100. | 4-[3,5-di(trifluoromethyl)phenyl]-oxazol-2-yl |
| 2101. | 4-(2,3-dimethoxyphenyl)-oxazol-2-yl |
| 2102. | 4-(2,4-dimethoxyphenyl)-oxazol-2-yl |
| 2103. | 4-(2,5-dimethoxyphenyl)-oxazol-2-yl |
| 2104. | 4-(2,6-dimethoxyphenyl)-oxazol-2-yl |
| 2105. | 4-(3,4-dimethoxyphenyl)-oxazol-2-yl |
| 2106. | 4-(3,5-dimethoxyphenyl)-oxazol-2-yl |
| 2107. | 4-(o-CN-phenoxy)-oxazol-2-yl |
| 2108. | 4-(m-CN-phenoxy)-oxazol-2-yl |
| 2109. | 4-(p-CN-phenoxy)-oxazol-2-yl |
| 2110. | 4-(o-NO₂-phenoxy)-oxazol-2-yl |
| 2111. | 4-(m-NO₂-phenoxy)-oxazol-2-yl |
| 2112. | 4-(p-NO₂-phenoxy)-oxazol-2-yl |
| 2113. | 4-(o-F-phenoxy)-oxazol-2-yl |
| 2114. | 4-(m-F-phenoxy)-oxazol-2-yl |
| 2115. | 4-(p-F-phenoxy)-oxazol-2-yl |
| 2116. | 4-(o-Cl-phenoxy)-oxazol-2-yl |
| 2117. | 4-(m-Cl-phenoxy)-oxazol-2-yl |
| 2118. | 4-(p-Cl-phenoxy)-oxazol-2-yl |
| 2119. | 4-(o-Br-phenoxy)-oxazol-2-yl |
| 2120. | 4-(m-Br-phenoxy)-oxazol-2-yl |
| 2121. | 4-(p-Br-phenoxy)-oxazol-2-yl |
| 2122. | 4-(o-CH₃-phenoxy)-oxazol-2-yl |
| 2123. | 4-(m-CH₃-phenoxy)-oxazol-2-yl |
| 2124. | 4-(p-CH₃-phenoxy)-oxazol-2-yl |
| 2125. | 4-(o-CF₃-phenoxy)-oxazol-2-yl |
| 2126. | 4-(m-CF₃-phenoxy)-oxazol-2-yl |
| 2127. | 4-(p-CF₃-phenoxy)-oxazol-2-yl |
| 2128. | 4-(o-CF₃-phenoxy)-oxazol-2-yl |
| 2129. | 4-(m-CF₃-phenoxy)-oxazol-2-yl |
| 2130. | 4-(p-CF₃-phenoxy)-oxazol-2-yl |
| 2131. | 4-(o-OCH₃-phenoxy)-oxazol-2-yl |
| 2132. | 4-(m-OCH₃-phenoxy)-oxazol-2-yl |
| 2133. | 4-(p-OCH₃-phenoxy)-oxazol-2-yl |
| 2134. | 4-(o-OCF₃-phenoxy)-oxazol-2-yl |
| 2135. | 4-(m-OCF₃-phenoxy)-oxazol-2-yl |
| 2136. | 4-(p-OCF₃-phenoxy)-oxazol-2-yl |
| 2137. | 4-(o-COOCH₃-phenoxy)-oxazol-2-yl |
| 2138. | 4-(m-COOCH₃-phenoxy)-oxazol-2-yl |
| 2139. | 4-(p-COOCH₃-phenoxy)-oxazol-2-yl |
| 2140. | 4-[o-N(CH₃)₂-phenoxy]-oxazol-2-yl |
| 2141. | 4-[m-N(CH₃)₂-phenoxy]-oxazol-2-yl |

TABLE A-continued

| no. | R³-A- |
|---|---|
| 2142. | 4-[p-N(CH₃)₂-phenoxy]-oxazol-2-yl |
| 2143. | 4-(2,3-dicyanophenoxy)-oxazol-2-yl |
| 2144. | 4-(2,4-dicyanophenoxy)-oxazol-2-yl |
| 2145. | 4-(2,5-dicyanophenoxy)-oxazol-2-yl |
| 2146. | 4-(2,6-dicyanophenoxy)-oxazol-2-yl |
| 2147. | 4-(3,4-dicyanophenoxy)-oxazol-2-yl |
| 2148. | 4-(3,5-dicyanophenoxy)-oxazol-2-yl |
| 2149. | 4-(2,3-difluorophenoxy)-oxazol-2-yl |
| 2150. | 4-(2,4-difluorophenoxy)-oxazol-2-yl |
| 2151. | 4-(2,5-difluorophenoxy)-oxazol-2-yl |
| 2152. | 4-(2,6-difluorophenoxy)-oxazol-2-yl |
| 2153. | 4-(3,4-difluorophenoxy)-oxazol-2-yl |
| 2154. | 4-(3,5-difluorophenoxy)-oxazol-2-yl |
| 2155. | 4-(2,3-dichlorophenoxy)-oxazol-2-yl |
| 2156. | 4-(2,4-dichlorophenoxy)-oxazol-2-yl |
| 2157. | 4-(2,5-dichlorophenoxy)-oxazol-2-yl |
| 2158. | 4-(2,6-dichlorophenoxy)-oxazol-2-yl |
| 2159. | 4-(3,4-dichlorophenoxy)-oxazol-2-yl |
| 2160. | 4-(3,5-dichlorophenoxy)-oxazol-2-yl |
| 2161. | 4-(2,3-dibromophenoxy)-oxazol-2-yl |
| 2162. | 4-(2,4-dibromophenoxy)-oxazol-2-yl |
| 2163. | 4-(2,5-dibromophenoxy)-oxazol-2-yl |
| 2164. | 4-(2,6-dibromophenoxy)-oxazol-2-yl |
| 2165. | 4-(3,4-dibromophenoxy)-oxazol-2-yl |
| 2166. | 4-(3,5-dibromophenoxy)-oxazol-2-yl |
| 2167. | 4-(2,3-dimethylphenoxy)-oxazol-2-yl |
| 2168. | 4-(2,4-dimethylphenoxy)-oxazol-2-yl |
| 2169. | 4-(2,5-dimethylphenoxy)-oxazol-2-yl |
| 2170. | 4-(2,6-dimethylphenoxy)-oxazol-2-yl |
| 2171. | 4-(3,4-dimethylphenoxy)-oxazol-2-yl |
| 2172. | 4-(3,5-dimethylphenoxy)-oxazol-2-yl |
| 2173. | 4-[2,3-di(trifluoromethyl)phenoxy]-oxazol-2-yl |
| 2174. | 4-[2,4-di(trifluoromethyl)phenoxy]-oxazol-2-yl |
| 2175. | 4-[2,5-di(trifluoromethyl)phenoxy]-oxazol-2-yl |
| 2176. | 4-[2,6-di(trifluoromethyl)phenoxy]-oxazol-2-yl |
| 2177. | 4-[3,4-di(trifluoromethyl)phenoxy]-oxazol-2-yl |
| 2178. | 4-[3,5-di(trifluoromethyl)phenoxy]-oxazol-2-yl |
| 2179. | 4-(2,3-dimethoxyphenoxy)-oxazol-2-yl |
| 2180. | 4-(2,4-dimethoxyphenoxy)-oxazol-2-yl |
| 2181. | 4-(2,5-dimethoxyphenoxy)-oxazol-2-yl |
| 2182. | 4-(2,6-dimethoxyphenoxy)-oxazol-2-yl |
| 2183. | 4-(3,4-dimethoxyphenoxy)-oxazol-2-yl |
| 2184. | 4-(3,5-dimethoxyphenoxy)-oxazol-2-yl |
| 2185. | 4-(o-CN-phenyl)-thiazol-2-yl |
| 2186. | 4-(m-CN-phenyl)-thiazol-2-yl |
| 2187. | 4-(p-CN-phenyl)-thiazol-2-yl |
| 2188. | 4-(o-NO₂-phenyl)-thiazol-2-yl |
| 2189. | 4-(m-NO₂-phenyl)-thiazol-2-yl |
| 2190. | 4-(p-NO₂-phenyl)-thiazol-2-yl |
| 2191. | 4-(o-F-phenyl)-thiazol-2-yl |
| 2192. | 4-(m-F-phenyl)-thiazol-2-yl |
| 2193. | 4-(p-F-phenyl)-thiazol-2-yl |
| 2194. | 4-(o-Cl-phenyl)-thiazol-2-yl |
| 2195. | 4-(m-Cl-phenyl)-thiazol-2-yl |
| 2196. | 4-(p-Cl-phenyl)-thiazol-2-yl |
| 2197. | 4-(o-Br-phenyl)-thiazol-2-yl |
| 2198. | 4-(m-Br-phenyl)-thiazol-2-yl |
| 2199. | 4-(p-Br-phenyl)-thiazol-2-yl |
| 2200. | 4-(o-CH₃-phenyl)-thiazol-2-yl |
| 2201. | 4-(m-CH₃-phenyl)-thiazol-2-yl |
| 2202. | 4-(p-CH₃-phenyl)-thiazol-2-yl |
| 2203. | 4-(o-CF₃-phenyl)-thiazol-2-yl |
| 2204. | 4-(m-CF₃-phenyl)-thiazol-2-yl |
| 2205. | 4-(p-CF₃-phenyl)-thiazol-2-yl |
| 2206. | 4-(o-CF₃-phenyl)-thiazol-2-yl |
| 2207. | 4-(m-CF₃-phenyl)-thiazol-2-yl |
| 2208. | 4-(p-CF₃-phenyl)-thiazol-2-yl |
| 2209. | 4-(o-OCH₃-phenyl)-thiazol-2-yl |
| 2210. | 4-(m-OCH₃-phenyl)-thiazol-2-yl |
| 2211. | 4-(p-OCH₃-phenyl)-thiazol-2-yl |
| 2212. | 4-(o-OCF₃-phenyl)-thiazol-2-yl |
| 2213. | 4-(m-OCF₃-phenyl)-thiazol-2-yl |
| 2214. | 4-(p-OCF₃-phenyl)-thiazol-2-yl |
| 2215. | 4-(o-COOCH₃-phenyl)-thiazol-2-yl |
| 2216. | 4-(m-COOCH₃-phenyl)-thiazol-2-yl |
| 2217. | 4-(p-COOCH₃-phenyl)-thiazol-2-yl |
| 2218. | 4-[o-N(CH₃)₂-phenyl]-thiazol-2-yl |
| 2219. | 4-[m-N(CH₃)₂-phenyl]-thiazol-2-yl |
| 2220. | 4-[p-N(CH₃)₂-phenyl]-thiazol-2-yl |
| 2221. | 4-(2,3-dicyanophenyl)-thiazol-2-yl |
| 2222. | 4-(2,4-dicyanophenyl)-thiazol-2-yl |
| 2223. | 4-(2,5-dicyanophenyl)-thiazol-2-yl |
| 2224. | 4-(2,6-dicyanophenyl)-thiazol-2-yl |
| 2225. | 4-(3,4-dicyanophenyl)-thiazol-2-yl |
| 2226. | 4-(3,5-dicyanophenyl)-thiazol-2-yl |
| 2227. | 4-(2,3-difluorophenyl)-thiazol-2-yl |
| 2228. | 4-(2,4-difluorophenyl)-thiazol-2-yl |
| 2229. | 4-(2,5-difluorophenyl)-thiazol-2-yl |
| 2230. | 4-(2,6-difluorophenyl)-thiazol-2-yl |
| 2231. | 4-(3,4-difluorophenyl)-thiazol-2-yl |
| 2232. | 4-(3,5-difluorophenyl)-thiazol-2-yl |
| 2233. | 4-(2,3-dichlorophenyl)-thiazol-2-yl |
| 2234. | 4-(2,4-dichlorophenyl)-thiazol-2-yl |
| 2235. | 4-(2,5-dichlorophenyl)-thiazol-2-yl |
| 2236. | 4-(2,6-dichlorophenyl)-thiazol-2-yl |
| 2237. | 4-(3,4-dichlorophenyl)-thiazol-2-yl |
| 2238. | 4-(3,5-dichlorophenyl)-thiazol-2-yl |
| 2239. | 4-(2,3-dibromophenyl)-thiazol-2-yl |
| 2240. | 4-(2,4-dibromophenyl)-thiazol-2-yl |
| 2241. | 4-(2,5-dibromophenyl)-thiazol-2-yl |
| 2242. | 4-(2,6-dibromophenyl)-thiazol-2-yl |
| 2243. | 4-(3,4-dibromophenyl)-thiazol-2-yl |

TABLE A-continued

| no. | R³-A- |
|---|---|
| 2244. | 4-(3,5-dibromophenyl)-thiazol-2-yl |
| 2245. | 4-(2,3-dimethylphenyl)-thiazol-2-yl |
| 2246. | 4-(2,4-dimethylphenyl)-thiazol-2-yl |
| 2247. | 4-(2,5-dimethylphenyl)-thiazol-2-yl |
| 2248. | 4-(2,6-dimethylphenyl)-thiazol-2-yl |
| 2249. | 4-(3,4-dimethylphenyl)-thiazol-2-yl |
| 2250. | 4-(3,5-dimethylphenyl)-thiazol-2-yl |
| 2251. | 4-[2,3-di(trifluoromethyl)phenyl]-thiazol-2-yl |
| 2252. | 4-[2,4-di(trifluoromethyl)phenyl]-thiazol-2-yl |
| 2253. | 4-[2,5-di(trifluoromethyl)phenyl]-thiazol-2-yl |
| 2254. | 4-[2,6-di(trifluoromethyl)phenyl]-thiazol-2-yl |
| 2255. | 4-[3,4-di(trifluoromethyl)phenyl]-thiazol-2-yl |
| 2256. | 4-[3,5-di(trifluoromethyl)phenyl]-thiazol-2-yl |
| 2257. | 4-(2,3-dimethoxyphenyl)-thiazol-2-yl |
| 2258. | 4-(2,4-dimethoxyphenyl)-thiazol-2-yl |
| 2259. | 4-(2,5-dimethoxyphenyl)-thiazol-2-yl |
| 2260. | 4-(2,6-dimethoxyphenyl)-thiazol-2-yl |
| 2261. | 4-(3,4-dimethoxyphenyl)-thiazol-2-yl |
| 2262. | 4-(3,5-dimethoxyphenyl)-thiazol-2-yl |
| 2263. | 4-(o-CN-phenoxy)-thiazol-2-yl |
| 2264. | 4-(m-CN-phenoxy)-thiazol-2-yl |
| 2265. | 4-(p-CN-phenoxy)-thiazol-2-yl |
| 2266. | 4-(o-NO$_2$-phenoxy)-thiazol-2-yl |
| 2267. | 4-(m-NO$_2$-phenoxy)-thiazol-2-yl |
| 2268. | 4-(p-NO$_2$-phenoxy)-thiazol-2-yl |
| 2269. | 4-(o-F-phenoxy)-thiazol-2-yl |
| 2270. | 4-(m-F-phenoxy)-thiazol-2-yl |
| 2271. | 4-(p-F-phenoxy)-thiazol-2-yl |
| 2272. | 4-(o-Cl-phenoxy)-thiazol-2-yl |
| 2273. | 4-(m-Cl-phenoxy)-thiazol-2-yl |
| 2274. | 4-(p-Cl-phenoxy)-thiazol-2-yl |
| 2275. | 4-(o-Br-phenoxy)-thiazol-2-yl |
| 2276. | 4-(m-Br-phenoxy)-thiazol-2-yl |
| 2277. | 4-(p-Br-phenoxy)-thiazol-2-yl |
| 2278. | 4-(o-CH$_3$-phenoxy)-thiazol-2-yl |
| 2279. | 4-(m-CH$_3$-phenoxy)-thiazol-2-yl |
| 2280. | 4-(p-CH$_3$-phenoxy)-thiazol-2-yl |
| 2281. | 4-(o-CF$_3$-phenoxy)-thiazol-2-yl |
| 2282. | 4-(m-CF$_3$-phenoxy)-thiazol-2-yl |
| 2283. | 4-(p-CF$_3$-phenoxy)-thiazol-2-yl |
| 2284. | 4-(o-CF$_3$-phenoxy)-thiazol-2-yl |
| 2285. | 4-(m-CF$_3$-phenoxy)-thiazol-2-yl |
| 2286. | 4-(p-CF$_3$-phenoxy)-thiazol-2-yl |
| 2287. | 4-(o-OCH$_3$-phenoxy)-thiazol-2-yl |
| 2288. | 4-(m-OCH$_3$-phenoxy)-thiazol-2-yl |
| 2289. | 4-(p-OCH$_3$-phenoxy)-thiazol-2-yl |
| 2290. | 4-(o-OCF$_3$-phenoxy)-thiazol-2-yl |
| 2291. | 4-(m-OCF$_3$-phenoxy)-thiazol-2-yl |
| 2292. | 4-(p-OCF$_3$-phenoxy)-thiazol-2-yl |
| 2293. | 4-(o-COOCH$_3$-phenoxy)-thiazol-2-yl |
| 2294. | 4-(m-COOCH$_3$-phenoxy)-thiazol-2-yl |
| 2295. | 4-(p-COOCH$_3$-phenoxy)-thiazol-2-yl |
| 2296. | 4-[o-N(CH$_3$)$_2$-phenoxy]-thiazol-2-yl |
| 2297. | 4-[m-N(CH$_3$)$_2$-phenoxy]-thiazol-2-yl |
| 2298. | 4-[p-N(CH$_3$)$_2$-phenoxy]-thiazol-2-yl |
| 2299. | 4-(2,3-dicyanophenoxy)-thiazol-2-yl |
| 2300. | 4-(2,4-dicyanophenoxy)-thiazol-2-yl |
| 2301. | 4-(2,5-dicyanophenoxy)-thiazol-2-yl |
| 2302. | 4-(2,6-dicyanophenoxy)-thiazol-2-yl |
| 2303. | 4-(3,4-dicyanophenoxy)-thiazol-2-yl |
| 2304. | 4-(3,5-dicyanophenoxy)-thiazol-2-yl |
| 2305. | 4-(2,3-difluorophenoxy)-thiazol-2-yl |
| 2306. | 4-(2,4-difluorophenoxy)-thiazol-2-yl |
| 2307. | 4-(2,5-difluorophenoxy)-thiazol-2-yl |
| 2308. | 4-(2,6-difluorophenoxy)-thiazol-2-yl |
| 2309. | 4-(3,4-difluorophenoxy)-thiazol-2-yl |
| 2310. | 4-(3,5-difluorophenoxy)-thiazol-2-yl |
| 2311. | 4-(2,3-dichlorophenoxy)-thiazol-2-yl |
| 2312. | 4-(2,4-dichlorophenoxy)-thiazol-2-yl |
| 2313. | 4-(2,5-dichlorophenoxy)-thiazol-2-yl |
| 2314. | 4-(2,6-dichlorophenoxy)-thiazol-2-yl |
| 2315. | 4-(3,4-dichlorophenoxy)-thiazol-2-yl |
| 2316. | 4-(3,5-dichlorophenoxy)-thiazol-2-yl |
| 2317. | 4-(2,3-dibromophenoxy)-thiazol-2-yl |
| 2318. | 4-(2,4-dibromophenoxy)-thiazol-2-yl |
| 2319. | 4-(2,5-dibromophenoxy)-thiazol-2-yl |
| 2320. | 4-(2,6-dibromophenoxy)-thiazol-2-yl |
| 2321. | 4-(3,4-dibromophenoxy)-thiazol-2-yl |
| 2322. | 4-(3,5-dibromophenoxy)-thiazol-2-yl |
| 2323. | 4-(2,3-dimethylphenoxy)-thiazol-2-yl |
| 2324. | 4-(2,4-dimethylphenoxy)-thiazol-2-yl |
| 2325. | 4-(2,5-dimethylphenoxy)-thiazol-2-yl |
| 2326. | 4-(2,6-dimethylphenoxy)-thiazol-2-yl |
| 2327. | 4-(3,4-dimethylphenoxy)-thiazol-2-yl |
| 2328. | 4-(3,5-dimethylphenoxy)-thiazol-2-yl |
| 2329. | 4-[2,3-di(trifluoromethyl)phenoxy]-thiazol-2-yl |
| 2330. | 4-[2,4-di(trifluoromethyl)phenoxy]-thiazol-2-yl |
| 2331. | 4-[2,5-di(trifluoromethyl)phenoxy]-thiazol-2-yl |
| 2332. | 4-[2,6-di(trifluoromethyl)phenoxy]-thiazol-2-yl |
| 2333. | 4-[3,4-di(trifluoromethyl)phenoxy]-thiazol-2-yl |
| 2334. | 4-[3,5-di(trifluoromethyl)phenoxy]-thiazol-2-yl |
| 2335. | 4-(2,3-dimethoxyphenoxy)-thiazol-2-yl |
| 2336. | 4-(2,4-dimethoxyphenoxy)-thiazol-2-yl |

TABLE A-continued

| no. | R³-A- |
|---|---|
| 2337. | 4-(2,5-dimethoxyphenoxy)-thiazol-2-yl |
| 2338. | 4-(2,6-dimethoxyphenoxy)-thiazol-2-yl |
| 2339. | 4-(3,4-dimethoxyphenoxy)-thiazol-2-yl |
| 2340. | 4-(3,5-dimethoxyphenoxy)-thiazol-2-yl |
| 2341. | 5-(o-CN-phenyl)-oxazol-2-yl |
| 2342. | 5-(m-CN-phenyl)-oxazol-2-yl |
| 2343. | 5-(p-CN-phenyl)-oxazol-2-yl |
| 2344. | 5-(o-NO₂-phenyl)-oxazol-2-yl |
| 2345. | 5-(m-NO₂-phenyl)-oxazol-2-yl |
| 2346. | 5-(p-NO₂-phenyl)-oxazol-2-yl |
| 2347. | 5-(o-F-phenyl)-oxazol-2-yl |
| 2348. | 5-(m-F-phenyl)-oxazol-2-yl |
| 2349. | 5-(p-F-phenyl)-oxazol-2-yl |
| 2350. | 5-(o-Cl-phenyl)-oxazol-2-yl |
| 2351. | 5-(m-Cl-phenyl)-oxazol-2-yl |
| 2352. | 5-(p-Cl-phenyl)-oxazol-2-yl |
| 2353. | 5-(o-Br-phenyl)-oxazol-2-yl |
| 2354. | 5-(m-Br-phenyl)-oxazol-2-yl |
| 2355. | 5-(p-Br-phenyl)-oxazol-2-yl |
| 2356. | 5-(o-CH₃-phenyl)-oxazol-2-yl |
| 2357. | 5-(m-CH₃-phenyl)-oxazol-2-yl |
| 2358. | 5-(p-CH₃-phenyl)-oxazol-2-yl |
| 2359. | 5-(o-CF₃-phenyl)-oxazol-2-yl |
| 2360. | 5-(m-CF₃-phenyl)-oxazol-2-yl |
| 2361. | 5-(p-CF₃-phenyl)-oxazol-2-yl |
| 2362. | 5-(o-CF₃-phenyl)-oxazol-2-yl |
| 2363. | 5-(m-CF₃-phenyl)-oxazol-2-yl |
| 2364. | 5-(p-CF₃-phenyl)-oxazol-2-yl |
| 2365. | 5-(o-OCH₃-phenyl)-oxazol-2-yl |
| 2366. | 5-(m-OCH₃-phenyl)-oxazol-2-yl |
| 2367. | 5-(p-OCH₃-phenyl)-oxazol-2-yl |
| 2368. | 5-(o-OCF₃-phenyl)-oxazol-2-yl |
| 2369. | 5-(m-OCF₃-phenyl)-oxazol-2-yl |
| 2370. | 5-(p-OCF₃-phenyl)-oxazol-2-yl |
| 2371. | 5-(o-COOCH₃-phenyl)-oxazol-2-yl |
| 2372. | 5-(m-COOCH₃-phenyl)-oxazol-2-yl |
| 2373. | 5-(p-COOCH₃-phenyl)-oxazol-2-yl |
| 2374. | 5-[o-N(CH₃)₂-phenyl]-oxazol-2-yl |
| 2375. | 5-[m-N(CH₃)₂-phenyl]-oxazol-2-yl |
| 2376. | 5-[p-N(CH₃)₂-phenyl]-oxazol-2-yl |
| 2377. | 5-(2,3-dicyanophenyl)-oxazol-2-yl |
| 2378. | 5-(2,4-dicyanophenyl)-oxazol-2-yl |
| 2379. | 5-(2,5-dicyanophenyl)-oxazol-2-yl |
| 2380. | 5-(2,6-dicyanophenyl)-oxazol-2-yl |
| 2381. | 5-(3,4-dicyanophenyl)-oxazol-2-yl |
| 2382. | 5-(3,5-dicyanophenyl)-oxazol-2-yl |
| 2383. | 5-(2,3-difluorophenyl)-oxazol-2-yl |
| 2384. | 5-(2,4-difluorophenyl)-oxazol-2-yl |
| 2385. | 5-(2,5-difluorophenyl)-oxazol-2-yl |
| 2386. | 5-(2,6-difluorophenyl)-oxazol-2-yl |
| 2387. | 5-(3,4-difluorophenyl)-oxazol-2-yl |
| 2388. | 5-(3,5-difluorophenyl)-oxazol-2-yl |
| 2389. | 5-(2,3-dichlorophenyl)-oxazol-2-yl |
| 2390. | 5-(2,4-dichlorophenyl)-oxazol-2-yl |
| 2391. | 5-(2,5-dichlorophenyl)-oxazol-2-yl |
| 2392. | 5-(2,6-dichlorophenyl)-oxazol-2-yl |
| 2393. | 5-(3,4-dichlorophenyl)-oxazol-2-yl |
| 2394. | 5-(3,5-dichlorophenyl)-oxazol-2-yl |
| 2395. | 5-(2,3-dibromophenyl)-oxazol-2-yl |
| 2396. | 5-(2,4-dibromophenyl)-oxazol-2-yl |
| 2397. | 5-(2,5-dibromophenyl)-oxazol-2-yl |
| 2398. | 5-(2,6-dibromophenyl)-oxazol-2-yl |
| 2399. | 5-(3,4-dibromophenyl)-oxazol-2-yl |
| 2400. | 5-(3,5-dibromophenyl)-oxazol-2-yl |
| 2401. | 5-(2,3-dimethylphenyl)-oxazol-2-yl |
| 2402. | 5-(2,4-dimethylphenyl)-oxazol-2-yl |
| 2403. | 5-(2,5-dimethylphenyl)-oxazol-2-yl |
| 2404. | 5-(2,6-dimethylphenyl)-oxazol-2-yl |
| 2405. | 5-(3,4-dimethylphenyl)-oxazol-2-yl |
| 2406. | 5-(3,5-dimethylphenyl)-oxazol-2-yl |
| 2407. | 5-[2,3-di(trifluoromethyl)phenyl]-oxazol-2-yl |
| 2408. | 5-[2,4-di(trifluoromethyl)phenyl]-oxazol-2-yl |
| 2409. | 5-[2,5-di(trifluoromethyl)phenyl]-oxazol-2-yl |
| 2410. | 5-[2,6-di(trifluoromethyl)phenyl]-oxazol-2-yl |
| 2411. | 5-[3,4-di(trifluoromethyl)phenyl]-oxazol-2-yl |
| 2412. | 5-[3,5-di(trifluoromethyl)phenyl]-oxazol-2-yl |
| 2413. | 5-(2,3-dimethoxyphenyl)-oxazol-2-yl |
| 2414. | 5-(2,4-dimethoxyphenyl)-oxazol-2-yl |
| 2415. | 5-(2,5-dimethoxyphenyl)-oxazol-2-yl |
| 2416. | 5-(2,6-dimethoxyphenyl)-oxazol-2-yl |
| 2417. | 5-(3,4,-dimethoxyphenyl)-oxazol-2-yl |
| 2418. | 5-(3,5-dimethoxyphenyl)-oxazol-2-yl |
| 2419. | 5-(o-CN-phenoxy)-oxazol-2-yl |
| 2420. | 5-(m-CN-phenoxy)-oxazol-2-yl |
| 2421. | 5-(p-CN-phenoxy)-oxazol-2-yl |
| 2422. | 5-(o-NO₂-phenoxy)-oxazol-2-yl |
| 2423. | 5-(m-NO₂-phenoxy)-oxazol-2-yl |
| 2424. | 5-(p-NO₂-phenoxy)-oxazol-2-yl |
| 2425. | 5-(o-F-phenoxy)-oxazol-2-yl |
| 2426. | 5-(m-F-phenoxy)-oxazol-2-yl |
| 2427. | 5-(p-F-phenoxy)-oxazol-2-yl |
| 2428. | 5-(o-Cl-phenoxy)-oxazol-2-yl |
| 2429. | 5-(m-Cl-phenoxy)-oxazol-2-yl |
| 2430. | 5-(p-Cl-phenoxy)-oxazol-2-yl |
| 2431. | 5-(o-Br-phenoxy)-oxazol-2-yl |
| 2432. | 5-(m-Br-phenoxy)-oxazol-2-yl |
| 2433. | 5-(p-Br-phenoxy)-oxazol-2-yl |
| 2434. | 5-(o-CH₃-phenoxy)-oxazol-2-yl |
| 2435. | 5-(m-CH₃-phenoxy)-oxazol-2-yl |
| 2436. | 5-(p-CH₃-phenoxy)-oxazol-2-yl |
| 2437. | 5-(o-CF₃-phenoxy)-oxazol-2-yl |
| 2438. | 5-(m-CF₃-phenoxy)-oxazol-2-yl |
| 2439. | 5-(p-CF₃-phenoxy)-oxazol-2-yl |
| 2440. | 5-(o-CF₃-phenoxy)-oxazol-2-yl |
| 2441. | 5-(m-CF₃-phenoxy)-oxazol-2-yl |
| 2442. | 5-(p-CF₃-phenoxy)-oxazol-2-yl |
| 2443. | 5-(o-OCH₃-phenoxy)-oxazol-2-yl |
| 2444. | 5-(m-OCH₃-phenoxy)-oxazol-2-yl |
| 2445. | 5-(p-OCH₃-phenoxy)-oxazol-2-yl |
| 2446. | 5-(o-OCF₃-phenoxy)-oxazol-2-yl |
| 2447. | 5-(m-OCF₃-phenoxy)-oxazol-2-yl |
| 2448. | 5-(p-OCF₃-phenoxy)-oxazol-2-yl |
| 2449. | 5-(o-COOCH₃-phenoxy)-oxazol-2-yl |
| 2450. | 5-(m-COOCH₃-phenoxy)-oxazol-2-yl |
| 2451. | 5-(p-COOCH₃-phenoxy)-oxazol-2-yl |
| 2452. | 5-[o-N(CH₃)₂-phenoxy]-oxazol-2-yl |
| 2453. | 5-[m-N(CH₃)₂-phenoxy]-oxazol-2-yl |
| 2454. | 5-[p-N(CH₃)₂-phenoxy]-oxazol-2-yl |

TABLE A-continued

| no. | R³-A- |
|---|---|
| 2455. | 5-(2,3-dicyanophenoxy)-oxazol-2-yl |
| 2456. | 5-(2,4-dicyanophenoxy)-oxazol-2-yl |
| 2457. | 5-(2,5-dicyanophenoxy)-oxazol-2-yl |
| 2458. | 5-(2,6-dicyanophenoxy)-oxazol-2-yl |
| 2459. | 5-(3,4-dicyanophenoxy)-oxazol-2-yl |
| 2460. | 5-(3,5-dicyanophenoxy)-oxazol-2-yl |
| 2461. | 5-(2,3-difluorophenoxy)-oxazol-2-yl |
| 2462. | 5-(2,4-difluorophenoxy)-oxazol-2-yl |
| 2463. | 5-(2,5-difluorophenoxy)-oxazol-2-yl |
| 2464. | 5-(2,6-difluorophenoxy)-oxazol-2-yl |
| 2465. | 5-(3,4-difluorophenoxy)-oxazol-2-yl |
| 2466. | 5-(3,5-difluorophenoxy)-oxazol-2-yl |
| 2467. | 5-(2,3-dichlorophenoxy)-oxazol-2-yl |
| 2468. | 5-(2,4-dichlorophenoxy)-oxazol-2-yl |
| 2469. | 5-(2,5-dichlorophenoxy)-oxazol-2-yl |
| 2470. | 5-(2,6-dichlorophenoxy)-oxazol-2-yl |
| 2471. | 5-(3,4-dichlorophenoxy)-oxazol-2-yl |
| 2472. | 5-(3,5-dichlorophenoxy)-oxazol-2-yl |
| 2473. | 5-(2,3-dibromophenoxy)-oxazol-2-yl |
| 2474. | 5-(2,4-dibromophenoxy)-oxazol-2-yl |
| 2475. | 5-(2,5-dibromophenoxy)-oxazol-2-yl |
| 2476. | 5-(2,6-dibromophenoxy)-oxazol-2-yl |
| 2477. | 5-(3,4-dibromophenoxy)-oxazol-2-yl |
| 2478. | 5-(3,5-dibromophenoxy)-oxazol-2-yl |
| 2479. | 5-(2,3-dimethylphenoxy)-oxazol-2-yl |
| 2480. | 5-(2,4-dimethylphenoxy)-oxazol-2-yl |
| 2481. | 5-(2,5-dimethylphenoxy)-oxazol-2-yl |
| 2482. | 5-(2,6-dimethylphenoxy)-oxazol-2-yl |
| 2483. | 5-(3,4-dimethylphenoxy)-oxazol-2-yl |
| 2484. | 5-(3,5-dimethylphenoxy)-oxazol-2-yl |
| 2485. | 5-[2,3-di(trifluoromethyl)phenoxy]-oxazol-2-yl |
| 2486. | 5-[2,4-di(trifluoromethyl)phenoxy]-oxazol-2-yl |
| 2487. | 5-[2,5-di(trifluoromethyl)phenoxy]-oxazol-2-yl |
| 2488. | 5-[2,6-di(trifluoromethyl)phenoxy]-oxazol-2-yl |
| 2489. | 5-[3,4-di(trifluoromethyl)phenoxy]-oxazol-2-yl |
| 2490. | 5-[3,5-di(trifluoromethyl)phenoxy]-oxazol-2-yl |
| 2491. | 5-(2,3-dimethoxyphenoxy)-oxazol-2-yl |
| 2492. | 5-(2,4-dimethoxyphenoxy)-oxazol-2-yl |
| 2493. | 5-(2,5-dimethoxyphenoxy)-oxazol-2-yl |
| 2494. | 5-(2,6-dimethoxyphenoxy)-oxazol-2-yl |
| 2495. | 5-(3,4-dimethoxyphenoxy)-oxazol-2-yl |
| 2496. | 5-(3,5-dimethoxyphenoxy)-oxazol-2-yl |
| 2497. | 5-(o-CN-phenyl)-thiazol-2-yl |
| 2498. | 5-(m-CN-phenyl)-thiazol-2-yl |
| 2499. | 5-(p-CN-phenyl)-thiazol-2-yl |
| 2500. | 5-(o-NO$_2$-phenyl)-thiazol-2-yl |
| 2501. | 5-(m-NO$_2$-phenyl)-thiazol-2-yl |
| 2502. | 5-(p-NO$_2$-phenyl)-thiazol-2-yl |
| 2503. | 5-(o-F-phenyl)-thiazol-2-yl |
| 2504. | 5-(m-F-phenyl)-thiazol-2-yl |
| 2505. | 5-(p-F-phenyl)-thiazol-2-yl |
| 2506. | 5-(o-Cl-phenyl)-thiazol-2-yl |
| 2507. | 5-(m-Cl-phenyl)-thiazol-2-yl |
| 2508. | 5-(p-Cl-phenyl)-thiazol-2-yl |
| 2509. | 5-(o-Br-phenyl)-thiazol-2-yl |
| 2510. | 5-(m-Br-phenyl)-thiazol-2-yl |
| 2511. | 5-(p-Br-phenyl)-thiazol-2-yl |
| 2512. | 5-(o-CH$_3$-phenyl)-thiazol-2-yl |
| 2513. | 5-(m-CH$_3$-phenyl)-thiazol-2-yl |
| 2514. | 5-(p-CH$_3$-phenyl)-thiazol-2-yl |
| 2515. | 5-(o-CF$_3$-phenyl)-thiazol-2-yl |
| 2516. | 5-(m-CF$_3$-phenyl)-thiazol-2-yl |
| 2517. | 5-(p-CF$_3$-phenyl)-thiazol-2-yl |
| 2518. | 5-(o-CF$_3$-phenyl)-thiazol-2-yl |
| 2519. | 5-(m-CF$_3$-phenyl)-thiazol-2-yl |
| 2520. | 5-(p-CF$_3$-phenyl)-thiazol-2-yl |
| 2521. | 5-(o-OCH$_3$-phenyl)-thiazol-2-yl |
| 2522. | 5-(m-OCH$_3$-phenyl)-thiazol-2-yl |
| 2523. | 5-(p-OCH$_3$-phenyl)-thiazol-2-yl |
| 2524. | 5-(o-OCF$_3$-phenyl)-thiazol-2-yl |
| 2525. | 5-(m-OCF$_3$-phenyl)-thiazol-2-yl |
| 2526. | 5-(p-OCF$_3$-phenyl)-thiazol-2-yl |
| 2527. | 5-(o-COOCH$_3$-phenyl)-thiazol-2-yl |
| 2528. | 5-(m-COOCH$_3$-phenyl)-thiazol-2-yl |
| 2529. | 5-(p-COOCH$_3$-phenyl)-thiazol-2-yl |
| 2530. | 5-[o-N(CH$_3$)$_2$-phenyl]-thiazol-2-yl |
| 2531. | 5-[m-N(CH$_3$)$_2$-phenyl]-thiazol-2-yl |
| 2532. | 5-[p-N(CH$_3$)$_2$-phenyl]-thiazol-2-yl |
| 2533. | 5-(2,3-dicyanophenyl)-thiazol-2-yl |
| 2534. | 5-(2,4-dicyanophenyl)-thiazol-2-yl |
| 2535. | 5-(2,5-dicyanophenyl)-thiazol-2-yl |
| 2536. | 5-(2,6-dicyanophenyl)-thiazol-2-yl |
| 2537. | 5-(3,4-dicyanophenyl)-thiazol-2-yl |
| 2538. | 5-(3,5-dicyanophenyl)-thiazol-2-yl |
| 2539. | 5-(2,3-difluorophenyl)-thiazol-2-yl |
| 2540. | 5-(2,4-difluorophenyl)-thiazol-2-yl |
| 2541. | 5-(2,5-difluorophenyl)-thiazol-2-yl |
| 2542. | 5-(2,6-difluorophenyl)-thiazol-2-yl |
| 2543. | 5-(3,4-difluorophenyl)-thiazol-2-yl |
| 2544. | 5-(3,5-difluorophenyl)-thiazol-2-yl |
| 2545. | 5-(2,3-dichlorophenyl)-thiazol-2-yl |
| 2546. | 5-(2,4-dichlorophenyl)-thiazol-2-yl |
| 2547. | 5-(2,5-dichlorophenyl)-thiazol-2-yl |
| 2548. | 5-(2,6-dichlorophenyl)-thiazol-2-yl |
| 2549. | 5-(3,4-dichlorophenyl)-thiazol-2-yl |
| 2550. | 5-(3,5-dichlorophenyl)-thiazol-2-yl |
| 2551. | 5-(2,3-dibromophenyl)-thiazol-2-yl |
| 2552. | 5-(2,4-dibromophenyl)-thiazol-2-yl |
| 2553. | 5-(2,5-dibromophenyl)-thiazol-2-yl |
| 2554. | 5-(2,6-dibromophenyl)-thiazol-2-yl |
| 2555. | 5-(3,4-dibromophenyl)-thiazol-2-yl |
| 2556. | 5-(3,5-dibromophenyl)-thiazol-2-yl |
| 2557. | 5-(2,3-dimethylphenyl)-thiazol-2-yl |

TABLE A-continued

| no. | R³-A- |
|---|---|
| 2558. | 5-(2,4-dimethylphenyl)-thiazol-2-yl |
| 2559. | 5-(2,5-dimethylphenyl)-thiazol-2-yl |
| 2560. | 5-(2,6-dimethylphenyl)-thiazol-2-yl |
| 2561. | 5-(3,4-dimethylphenyl)-thiazol-2-yl |
| 2562. | 5-(3,5-dimethylphenyl)-thiazol-2-yl |
| 2563. | 5-[2,3-di(trifluoromethyl)phenyl]-thiazol-2-yl |
| 2564. | 5-[2,4-di(trifluoromethyl)phenyl]-thiazol-2-yl |
| 2565. | 5-[2,5-di(trifluoromethyl)phenyl]-thiazol-2-yl |
| 2566. | 5-[2,6-di(trifluoromethyl)phenyl]-thiazol-2-yl |
| 2567. | 5-[3,4-di(trifluoromethyl)phenyl]-thiazol-2-yl |
| 2568. | 5-[3,5-di(trifluoromethyl)phenyl]-thiazol-2-yl |
| 2569. | 5-(2,3-dimethoxyphenyl)-thiazol-2-yl |
| 2570. | 5-(2,4-dimethoxyphenyl)-thiazol-2-yl |
| 2571. | 5-(2,5-dimethoxyphenyl)-thiazol-2-yl |
| 2572. | 5-(2,6-dimethoxyphenyl)-thiazol-2-yl |
| 2573. | 5-(3,4-dimethoxyphenyl)-thiazol-2-yl |
| 2574. | 5-(3,5-dimethoxyphenyl)-thiazol-2-yl |
| 2575. | 5-(o-CN-phenoxy)-thiazol-2-yl |
| 2576. | 5-(m-CN-phenoxy)-thiazol-2-yl |
| 2577. | 5-(p-CN-phenoxy)-thiazol-2-yl |
| 2578. | 5-(o-NO₂-phenoxy)-thiazol-2-yl |
| 2579. | 5-(m-NO₂-phenoxy)-thiazol-2-yl |
| 2580. | 5-(p-NO₂-phenoxy)-thiazol-2-yl |
| 2581. | 5-(o-F-phenoxy)-thiazol-2-yl |
| 2582. | 5-(m-F-phenoxy)-thiazol-2-yl |
| 2583. | 5-(p-F-phenoxy)-thiazol-2-yl |
| 2584. | 5-(o-Cl-phenoxy)-thiazol-2-yl |
| 2585. | 5-(m-Cl-phenoxy)-thiazol-2-yl |
| 2586. | 5-(p-Cl-phenoxy)-thiazol-2-yl |
| 2587. | 5-(o-Br-phenoxy)-thiazol-2-yl |
| 2588. | 5-(m-Br-phenoxy)-thiazol-2-yl |
| 2589. | 5-(p-Br-phenoxy)-thiazol-2-yl |
| 2590. | 5-(o-CH₃-phenoxy)-thiazol-2-yl |
| 2591. | 5-(m-CH₃-phenoxy)-thiazol-2-yl |
| 2592. | 5-(p-CH₃-phenoxy)-thiazol-2-yl |
| 2593. | 5-(o-CF₃-phenoxy)-thiazol-2-yl |
| 2594. | 5-(m-CF₃-phenoxy)-thiazol-2-yl |
| 2595. | 5-(p-CF₃-phenoxy)-thiazol-2-yl |
| 2596. | 5-(o-CF₃-phenoxy)-thiazol-2-yl |
| 2597. | 5-(m-CF₃-phenoxy)-thiazol-2-yl |
| 2598. | 5-(p-CF₃-phenoxy)-thiazol-2-yl |
| 2599. | 5-(o-OCH₃-phenoxy)-thiazol-2-yl |
| 2600. | 5-(m-OCH₃-phenoxy)-thiazol-2-yl |
| 2601. | 5-(p-OCH₃-phenoxy)-thiazol-2-yl |
| 2602. | 5-(o-OCF₃-phenoxy)-thiazol-2-yl |
| 2603. | 5-(m-OCF₃-phenoxy)-thiazol-2-yl |
| 2604. | 5-(p-OCF₃-phenoxy)-thiazol-2-yl |
| 2605. | 5-(o-COOCH₃-phenoxy)-thiazol-2-yl |
| 2606. | 5-(m-COOCH₃-phenoxy)-thiazol-2-yl |
| 2607. | 5-(p-COOCH₃-phenoxy)-thiazol-2-yl |
| 2608. | 5-[o-N(CH₃)₂-phenoxy]-thiazol-2-yl |
| 2609. | 5-[m-N(CH₃)₂-phenoxy]-thiazol-2-yl |
| 2610. | 5-[p-N(CH₃)₂-phenoxy]-thiazol-2-yl |
| 2611. | 5-(2,3-dicyanophenoxy)-thiazol-2-yl |
| 2612. | 5-(2,4-dicyanophenoxy)-thiazol-2-yl |
| 2613. | 5-(2,5-dicyanophenoxy)-thiazol-2-yl |
| 2614. | 5-(2,6-dicyanophenoxy)-thiazol-2-yl |
| 2615. | 5-(3,4-dicyanophenoxy)-thiazol-2-yl |
| 2616. | 5-(3,5-dicyanophenoxy)-thiazol-2-yl |
| 2617. | 5-(2,3-difluorophenoxy)-thiazol-2-yl |
| 2618. | 5-(2,4-difluorophenoxy)-thiazol-2-yl |
| 2619. | 5-(2,5-difluorophenoxy)-thiazol-2-yl |
| 2620. | 5-(2,6-difluorophenoxy)-thiazol-2-yl |
| 2621. | 5-(3,4-difluorophenoxy)-thiazol-2-yl |
| 2622. | 5-(3,5-difluorophenoxy)-thiazol-2-yl |
| 2623. | 5-(2,3-dichlorophenoxy)-thiazol-2-yl |
| 2624. | 5-(2,4-dichlorophenoxy)-thiazol-2-yl |
| 2625. | 5-(2,5-dichlorophenoxy)-thiazol-2-yl |
| 2626. | 5-(2,6-dichlorophenoxy)-thiazol-2-yl |
| 2627. | 5-(3,4-dichlorophenoxy)-thiazol-2-yl |
| 2628. | 5-(3,5-dichlorophenoxy)-thiazol-2-yl |
| 2629. | 5-(2,3-dibromophenoxy)-thiazol-2-yl |
| 2630. | 5-(2,4-dibromophenoxy)-thiazol-2-yl |
| 2631. | 5-(2,5-dibromophenoxy)-thiazol-2-yl |
| 2632. | 5-(2,6-dibromophenoxy)-thiazol-2-yl |
| 2633. | 5-(3,4-dibromophenoxy)-thiazol-2-yl |
| 2634. | 5-(3,5-dibromophenoxy)-thiazol-2-yl |
| 2635. | 5-(2,3-dimethylphenoxy)-thiazol-2-yl |
| 2636. | 5-(2,4-dimethylphenoxy)-thiazol-2-yl |
| 2637. | 5-(2,5-dimethylphenoxy)-thiazol-2-yl |
| 2638. | 5-(2,6-dimethylphenoxy)-thiazol-2-yl |
| 2639. | 5-(3,4-dimethylphenoxy)-thiazol-2-yl |
| 2640. | 5-(3,5-dimethylphenoxy)-thiazol-2-yl |
| 2641. | 5-[2,3-di(trifluoromethyl)phenoxy]-thiazol-2-yl |
| 2642. | 5-[2,4-di(trifluoromethyl)phenoxy]-thiazol-2-yl |
| 2643. | 5-[2,5-di(trifluoromethyl)phenoxy]-thiazol-2-yl |
| 2644. | 5-[2,6-di(trifluoromethyl)phenoxy]-thiazol-2-yl |
| 2645. | 5-[3,4-di(trifluoromethyl)phenoxy]-thiazol-2-yl |
| 2646. | 5-[3,5-di(trifluoromethyl)phenoxy]-thiazol-2-yl |
| 2647. | 5-(2,3-dimethoxyphenoxy)-thiazol-2-yl |
| 2648. | 5-(2,4-dimethoxyphenoxy)-thiazol-2-yl |
| 2649. | 5-(2,5-dimethoxyphenoxy)-thiazol-2-yl |
| 2650. | 5-(2,6-dimethoxyphenoxy)-thiazol-2-yl |

TABLE A-continued

| no. | R³-A- |
|---|---|
| 2651. | 5-(3,4-dimethoxyphenoxy)-thiazol-2-yl |
| 2652. | 5-(3,5-dimethoxyphenoxy)-thiazol-2-yl |
| 2653. | 2-(o-CN-phenyl)-oxazol-5-yl |
| 2654. | 2-(m-CN-phenyl)-oxazol-5-yl |
| 2655. | 2-(p-CN-phenyl)-oxazol-5-yl |
| 2656. | 2-(o-NO$_2$-phenyl)-oxazol-5-yl |
| 2657. | 2-(m-NO$_2$-phenyl)-oxazol-5-yl |
| 2658. | 2-(p-NO$_2$-phenyl)-oxazol-5-yl |
| 2659. | 2-(o-F-phenyl)-oxazol-5-yl |
| 2660. | 2-(m-F-phenyl)-oxazol-5-yl |
| 2661. | 2-(p-F-phenyl)-oxazol-5-yl |
| 2662. | 2-(o-Cl-phenyl)-oxazol-5-yl |
| 2663. | 2-(m-Cl-phenyl)-oxazol-5-yl |
| 2664. | 2-(p-Cl-phenyl)-oxazol-5-yl |
| 2665. | 2-(o-Br-phenyl)-oxazol-5-yl |
| 2666. | 2-(m-Br-phenyl)-oxazol-5-yl |
| 2667. | 2-(p-Br-phenyl)-oxazol-5-yl |
| 2668. | 2-(o-CH$_3$-phenyl)-oxazol-5-yl |
| 2669. | 2-(m-CH$_3$-phenyl)-oxazol-5-yl |
| 2670. | 2-(p-CH$_3$-phenyl)-oxazol-5-yl |
| 2671. | 2-(o-CF$_3$-phenyl)-oxazol-5-yl |
| 2672. | 2-(m-CF$_3$-phenyl)-oxazol-5-yl |
| 2673. | 2-(p-CF$_3$-phenyl)-oxazol-5-yl |
| 2674. | 2-(o-CF$_3$-phenyl)-oxazol-5-yl |
| 2675. | 2-(m-CF$_3$-phenyl)-oxazol-5-yl |
| 2676. | 2-(p-CF$_3$-phenyl)-oxazol-5-yl |
| 2677. | 2-(o-OCH$_3$-phenyl)-oxazol-5-yl |
| 2678. | 2-(m-OCH$_3$-phenyl)-oxazol-5-yl |
| 2679. | 2-(p-OCH$_3$-phenyl)-oxazol-5-yl |
| 2680. | 2-(o-OCF$_3$-phenyl)-oxazol-5-yl |
| 2681. | 2-(m-OCF$_3$-phenyl)-oxazol-5-yl |
| 2682. | 2-(p-OCF$_3$-phenyl)-oxazol-5-yl |
| 2683. | 2-(o-COOCH$_3$-phenyl)-oxazol-5-yl |
| 2684. | 2-(m-COOCH$_3$-phenyl)-oxazol-5-yl |
| 2685. | 2-(p-COOCH$_3$-phenyl)-oxazol-5-yl |
| 2686. | 2-[o-N(CH$_3$)$_2$-phenyl]-oxazol-5-yl |
| 2687. | 2-[m-N(CH$_3$)$_2$-phenyl]-oxazol-5-yl |
| 2688. | 2-[p-N(CH$_3$)$_2$-phenyl]-oxazol-5-yl |
| 2689. | 2-(2,3-dicyanophenyl)-oxazol-5-yl |
| 2690. | 2-(2,4-dicyanophenyl)-oxazol-5-yl |
| 2691. | 2-(2,5-dicyanophenyl)-oxazol-5-yl |
| 2692. | 2-(2,6-dicyanophenyl)-oxazol-5-yl |
| 2693. | 2-(3,4-dicyanophenyl)-oxazol-5-yl |
| 2694. | 2-(3,5-dicyanophenyl)-oxazol-5-yl |
| 2695. | 2-(2,3-difluorophenyl)-oxazol-5-yl |
| 2696. | 2-(2,4-difluorophenyl)-oxazol-5-yl |
| 2697. | 2-(2,5-difluorophenyl)-oxazol-5-yl |
| 2698. | 2-(2,6-difluorophenyl)-oxazol-5-yl |
| 2699. | 2-(3,4-difluorophenyl)-oxazol-5-yl |
| 2700. | 2-(3,5-difluorophenyl)-oxazol-5-yl |
| 2701. | 2-(2,3-dichlorophenyl)-oxazol-5-yl |
| 2702. | 2-(2,4-dichlorophenyl)-oxazol-5-yl |
| 2703. | 2-(2,5-dichlorophenyl)-oxazol-5-yl |
| 2704. | 2-(2,6-dichlorophenyl)-oxazol-5-yl |
| 2705. | 2-(3,4-dichlorophenyl)-oxazol-5-yl |
| 2706. | 2-(3,5-dichlorophenyl)-oxazol-5-yl |
| 2707. | 2-(2,3-dibromophenyl)-oxazol-5-yl |
| 2708. | 2-(2,4-dibromophenyl)-oxazol-5-yl |
| 2709. | 2-(2,5-dibromophenyl)-oxazol-5-yl |
| 2710. | 2-(2,6-dibromophenyl)-oxazol-5-yl |
| 2711. | 2-(3,4-dibromophenyl)-oxazol-5-yl |
| 2712. | 2-(3,5-dibromophenyl)-oxazol-5-yl |
| 2713. | 2-(2,3-dimethylphenyl)-oxazol-5-yl |
| 2714. | 2-(2,4-dimethylphenyl)-oxazol-5-yl |
| 2715. | 2-(2,5-dimethylphenyl)-oxazol-5-yl |
| 2716. | 2-(2,6-dimethylphenyl)-oxazol-5-yl |
| 2717. | 2-(3,4-dimethylphenyl)-oxazol-5-yl |
| 2718. | 2-(3,5-dimethylphenyl)-oxazol-5-yl |
| 2719. | 2-[2,3-di(trifluoromethyl)phenyl]-oxazol-5-yl |
| 2720. | 2-[2,4-di(trifluoromethyl)phenyl]-oxazol-5-yl |
| 2721. | 2-[2,5-di(trifluoromethyl)phenyl]-oxazol-5-yl |
| 2722. | 2-[2,6-di(trifluoromethyl)phenyl]-oxazol-5-yl |
| 2723. | 2-[3,4-di(trifluoromethyl)phenyl]-oxazol-5-yl |
| 2724. | 2-[3,5-di(trifluoromethyl)phenyl]-oxazol-5-yl |
| 2725. | 2-(2,3-dimethoxyphenyl)-oxazol-5-yl |
| 2726. | 2-(2,4-dimethoxyphenyl)-oxazol-5-yl |
| 2727. | 2-(2,5-dimethoxyphenyl)-oxazol-5-yl |
| 2728. | 2-(2,6-dimethoxyphenyl)-oxazol-5-yl |
| 2729. | 2-(3,4-dimethoxyphenyl)-oxazol-5-yl |
| 2730. | 2-(3,5-dimethoxyphenyl)-oxazol-5-yl |
| 2731. | 2-(o-CN-phenoxy)-oxazol-5-yl |
| 2732. | 2-(m-CN-phenoxy)-oxazol-5-yl |
| 2733. | 2-(p-CN-phenoxy)-oxazol-5-yl |
| 2734. | 2-(o-NO$_2$-phenoxy)-oxazol-5-yl |
| 2735. | 2-(m-NO$_2$-phenoxy)-oxazol-5-yl |
| 2736. | 2-(p-NO$_2$-phenoxy)-oxazol-5-yl |
| 2737. | 2-(o-F-phenoxy)-oxazol-5-yl |
| 2738. | 2-(m-F-phenoxy)-oxazol-5-yl |
| 2739. | 2-(p-F-phenoxy)-oxazol-5-yl |
| 2740. | 2-(o-Cl-phenoxy)-oxazol-5-yl |
| 2741. | 2-(m-Cl-phenoxy)-oxazol-5-yl |
| 2742. | 2-(p-Cl-phenoxy)-oxazol-5-yl |
| 2743. | 2-(o-Br-phenoxy)-oxazol-5-yl |
| 2744. | 2-(m-Br-phenoxy)-oxazol-5-yl |
| 2745. | 2-(p-Br-phenoxy)-oxazol-5-yl |
| 2746. | 2-(o-CH$_3$-phenoxy)-oxazol-5-yl |
| 2747. | 2-(m-CH$_3$-phenoxy)-oxazol-5-yl |
| 2748. | 2-(p-CH$_3$-phenoxy)-oxazol-5-yl |
| 2749. | 2-(o-CF$_3$-phenoxy)-oxazol-5-yl |
| 2750. | 2-(m-CF$_3$-phenoxy)-oxazol-5-yl |
| 2751. | 2-(p-CF$_3$-phenoxy)-oxazol-5-yl |
| 2752. | 2-(o-CF$_3$-phenoxy)-oxazol-5-yl |
| 2753. | 2-(m-CF$_3$-phenoxy)-oxazol-5-yl |
| 2754. | 2-(p-CF$_3$-phenoxy)-oxazol-5-yl |
| 2755. | 2-(o-OCH$_3$-phenoxy)-oxazol-5-yl |
| 2756. | 2-(m-OCH$_3$-phenoxy)-oxazol-5-yl |
| 2757. | 2-(p-OCH$_3$-phenoxy)-oxazol-5-yl |
| 2758. | 2-(o-OCF$_3$-phenoxy)-oxazol-5-yl |
| 2759. | 2-(m-OCF$_3$-phenoxy)-oxazol-5-yl |
| 2760. | 2-(p-OCF$_3$-phenoxy)-oxazol-5-yl |
| 2761. | 2-(o-COOCH$_3$-phenoxy)-oxazol-5-yl |
| 2762. | 2-(m-COOCH$_3$-phenoxy)-oxazol-5-yl |
| 2763. | 2-(p-COOCH$_3$-phenoxy)-oxazol-5-yl |
| 2764. | 2-[o-N(CH$_3$)$_2$-phenoxy]-oxazol-5-yl |
| 2765. | 2-[m-N(CH$_3$)$_2$-phenoxy]-oxazol-5-yl |
| 2766. | 2-[p-N(CH$_3$)$_2$-phenoxy]-oxazol-5-yl |
| 2767. | 2-(2,3-dicyanophenoxy)-oxazol-5-yl |
| 2768. | 2-(2,4-dicyanophenoxy)-oxazol-5-yl |

TABLE A-continued

| no. | R³-A- |
|---|---|
| 2769. | 2-(2,5-dicyanophenoxy)-oxazol-5-yl |
| 2770. | 2-(2,6-dicyanophenoxy)-oxazol-5-yl |
| 2771. | 2-(3,4-dicyanophenoxy)-oxazol-5-yl |
| 2772. | 2-(3,5-dicyanophenoxy)-oxazol-5-yl |
| 2773. | 2-(2,3-difluorophenoxy)-oxazol-5-yl |
| 2774. | 2-(2,4-difluorophenoxy)-oxazol-5-yl |
| 2775. | 2-(2,5-difluorophenoxy)-oxazol-5-yl |
| 2776. | 2-(2,6-difluorophenoxy)-oxazol-5-yl |
| 2777. | 2-(3,4-difluorophenoxy)-oxazol-5-yl |
| 2778. | 2-(3,5-difluorophenoxy)-oxazol-5-yl |
| 2779. | 2-(2,3-dichlorophenoxy)-oxazol-5-yl |
| 2780. | 2-(2,4-dichlorophenoxy)-oxazol-5-yl |
| 2781. | 2-(2,5-dichlorophenoxy)-oxazol-5-yl |
| 2782. | 2-(2,6-dichlorophenoxy)-oxazol-5-yl |
| 2783. | 2-(3,4-dichlorophenoxy)-oxazol-5-yl |
| 2784. | 2-(3,5-dichlorophenoxy)-oxazol-5-yl |
| 2785. | 2-(2,3-dibromophenoxy)-oxazol-5-yl |
| 2786. | 2-(2,4-dibromophenoxy)-oxazol-5-yl |
| 2787. | 2-(2,5-dibromophenoxy)-oxazol-5-yl |
| 2788. | 2-(2,6-dibromophenoxy)-oxazol-5-yl |
| 2789. | 2-(3,4-dibromophenoxy)-oxazol-5-yl |
| 2790. | 2-(3,5-dibromophenoxy)-oxazol-5-yl |
| 2791. | 2-(2,3-dimethylphenoxy)-oxazol-5-yl |
| 2792. | 2-(2,4-dimethylphenoxy)-oxazol-5-yl |
| 2793. | 2-(2,5-dimethylphenoxy)-oxazol-5-yl |
| 2794. | 2-(2,6-dimethylphenoxy)-oxazol-5-yl |
| 2795. | 2-(3,4-dimethylphenoxy)-oxazol-5-yl |
| 2796. | 2-(3,5-dimethylphenoxy)-oxazol-5-yl |
| 2797. | 2-[2,3-di(trifluoromethyl)phenoxy]-oxazol-5-yl |
| 2798. | 2-[2,4-di(trifluoromethyl)phenoxy]-oxazol-5-yl |
| 2799. | 2-[2,5-di(trifluoromethyl)phenoxy]-oxazol-5-yl |
| 2800. | 2-[2,6-di(trifluoromethyl)phenoxy]-oxazol-5-yl |
| 2801. | 2-[3,4-di(trifluoromethyl)phenoxy]-oxazol-5-yl |
| 2802. | 2-[3,5-di(trifluoromethyl)phenoxy]-oxazol-5-yl |
| 2803. | 2-(2,3-dimethoxyphenoxy)-oxazol-5-yl |
| 2804. | 2-(2,4-dimethoxyphenoxy)-oxazol-5-yl |
| 2805. | 2-(2,5-dimethoxyphenoxy)-oxazol-5-yl |
| 2806. | 2-(2,6-dimethoxyphenoxy)-oxazol-5-yl |
| 2807. | 2-(3,4-dimethoxyphenoxy)-oxazol-5-yl |
| 2808. | 2-(3,5-dimethoxyphenoxy)-oxazol-5-yl |
| 2809. | 2-(o-CN-phenyl)-thiazol-5-yl |
| 2810. | 2-(m-CN-phenyl)-thiazol-5-yl |
| 2811. | 2-(p-CN-phenyl)-thiazol-5-yl |
| 2812. | 2-(o-NO$_2$-phenyl)-thiazol-5-yl |
| 2813. | 2-(m-NO$_2$-phenyl)-thiazol-5-yl |
| 2814. | 2-(p-NO$_2$-phenyl)-thiazol-5-yl |
| 2815. | 2-(o-F-phenyl)-thiazol-5-yl |
| 2816. | 2-(m-F-phenyl)-thiazol-5-yl |
| 2817. | 2-(p-F-phenyl)-thiazol-5-yl |
| 2818. | 2-(o-Cl-phenyl)-thiazol-5-yl |
| 2819. | 2-(m-Cl-phenyl)-thiazol-5-yl |
| 2820. | 2-(p-Cl-phenyl)-thiazol-5-yl |
| 2821. | 2-(o-Br-phenyl)-thiazol-5-yl |
| 2822. | 2-(m-Br-phenyl)-thiazol-5-yl |
| 2823. | 2-(p-Br-phenyl)-thiazol-5-yl |
| 2824. | 2-(o-CH$_3$-phenyl)-thiazol-5-yl |
| 2825. | 2-(m-CH$_3$-phenyl)-thiazol-5-yl |
| 2826. | 2-(p-CH$_3$-phenyl)-thiazol-5-yl |
| 2827. | 2-(o-CF$_3$-phenyl)-thiazol-5-yl |
| 2828. | 2-(m-CF$_3$-phenyl)-thiazol-5-yl |
| 2829. | 2-(p-CF$_3$-phenyl)-thiazol-5-yl |
| 2830. | 2-(o-CF$_3$-phenyl)-thiazol-5-yl |
| 2831. | 2-(m-CF$_3$-phenyl)-thiazol-5-yl |
| 2832. | 2-(p-CF$_3$-phenyl)-thiazol-5-yl |
| 2833. | 2-(o-OCH$_3$-phenyl)-thiazol-5-yl |
| 2834. | 2-(m-OCH$_3$-phenyl)-thiazol-5-yl |
| 2835. | 2-(p-OCH$_3$-phenyl)-thiazol-5-yl |
| 2836. | 2-(o-OCF$_3$-phenyl)-thiazol-5-yl |
| 2837. | 2-(m-OCF$_3$-phenyl)-thiazol-5-yl |
| 2838. | 2-(p-OCF$_3$-phenyl)-thiazol-5-yl |
| 2839. | 2-(o-COOCH$_3$-phenyl)-thiazol-5-yl |
| 2840. | 2-(m-COOCH$_3$-phenyl)-thiazol-5-yl |
| 2841. | 2-(p-COOCH$_3$-phenyl)-thiazol-5-yl |
| 2842. | 2-[o-N(CH$_3$)$_2$-phenyl]-thiazol-5-yl |
| 2843. | 2-[m-N(CH$_3$)$_2$-phenyl]-thiazol-5-yl |
| 2844. | 2-[p-N(CH$_3$)$_2$-phenyl]-thiazol-5-yl |
| 2845. | 2-(2,3-dicyanophenyl)-thiazol-5-yl |
| 2846. | 2-(2,4-dicyanophenyl)-thiazol-5-yl |
| 2847. | 2-(2,5-dicyanophenyl)-thiazol-5-yl |
| 2848. | 2-(2,6-dicyanophenyl)-thiazol-5-yl |
| 2849. | 2-(3,4-dicyanophenyl)-thiazol-5-yl |
| 2850. | 2-(3,5-dicyanophenyl)-thiazol-5-yl |
| 2851. | 2-(2,3-difluorophenyl)-thiazol-5-yl |
| 2852. | 2-(2,4-difluorophenyl)-thiazol-5-yl |
| 2853. | 2-(2,5-difluorophenyl)-thiazol-5-yl |
| 2854. | 2-(2,6-difluorophenyl)-thiazol-5-yl |
| 2855. | 2-(3,4-difluorophenyl)-thiazol-5-yl |
| 2856. | 2-(3,5-difluorophenyl)-thiazol-5-yl |
| 2857. | 2-(2,3-dichlorophenyl)-thiazol-5-yl |
| 2858. | 2-(2,4-dichlorophenyl)-thiazol-5-yl |
| 2859. | 2-(2,5-dichlorophenyl)-thiazol-5-yl |
| 2860. | 2-(2,6-dichlorophenyl)-thiazol-5-yl |
| 2861. | 2-(3,4-dichlorophenyl)-thiazol-5-yl |
| 2862. | 2-(3,5-dichlorophenyl)-thiazol-5-yl |
| 2863. | 2-(2,3-dibromophenyl)-thiazol-5-yl |
| 2864. | 2-(2,4-dibromophenyl)-thiazol-5-yl |
| 2865. | 2-(2,5-dibromophenyl)-thiazol-5-yl |
| 2866. | 2-(2,6-dibromophenyl)-thiazol-5-yl |
| 2867. | 2-(3,4-dibromophenyl)-thiazol-5-yl |
| 2868. | 2-(3,5-dibromophenyl)-thiazol-5-yl |
| 2869. | 2-(2,3-dimethylphenyl)-thiazol-5-yl |
| 2870. | 2-(2,4-dimethylphenyl)-thiazol-5-yl |
| 2871. | 2-(2,5-dimethylphenyl)-thiazol-5-yl |

TABLE A-continued

| no. | R³-A- |
|---|---|
| 2872. | 2-(2,6-dimethylphenyl)-thiazol-5-yl |
| 2873. | 2-(3,4-dimethylphenyl)-thiazol-5-yl |
| 2874. | 2-(3,5-dimethylphenyl)-thiazol-5-yl |
| 2875. | 2-[2,3-di(trifluoromethyl)phenyl]-thiazol-5-yl |
| 2876. | 2-[2,4-di(trifluoromethyl)phenyl]-thiazol-5-yl |
| 2877. | 2-[2,5-di(trifluoromethyl)phenyl]-thiazol-5-yl |
| 2878. | 2-[2,6-di(trifluoromethyl)phenyl]-thiazol-5-yl |
| 2879. | 2-[3,4-di(trifluoromethyl)phenyl]-thiazol-5-yl |
| 2880. | 2-[3,5-di(trifluoromethyl)phenyl]-thiazol-5-yl |
| 2881. | 2-(2,3-dimethoxyphenyl)-thiazol-5-yl |
| 2882. | 2-(2,4-dimethoxyphenyl)-thiazol-5-yl |
| 2883. | 2-(2,5-dimethoxyphenyl)-thiazol-5-yl |
| 2884. | 2-(2,6-dimethoxyphenyl)-thiazol-5-yl |
| 2885. | 2-(3,4-dimethoxyphenyl)-thiazol-5-yl |
| 2886. | 2-(3,5-dimethoxyphenyl)-thiazol-5-yl |
| 2887. | 2-(o-CN-phenoxy)-thiazol-5-yl |
| 2888. | 2-(m-CN-phenoxy)-thiazol-5-yl |
| 2889. | 2-(p-CN-phenoxy)-thiazol-5-yl |
| 2890. | 2-(o-NO₂-phenoxy)-thiazol-5-yl |
| 2891. | 2-(m-NO₂-phenoxy)-thiazol-5-yl |
| 2892. | 2-(p-NO₂-phenoxy)-thiazol-5-yl |
| 2893. | 2-(o-F-phenoxy)-thiazol-5-yl |
| 2894. | 2-(m-F-phenoxy)-thiazol-5-yl |
| 2895. | 2-(p-F-phenoxy)-thiazol-5-yl |
| 2896. | 2-(o-Cl-phenoxy)-thiazol-5-yl |
| 2897. | 2-(m-Cl-phenoxy)-thiazol-5-yl |
| 2898. | 2-(p-Cl-phenoxy)-thiazol-5-yl |
| 2899. | 2-(o-Br-phenoxy)-thiazol-5-yl |
| 2900. | 2-(m-Br-phenoxy)-thiazol-5-yl |
| 2901. | 2-(p-Br-phenoxy)-thiazol-5-yl |
| 2902. | 2-(o-CH₃-phenoxy)-thiazol-5-yl |
| 2903. | 2-(m-CH₃-phenoxy)-thiazol-5-yl |
| 2904. | 2-(p-CH₃-phenoxy)-thiazol-5-yl |
| 2905. | 2-(o-CF₃-phenoxy)-thiazol-5-yl |
| 2906. | 2-(m-CF₃-phenoxy)-thiazol-5-yl |
| 2907. | 2-(p-CF₃-phenoxy)-thiazol-5-yl |
| 2908. | 2-(o-CF₃-phenoxy)-thiazol-5-yl |
| 2909. | 2-(m-CF₃-phenoxy)-thiazol-5-yl |
| 2910. | 2-(p-CF₃-phenoxy)-thiazol-5-yl |
| 2911. | 2-(o-OCH₃-phenoxy)-thiazol-5-yl |
| 2912. | 2-(m-OCH₃-phenoxy)-thiazol-5-yl |
| 2913. | 2-(p-OCH₃-phenoxy)-thiazol-5-yl |
| 2914. | 2-(o-OCF₃-phenoxy)-thiazol-5-yl |
| 2915. | 2-(m-OCF₃-phenoxy)-thiazol-5-yl |
| 2916. | 2-(p-OCF₃-phenoxy)-thiazol-5-yl |
| 2917. | 2-(o-COOCH₃-phenoxy)-thiazol-5-yl |
| 2918. | 2-(m-COOCH₃-phenoxy)-thiazol-5-yl |
| 2919. | 2-(p-COOCH₃-phenoxy)-thiazol-5-yl |
| 2920. | 2-[o-N(CH₃)₂-phenoxy]-thiazol-5-yl |
| 2921. | 2-[m-N(CH₃)₂-phenoxy]-thiazol-5-yl |
| 2922. | 2-[p-N(CH₃)₂-phenoxy]-thiazol-5-yl |
| 2923. | 2-(2,3-dicyanophenoxy)-thiazol-5-yl |
| 2924. | 2-(2,4-dicyanophenoxy)-thiazol-5-yl |
| 2925. | 2-(2,5-dicyanophenoxy)-thiazol-5-yl |
| 2926. | 2-(2,6-dicyanophenoxy)-thiazol-5-yl |
| 2927. | 2-(3,4-dicyanophenoxy)-thiazol-5-yl |
| 2928. | 2-(3,5-dicyanophenoxy)-thiazol-5-yl |
| 2929. | 2-(2,3-difluorophenoxy)-thiazol-5-yl |
| 2930. | 2-(2,4-difluorophenoxy)-thiazol-5-yl |
| 2931. | 2-(2,5-difluorophenoxy)-thiazol-5-yl |
| 2932. | 2-(2,6-difluorophenoxy)-thiazol-5-yl |
| 2933. | 2-(3,4-difluorophenoxy)-thiazol-5-yl |
| 2934. | 2-(3,5-difluorophenoxy)-thiazol-5-yl |
| 2935. | 2-(2,3-dichlorophenoxy)-thiazol-5-yl |
| 2936. | 2-(2,4-dichlorophenoxy)-thiazol-5-yl |
| 2937. | 2-(2,5-dichlorophenoxy)-thiazol-5-yl |
| 2938. | 2-(2,6-dichlorophenoxy)-thiazol-5-yl |
| 2939. | 2-(3,4-dichlorophenoxy)-thiazol-5-yl |
| 2940. | 2-(3,5-dichlorophenoxy)-thiazol-5-yl |
| 2941. | 2-(2,3-dibromophenoxy)-thiazol-5-yl |
| 2942. | 2-(2,4-dibromophenoxy)-thiazol-5-yl |
| 2943. | 2-(2,5-dibromophenoxy)-thiazol-5-yl |
| 2944. | 2-(2,6-dibromophenoxy)-thiazol-5-yl |
| 2945. | 2-(3,4-dibromophenoxy)-thiazol-5-yl |
| 2946. | 2-(3,5-dibromophenoxy)-thiazol-5-yl |
| 2947. | 2-(2,3-dimethylphenoxy)-thiazol-5-yl |
| 2948. | 2-(2,4-dimethylphenoxy)-thiazol-5-yl |
| 2949. | 2-(2,5-dimethylphenoxy)-thiazol-5-yl |
| 2950. | 2-(2,6-dimethylphenoxy)-thiazol-5-yl |
| 2951. | 2-(3,4-dimethylphenoxy)-thiazol-5-yl |
| 2952. | 2-(3,5-dimethylphenoxy)-thiazol-5-yl |
| 2953. | 2-[2,3-di(trifluoromethyl)phenoxy]-thiazol-5-yl |
| 2954. | 2-[2,4-di(trifluoromethyl)phenoxy]-thiazol-5-yl |
| 2955. | 2-[2,5-di(trifluoromethyl)phenoxy]-thiazol-5-yl |
| 2956. | 2-[2,6-di(trifluoromethyl)phenoxy]-thiazol-5-yl |
| 2957. | 2-[3,4-di(trifluoromethyl)phenoxy]-thiazol-5-yl |
| 2958. | 2-[3,5-di(trifluoromethyl)phenoxy]-thiazol-5-yl |
| 2959. | 2-(2,3-dimethoxyphenoxy)-thiazol-5-yl |
| 2960. | 2-(2,4-dimethoxyphenoxy)-thiazol-5-yl |
| 2961. | 2-(2,5-dimethoxyphenoxy)-thiazol-5-yl |
| 2962. | 2-(2,6-dimethoxyphenoxy)-thiazol-5-yl |
| 2963. | 2-(3,4-dimethoxyphenoxy)-thiazol-5-yl |
| 2964. | 2-(3,5-dimethoxyphenoxy)-thiazol-5-yl |

TABLE A-continued

| no. | R³-A- |
|---|---|
| 2965. | 2-(o-CN-phenyl)-oxazol-4-yl |
| 2966. | 2-(m-CN-phenyl)-oxazol-4-yl |
| 2967. | 2-(p-CN-phenyl)-oxazol-4-yl |
| 2968. | 2-(o-NO₂-phenyl)-oxazol-4-yl |
| 2969. | 2-(m-NO₂-phenyl)-oxazol-4-yl |
| 2970. | 2-(p-NO₂-phenyl)-oxazol-4-yl |
| 2971. | 2-(o-F-phenyl)-oxazol-4-yl |
| 2972. | 2-(m-F-phenyl)-oxazol-4-yl |
| 2973. | 2-(p-F-phenyl)-oxazol-4-yl |
| 2974. | 2-(o-Cl-phenyl)-oxazol-4-yl |
| 2975. | 2-(m-Cl-phenyl)-oxazol-4-yl |
| 2976. | 2-(p-Cl-phenyl)-oxazol-4-yl |
| 2977. | 2-(o-Br-phenyl)-oxazol-4-yl |
| 2978. | 2-(m-Br-phenyl)-oxazol-4-yl |
| 2979. | 2-(p-Br-phenyl)-oxazol-4-yl |
| 2980. | 2-(o-CH₃-phenyl)-oxazol-4-yl |
| 2981. | 2-(m-CH₃-phenyl)-oxazol-4-yl |
| 2982. | 2-(p-CH₃-phenyl)-oxazol-4-yl |
| 2983. | 2-(o-CF₃-phenyl)-oxazol-4-yl |
| 2984. | 2-(m-CF₃-phenyl)-oxazol-4-yl |
| 2985. | 2-(p-CF₃-phenyl)-oxazol-4-yl |
| 2986. | 2-(o-CF₃-phenyl)-oxazol-4-yl |
| 2987. | 2-(m-CF₃-phenyl)-oxazol-4-yl |
| 2988. | 2-(p-CF₃-phenyl)-oxazol-4-yl |
| 2989. | 2-(o-OCH₃-phenyl)-oxazol-4-yl |
| 2990. | 2-(m-OCH₃-phenyl)-oxazol-4-yl |
| 2991. | 2-(p-OCH₃-phenyl)-oxazol-4-yl |
| 2992. | 2-(o-OCF₃-phenyl)-oxazol-4-yl |
| 2993. | 2-(m-OCF₃-phenyl)-oxazol-4-yl |
| 2994. | 2-(p-OCF₃-phenyl)-oxazol-4-yl |
| 2995. | 2-(o-COOCH₃-phenyl)-oxazol-4-yl |
| 2996. | 2-(m-COOCH₃-phenyl)-oxazol-4-yl |
| 2997. | 2-(p-COOCH₃-phenyl)-oxazol-4-yl |
| 2998. | 2-[o-N(CH₃)₂-phenyl]-oxazol-4-yl |
| 2999. | 2-[m-N(CH₃)₂-phenyl]-oxazol-4-yl |
| 3000. | 2-[p-N(CH₃)₂-phenyl]-oxazol-4-yl |
| 3001. | 2-(2,3-dicyanophenyl)-oxazol-4-yl |
| 3002. | 2-(2,4-dicyanophenyl)-oxazol-4-yl |
| 3003. | 2-(2,5-dicyanophenyl)-oxazol-4-yl |
| 3004. | 2-(2,6-dicyanophenyl)-oxazol-4-yl |
| 3005. | 2-(3,4-dicyanophenyl)-oxazol-4-yl |
| 3006. | 2-(3,5-dicyanophenyl)-oxazol-4-yl |
| 3007. | 2-(2,3-difluorophenyl)-oxazol-4-yl |
| 3008. | 2-(2,4-difluorophenyl)-oxazol-4-yl |
| 3009. | 2-(2,5-difluorophenyl)-oxazol-4-yl |
| 3010. | 2-(2,6-difluorophenyl)-oxazol-4-yl |
| 3011. | 2-(3,4-difluorophenyl)-oxazol-4-yl |
| 3012. | 2-(3,5-difluorophenyl)-oxazol-4-yl |
| 3013. | 2-(2,3-dichlorophenyl)-oxazol-4-yl |
| 3014. | 2-(2,4-dichlorophenyl)-oxazol-4-yl |
| 3015. | 2-(2,5-diohlorophenyl)-oxazol-4-yl |
| 3016. | 2-(2,6-dichlorophenyl)-oxazol-4-yl |
| 3017. | 2-(3,4-dichlorophenyl)-oxazol-4-yl |
| 3018. | 2-(3,5-dichlorophenyl)-oxazol-4-yl |
| 3019. | 2-(2,3-dibromophenyl)-oxazol-4-yl |
| 3020. | 2-(2,4-dibromophenyl)-oxazol-4-yl |
| 3021. | 2-(2,5-dibromophenyl)-oxazol-4-yl |
| 3022. | 2-(2,6-dibromophenyl)-oxazol-4-yl |
| 3023. | 2-(3,4-dibromophenyl)-oxazol-4-yl |
| 3024. | 2-(3,5-dibromophenyl)-oxazol-4-yl |
| 3025. | 2-(2,3-dimethylphenyl)-oxazol-4-yl |
| 3026. | 2-(2,4-dimethylphenyl)-oxazol-4-yl |
| 3027. | 2-(2,5-dimethylphenyl)-oxazol-4-yl |
| 3028. | 2-(2,6-dimethylphenyl)-oxazol-4-yl |
| 3029. | 2-(3,4-dimethylphenyl)-oxazol-4-yl |
| 3030. | 2-(3,5-dimethylphenyl)-oxazol-4-yl |
| 3031. | 2-[2,3-di(trifluoromethyl)phenyl]-oxazol-4-yl |
| 3032. | 2-[2,4-di(trifluoromethyl)phenyl]-oxazol-4-yl |
| 3033. | 2-[2,5-di(trifluoromethyl)phenyl]-oxazol-4-yl |
| 3034. | 2-[2,6-di(trifluoromethyl)phenyl]-oxazol-4-yl |
| 3035. | 2-[3,4-di(trifluoromethyl)phenyl]-oxazol-4-yl |
| 3036. | 2-[3,5-di(trifluoromethyl)phenyl]-oxazol-4-yl |
| 3037. | 2-(2,3-dimethoxyphenyl)-oxazol-4-yl |
| 3038. | 2-(2,4-dimethoxyphenyl)-oxazol-4-yl |
| 3039. | 2-(2,5-dimethoxyphenyl)-oxazol-4-yl |
| 3040. | 2-(2,6-dimethoxyphenyl)-oxazol-4-yl |
| 3041. | 2-(3,4-dimethoxyphenyl)-oxazol-4-yl |
| 3042. | 2-(3,5-dimethoxyphenyl)-oxazol-4-yl |
| 3043. | 2-(o-CN-phenoxy)-oxazol-4-yl |
| 3044. | 2-(m-CN-phenoxy)-oxazol-4-yl |
| 3045. | 2-(p-CN-phenoxy)-oxazol-4-yl |
| 3046. | 2-(o-NO₂-phenoxy)-oxazol-4-yl |
| 3047. | 2-(m-NO₂-phenoxy)-oxazol-4-yl |
| 3048. | 2-(p-NO₂-phenoxy)-oxazol-4-yl |
| 3049. | 2-(o-F-phenoxy)-oxazol-4-yl |
| 3050. | 2-(m-F-phenoxy)-oxazol-4-yl |
| 3051. | 2-(p-F-phenoxy)-oxazol-4-yl |
| 3052. | 2-(o-Cl-phenoxy)-oxazol-4-yl |
| 3053. | 2-(m-Cl-phenoxy)-oxazol-4-yl |
| 3054. | 2-(p-Cl-phenoxy)-oxazol-4-yl |
| 3055. | 2-(o-Br-phenoxy)-oxazol-4-yl |
| 3056. | 2-(m-Br-phenoxy)-oxazol-4-yl |
| 3057. | 2-(p-Br-phenoxy)-oxazol-4-yl |
| 3058. | 2-(o-CH₃-phenoxy)-oxazol-4-yl |
| 3059. | 2-(m-CH₃-phenoxy)-oxazol-4-yl |
| 3060. | 2-(p-CH₃-phenoxy)-oxazol-4-yl |
| 3061. | 2-(o-CF₃-phenoxy)-oxazol-4-yl |
| 3062. | 2-(m-CF₃-phenoxy)-oxazol-4-yl |
| 3063. | 2-(p-CF₃-phenoxy)-oxazol-4-yl |
| 3064. | 2-(o-CF₃-phenoxy)-oxazol-4-yl |
| 3065. | 2-(m-CF₃-phenoxy)-oxazol-4-yl |
| 3066. | 2-(p-CF₃-phenoxy)-oxazol-4-yl |
| 3067. | 2-(o-OCH₃-phenoxy)-oxazol-4-yl |
| 3068. | 2-(m-OCH₃-phenoxy)-oxazol-4-yl |
| 3069. | 2-(p-OCH₃-phenoxy)-oxazol-4-yl |
| 3070. | 2-(o-OCF₃-phenoxy)-oxazol-4-yl |
| 3071. | 2-(m-OCF₃-phenoxy)-oxazol-4-yl |
| 3072. | 2-(p-OCF₃-phenoxy)-oxazol-4-yl |
| 3073. | 2-(o-COOCH₃-phenoxy)-oxazol-4-yl |
| 3074. | 2-(m-COOCH₃-phenoxy)-oxazol-4-yl |
| 3075. | 2-(p-COOCH₃-phenoxy)-oxazol-4-yl |
| 3076. | 2-[o-N(CH₃)₂-phenoxy]-oxazol-4-yl |
| 3077. | 2-[m-N(CH₃)₂-phenoxy]-oxazol-4-yl |
| 3078. | 2-[p-N(CH₃)₂-phenoxy]-oxazol-4-yl |
| 3079. | 2-(2,3-dicyanophenoxy)-oxazol-4-yl |
| 3080. | 2-(2,4-dicyanophenoxy)-oxazol-4-yl |
| 3081. | 2-(2,5-dicyanophenoxy)-oxazol-4-yl |
| 3082. | 2-(2,6-dicyanophenoxy)-oxazol-4-yl |

TABLE A-continued

| no. | R³-A- |
|---|---|
| 3083. | 2-(3,4-dicyanophenoxy)-oxazol-4-yl |
| 3084. | 2-(3,5-dicyanophenoxy)-oxazol-4-yl |
| 3085. | 2-(2,3-difluorophenoxy)-oxazol-4-yl |
| 3086. | 2-(2,4-difluorophenoxy)-oxazol-4-yl |
| 3087. | 2-(2,5-difluorophenoxy)-oxazol-4-yl |
| 3088. | 2-(2,6-difluorophenoxy)-oxazol-4-yl |
| 3089. | 2-(3,4-difluorophenoxy)-oxazol-4-yl |
| 3090. | 2-(3,5-difluorophenoxy)-oxazol-4-yl |
| 3091. | 2-(2,3-dichlorophenoxy)-oxazol-4-yl |
| 3092. | 2-(2,4-dichlorophenoxy)-oxazol-4-yl |
| 3093. | 2-(2,5-dichlorophenoxy)-oxazol-4-yl |
| 3094. | 2-(2,6-dichlorophenoxy)-oxazol-4-yl |
| 3095. | 2-(3,4-dichlorophenoxy)-oxazol-4-yl |
| 3096. | 2-(3,5-dichlorophenoxy)-oxazol-4-yl |
| 3097. | 2-(2,3-dibromophenoxy)-oxazol-4-yl |
| 3098. | 2-(2,4-dibromophenoxy)-oxazol-4-yl |
| 3099. | 2-(2,5-dibromophenoxy)-oxazol-4-yl |
| 3100. | 2-(2,6-dibromophenoxy)-oxazol-4-yl |
| 3101. | 2-(3,4-dibromophenoxy)-oxazol-4-yl |
| 3102. | 2-(3,5-dibromophenoxy)-oxazol-4-yl |
| 3103. | 2-(2,3-dimethylphenoxy)-oxazol-4-yl |
| 3104. | 2-(2,4-dimethylphenoxy)-oxazol-4-yl |
| 3105. | 2-(2,5-dimethylphenoxy)-oxazol-4-yl |
| 3106. | 2-(2,6-dimethylphenoxy)-oxazol-4-yl |
| 3107. | 2-(3,4-dimethylphenoxy)-oxazol-4-yl |
| 3108. | 2-(3,5-dimethylphenoxy)-oxazol-4-yl |
| 3109. | 2-[2,3-di(trifluoromethyl)phenoxy]-oxazol-4-yl |
| 3110. | 2-[2,4-di(trifluoromethyl)phenoxy]-oxazol-4-yl |
| 3111. | 2-[2,5-di(trifluoromethyl)phenoxy]-oxazol-4-yl |
| 3112. | 2-[2,6-di(trifluoromethyl)phenoxy]-oxazol-4-yl |
| 3113. | 2-[3,4-di(trifluoromethyl)phenoxy]-oxazol-4-yl |
| 3114. | 2-[3,5-di(trifluoromethyl)phenoxy]-oxazol-4-yl |
| 3115. | 2-(2,3-dimethoxyphenoxy)-oxazol-4-yl |
| 3116. | 2-(2,4-dimethoxyphenoxy)-oxazol-4-yl |
| 3117. | 2-(2,5-dimethoxyphenoxy)-oxazol-4-yl |
| 3118. | 2-(2,6-dimethoxyphenoxy)-oxazol-4-yl |
| 3119. | 2-(3,4-dimethoxyphenoxy)-oxazol-4-yl |
| 3120. | 2-(3,5-dimethoxyphenoxy)-oxazol-4-yl |
| 3121. | 2-(o-CN-phenyl)-thiazol-4-yl |
| 3122. | 2-(m-CN-phenyl)-thiazol-4-yl |
| 3123. | 2-(p-CN-phenyl)-thiazol-4-yl |
| 3124. | 2-(o-NO₂-phenyl)-thiazol-4-yl |
| 3125. | 2-(m-NO₂-phenyl)-thiazol-4-yl |
| 3126. | 2-(p-NO₂-phenyl)-thiazol-4-yl |
| 3127. | 2-(o-F-phenyl)-thiazol-4-yl |
| 3128. | 2-(m-F-phenyl)-thiazol-4-yl |
| 3129. | 2-(p-F-phenyl)-thiazol-4-yl |
| 3130. | 2-(o-Cl-phenyl)-thiazol-4-yl |
| 3131. | 2-(m-Cl-phenyl)-thiazol-4-yl |
| 3132. | 2-(p-Cl-phenyl)-thiazol-4-yl |
| 3133. | 2-(o-Br-phenyl)-thiazol-4-yl |
| 3134. | 2-(m-Br-phenyl)-thiazol-4-yl |
| 3135. | 2-(p-Br-phenyl)-thiazol-4-yl |
| 3136. | 2-(o-CH₃-phenyl)-thiazol-4-yl |
| 3137. | 2-(m-CH₃-phenyl)-thiazol-4-yl |
| 3138. | 2-(p-CH₃-phenyl)-thiazol-4-yl |
| 3139. | 2-(o-CF₃-phenyl)-thiazol-4-yl |
| 3140. | 2-(m-CF₃-phenyl)-thiazol-4-yl |
| 3141. | 2-(p-CF₃-phenyl)-thiazol-4-yl |
| 3142. | 2-(o-CF₃-phenyl)-thiazol-4-yl |
| 3143. | 2-(m-CF₃-phenyl)-thiazol-4-yl |
| 3144. | 2-(p-CF₃-phenyl)-thiazol-4-yl |
| 3145. | 2-(o-OCH₃-phenyl)-thiazol-4-yl |
| 3146. | 2-(m-OCH₃-phenyl)-thiazol-4-yl |
| 3147. | 2-(p-OCH₃-phenyl)-thiazol-4-yl |
| 3148. | 2-(o-OCF₃-phenyl)-thiazol-4-yl |
| 3149. | 2-(m-OCF₃-phenyl)-thiazol-4-yl |
| 3150. | 2-(p-OCF₃-phenyl)-thiazol-4-yl |
| 3151. | 2-(o-COOCH₃-phenyl)-thiazol-4-yl |
| 3152. | 2-(m-COOCH₃-phenyl)-thiazol-4-yl |
| 3153. | 2-(p-COOCH₃-phenyl)-thiazol-4-yl |
| 3154. | 2-[o-N(CH₃)₂-phenyl]-thiazol-4-yl |
| 3155. | 2-[m-N(CH₃)₂-phenyl]-thiazol-4-yl |
| 3156. | 2-[p-N(CH₃)₂-phenyl]-thiazol-4-yl |
| 3157. | 2-(2,3-dicyanophenyl)-thiazol-4-yl |
| 3158. | 2-(2,4-dicyanophenyl)-thiazol-4-yl |
| 3159. | 2-(2,5-dicyanophenyl)-thiazol-4-yl |
| 3160. | 2-(2,6-dicyanophenyl)-thiazol-4-yl |
| 3161. | 2-(3,4-dicyanophenyl)-thiazol-4-yl |
| 3162. | 2-(3,5-dicyanophenyl)-thiazol-4-yl |
| 3163. | 2-(2,3-difluorophenyl)-thiazol-4-yl |
| 3164. | 2-(2,4-difluorophenyl)-thiazol-4-yl |
| 3165. | 2-(2,5-difluorophenyl)-thiazol-4-yl |
| 3166. | 2-(2,6-difluorophenyl)-thiazol-4-yl |
| 3167. | 2-(3,4-difluorophenyl)-thiazol-4-yl |
| 3168. | 2-(3,5-difluorophenyl)-thiazol-4-yl |
| 3169. | 2-(2,3-dichlorophenyl)-thiazol-4-yl |
| 3170. | 2-(2,4-dichlorophenyl)-thiazol-4-yl |
| 3171. | 2-(2,5-dichlorophenyl)-thiazol-4-yl |
| 3172. | 2-(2,6-dichlorophenyl)-thiazol-4-yl |
| 3173. | 2-(3,4-dichlorophenyl)-thiazol-4-yl |
| 3174. | 2-(3,5-dichlorophenyl)-thiazol-4-yl |
| 3175. | 2-(2,3-dibromophenyl)-thiazol-4-yl |
| 3176. | 2-(2,4-dibromophenyl)-thiazol-4-yl |
| 3177. | 2-(2,5-dibromophenyl)-thiazol-4-yl |
| 3178. | 2-(2,6-dibromophenyl)-thiazol-4-yl |
| 3179. | 2-(3,4-dibromophenyl)-thiazol-4-yl |
| 3180. | 2-(3,5-dibromophenyl)-thiazol-4-yl |
| 3181. | 2-(2,3-dimethylphenyl)-thiazol-4-yl |
| 3182. | 2-(2,4-dimethylphenyl)-thiazol-4-yl |
| 3183. | 2-(2,5-dimethylphenyl)-thiazol-4-yl |
| 3184. | 2-(2,6-dimethylphenyl)-thiazol-4-yl |
| 3185. | 2-(3,4-dimethylphenyl)-thiazol-4-yl |

TABLE A-continued

| no. | R³-A- |
|---|---|
| 3186. | 2-(3,5-dimethylphenyl)-thiazol-4-yl |
| 3187. | 2-[2,3-di(trifluoromethyl)phenyl]-thiazol-4-yl |
| 3188. | 2-[2,4-di(trifluoromethyl)phenyl]-thiazol-4-yl |
| 3189. | 2-[2,5-di(trifluoromethyl)phenyl]-thiazol-4-yl |
| 3190. | 2-[2,6-di(trifluoromethyl)phenyl]-thiazol-4-yl |
| 3191. | 2-[3,4-di(trifluoromethyl)phenyl]-thiazol-4-yl |
| 3192. | 2-[3,5-di(trifluoromethyl)phenyl]-thiazol-4-yl |
| 3193. | 2-(2,3-dimethoxyphenyl)-thiazol-4-yl |
| 3194. | 2-(2,4-dimethoxyphenyl)-thiazol-4-yl |
| 3195. | 2-(2,5-dimethoxyphenyl)-thiazol-4-yl |
| 3196. | 2-(2,6-dimethoxyphenyl)-thiazol-4-yl |
| 3197. | 2-(3,4-dimethoxyphenyl)-thiazol-4-yl |
| 3198. | 2-(3,5-dimethoxyphenyl)-thiazol-4-yl |
| 3199. | 2-(o-CN-phenoxy)-thiazol-4-yl |
| 3200. | 2-(m-CN-phenoxy)-thiazol-4-yl |
| 3201. | 2-(p-CN-phenoxy)-thiazol-4-yl |
| 3202. | 2-(o-NO₂-phenoxy)-thiazol-4-yl |
| 3203. | 2-(m-NO₂-phenoxy)-thiazol-4-yl |
| 3204. | 2-(p-NO₂-phenoxy)-thiazol-4-yl |
| 3205. | 2-(o-F-phenoxy)-thiazol-4-yl |
| 3206. | 2-(m-F-phenoxy)-thiazol-4-yl |
| 3207. | 2-(p-F-phenoxy)-thiazol-4-yl |
| 3208. | 2-(o-Cl-phenoxy)-thiazol-4-yl |
| 3209. | 2-(m-Cl-phenoxy)-thiazol-4-yl |
| 3210. | 2-(p-Cl-phenoxy)-thiazol-4-yl |
| 3211. | 2-(o-Br-phenoxy)-thiazol-4-yl |
| 3212. | 2-(m-Br-phenoxy)-thiazol-4-yl |
| 3213. | 2-(p-Br-phenoxy)-thiazol-4-yl |
| 3214. | 2-(o-CH₃-phenoxy)-thiazol-4-yl |
| 3215. | 2-(m-CH₃-phenoxy)-thiazol-4-yl |
| 3216. | 2-(p-CH₃-phenoxy)-thiazol-4-yl |
| 3217. | 2-(o-CF₃-phenoxy)-thiazol-4-yl |
| 3218. | 2-(m-CF₃-phenoxy)-thiazol-4-yl |
| 3219. | 2-(p-CF₃-phenoxy)-thiazol-4-yl |
| 3220. | 2-(o-CF₃-phenoxy)-thiazol-4-yl |
| 3221. | 2-(m-CF₃-phenoxy)-thiazol-4-yl |
| 3222. | 2-(p-CF₃-phenoxy)-thiazol-4-yl |
| 3223. | 2-(o-OCH₃-phenoxy)-thiazol-4-yl |
| 3224. | 2-(m-OCH₃-phenoxy)-thiazol-4-yl |
| 3225. | 2-(p-OCH₃-phenoxy)-thiazol-4-yl |
| 3226. | 2-(o-OCF₃-phenoxy)-thiazol-4-yl |
| 3227. | 2-(m-OCF₃-phenoxy)-thiazol-4-yl |
| 3228. | 2-(p-OCF₃-phenoxy)-thiazol-4-yl |
| 3229. | 2-(o-COOCH₃-phenoxy)-thiazol-4-yl |
| 3230. | 2-(m-COOCH₃-phenoxy)-thiazol-4-yl |
| 3231. | 2-(p-COOCH₃-phenoxy)-thiazol-4-yl |
| 3232. | 2-[o-N(CH₃)₂-phenoxy]-thiazol-4-yl |
| 3233. | 2-[m-N(CH₃)₂-phenoxy]-thiazol-4-yl |
| 3234. | 2-[p-N(CH₃)₂-phenoxy]-thiazol-4-yl |
| 3235. | 2-(2,3-dicyanophenoxy)-thiazol-4-yl |
| 3236. | 2-(2,4-dicyanophenoxy)-thiazol-4-yl |
| 3237. | 2-(2,5-dicyanophenoxy)-thiazol-4-yl |
| 3238. | 2-(2,6-dicyanophenoxy)-thiazol-4-yl |
| 3239. | 2-(3,4-dicyanophenoxy)-thiazol-4-yl |
| 3240. | 2-(3,5-dicyanophenoxy)-thiazol-4-yl |
| 3241. | 2-(2,3-difluorophenoxy)-thiazol-4-yl |
| 3242. | 2-(2,4-difluorophenoxy)-thiazol-4-yl |
| 3243. | 2-(2,5-difluorophenoxy)-thiazol-4-yl |
| 3244. | 2-(2,6-difluorophenoxy)-thiazol-4-yl |
| 3245. | 2-(3,4-difluorophenoxy)-thiazol-4-yl |
| 3246. | 2-(3,5-difluorophenoxy)-thiazol-4-yl |
| 3247. | 2-(2,3-dichlorophenoxy)-thiazol-4-yl |
| 3248. | 2-(2,4-dichlorophenoxy)-thiazol-4-yl |
| 3249. | 2-(2,5-dichlorophenoxy)-thiazol-4-yl |
| 3250. | 2-(2,6-dichlorophenoxy)-thiazol-4-yl |
| 3251. | 2-(3,4-dichlorophenoxy)-thiazol-4-yl |
| 3252. | 2-(3,5-dichlorophenoxy)-thiazol-4-yl |
| 3253. | 2-(2,3-dibromophenoxy)-thiazol-4-yl |
| 3254. | 2-(2,4-dibromophenoxy)-thiazol-4-yl |
| 3255. | 2-(2,5-dibromophenoxy)-thiazol-4-yl |
| 3256. | 2-(2,6-dibromophenoxy)-thiazol-4-yl |
| 3257. | 2-(3,4-dibromophenoxy)-thiazol-4-yl |
| 3258. | 2-(3,5-dibromophenoxy)-thiazol-4-yl |
| 3259. | 2-(2,3-dimethylphenoxy)-thiazol-4-yl |
| 3260. | 2-(2,4-dimethylphenoxy)-thiazol-4-yl |
| 3261. | 2-(2,5-dimethylphenoxy)-thiazol-4-yl |
| 3262. | 2-(2,6-dimethylphenoxy)-thiazol-4-yl |
| 3263. | 2-(3,4-dimethylphenoxy)-thiazol-4-yl |
| 3264. | 2-(3,5-dimethylphenoxy)-thiazol-4-yl |
| 3265. | 2-[2,3-di(trifluoromethyl)phenoxy]-thiazol-4-yl |
| 3266. | 2-[2,4-di(trifluoromethyl)phenoxy]-thiazol-4-yl |
| 3267. | 2-[2,5-di(trifluoromethyl)phenoxy]-thiazol-4-yl |
| 3268. | 2-[2,6-di(trifluoromethyl)phenoxy]-thiazol-4-yl |
| 3269. | 2-[3,4-di(trifluoromethyl)phenoxy]-thiazol-4-yl |
| 3270. | 2-[3,5-di(trifluoromethyl)phenoxy]-thiazol-4-yl |
| 3271. | 2-(2,3-dimethoxyphenoxy)-thiazol-4-yl |
| 3272. | 2-(2,4-dimethoxyphenoxy)-thiazol-4-yl |
| 3273. | 2-(2,5-dimethoxyphenoxy)-thiazol-4-yl |
| 3274. | 2-(2,6-dimethoxyphenoxy)-thiazol-4-yl |
| 3275. | 2-(3,4-dimethoxyphenoxy)-thiazol-4-yl |
| 3276. | 2-(3,5-dimethoxyphenoxy)-thiazol-4-yl |
| 3277. | 1-(o-CN-phenyl)-1H-pyrrol-3-yl |
| 3278. | 1-(m-CN-phenyl)-1H-pyrrol-3-yl |
| 3279. | 1-(p-CN-phenyl)-1H-pyrrol-3-yl |
| 3280. | 1-(o-NO₂-phenyl)-1H-pyrrol-3-yl |

TABLE A-continued

| no. | R³-A- |
|---|---|
| 3281. | 1-(m-NO₂-phenyl)-1H-pyrrol-3-yl |
| 3282. | 1-(p-NO₂-phenyl)-1H-pyrrol-3-yl |
| 3283. | 1-(o-F-phenyl)-1H-pyrrol-3-yl |
| 3284. | 1-(m-F-phenyl)-1H-pyrrol-3-yl |
| 3285. | 1-(p-F-phenyl)-1H-pyrrol-3-yl |
| 3286. | 1-(o-Cl-phenyl)-1H-pyrrol-3-yl |
| 3287. | 1-(m-Cl-phenyl)-1H-pyrrol-3-yl |
| 3288. | 1-(p-Cl-phenyl)-1H-pyrrol-3-yl |
| 3289. | 1-(o-Br-phenyl)-1H-pyrrol-3-yl |
| 3290. | 1-(m-Br-phenyl)-1H-pyrrol-3-yl |
| 3291. | 1-(p-Br-phenyl)-1H-pyrrol-3-yl |
| 3292. | 1-(o-CH₃-phenyl)-1H-pyrrol-3-yl |
| 3293. | 1-(m-CH₃-phenyl)-1H-pyrrol-3-yl |
| 3294. | 1-(p-CH₃-phenyl)-1H-pyrrol-3-yl |
| 3295. | 1-(o-CF₃-phenyl)-1H-pyrrol-3-yl |
| 3296. | 1-(m-CF₃-phenyl)-1H-pyrrol-3-yl |
| 3297. | 1-(p-CF₃-phenyl)-1H-pyrrol-3-yl |
| 3298. | 1-(o-CF₃-phenyl)-1H-pyrrol-3-yl |
| 3299. | 1-(m-CF₃-phenyl)-1H-pyrrol-3-yl |
| 3300. | 1-(p-CF₃-phenyl)-1H-pyrrol-3-yl |
| 3301. | 1-(o-OCH₃-phenyl)-1H-pyrrol-3-yl |
| 3302. | 1-(m-OCH₃-phenyl)-1H-pyrrol-3-yl |
| 3303. | 1-(p-OCH₃-phenyl)-1H-pyrrol-3-yl |
| 3304. | 1-(o-OCF₃-phenyl)-1H-pyrrol-3-yl |
| 3305. | 1-(m-OCF₃-phenyl)-1H-pyrrol-3-yl |
| 3306. | 1-(p-OCF₃-phenyl)-1H-pyrrol-3-yl |
| 3307. | 1-(o-COOCH₃-phenyl)-1H-pyrrol-3-yl |
| 3308. | 1-(m-COOCH₃-phenyl)-1H-pyrrol-3-yl |
| 3309. | 1-(p-COOCH₃-phenyl)-1H-pyrrol-3-yl |
| 3310. | 1-[o-N(CH₃)₂-phenyl]-1H-pyrrol-3-yl |
| 3311. | 1-[m-N(CH₃)₂-phenyl]-1H-pyrrol-3-yl |
| 3312. | 1-[p-N(CH₃)₂-phenyl]-1H-pyrrol-3-yl |
| 3313. | 1-(2,3-dicyanophenyl)-1H-pyrrol-3-yl |
| 3314. | 1-(2,4-dicyanophenyl)-1H-pyrrol-3-yl |
| 3315. | 1-(2,5-dicyanophenyl)-1H-pyrrol-3-yl |
| 3316. | 1-(2,6-dicyanophenyl)-1H-pyrrol-3-yl |
| 3317. | 1-(3,4-dicyanophenyl)-1H-pyrrol-3-yl |
| 3318. | 1-(3,5-dicyanophenyl)-1H-pyrrol-3-yl |
| 3319. | 1-(2,3-difluorophenyl)-1H-pyrrol-3-yl |
| 3320. | 1-(2,4-difluorophenyl)-1H-pyrrol-3-yl |
| 3321. | 1-(2,5-difluorophenyl)-1H-pyrrol-3-yl |
| 3322. | 1-(2,6-difluorophenyl)-1H-pyrrol-3-yl |
| 3323. | 1-(3,4-difluorophenyl)-1H-pyrrol-3-yl |
| 3324. | 1-(3,5-difluorophenyl)-1H-pyrrol-3-yl |
| 3325. | 1-(2,3-dichlorophenyl)-1H-pyrrol-3-yl |
| 3326. | 1-(2,4-dichlorophenyl)-1H-pyrrol-3-yl |
| 3327. | 1-(2,5-dichlorophenyl)-1H-pyrrol-3-yl |
| 3328. | 1-(2,6-dichlorophenyl)-1H-pyrrol-3-yl |
| 3329. | 1-(3,4-dichlorophenyl)-1H-pyrrol-3-yl |
| 3330. | 1-(3,5-dichlorophenyl)-1H-pyrrol-3-yl |
| 3331. | 1-(2,3-dibromophenyl)-1H-pyrrol-3-yl |
| 3332. | 1-(2,4-dibromophenyl)-1H-pyrrol-3-yl |
| 3333. | 1-(2,5-dibromophenyl)-1H-pyrrol-3-yl |
| 3334. | 1-(2,6-dibromophenyl)-1H-pyrrol-3-yl |
| 3335. | 1-(3,4-dibromophenyl)-1H-pyrrol-3-yl |
| 3336. | 1-(3,5-dibromophenyl)-1H-pyrrol-3-yl |
| 3337. | 1-(2,3-dimethylphenyl)-1H-pyrrol-3-yl |
| 3338. | 1-(2,4-dimethylphenyl)-1H-pyrrol-3-yl |
| 3339. | 1-(2,5-dimethylphenyl)-1H-pyrrol-3-yl |
| 3340. | 1-(2,6-dimethylphenyl)-1H-pyrrol-3-yl |
| 3341. | 1-(3,4-dimethylphenyl)-1H-pyrrol-3-yl |
| 3342. | 1-(3,5-dimethylphenyl)-1H-pyrrol-3-yl |
| 3343. | 1-[2,3-di(trifluoromethyl)phenyl]-1H-pyrrol-3-yl |
| 3344. | 1-[2,4-di(trifluoromethyl)phenyl]-1H-pyrrol-3-yl |
| 3345. | 1-[2,5-di(trifluoromethyl)phenyl]-1H-pyrrol-3-yl |
| 3346. | 1-[2,6-di(trifluoromethyl)phenyl]-1H-pyrrol-3-yl |
| 3347. | 1-[3,4-di(trifluoromethyl)phenyl]-1H-pyrrol-3-yl |
| 3348. | 1-[3,5-di(trifluoromethyl)phenyl]-1H-pyrrol-3-yl |
| 3349. | 1-(2,3-dimethoxyphenyl)-1H-pyrrol-3-yl |
| 3350. | 1-(2,4-dimethoxyphenyl)-1H-pyrrol-3-yl |
| 3351. | 1-(2,5-dimethoxyphenyl)-1H-pyrrol-3-yl |
| 3352. | 1-(2,6-dimethoxyphenyl)-1H-pyrrol-3-yl |
| 3353. | 1-(3,4-dimethoxyphenyl)-1H-pyrrol-3-yl |
| 3354. | 1-(3,5-dimethoxyphenyl)-1H-pyrrol-3-yl |
| 3355. | 1-(o-CN-phenoxy)-1H-pyrrol-3-yl |
| 3356. | 1-(m-CN-phenoxy)-1H-pyrrol-3-yl |
| 3357. | 1-(p-CN-phenoxy)-1H-pyrrol-3-yl |
| 3358. | 1-(o-NO₂-phenoxy)-1H-pyrrol-3-yl |
| 3359. | 1-(m-NO₂-phenoxy)-1H-pyrrol-3-yl |
| 3360. | 1-(p-NO₂-phenoxy)-1H-pyrrol-3-yl |
| 3361. | 1-(o-F-phenoxy)-1H-pyrrol-3-yl |
| 3362. | 1-(m-F-phenoxy)-1H-pyrrol-3-yl |
| 3363. | 1-(p-F-phenoxy)-1H-pyrrol-3-yl |
| 3364. | 1-(o-Cl-phenoxy)-1H-pyrrol-3-yl |
| 3365. | 1-(m-Cl-phenoxy)-1H-pyrrol-3-yl |
| 3366. | 1-(p-Cl-phenoxy)-1H-pyrrol-3-yl |
| 3367. | 1-(o-Br-phenoxy)-1H-pyrrol-3-yl |
| 3368. | 1-(m-Br-phenoxy)-1H-pyrrol-3-yl |
| 3369. | 1-(p-Br-phenoxy)-1H-pyrrol-3-yl |
| 3370. | 1-(o-CH₃-phenoxy)-1H-pyrrol-3-yl |
| 3371. | 1-(m-CH₃-phenoxy)-1H-pyrrol-3-yl |
| 3372. | 1-(p-CH₃-phenoxy)-1H-pyrrol-3-yl |
| 3373. | 1-(o-CF₃-phenoxy)-1H-pyrrol-3-yl |
| 3374. | 1-(m-CF₃-phenoxy)-1H-pyrrol-3-yl |
| 3375. | 1-(p-CF₃-phenoxy)-1H-pyrrol-3-yl |
| 3376. | 1-(o-CF₃-phenoxy)-1H-pyrrol-3-yl |
| 3377. | 1-(m-CF₃-phenoxy)-1H-pyrrol-3-yl |
| 3378. | 1-(p-CF₃-phenoxy)-1H-pyrrol-3-yl |
| 3379. | 1-(o-OCH₃-phenoxy)-1H-pyrrol-3-yl |
| 3380. | 1-(m-OCH₃-phenoxy)-1H-pyrrol-3-yl |
| 3381. | 1-(p-OCH₃-phenoxy)-1H-pyrrol-3-yl |

TABLE A-continued

| no. | R³-A- |
|---|---|
| 3382. | 1-(o-OCF₃-phenoxy)-1H-pyrrol-3-yl |
| 3383. | 1-(m-OCF₃-phenoxy)-1H-pyrrol-3-yl |
| 3384. | 1-(p-OCF₃-phenoxy)-1H-pyrrol-3-yl |
| 3385. | 1-(o-COOCH₃-phenoxy)-1H-pyrrol-3-yl |
| 3386. | 1-(m-COOCH₃-phenoxy)-1H-pyrrol-3-yl |
| 3387. | 1-(p-COOCH₃-phenoxy)-1H-pyrrol-3-yl |
| 3388. | 1-[o-N(CH₃)₂-phenoxy]-1H-pyrrol-3-yl |
| 3389. | 1-[m-N(CH₃)₂-phenoxy]-1H-pyrrol-3-yl |
| 3390. | 1-[p-N(CH₃)₂-phenoxy]-1H-pyrrol-3-yl |
| 3391. | 1-(2,3-dicyanophenoxy)-1H-pyrrol-3-yl |
| 3392. | 1-(2,4-dicyanophenoxy)-1H-pyrrol-3-yl |
| 3393. | 1-(2,5-dicyanophenoxy)-1H-pyrrol-3-yl |
| 3394. | 1-(2,6-dicyanophenoxy)-1H-pyrrol-3-yl |
| 3395. | 1-(3,4-dicyanophenoxy)-1H-pyrrol-3-yl |
| 3396. | 1-(3,5-dicyanophenoxy)-1H-pyrrol-3-yl |
| 3397. | 1-(2,3-difluorophenoxy)-1H-pyrrol-3-yl |
| 3398. | 1-(2,4-difluorophenoxy)-1H-pyrrol-3-yl |
| 3399. | 1-(2,5-difluorophenoxy)-1H-pyrrol-3-yl |
| 3400. | 1-(2,6-difluorophenoxy)-1H-pyrrol-3-yl |
| 3401. | 1-(3,4-difluorophenoxy)-1H-pyrrol-3-yl |
| 3402. | 1-(3,5-difluorophenoxy)-1H-pyrrol-3-yl |
| 3403. | 1-(2,3-dichlorophenoxy)-1H-pyrrol-3-yl |
| 3404. | 1-(2,4-dichlorophenoxy)-1H-pyrrol-3-yl |
| 3405. | 1-(2,5-dichlorophenoxy)-1H-pyrrol-3-yl |
| 3406. | 1-(2,6-dichlorophenoxy)-1H-pyrrol-3-yl |
| 3407. | 1-(3,4-dichlorophenoxy)-1H-pyrrol-3-yl |
| 3408. | 1-(3,5-dichlorophenoxy)-1H-pyrrol-3-yl |
| 3409. | 1-(2,3-dibromophenoxy)-1H-pyrrol-3-yl |
| 3410. | 1-(2,4-dibromophenoxy)-1H-pyrrol-3-yl |
| 3411. | 1-(2,5-dibromophenoxy)-1H-pyrrol-3-yl |
| 3412. | 1-(2,6-dibromophenoxy)-1H-pyrrol-3-yl |
| 3413. | 1-(3,4-dibromophenoxy)-1H-pyrrol-3-yl |
| 3414. | 1-(3,5-dibromophenoxy)-1H-pyrrol-3-yl |
| 3415. | 1-(2,3-dimethylphenoxy)-1H-pyrrol-3-yl |
| 3416. | 1-(2,4-dimethylphenoxy)-1H-pyrrol-3-yl |
| 3417. | 1-(2,5-dimethylphenoxy)-1H-pyrrol-3-yl |
| 3418. | 1-(2,6-dimethylphenoxy)-1H-pyrrol-3-yl |
| 3419. | 1-(3,4-dimethylphenoxy)-1H-pyrrol-3-yl |
| 3420. | 1-(3,5-dimethylphenoxy)-1H-pyrrol-3-yl |
| 3421. | 1-[2,3-di(trifluoromethyl)phenoxy]-1H-pyrrol-3-yl |
| 3422. | 1-[2,4-di(trifluoromethyl)phenoxy]-1H-pyrrol-3-yl |
| 3423. | 1-[2,5-di(trifluoromethyl)phenoxy]-1H-pyrrol-3-yl |
| 3424. | 1-[2,6-di(trifluoromethyl)phenoxy]-1H-pyrrol-3-yl |
| 3425. | 1-[3,4-di(trifluoromethyl)phenoxy]-1H-pyrrol-3-yl |
| 3426. | 1-[3,5-di(trifluoromethyl)phenoxy]-1H-pyrrol-3-yl |
| 3427. | 1-(2,3-dimethoxyphenoxy)-1H-pyrrol-3-yl |
| 3428. | 1-(2,4-dimethoxyphenoxy)-1H-pyrrol-3-yl |
| 3429. | 1-(2,5-dimethoxyphenoxy)-1H-pyrrol-3-yl |
| 3430. | 1-(2,6-dimethoxyphenoxy)-1H-pyrrol-3-yl |
| 3431. | 1-(3,4-dimethoxyphenoxy)-1H-pyrrol-3-yl |
| 3432. | 1-(3,5-dimethoxyphenoxy)-1H-pyrrol-3-yl |
| 3433. | 1-methyl-5-(o-CN-phenyl)-1H-pyrrol-3-yl |
| 3434. | 1-methyl-5-(m-CN-phenyl)-1H-pyrrol-3-yl |
| 3435. | 1-methyl-5-(p-CN-phenyl)-1H-pyrrol-3-yl |
| 3436. | 1-methyl-5-(o-NO₂-phenyl)-1H-pyrrol-3-yl |
| 3437. | 1-methyl-5-(m-NO₂-phenyl)-1H-pyrrol-3-yl |
| 3438. | 1-methyl-5-(p-NO₂-phenyl)-1H-pyrrol-3-yl |
| 3439. | 1-methyl-5-(o-F-phenyl)-1H-pyrrol-3-yl |
| 3440. | 1-methyl-5-(m-F-phenyl)-1H-pyrrol-3-yl |
| 3441. | 1-methyl-5-(p-F-phenyl)-1H-pyrrol-3-yl |
| 3442. | 1-methyl-5-(o-Cl-phenyl)-1H-pyrrol-3-yl |
| 3443. | 1-methyl-5-(m-Cl-phenyl)-1H-pyrrol-3-yl |
| 3444. | 1-methyl-5-(p-Cl-phenyl)-1H-pyrrol-3-yl |
| 3445. | 1-methyl-5-(o-Br-phenyl)-1H-pyrrol-3-yl |
| 3446. | 1-methyl-5-(m-Br-phenyl)-1H-pyrrol-3-yl |
| 3447. | 1-methyl-5-(p-Br-phenyl)-1H-pyrrol-3-yl |
| 3448. | 1-methyl-5-(o-CH₃-phenyl)-1H-pyrrol-3-yl |
| 3449. | 1-methyl-5-(m-CH₃-phenyl)-1H-pyrrol-3-yl |
| 3450. | 1-methyl-5-(p-CH₃-phenyl)-1H-pyrrol-3-yl |
| 3451. | 1-methyl-5-(o-CF₃-phenyl)-1H-pyrrol-3-yl |
| 3452. | 1-methyl-5-(m-CF₃-phenyl)-1H-pyrrol-3-yl |
| 3453. | 1-methyl-5-(p-CF₃-phenyl)-1H-pyrrol-3-yl |
| 3454. | 1-methyl-5-(o-CF₃-phenyl)-1H-pyrrol-3-yl |
| 3455. | 1-methyl-5-(m-CF₃-phenyl)-1H-pyrrol-3-yl |
| 3456. | 1-methyl-5-(p-CF₃-phenyl)-1H-pyrrol-3-yl |
| 3457. | 1-methyl-5-(o-OCH₃-phenyl)-1H-pyrrol-3-yl |
| 3458. | 1-methyl-5-(m-OCH₃-phenyl)-1H-pyrrol-3-yl |
| 3459. | 1-methyl-5-(p-OCH₃-phenyl)-1H-pyrrol-3-yl |

TABLE A-continued

| no. | R³-A- |
|---|---|
| 3460. | 1-methyl-5-(o-OCF₃-phenyl)-1H-pyrrol-3-yl |
| 3461. | 1-methyl-5-(m-OCF₃-phenyl)-1H-pyrrol-3-yl |
| 3462. | 1-methyl-5-(p-OCF₃-phenyl)-1H-pyrrol-3-yl |
| 3463. | 1-methyl-5-(o-COOCH₃-phenyl)-1H-pyrrol-3-yl |
| 3464. | 1-methyl-5-(m-COOCH₃-phenyl)-1H-pyrrol-3-yl |
| 3465. | 1-methyl-5-(p-COOCH₃-phenyl)-1H-pyrrol-3-yl |
| 3466. | 1-methyl-5-[o-N(CH₃)₂-phenyl]-1H-pyrrol-3-yl |
| 3467. | 1-methyl-5-[m-N(CH₃)₂-phenyl]-1H-pyrrol-3-yl |
| 3468. | 1-methyl-5-[p-N(CH₃)₂-phenyl]-1H-pyrrol-3-yl |
| 3469. | 1-methyl-5-(2,3-dicyanophenyl)-1H-pyrrol-3-yl |
| 3470. | 1-methyl-5-(2,4-dicyanophenyl)-1H-pyrrol-3-yl |
| 3471. | 1-methyl-5-(2,5-dicyanophenyl)-1H-pyrrol-3-yl |
| 3472. | 1-methyl-5-(2,6-dicyanophenyl)-1H-pyrrol-3-yl |
| 3473. | 1-methyl-5-(3,4-dicyanphenyl)-1H-pyrrol-3-yl |
| 3474. | 1-methyl-5-(3,5-dicyanophenyl)-1H-pyrrol-3-yl |
| 3475. | 1-methyl-5-(2,3-difluorophenyl)-1H-pyrrol-3-yl |
| 3476. | 1-methyl-5-(2,4-difluorophenyl)-1H-pyrrol-3-yl |
| 3477. | 1-methyl-5-(2,5-difluorophenyl)-1H-pyrrol-3-yl |
| 3478. | 1-methyl-5-(2,6-difluorophenyl)-1H-pyrrol-3-yl |
| 3479. | 1-methyl-5-(3,4-difluorophenyl)-1H-pyrrol-3-yl |
| 3480. | 1-methyl-5-(3,5-difluorophenyl)-1H-pyrrol-3-yl |
| 3481. | 1-methyl-5-(2,3-dichlorophenyl)-1H-pyrrol-3-yl |
| 3482. | 1-methyl-5-(2,4-dichlorophenyl)-1H-pyrrol-3-yl |
| 3483. | 1-methyl-5-(2,5-dichlorophenyl)-1H-pyrrol-3-yl |
| 3484. | 1-methyl-5-(2,6-dichlorophenyl)-1H-pyrrol-3-yl |
| 3485. | 1-methyl-5-(3,4-dichlorophenyl)-1H-pyrrol-3-yl |
| 3486. | 1-methyl-5-(3,5-dichlorophenyl)-1H-pyrrol-3-yl |
| 3487. | 1-methyl-5-(2,3-dibromophenyl)-1H-pyrrol-3-yl |
| 3488. | 1-methyl-5-(2,4-dibromophenyl)-1H-pyrrol-3-yl |
| 3489. | 1-methyl-5-(2,5-dibromophenyl)-1H-pyrrol-3-yl |
| 3490. | 1-methyl-5-(2,6-dibromophenyl)-1H-pyrrol-3-yl |
| 3491. | 1-methyl-5-(3,4-dibromophenyl)-1H-pyrrol-3-yl |
| 3492. | 1-methyl-5-(3,5-dibromophenyl)-1H-pyrrol-3-yl |
| 3493. | 1-methyl-5-(2,3-dimethylphenyl)-1H-pyrrol-3-yl |
| 3494. | 1-methyl-5-(2,4-dimethylphenyl)-1H-pyrrol-3-yl |
| 3495. | 1-methyl-5-(2,5-dimethylphenyl)-1H-pyrrol-3-yl |
| 3496. | 1-methyl-5-(2,6-dimethylphenyl)-1H-pyrrol-3-yl |
| 3497. | 1-methyl-5-(3,4-dimethylphenyl)-1H-pyrrol-3-yl |
| 3498. | 1-methyl-5-(3,5-dimethylphenyl)-1H-pyrrol-3-yl |
| 3499. | 1-methyl-5-[2,3-di(trifluoromethyl)phenyl]-1H-pyrrol-3-yl |
| 3500. | 1-methyl-5-[2,4-di(trifluoromethyl)phenyl]-1H-pyrrol-3-yl |
| 3501. | 1-methyl-5-[2,5-di(trifluoromethyl)phenyl]-1H-pyrrol-3-yl |
| 3502. | 1-methyl-5-[2,6-di(trifluoromethyl)phenyl]-1H-pyrrol-3-yl |
| 3503. | 1-methyl-5-[3,4-di(trifluoromethyl)phenyl]-1H-pyrrol-3-yl |
| 3504. | 1-methyl-5-[3,5-di(trifluoromethyl)phenyl]-1H-pyrrol-3-yl |
| 3505. | 1-methyl-5-(2,3-dimethoxyphenyl)-1H-pyrrol-3-yl |
| 3506. | 1-methyl-5-(2,4-dimethoxyphenyl)-1H-pyrrol-3-yl |
| 3507. | 1-methyl-5-(2,5-dimethoxyphenyl)-1H-pyrrol-3-yl |
| 3508. | 1-methyl-5-(2,6-dimethoxyphenyl)-1H-pyrrol-3-yl |
| 3509. | 1-methyl-5-(3,4-dimethoxyphenyl)-1H-pyrrol-3-yl |
| 3510. | 1-methyl-5-(3,5-dimethoxyphenyl)-1H-pyrrol-3-yl |
| 3511. | 1-methyl-5-(o-CN-phenoxy)-1H-pyrrol-3-yl |
| 3512. | 1-methyl-5-(m-CN-phenoxy)-1H-pyrrol-3-yl |
| 3513. | 1-methyl-5-(p-CN-phenoxy)-1H-pyrrol-3-yl |
| 3514. | 1-methyl-5-(o-NO₂-phenoxy)-1H-pyrrol-3-yl |
| 3515. | 1-methyl-5-(m-NO₂-phenoxy)-1H-pyrrol-3-yl |
| 3516. | 1-methyl-5-(p-NO₂-phenoxy)-1H-pyrrol-3-yl |
| 3517. | 1-methyl-5-(o-F-phenoxy)-1H-pyrrol-3-yl |
| 3518. | 1-methyl-5-(m-F-phenoxy)-1H-pyrrol-3-yl |
| 3519. | 1-methyl-5-(p-F-phenoxy)-1H-pyrrol-3-yl |
| 3520. | 1-methyl-5-(o-Cl-phenoxy)-1H-pyrrol-3-yl |
| 3521. | 1-methyl-5-(m-Cl-phenoxy)-1H-pyrrol-3-yl |
| 3522. | 1-methyl-5-(p-Cl-phenoxy)-1H-pyrrol-3-yl |
| 3523. | 1-methyl-5-(o-Br-phenoxy)-1H-pyrrol-3-yl |
| 3524. | 1-methyl-5-(m-Br-phenoxy)-1H-pyrrol-3-yl |
| 3525. | 1-methyl-5-(p-Br-phenoxy)-1H-pyrrol-3-yl |
| 3526. | 1-methyl-5-(o-CH₃-phenoxy)-1H-pyrrol-3-yl |
| 3527. | 1-methyl-5-(m-CH₃-phenoxy)-1H-pyrrol-3-yl |
| 3528. | 1-methyl-5-(p-CH₃-phenoxy)-1H-pyrrol-3-yl |
| 3529. | 1-methyl-5-(o-CF₃-phenoxy)-1H-pyrrol-3-yl |
| 3530. | 1-methyl-5-(m-CF₃-phenoxy)-1H-pyrrol-3-yl |
| 3531. | 1-methyl-5-(p-CF₃-phenoxy)-1H-pyrrol-3-yl |
| 3532. | 1-methyl-5-(o-CF₃-phenoxy)-1H-pyrrol-3-yl |
| 3533. | 1-methyl-5-(m-CF₃-phenoxy)-1H-pyrrol-3-yl |
| 3534. | 1-methyl-5-(p-CF₃-phenoxy)-1H-pyrrol-3-yl |
| 3535. | 1-methyl-5-(o-OCH₃-phenoxy)-1H-pyrrol-3-yl |
| 3536. | 1-methyl-5-(m-OCH₃-phenoxy)-1H-pyrrol-3-yl |
| 3537. | 1-methyl-5-(p-OCH₃-phenoxy)-1H-pyrrol-3-yl |

TABLE A-continued

| no. | R³-A- |
|---|---|
| 3538. | 1-methyl-5-(o-OCF₃-phenoxy)-1H-pyrrol-3-yl |
| 3539. | 1-methyl-5-(m-OCF₃-phenoxy)-1H-pyrrol-3-yl |
| 3540. | 1-methyl-5-(p-OCF₃-phenoxy)-1H-pyrrol-3-yl |
| 3541. | 1-methyl-5-(o-COOCH₃-phenoxy)-1H-pyrrol-3-yl |
| 3542. | 1-methyl-5-(m-COOCH₃-phenoxy)-1H-pyrrol-3-yl |
| 3543. | 1-methyl-5-(p-COOCH₃-phenoxy)-1H-pyrrol-3-yl |
| 3544. | 1-methyl-5-[o-N(CH₃)₂-phenoxy]-1H-pyrrol-3-yl |
| 3545. | 1-methyl-5-[m-N(CH₃)₂-phenoxy]-1H-pyrrol-3-yl |
| 3546. | 1-methyl-5-[p-N(CH₃)₂-phenoxy]-1H-pyrrol-3-yl |
| 3547. | 1-methyl-5-(2,3-dicyanophenoxy)-1H-pyrrol-3-yl |
| 3548. | 1-methyl-5-(2,4-dicyanophenoxy)-1H-pyrrol-3-yl |
| 3549. | 1-methyl-5-(2,5-dicyanophenoxy)-1H-pyrrol-3-yl |
| 3550. | 1-methyl-5-(2,6-dicyanophenoxy)-1H-pyrrol-3-yl |
| 3551. | 1-methyl-5-(3,4-dicyanophenoxy)-1H-pyrrol-3-yl |
| 3552. | 1-methyl-5-(3,5-dicyanophenoxy)-1H-pyrrol-3-yl |
| 3553. | 1-methyl-5-(2,3-difluorophenoxy)-1H-pyrrol-3-yl |
| 3554. | 1-methyl-5-(2,4-difluorophenoxy)-1H-pyrrol-3-yl |
| 3555. | 1-methyl-5-(2,5-difluorophenoxy)-1H-pyrrol-3-yl |
| 3556. | 1-methyl-5-(2,6-difluorophenoxy)-1H-pyrrol-3-yl |
| 3557. | 1-methyl-5-(3,4-difluorophenoxy)-1H-pyrrol-3-yl |
| 3558. | 1-methyl-5-(3,5-difluorophenoxy)-1H-pyrrol-3-yl |
| 3559. | 1-methyl-5-(2,3-dichlorophenoxy)-1H-pyrrol-3-yl |
| 3560. | 1-methyl-5-(2,4-dichlorophenoxy)-1H-pyrrol-3-yl |
| 3561. | 1-methyl-5-(2,5-dichlorophenoxy)-1H-pyrrol-3-yl |
| 3562. | 1-methyl-5-(2,6-dichlorophenoxy)-1H-pyrrol-3-yl |
| 3563. | 1-methyl-5-(3,4-dichlorophenoxy)-1H-pyrrol-3-yl |
| 3564. | 1-methyl-5-(3,5-dichlorophenoxy)-1H-pyrrol-3-yl |
| 3565. | 1-methyl-5-(2,3-dibromophenoxy)-1H-pyrrol-3-yl |
| 3566. | 1-methyl-5-(2,4-dibromophenoxy)-1H-pyrrol-3-yl |
| 3567. | 1-methyl-5-(2,5-dibromophenoxy)-1H-pyrrol-3-yl |
| 3568. | 1-methyl-5-(2,6-dibromophenoxy)-1H-pyrrol-3-yl |
| 3569. | 1-methyl-5-(3,4-dibromophenoxy)-1H-pyrrol-3-yl |
| 3570. | 1-methyl-5-(3,5-dibromophenoxy)-1H-pyrrol-3-yl |
| 3571. | 1-methyl-5-(2,3-dimethylphenoxy)-1H-pyrrol-3-yl |
| 3572. | 1-methyl-5-(2,4-dimethylphenoxy)-1H-pyrrol-3-yl |
| 3573. | 1-methyl-5-(2,5-dimethylphenoxy)-1H-pyrrol-3-yl |
| 3574. | 1-methyl-5-(2,6-dimethylphenoxy)-1H-pyrrol-3-yl |
| 3575. | 1-methyl-5-(3,4-dimethylphenoxy)-1H-pyrrol-3-yl |
| 3576. | 1-methyl-5-(3,5-dimethylphenoxy)-1H-pyrrol-3-yl |
| 3577. | 1-methyl-5-[2,3-di(trifluoromethyl)phenoxy]-1H-pyrrol-3-yl |
| 3578. | 1-methyl-5-[2,4-di(trifluoromethyl)phenoxy]-1H-pyrrol-3-yl |
| 3579. | 1-methyl-5-[2,5-di(trifluoromethyl)phenoxy]-1H-pyrrol-3-yl |
| 3580. | 1-methyl-5-[2,6-di(trifluoromethyl)phenoxy]-1H-pyrrol-3-yl |
| 3581. | 1-methyl-5-[3,4-di(trifluoromethyl)phenoxy]-1H-pyrrol-3-yl |
| 3582. | 1-methyl-5-[3,5-di(trifluoromethyl)phenoxy]-1H-pyrrol-3-yl |
| 3583. | 1-methyl-5-(2,3-dimethoxyphenoxy)-1H-pyrrol-3-yl |
| 3584. | 1-methyl-5-(2,4-dimethoxyphenoxy)-1H-pyrrol-3-yl |
| 3585. | 1-methyl-5-(2,5-dimethoxyphenoxy)-1H-pyrrol-3-yl |
| 3586. | 1-methyl-5-(2,6-dimethoxyphenoxy)-1H-pyrrol-3-yl |
| 3587. | 1-methyl-5-(3,4-dimethoxyphenoxy)-1H-pyrrol-3-yl |
| 3588. | 1-methyl-5-(3,5-dimethoxyphenoxy)-1H-pyrrol-3-yl |
| 3589. | 1-methyl-5-(o-CN-phenyl)-1H-pyrrol-2-yl |
| 3590. | 1-methyl-5-(m-CN-phenyl)-1H-pyrrol-2-yl |
| 3591. | 1-methyl-5-(p-CN-phenyl)-1H-pyrrol-2-yl |
| 3592. | 1-methyl-5-(o-NO₂-phenyl)-1H-pyrrol-2-yl |
| 3593. | 1-methyl-5-(m-NO₂-phenyl)-1H-pyrrol-2-yl |
| 3594. | 1-methyl-5-(p-NO₂-phenyl)-1H-pyrrol-2-yl |
| 3595. | 1-methyl-5-(o-F-phenyl)-1H-pyrrol-2-yl |
| 3596. | 1-methyl-5-(m-F-phenyl)-1H-pyrrol-2-yl |
| 3597. | 1-methyl-5-(p-F-phenyl)-1H-pyrrol-2-yl |
| 3598. | 1-methyl-5-(o-Cl-phenyl)-1H-pyrrol-2-yl |
| 3599. | 1-methyl-5-(m-Cl-phenyl)-1H-pyrrol-2-yl |
| 3600. | 1-methyl-5-(p-Cl-phenyl)-1H-pyrrol-2-yl |
| 3601. | 1-methyl-5-(o-Br-phenyl)-1H-pyrrol-2-yl |
| 3602. | 1-methyl-5-(m-Br-phenyl)-1H-pyrrol-2-yl |
| 3603. | 1-methyl-5-(p-Br-phenyl)-1H-pyrrol-2-yl |
| 3604. | 1-methyl-5-(o-CH₃-phenyl)-1H-pyrrol-2-yl |
| 3605. | 1-methyl-5-(m-CH₃-phenyl)-1H-pyrrol-2-yl |
| 3606. | 1-methyl-5-(p-CH₃-phenyl)-1H-pyrrol-2-yl |
| 3607. | 1-methyl-5-(o-CF₃-phenyl)-1H-pyrrol-2-yl |
| 3608. | 1-methyl-5-(m-CF₃-phenyl)-1H-pyrrol-2-yl |
| 3609. | 1-methyl-5-(p-CF₃-phenyl)-1H-pyrrol-2-yl |
| 3610. | 1-methyl-5-(o-CF₃-phenyl)-1H-pyrrol-2-yl |
| 3611. | 1-methyl-5-(m-CF₃-phenyl)-1H-pyrrol-2-yl |
| 3612. | 1-methyl-5-(p-CF₃-phenyl)-1H-pyrrol-2-yl |
| 3613. | 1-methyl-5-(o-OCH₃-phenyl)-1H-pyrrol-2-yl |
| 3614. | 1-methyl-5-(m-OCH₃-phenyl)-1H-pyrrol-2-yl |

TABLE A-continued

| no. | R³-A- |
|---|---|
| 3615. | 1-methyl-5-(p-OCH₃-phenyl)-1H-pyrrol-2-yl |
| 3616. | 1-methyl-5-(o-OCF₃-phenyl)-1H-pyrrol-2-yl |
| 3617. | 1-methyl-5-(m-OCF₃-phenyl)-1H-pyrrol-2-yl |
| 3618. | 1-methyl-5-(p-OCF₃-phenyl)-1H-pyrrol-2-yl |
| 3619. | 1-methyl-5-(o-COOCH₃-phenyl)-1H-pyrrol-2-yl |
| 3620. | 1-methyl-5-(m-COOCH₃-phenyl)-1H-pyrrol-2-yl |
| 3621. | 1-methyl-5-(p-COOCH₃-phenyl)-1H-pyrrol-2-yl |
| 3622. | 1-methyl-5-[o-N(CH₃)₂-phenyl]-1H-pyrrol-2-yl |
| 3623. | 1-methyl-5-[m-N(CH₃)₂-phenyl]-1H-pyrrol-2-yl |
| 3624. | 1-methyl-5-[p-N(CH₃)₂-phenyl]-1H-pyrrol-2-yl |
| 3625. | 1-methyl-5-(2,3-dicyanophenyl)-1H-pyrrol-2-yl |
| 3626. | 1-methyl-5-(2,4-dicyanophenyl)-1H-pyrrol-2-yl |
| 3627. | 1-methyl-5-(2,5-dicyanophenyl)-1H-pyrrol-2-yl |
| 3628. | 1-methyl-5-(2,6-dicyanophenyl)-1H-pyrrol-2-yl |
| 3629. | 1-methyl-5-(3,4-dicyanophenyl)-1H-pyrrol-2-yl |
| 3630. | 1-methyl-5-(3,5-dicyanophenyl)-1H-pyrrol-2-yl |
| 3631. | 1-methyl-5-(2,3-difluorophenyl)-1H-pyrrol-2-yl |
| 3632. | 1-methyl-5-(2,4-difluorophenyl)-1H-pyrrol-2-yl |
| 3633. | 1-methyl-5-(2,5-difluorophenyl)-1H-pyrrol-2-yl |
| 3634. | 1-methyl-5-(2,6-difluorophenyl)-1H-pyrrol-2-yl |
| 3635. | 1-methyl-5-(3,4-difluorophenyl)-1H-pyrrol-2-yl |
| 3636. | 1-methyl-5-(3,5-difluorophenyl)-1H-pyrrol-2-yl |
| 3637. | 1-methyl-5-(2,3-dichlorophenyl)-1H-pyrrol-2-yl |
| 3638. | 1-methyl-5-(2,4-dichlorophenyl)-1H-pyrrol-2-yl |
| 3639. | 1-methyl-5-(2,5-dichlorophenyl)-1H-pyrrol-2-yl |
| 3640. | 1-methyl-5-(2,6-dichlorophenyl)-1H-pyrrol-2-yl |
| 3641. | 1-methyl-5-(3,4-dichlorophenyl)-1H-pyrrol-2-yl |
| 3642. | 1-methyl-5-(3,5-dichlorophenyl)-1H-pyrrol-2-yl |
| 3643. | 1-methyl-5-(2,3-dibromophenyl)-1H-pyrrol-2-yl |
| 3644. | 1-methyl-5-(2,4-dibromophenyl)-1H-pyrrol-2-yl |
| 3645. | 1-methyl-5-(2,5-dibromophenyl)-1H-pyrrol-2-yl |
| 3646. | 1-methyl-5-(2,6-dibromophenyl)-1H-pyrrol-2-yl |
| 3647. | 1-methyl-5-(3,4-dibromophenyl)-1H-pyrrol-2-yl |
| 3648. | 1-methyl-5-(3,5-dibromophenyl)-1H-pyrrol-2-yl |
| 3649. | 1-methyl-5-(2,3-dimethylphenyl)-1H-pyrrol-2-yl |
| 3650. | 1-methyl-5-(2,4-dimethylphenyl)-1H-pyrrol-2-yl |
| 3651. | 1-methyl-5-(2,5-dimethylphenyl)-1H-pyrrol-2-yl |
| 3652. | 1-methyl-5-(2,6-dimethylphenyl)-1H-pyrrol-2-yl |
| 3653. | 1-methyl-5-(3,4-dimethylphenyl)-1H-pyrrol-2-yl |
| 3654. | 1-methyl-5-(3,5-dimethylphenyl)-1H-pyrrol-2-yl |
| 3655. | 1-methyl-5-[2,3-di(trifluoromethyl)phenyl]-1H-pyrrol-2-yl |
| 3656. | 1-methyl-5-[2,4-di(trifluoromethyl)phenyl]-1H-pyrrol-2-yl |
| 3657. | 1-methyl-5-[2,5-di(trifluoromethyl)phenyl]-1H-pyrrol-2-yl |
| 3658. | 1-methyl-5-[2,6-di(trifluoromethyl)phenyl]-1H-pyrrol-2-yl |
| 3659. | 1-methyl-5-[3,4-di(trifluoromethyl)phenyl]-1H-pyrrol-2-yl |
| 3660. | 1-methyl-5-[3,5-di(trifluoromethyl)phenyl]-1H-pyrrol-2-yl |
| 3661. | 1-methyl-5-(2,3-dimethoxyphenyl)-1H-pyrrol-2-yl |
| 3662. | 1-methyl-5-(2,4-dimethoxyphenyl)-1H-pyrrol-2-yl |
| 3663. | 1-methyl-5-(2,5-dimethoxyphenyl)-1H-pyrrol-2-yl |
| 3664. | 1-methyl-5-(2,6-dimethoxyphenyl)-1H-pyrrol-2-yl |
| 3665. | 1-methyl-5-(3,4-dimethoxyphenyl)-1H-pyrrol-2-yl |
| 3666. | 1-methyl-5-(3,5-dimethoxyphenyl)-1H-pyrrol-2-yl |
| 3667. | 1-methyl-5-(o-CN-phenoxy)-1H-pyrrol-2-yl |
| 3668. | 1-methyl-5-(m-CN-phenoxy)-1H-pyrrol-2-yl |
| 3669. | 1-methyl-5-(p-CN-phenoxy)-1H-pyrrol-2-yl |
| 3670. | 1-methyl-5-(o-NO₂-phenoxy)-1H-pyrrol-2-yl |
| 3671. | 1-methyl-5-(m-NO₂-phenoxy)-1H-pyrrol-2-yl |
| 3672. | 1-methyl-5-(p-NO₂-phenoxy)-1H-pyrrol-2-yl |
| 3673. | 1-methyl-5-(o-F-phenoxy)-1H-pyrrol-2-yl |
| 3674. | 1-methyl-5-(m-F-phenoxy)-1H-pyrrol-2-yl |
| 3675. | 1-methyl-5-(p-F-phenoxy)-1H-pyrrol-2-yl |
| 3676. | 1-methyl-5-(o-Cl-phenoxy)-1H-pyrrol-2-yl |
| 3677. | 1-methyl-5-(m-Cl-phenoxy)-1H-pyrrol-2-yl |
| 3678. | 1-methyl-5-(p-Cl-phenoxy)-1H-pyrrol-2-yl |
| 3679. | 1-methyl-5-(o-Br-phenoxy)-1H-pyrrol-2-yl |
| 3680. | 1-methyl-5-(m-Br-phenoxy)-1H-pyrrol-2-yl |
| 3681. | 1-methyl-5-(p-Br-phenoxy)-1H-pyrrol-2-yl |
| 3682. | 1-methyl-5-(o-CH₃-phenoxy)-1H-pyrrol-2-yl |
| 3683. | 1-methyl-5-(m-CH₃-phenoxy)-1H-pyrrol-2-yl |
| 3684. | 1-methyl-5-(p-CH₃-phenoxy)-1H-pyrrol-2-yl |
| 3685. | 1-methyl-5-(o-CF₃-phenoxy)-1H-pyrrol-2-yl |
| 3686. | 1-methyl-5-(m-CF₃-phenoxy)-1H-pyrrol-2-yl |
| 3687. | 1-methyl-5-(p-CF₃-phenoxy)-1H-pyrrol-2-yl |
| 3688. | 1-methyl-5-(o-CF₃-phenoxy)-1H-pyrrol-2-yl |
| 3689. | 1-methyl-5-(m-CF₃-phenoxy)-1H-pyrrol-2-yl |
| 3690. | 1-methyl-5-(p-CF₃-phenoxy)-1H-pyrrol-2-yl |
| 3691. | 1-methyl-5-(o-OCH₃-phenoxy)-1H-pyrrol-2-yl |
| 3692. | 1-methyl-5-(m-OCH₃-phenoxy)-1H-pyrrol-2-yl |

TABLE A-continued

| no. | R³-A- |
|---|---|
| 3693. | 1-methyl-5-(p-OCH₃-phenoxy)-1H-pyrrol-2-yl |
| 3694. | 1-methyl-5-(o-OCF₃-phenoxy)-1H-pyrrol-2-yl |
| 3695. | 1-methyl-5-(m-OCF₃-phenoxy)-1H-pyrrol-2-yl |
| 3696. | 1-methyl-5-(p-OCF₃-phenoxy)-1H-pyrrol-2-yl |
| 3697. | 1-methyl-5-(o-COOCH₃-phenoxy)-1H-pyrrol-2-yl |
| 3698. | 1-methyl-5-(m-COOCH₃-phenoxy)-1H-pyrrol-2-yl |
| 3699. | 1-methyl-5-(p-COOCH₃-phenoxy)-1H-pyrrol-2-yl |
| 3700. | 1-methyl-5-[o-N(CH₃)₂-phenoxy]-1H-pyrrol-2-yl |
| 3701. | 1-methyl-5-[m-N(CH₃)₂-phenoxy]-1H-pyrrol-2-yl |
| 3702. | 1-methyl-5-[p-N(CH₃)₂-phenoxy]-1H-pyrrol-2-yl |
| 3703. | 1-methyl-5-(2,3-dicyanophenoxy)-1H-pyrrol-2-yl |
| 3704. | 1-methyl-5-(2,4-dicyanophenoxy)-1H-pyrrol-2-yl |
| 3705. | 1-methyl-5-(2,5-dicyanophenoxy)-1H-pyrrol-2-yl |
| 3706. | 1-methyl-5-(2,6-dicyanophenoxy)-1H-pyrrol-2-yl |
| 3707. | 1-methyl-5-(3,4-dicyanophenoxy)-1H-pyrrol-2-yl |
| 3708. | 1-methyl-5-(3,5-dicyanophenoxy)-1H-pyrrol-2-yl |
| 3709. | 1-methyl-5-(2,3-difluorophenoxy)-1H-pyrrol-2-yl |
| 3710. | 1-methyl-5-(2,4-difluorophenoxy)-1H-pyrrol-2-yl |
| 3711. | 1-methyl-5-(2,5-difluorophenoxy)-1H-pyrrol-2-yl |
| 3712. | 1-methyl-5-(2,6-difluorophenoxy)-1H-pyrrol-2-yl |
| 3713. | 1-methyl-5-(3,4-difluorophenoxy)-1H-pyrrol-2-yl |
| 3714. | 1-methyl-5-(3,5-difluorophenoxy)-1H-pyrrol-2-yl |
| 3715. | 1-methyl-5-(2,3-dichlorophenoxy)-1H-pyrrol-2-yl |
| 3716. | 1-methyl-5-(2,4-dichlorophenoxy)-1H-pyrrol-2-yl |
| 3717. | 1-methyl-5-(2,5-dichlorophenoxy)-1H-pyrrol-2-yl |
| 3718. | 1-methyl-5-(2,6-dichlorophenoxy)-1H-pyrrol-2-yl |
| 3719. | 1-methyl-5-(3,4-dichlorophenoxy)-1H-pyrrol-2-yl |
| 3720. | 1-methyl-5-(3,5-dichlorophenoxy)-1H-pyrrol-2-yl |
| 3721. | 1-methyl-5-(2,3-dibromophenoxy)-1H-pyrrol-2-yl |
| 3722. | 1-methyl-5-(2,4-dibromophenoxy)-1H-pyrrol-2-yl |
| 3723. | 1-methyl-5-(2,5-dibromophenoxy)-1H-pyrrol-2-yl |
| 3724. | 1-methyl-5-(2,6-dibromophenoxy)-1H-pyrrol-2-yl |
| 3725. | 1-methyl-5-(3,4-dibromophenoxy)-1H-pyrrol-2-yl |
| 3726. | 1-methyl-5-(3,5-dibromophenoxy)-1H-pyrrol-2-yl |
| 3727. | 1-methyl-5-(2,3-dimethylphenoxy)-1H-pyrrol-2-yl |
| 3728. | 1-methyl-5-(2,4-dimethylphenoxy)-1H-pyrrol-2-yl |
| 3729. | 1-methyl-5-(2,5-dimethylphenoxy)-1H-pyrrol-2-yl |
| 3730. | 1-methyl-5-(2,6-dimethylphenoxy)-1H-pyrrol-2-yl |
| 3731. | 1-methyl-5-(3,4-dimethylphenoxy)-1H-pyrrol-2-yl |
| 3732. | 1-methyl-5-(3,5-dimethylphenoxy)-1H-pyrrol-2-yl |
| 3733. | 1-methyl-5-[2,3-di(trifluoromethyl)phenoxy]-1H-pyrrol-2-yl |
| 3734. | 1-methyl-5-[2,4-di(trifluoromethyl)phenoxy]-1H-pyrrol-2-yl |
| 3735. | 1-methyl-5-[2,5-di(trifluoromethyl)phenoxy]-1H-pyrrol-2-yl |
| 3736. | 1-methyl-5-[2,6-di(trifluoromethyl)phenoxy]-1H-pyrrol-2-yl |
| 3737. | 1-methyl-5-[3,4-di(trifluoromethyl)phenoxy]-1H-pyrrol-2-yl |
| 3738. | 1-methyl-5-[3,5-di(trifluoromethyl)phenoxy]-1H-pyrrol-2-yl |
| 3739. | 1-methyl-5-(2,3-dimethoxy-phenoxy)-1H-pyrrol-2-yl |
| 3740. | 1-methyl-5-(2,4-dimethoxy-phenoxy)-1H-pyrrol-2-yl |
| 3741. | 1-methyl-5-(2,5-dimethoxy-phenoxy)-1H-pyrrol-2-yl |
| 3742. | 1-methyl-5-(2,6-dimethoxy-phenoxy)-1H-pyrrol-2-yl |
| 3743. | 1-methyl-5-(3,4-dimethoxy-phenoxy)-1H-pyrrol-2-yl |
| 3744. | 1-methyl-5-(3,5-dimethoxy-phenoxy)-1H-pyrrol-2-yl |
| 3745. | 1-methyl-5-(o-CN-phenyl)-1H-pyrazol-3-yl |
| 3746. | 1-methyl-5-(m-CN-phenyl)-1H-pyrazol-3-yl |
| 3747. | 1-methyl-5-(p-CN-phenyl)-1H-pyrazol-3-yl |
| 3748. | 1-methyl-5-(o-NO₂-phenyl)-1H-pyrazol-3-yl |
| 3749. | 1-methyl-5-(m-NO₂-phenyl)-1H-pyrazol-3-yl |
| 3750. | 1-methyl-5-(p-NO₂-phenyl)-1H-pyrazol-3-yl |
| 3751. | 1-methyl-5-(o-F-phenyl)-1H-pyrazol-3-yl |
| 3752. | 1-methyl-5-(m-F-phenyl)-1H-pyrazol-3-yl |
| 3753. | 1-methyl-5-(p-F-phenyl)-1H-pyrazol-3-yl |
| 3754. | 1-methyl-5-(o-Cl-phenyl)-1H-pyrazol-3-yl |
| 3755. | 1-methyl-5-(m-Cl-phenyl)-1H-pyrazol-3-yl |
| 3756. | 1-methyl-5-(p-Cl-phenyl)-1H-pyrazol-3-yl |
| 3757. | 1-methyl-5-(o-Br-phenyl)-1H-pyrazol-3-yl |
| 3758. | 1-methyl-5-(m-Br-phenyl)-1H-pyrazol-3-yl |
| 3759. | 1-methyl-5-(p-Br-phenyl)-1H-pyrazol-3-yl |
| 3760. | 1-methyl-5-(o-CH₃-phenyl)-1H-pyrazol-3-yl |
| 3761. | 1-methyl-5-(m-CH₃-phenyl)-1H-pyrazol-3-yl |
| 3762. | 1-methyl-5-(p-CH₃-phenyl)-1H-pyrazol-3-yl |
| 3763. | 1-methyl-5-(o-CF₃-phenyl)-1H-pyrazol-3-yl |
| 3764. | 1-methyl-5-(m-CF₃-phenyl)-1H-pyrazol-3-yl |
| 3765. | 1-methyl-5-(p-CF₃-phenyl)-1H-pyrazol-3-yl |
| 3766. | 1-methyl-5-(o-CF₃-phenyl)-1H-pyrazol-3-yl |
| 3767. | 1-methyl-5-(m-CF₃-phenyl)-1H-pyrazol-3-yl |
| 3768. | 1-methyl-5-(p-CF₃-phenyl)-1H-pyrazol-3-yl |
| 3769. | 1-methyl-5-(o-OCH₃-phenyl)-1H-pyrazol-3-yl |

TABLE A-continued

| no. | R³-A- |
|---|---|
| 3770. | 1-methyl-5-(m-OCH₃-phenyl)-1H-pyrazol-3-yl |
| 3771. | 1-methyl-5-(p-OCH₃-phenyl)-1H-pyrazol-3-yl |
| 3772. | 1-methyl-5-(o-OCF₃-phenyl)-1H-pyrazol-3-yl |
| 3773. | 1-methyl-5-(m-OCF₃-phenyl)-1H-pyrazol-3-yl |
| 3774. | 1-methyl-5-(p-OCF₃-phenyl)-1H-pyrazol-3-yl |
| 3775. | 1-methyl-5-(o-COOCH₃-phenyl)-1H-pyrazol-3-yl |
| 3776. | 1-methyl-5-(m-COOCH₃-phenyl)-1H-pyrazol-3-yl |
| 3777. | 1-methyl-5-(p-COOCH₃-phenyl)-1H-pyrazol-3-yl |
| 3778. | 1-methyl-5-[o-N(CH₃)₂-phenyl]-1H-pyrazol-3-yl |
| 3779. | 1-methyl-5-[m-N(CH₃)₂-phenyl]-1H-pyrazol-3-yl |
| 3780. | 1-methyl-5-[p-N(CH₃)₂-phenyl]-1H-pyrazol-3-yl |
| 3781. | 1-methyl-5-(2,3-dicyanophenyl)-1H-pyrazol-3-yl |
| 3782. | 1-methyl-5-(2,4-dicyanophenyl)-1H-pyrazol-3-yl |
| 3783. | 1-methyl-5-(2,5-dicyanophenyl)-1H-pyrazol-3-yl |
| 3784. | 1-methyl-5-(2,6-dicyanophenyl)-1H-pyrazol-3-yl |
| 3785. | 1-methyl-5-(3,4-dicyanophenyl)-1H-pyrazol-3-yl |
| 3786. | 1-methyl-5-(3,5-dicyanophenyl)-1H-pyrazol-3-yl |
| 3787. | 1-methyl-5-(2,3-difluorophenyl)-1H-pyrazol-3-yl |
| 3788. | 1-methyl-5-(2,4-difluorophenyl)-1H-pyrazol-3-yl |
| 3789. | 1-methyl-5-(2,5-difluorophenyl)-1H-pyrazol-3-yl |
| 3790. | 1-methyl-5-(2,6-difluorophenyl)-1H-pyrazol-3-yl |
| 3791. | 1-methyl-5-(3,4-difluorophenyl)-1H-pyrazol-3-yl |
| 3792. | 1-methyl-5-(3,5-difluorophenyl)-1H-pyrazol-3-yl |
| 3793. | 1-methyl-5-(2,3-dichlorophenyl)-1H-pyrazol-3-yl |
| 3794. | 1-methyl-5-(2,4-dichlorophenyl)-1H-pyrazol-3-yl |
| 3795. | 1-methyl-5-(2,5-dichlorophenyl)-1H-pyrazol-3-yl |
| 3796. | 1-methyl-5-(2,6-dichlorophenyl)-1H-pyrazol-3-yl |
| 3797. | 1-methyl-5-(3,4-dichlorophenyl)-1H-pyrazol-3-yl |
| 3798. | 1-methyl-5-(3,5-dichlorophenyl)-1H-pyrazol-3-yl |
| 3799. | 1-methyl-5-(2,3-dibromophenyl)-1H-pyrazol-3-yl |
| 3800. | 1-methyl-5-(2,4-dibromophenyl)-1H-pyrazol-3-yl |
| 3801. | 1-methyl-5-(2,5-dibromophenyl)-1H-pyrazol-3-yl |
| 3802. | 1-methyl-5-(2,6-dibromophenyl)-1H-pyrazol-3-yl |
| 3803. | 1-methyl-5-(3,4-dibromophenyl)-1H-pyrazol-3-yl |
| 3804. | 1-methyl-5-(3,5-dibromophenyl)-1H-pyrazol-3-yl |
| 3805. | 1-methyl-5-(2,3-dimethylphenyl)-1H-pyrazol-3-yl |
| 3806. | 1-methyl-5-(2,4-dimethylphenyl)-1H-pyrazol-3-yl |
| 3807. | 1-methyl-5-(2,5-dimethylphenyl)-1H-pyrazol-3-yl |
| 3808. | 1-methyl-5-(2,6-dimethylphenyl)-1H-pyrazol-3-yl |
| 3809. | 1-methyl-5-(3,4-dimethylphenyl)-1H-pyrazol-3-yl |
| 3810. | 1-methyl-5-(3,5-dimethylphenyl)-1H-pyrazol-3-yl |
| 3811. | 1-methyl-5-[2,3-di(trifluoromethyl)phenyl]-1H-pyrazol-3-yl |
| 3812. | 1-methyl-5-[2,4-di(trifluoromethyl)phenyl]-1H-pyrazol-3-yl |
| 3813. | 1-methyl-5-[2,5-di(trifluoromethyl)phenyl]-1H-pyrazol-3-yl |
| 3814. | 1-methyl-5-[2,6-di(trifluoromethyl)phenyl]-1H-pyrazol-3-yl |
| 3815. | 1-methyl-5-[3,4-di(trifluoromethyl)phenyl]-1H-pyrazol-3-yl |
| 3816. | 1-methyl-5-[3,5-di(trifluoromethyl)phenyl]-1H-pyrazol-3-yl |
| 3817. | 1-methyl-5-(2,3-dimethoxyphenyl)-1H-pyrazol-3-yl |
| 3818. | 1-methyl-5-(2,4-dimethoxyphenyl)-1H-pyrazol-3-yl |
| 3819. | 1-methyl-5-(2,5-dimethoxyphenyl)-1H-pyrazol-3-yl |
| 3820. | 1-methyl-5-(2,6-dimethoxyphenyl)-1H-pyrazol-3-yl |
| 3821. | 1-methyl-5-(3,4-dimethoxyphenyl)-1H-pyrazol-3-yl |
| 3822. | 1-methyl-5-(3,5-dimethoxyphenyl)-1H-pyrazol-3-yl |
| 3823. | 1-methyl-5-(o-CN-phenoxy)-1H-pyrazol-3-yl |
| 3824. | 1-methyl-5-(m-CN-phenoxy)-1H-pyrazol-3-yl |
| 3825. | 1-methyl-5-(p-CN-phenoxy)-1H-pyrazol-3-yl |
| 3826. | 1-methyl-5-(o-NO₂-phenoxy)-1H-pyrazol-3-yl |
| 3827. | 1-methyl-5-(m-NO₂-phenoxy)-1H-pyrazol-3-yl |
| 3828. | 1-methyl-5-(p-NO₂-phenoxy)-1H-pyrazol-3-yl |
| 3829. | 1-methyl-5-(o-F-phenoxy)-1H-pyrazol-3-yl |
| 3830. | 1-methyl-5-(m-F-phenoxy)-1H-pyrazol-3-yl |
| 3831. | 1-methyl-5-(p-F-phenoxy)-1H-pyrazol-3-yl |
| 3832. | 1-methyl-5-(o-Cl-phenoxy)-1H-pyrazol-3-yl |
| 3833. | 1-methyl-5-(m-Cl-phenoxy)-1H-pyrazol-3-yl |
| 3834. | 1-methyl-5-(p-Cl-phenoxy)-1H-pyrazol-3-yl |
| 3835. | 1-methyl-5-(o-Br-phenoxy)-1H-pyrazol-3-yl |
| 3836. | 1-methyl-5-(m-Br-phenoxy)-1H-pyrazol-3-yl |
| 3837. | 1-methyl-5-(p-Br-phenoxy)-1H-pyrazol-3-yl |
| 3838. | 1-methyl-5-(o-CH₃-phenoxy)-1H-pyrazol-3-yl |
| 3839. | 1-methyl-5-(m-CH₃-phenoxy)-1H-pyrazol-3-yl |
| 3840. | 1-methyl-5-(p-CH₃-phenoxy)-1H-pyrazol-3-yl |
| 3841. | 1-methyl-5-(o-CF₃-phenoxy)-1H-pyrazol-3-yl |
| 3842. | 1-methyl-5-(m-CF₃-phenoxy)-1H-pyrazol-3-yl |
| 3843. | 1-methyl-5-(p-CF₃-phenoxy)-1H-pyrazol-3-yl |
| 3844. | 1-methyl-5-(o-CF₃-phenoxy)-1H-pyrazol-3-yl |

TABLE A-continued

| no. | R³-A- |
|---|---|
| 3845. | 1-methyl-5-(m-CF₃-phenoxy)-1H-pyrazol-3-yl |
| 3846. | 1-methyl-5-(p-CF₃-phenoxy)-1H-pyrazol-3-yl |
| 3847. | 1-methyl-5-(o-OCH₃-phenoxy)-1H-pyrazol-3-yl |
| 3848. | 1-methyl-5-(m-OCH₃-phenoxy)-1H-pyrazol-3-yl |
| 3849. | 1-methyl-5-(p-OCH₃-phenoxy)-1H-pyrazol-3-yl |
| 3850. | 1-methyl-5-(o-OCF₃-phenoxy)-1H-pyrazol-3-yl |
| 3851. | 1-methyl-5-(m-OCF₃-phenoxy)-1H-pyrazol-3-yl |
| 3852. | 1-methyl-5-(p-OCF₃-phenoxy)-1H-pyrazol-3-yl |
| 3853. | 1-methyl-5-(o-COOCH₃-phenoxy)-1H-pyrazol-3-yl |
| 3854. | 1-methyl-5-(m-COOCH₃-phenoxy)-1H-pyrazol-3-yl |
| 3855. | 1-methyl-5-(p-COOCH₃-phenoxy)-1H-pyrazol-3-yl |
| 3856. | 1-methyl-5-[o-N(CH₃)₂-phenoxy]-1H-pyrazol-3-yl |
| 3857. | 1-methyl-5-[m-N(CH₃)₂-phenoxy]-1H-pyrazol-3-yl |
| 3858. | 1-methyl-5-[p-N(CH₃)₂-phenoxy]-1H-pyrazol-3-yl |
| 3859. | 1-methyl-5-(2,3-dicyanophenoxy)-1H-pyrazol-3-yl |
| 3860. | 1-methyl-5-(2,4-dicyanophenoxy)-1H-pyrazol-3-yl |
| 3861. | 1-methyl-5-(2,5-dicyanophenoxy)-1H-pyrazol-3-yl |
| 3862. | 1-methyl-5-(2,6-dicyanophenoxy)-1H-pyrazol-3-yl |
| 3863. | 1-methyl-5-(3,4-dicyanophenoxy)-1H-pyrazol-3-yl |
| 3864. | 1-methyl-5-(3,5-dicyanophenoxy)-1H-pyrazol-3-yl |
| 3865. | 1-methyl-5-(2,3-difluorophenoxy)-1H-pyrazol-3-yl |
| 3866. | 1-methyl-5-(2,4-difluorophenoxy)-1H-pyrazol-3-yl |
| 3867. | 1-methyl-5-(2,5-difluorophenoxy)-1H-pyrazol-3-yl |
| 3868. | 1-methyl-5-(2,6-difluorophenoxy)-1H-pyrazol-3-yl |
| 3869. | 1-methyl-5-(3,4-difluorophenoxy)-1H-pyrazol-3-yl |
| 3870. | 1-methyl-5-(3,5-difluorophenoxy)-1H-pyrazol-3-yl |
| 3871. | 1-methyl-5-(2,3-dichlorophenoxy)-1H-pyrazol-3-yl |
| 3872. | 1-methyl-5-(2,4-dichlorophenoxy)-1H-pyrazol-3-yl |
| 3873. | 1-methyl-5-(2,5-dichlorophenoxy)-1H-pyrazol-3-yl |
| 3874. | 1-methyl-5-(2,6-dichlorophenoxy)-1H-pyrazol-3-yl |
| 3875. | 1-methyl-5-(3,4-dichlorophenoxy)-1H-pyrazol-3-yl |
| 3876. | 1-methyl-5-(3,5-dichlorophenoxy)-1H-pyrazol-3-yl |
| 3877. | 1-methyl-5-(2,3-dibromophenoxy)-1H-pyrazol-3-yl |
| 3878. | 1-methyl-5-(2,4-dibromophenoxy)-1H-pyrazol-3-yl |
| 3879. | 1-methyl-5-(2,5-dibromophenoxy)-1H-pyrazol-3-yl |
| 3880. | 1-methyl-5-(2,6-dibromophenoxy)-1H-pyrazol-3-yl |
| 3881. | 1-methyl-5-(3,4-dibromophenoxy)-1H-pyrazol-3-yl |
| 3882. | 1-methyl-5-(3,5-dibromophenoxy)-1H-pyrazol-3-yl |
| 3883. | 1-methyl-5-(2,3-dimethylphenoxy)-1H-pyrazol-3-yl |
| 3884. | 1-methyl-5-(2,4-dimethylphenoxy)-1H-pyrazol-3-yl |
| 3885. | 1-methyl-5-(2,5-dimethylphenoxy)-1H-pyrazol-3-yl |
| 3886. | 1-methyl-5-(2,6-dimethylphenoxy)-1H-pyrazol-3-yl |
| 3887. | 1-methyl-5-(3,4-dimethylphenoxy)-1H-pyrazol-3-yl |
| 3888. | 1-methyl-5-(3,5-dimethylphenoxy)-1H-pyrazol-3-yl |
| 3889. | 1-methyl-5-[2,3-di(trifluoromethyl)phenoxy]-1H-pyrazol-3-yl |
| 3890. | 1-methyl-5-[2,4-di(trifluoromethyl)phenoxy]-1H-pyrazol-3-yl |
| 3891. | 1-methyl-5-[2,5-di(trifluoromethyl)phenoxy]-1H-pyrazol-3-yl |
| 3892. | 1-methyl-5-[2,6-di(trifluoromethyl)phenoxy]-1H-pyrazol-3-yl |
| 3893. | 1-methyl-5-[3,4-di(trifluoromethyl)phenoxy]-1H-pyrazol-3-yl |
| 3894. | 1-methyl-5-[3,5-di(trifluoromethyl)phenoxy]-1H-pyrazol-3-yl |
| 3895. | 1-methyl-5-(2,3-dimethoxyphenoxy)-1H-pyrazol-3-yl |
| 3896. | 1-methyl-5-(2,4-dimethoxyphenoxy)-1H-pyrazol-3-yl |
| 3897. | 1-methyl-5-(2,5-dimethoxyphenoxy)-1H-pyrazol-3-yl |
| 3898. | 1-methyl-5-(2,6-dimethoxyphenoxy)-1H-pyrazol-3-yl |
| 3899. | 1-methyl-5-(3,4-dimethoxyphenoxy)-1H-pyrazol-3-yl |
| 3900. | 1-methyl-5-(3,5-dimethoxyphenoxy)-1H-pyrazol-3-yl |
| 3901. | 1-methyl-3-(o-CN-phenyl)-1H-pyrazol-5-yl |
| 3902. | 1-methyl-3-(m-CN-phenyl)-1H-pyrazol-5-yl |
| 3903. | 1-methyl-3-(p-CN-phenyl)-1H-pyrazol-5-yl |
| 3904. | 1-methyl-3-(o-NO₂-phenyl)-1H-pyrazol-5-yl |
| 3905. | 1-methyl-3-(m-NO₂-phenyl)-1H-pyrazol-5-yl |
| 3906. | 1-methyl-3-(p-NO₂-phenyl)-1H-pyrazol-5-yl |
| 3907. | 1-methyl-3-(o-F-phenyl)-1H-pyrazol-5-yl |
| 3908. | 1-methyl-3-(m-F-phenyl)-1H-pyrazol-5-yl |
| 3909. | 1-methyl-3-(p-F-phenyl)-1H-pyrazol-5-yl |
| 3910. | 1-methyl-3-(o-Cl-phenyl)-1H-pyrazol-5-yl |
| 3911. | 1-methyl-3-(m-Cl-phenyl)-1H-pyrazol-5-yl |
| 3912. | 1-methyl-3-(p-Cl-phenyl)-1H-pyrazol-5-yl |
| 3913. | 1-methyl-3-(o-Br-phenyl)-1H-pyrazol-5-yl |
| 3914. | 1-methyl-3-(m-Br-phenyl)-1H-pyrazol-5-yl |
| 3915. | 1-methyl-3-(p-Br-phenyl)-1H-pyrazol-5-yl |
| 3916. | 1-methyl-3-(o-CH₃-phenyl)-1H-pyrazol-5-yl |
| 3917. | 1-methyl-3-(m-CH₃-phenyl)-1H-pyrazol-5-yl |
| 3918. | 1-methyl-3-(p-CH₃-phenyl)-1H-pyrazol-5-yl |

TABLE A-continued

| no. | R³-A- |
|---|---|
| 3919. | 1-methyl-3-(o-CF₃-phenyl)-1H-pyrazol-5-yl |
| 3920. | 1-methyl-3-(m-CF₃-phenyl)-1H-pyrazol-5-yl |
| 3921. | 1-methyl-3-(p-CF₃-phenyl)-1H-pyrazol-5-yl |
| 3922. | 1-methyl-3-(o-CF₃-phenyl)-1H-pyrazol-5-yl |
| 3923. | 1-methyl-3-(m-CF₃-phenyl)-1H-pyrazol-5-yl |
| 3924. | 1-methyl-3-(p-CF₃-phenyl)-1H-pyrazol-5-yl |
| 3925. | 1-methyl-3-(o-OCH₃-phenyl)-1H-pyrazol-5-yl |
| 3926. | 1-methyl-3-(m-OCH₃-phenyl)-1H-pyrazol-5-yl |
| 3927. | 1-methyl-3-(p-OCH₃-phenyl)-1H-pyrazol-5-yl |
| 3928. | 1-methyl-3-(o-OCF₃-phenyl)-1H-pyrazol-5-yl |
| 3929. | 1-methyl-3-(m-OCF₃-phenyl)-1H-pyrazol-5-yl |
| 3930. | 1-methyl-3-(p-OCF₃-phenyl)-1H-pyrazol-5-yl |
| 3931. | 1-methyl-3-(o-COOCH₃-phenyl)-1H-pyrazol-5-yl |
| 3932. | 1-methyl-3-(m-COOCH₃-phenyl)-1H-pyrazol-5-yl |
| 3933. | 1-methyl-3-(p-COOCH₃-phenyl)-1H-pyrazol-5-yl |
| 3934. | 1-methyl-3-[o-N(CH₃)₂-phenyl]-1H-pyrazol-5-yl |
| 3935. | 1-methyl-3-[m-N(CH₃)₂-phenyl]-1H-pyrazol-5-yl |
| 3936. | 1-methyl-3-[p-N(CH₃)₂-phenyl]-1H-pyrazol-5-yl |
| 3937. | 1-methyl-3-(2,3-dicyanophenyl)-1H-pyrazol-5-yl |
| 3938. | 1-methyl-3-(2,4-dicyanophenyl)-1H-pyrazol-5-yl |
| 3939. | 1-methyl-3-(2,5-dicyanophenyl)-1H-pyrazol-5-yl |
| 3940. | 1-methyl-3-(2,6-dicyanophenyl)-1H-pyrazol-5-yl |
| 3941. | 1-methyl-3-(3,4-dicyanophenyl)-1H-pyrazol-5-yl |
| 3942. | 1-methyl-3-(3,5-dicyanophenyl)-1H-pyrazol-5-yl |
| 3943. | 1-methyl-3-(2,3-difluorophenyl)-1H-pyrazol-5-yl |
| 3944. | 1-methyl-3-(2,4-difluorophenyl)-1H-pyrazol-5-yl |
| 3945. | 1-methyl-3-(2,5-difluorophenyl)-1H-pyrazol-5-yl |
| 3946. | 1-methyl-3-(2,6-difluorophenyl)-1H-pyrazol-5-yl |
| 3947. | 1-methyl-3-(3,4-difluorophenyl)-1H-pyrazol-5-yl |
| 3948. | 1-methyl-3-(3,5-difluorophenyl)-1H-pyrazol-5-yl |
| 3949. | 1-methyl-3-(2,3-dichlorophenyl)-1H-pyrazol-5-yl |
| 3950. | 1-methyl-3-(2,4-dichlorophenyl)-1H-pyrazol-5-yl |
| 3951. | 1-methyl-3-(2,5-dichlorophenyl)-1H-pyrazol-5-yl |
| 3952. | 1-methyl-3-(2,6-dichlorophenyl)-1H-pyrazol-5-yl |
| 3953. | 1-methyl-3-(3,4-dichlorophenyl)-1H-pyrazol-5-yl |
| 3954. | 1-methyl-3-(3,5-dichlorophenyl)-1H-pyrazol-5-yl |
| 3955. | 1-methyl-3-(2,3-dibromophenyl)-1H-pyrazol-5-yl |
| 3956. | 1-methyl-3-(2,4-dibromophenyl)-1H-pyrazol-5-yl |
| 3957. | 1-methyl-3-(2,5-dibromophenyl)-1H-pyrazol-5-yl |
| 3958. | 1-methyl-3-(2,6-dibromophenyl)-1H-pyrazol-5-yl |
| 3959. | 1-methyl-3-(3,4-dibromophenyl)-1H-pyrazol-5-yl |
| 3960. | 1-methyl-3-(3,5-dibromophenyl)-1H-pyrazol-5-yl |
| 3961. | 1-methyl-3-(2,3-dimethylphenyl)-1H-pyrazol-5-yl |
| 3962. | 1-methyl-3-(2,4-dimethylphenyl)-1H-pyrazol-5-yl |
| 3963. | 1-methyl-3-(2,5-dimethylphenyl)-1H-pyrazol-5-yl |
| 3964. | 1-methyl-3-(2,6-dimethylphenyl)-1H-pyrazol-5-yl |
| 3965. | 1-methyl-3-(3,4-dimethylphenyl)-1H-pyrazol-5-yl |
| 3966. | 1-methyl-3-(3,5-dimethylphenyl)-1H-pyrazol-5-yl |
| 3967. | 1-methyl-3-[2,3-di(trifluoromethyl)phenyl]-1H-pyrazol-5-yl |
| 3968. | 1-methyl-3-[2,4-di(trifluoromethyl)phenyl]-1H-pyrazol-5-yl |
| 3969. | 1-methyl-3-[2,5-di(trifluoromethyl)phenyl]-1H-pyrazol-5-yl |
| 3970. | 1-methyl-3-[2,6-di(trifluoromethyl)phenyl]-1H-pyrazol-5-yl |
| 3971. | 1-methyl-3-[3,4-di(trifluoromethyl)phenyl]-1H-pyrazol-5-yl |
| 3972. | 1-methyl-3-[3,5-di(trifluoromethyl)phenyl]-1H-pyrazol-5-yl |
| 3973. | 1-methyl-3-(2,3-dimethoxyphenyl)-1H-pyrazol-5-yl |
| 3974. | 1-methyl-3-(2,4-dimethoxyphenyl)-1H-pyrazol-5-yl |
| 3975. | 1-methyl-3-(2,5-dimethoxyphenyl)-1H-pyrazol-5-yl |
| 3976. | 1-methyl-3-(2,6-dimethoxyphenyl)-1H-pyrazol-5-yl |
| 3977. | 1-methyl-3-(3,4-dimethoxyphenyl)-1H-pyrazol-5-yl |
| 3978. | 1-methyl-3-(3,5-dimethoxyphenyl)-1H-pyrazol-5-yl |
| 3979. | 1-methyl-3-(o-CN-phenoxy)-1H-pyrazol-5-yl |
| 3980. | 1-methyl-3-(m-CN-phenoxy)-1H-pyrazol-5-yl |
| 3981. | 1-methyl-3-(p-CN-phenoxy)-1H-pyrazol-5-yl |
| 3982. | 1-methyl-3-(o-NO₂-phenoxy)-1H-pyrazol-5-yl |
| 3983. | 1-methyl-3-(m-NO₂-phenoxy)-1H-pyrazol-5-yl |
| 3984. | 1-methyl-3-(p-NO₂-phenoxy)-1H-pyrazol-5-yl |
| 3985. | 1-methyl-3-(o-F-phenoxy)-1H-pyrazol-5-yl |
| 3986. | 1-methyl-3-(m-F-phenoxy)-1H-pyrazol-5-yl |
| 3987. | 1-methyl-3-(p-F-phenoxy)-1H-pyrazol-5-yl |
| 3988. | 1-methyl-3-(o-Cl-phenoxy)-1H-pyrazol-5-yl |
| 3989. | 1-methyl-3-(m-Cl-phenoxy)-1H-pyrazol-5-yl |
| 3990. | 1-methyl-3-(p-Cl-phenoxy)-1H-pyrazol-5-yl |
| 3991. | 1-methyl-3-(o-Br-phenoxy)-1H-pyrazol-5-yl |
| 3992. | 1-methyl-3-(m-Br-phenoxy)-1H-pyrazol-5-yl |
| 3993. | 1-methyl-3-(p-Br-phenoxy)-1H-pyrazol-5-yl |
| 3994. | 1-methyl-3-(o-CH₃-phenoxy)-1H-pyrazol-5-yl |
| 3995. | 1-methyl-3-(m-CH₃-phenoxy)-1H-pyrazol-5-yl |
| 3996. | 1-methyl-3-(p-CH₃-phenoxy)-1H-pyrazol-5-yl |

TABLE A-continued

| no. | R³-A- |
|---|---|
| 3997. | 1-methyl-3-(o-CF₃-phenoxy)-1H-pyrazol-5-yl |
| 3998. | 1-methyl-3-(m-CF₃-phenoxy)-1H-pyrazol-5-yl |
| 3999. | 1-methyl-3-(p-CF₃-phenoxy)-1H-pyrazol-5-yl |
| 4000. | 1-methyl-3-(o-CF₃-phenoxy)-1H-pyrazol-5-yl |
| 4001. | 1-methyl-3-(m-CF₃-phenoxy)-1H-pyrazol-5-yl |
| 4002. | 1-methyl-3-(p-CF₃-phenoxy)-1H-pyrazol-5-yl |
| 4003. | 1-methyl-3-(o-OCH₃-phenoxy)-1H-pyrazol-5-yl |
| 4004. | 1-methyl-3-(m-OCH₃-phenoxy)-1H-pyrazol-5-yl |
| 4005. | 1-methyl-3-(p-OCH₃-phenoxy)-1H-pyrazol-5-yl |
| 4006. | 1-methyl-3-(o-OCF₃-phenoxy)-1H-pyrazol-5-yl |
| 4007. | 1-methyl-3-(m-OCF₃-phenoxy)-1H-pyrazol-5-yl |
| 4008. | 1-methyl-3-(p-OCF₃-phenoxy)-1H-pyrazol-5-yl |
| 4009. | 1-methyl-3-(o-COOCH₃-phenoxy)-1H-pyrazol-5-yl |
| 4010. | 1-methyl-3-(m-COOCH₃-phenoxy)-1H-pyrazol-5-yl |
| 4011. | 1-methyl-3-(p-COOCH₃-phenoxy)-1H-pyrazol-5-yl |
| 4012. | 1-methyl-3-[o-N(CH₃)₂-phenoxy]-1H-pyrazol-5-yl |
| 4013. | 1-methyl-3-[m-N(CH₃)₂-phenoxy]-1H-pyrazol-5-yl |
| 4014. | 1-methyl-3-[p-N(CH₃)₂-phenoxy]-1H-pyrazol-5-yl |
| 4015. | 1-methyl-3-(2,3-dicyanophenoxy)-1H-pyrazol-5-yl |
| 4016. | 1-methyl-3-(2,4-dicyanophenoxy)-1H-pyrazol-5-yl |
| 4017. | 1-methyl-3-(2,5-dicyanophenoxy)-1H-pyrazol-5-yl |
| 4018. | 1-methyl-3-(2,6-dicyanophenoxy)-1H-pyrazol-5-yl |
| 4019. | 1-methyl-3-(3,4-dicyanophenoxy)-1H-pyrazol-5-yl |
| 4020. | 1-methyl-3-(3,5-dicyanophenoxy)-1H-pyrazol-5-yl |
| 4021. | 1-methyl-3-(2,3-difluorophenoxy)-1H-pyrazol-5-yl |
| 4022. | 1-methyl-3-(2,4-difluorophenoxy)-1H-pyrazol-5-yl |
| 4023. | 1-methyl-3-(2,5-difluorophenoxy)-1H-pyrazol-5-yl |
| 4024. | 1-methyl-3-(2,6-difluorophenoxy)-1H-pyrazol-5-yl |
| 4025. | 1-methyl-3-(3,4-difluorophenoxy)-1H-pyrazol-5-yl |
| 4026. | 1-methyl-3-(3,5-difluorophenoxy)-1H-pyrazol-5-yl |
| 4027. | 1-methyl-3-(2,3-dichlorophenoxy)-1H-pyrazol-5-yl |
| 4028. | 1-methyl-3-(2,4-dichlorophenoxy)-1H-pyrazol-5-yl |
| 4029. | 1-methyl-3-(2,5-dichlorophenoxy)-1H-pyrazol-5-yl |
| 4030. | 1-methyl-3-(2,6-dichlorophenoxy)-1H-pyrazol-5-yl |
| 4031. | 1-methyl-3-(3,4-dichlorophenoxy)-1H-pyrazol-5-yl |
| 4032. | 1-methyl-3-(3,5-dichlorophenoxy)-1H-pyrazol-5-yl |
| 4033. | 1-methyl-3-(2,3-dibromophenoxy)-1H-pyrazol-5-yl |
| 4034. | 1-methyl-3-(2,4-dibromophenoxy)-1H-pyrazol-5-yl |
| 4035. | 1-methyl-3-(2,5-dibromophenoxy)-1H-pyrazol-5-yl |
| 4036. | 1-methyl-3-(2,6-dibromophenoxy)-1H-pyrazol-5-yl |
| 4037. | 1-methyl-3-(3,4-dibromophenoxy)-1H-pyrazol-5-yl |
| 4038. | 1-methyl-3-(3,5-dibromophenoxy)-1H-pyrazol-5-yl |
| 4039. | 1-methyl-3-(2,3-dimethyl-phenoxy)-1H-pyrazol-5-yl |
| 4040. | 1-methyl-3-(2,4-dimethyl-phenoxy)-1H-pyrazol-5-yl |
| 4041. | 1-methyl-3-(2,5-dimethyl-phenoxy)-1H-pyrazol-5-yl |
| 4042. | 1-methyl-3-(2,6-dimethyl-phenoxy)-1H-pyrazol-5-yl |
| 4043. | 1-methyl-3-(3,4-dimethyl-phenoxy)-1H-pyrazol-5-yl |
| 4044. | 1-methyl-3-(3,5-dimethyl-phenoxy)-1H-pyrazol-5-yl |
| 4045. | 1-methyl-3-[2,3-di(trifluoro-methyl)phenoxy]-1H-pyrazol-5-yl |
| 4046. | 1-methyl-3-[2,4-di(trifluoro-methyl)phenoxy]-1H-pyrazol-5-yl |
| 4047. | 1-methyl-3-[2,5-di(trifluoro-methyl)phenoxy]-1H-pyrazol-5-yl |
| 4048. | 1-methyl-3-[2,6-di(trifluoro-methyl)phenoxy]-1H-pyrazol-5-yl |
| 4049. | 1-methyl-3-[3,4-di(trifluoro-methyl)phenoxy]-1H-pyrazol-5-yl |
| 4050. | 1-methyl-3-[3,5-di(trifluoro-methyl)phenoxy]-1H-pyrazol-5-yl |
| 4051. | 1-methyl-3-(2,3-dimethoxy-phenoxy)-1H-pyrazol-5-yl |
| 4052. | 1-methyl-3-(2,4-dimethoxy-phenoxy)-1H-pyrazol-5-yl |
| 4053. | 1-methyl-3-(2,5-dimethoxy-phenoxy)-1H-pyrazol-5-yl |
| 4054. | 1-methyl-3-(2,6-dimethoxy-phenoxy)-1H-pyrazol-5-yl |
| 4055. | 1-methyl-3-(3,4-dimethoxy-phenoxy)-1H-pyrazol-5-yl |
| 4056. | 1-methyl-3-(3,5-dimethoxy-phenoxy)-1H-pyrazol-5-yl |
| 4057. | 1-(o-CN-phenyl)-1H-pyrazol-3-yl |
| 4058. | 1-(m-CN-phenyl)-1H-pyrazol-3-yl |
| 4059. | 1-(p-CN-phenyl)-1H-pyrazol-3-yl |
| 4060. | 1-(o-NO₂-phenyl)-1H-pyrazol-3-yl |
| 4061. | 1-(m-NO₂-phenyl)-1H-pyrazol-3-yl |
| 4062. | 1-(p-NO₂-phenyl)-1H-pyrazol-3-yl |
| 4063. | 1-(o-F-phenyl)-1H-pyrazol-3-yl |
| 4064. | 1-(m-F-phenyl)-1H-pyrazol-3-yl |
| 4065. | 1-(p-F-phenyl)-1H-pyrazol-3-yl |
| 4066. | 1-(o-Cl-phenyl)-1H-pyrazol-3-yl |
| 4067. | 1-(m-Cl-phenyl)-1H-pyrazol-3-yl |
| 4068. | 1-(p-Cl-phenyl)-1H-pyrazol-3-yl |
| 4069. | 1-(o-Br-phenyl)-1H-pyrazol-3-yl |
| 4070. | 1-(m-Br-phenyl)-1H-pyrazol-3-yl |
| 4071. | 1-(p-Br-phenyl)-1H-pyrazol-3-yl |
| 4072. | 1-(o-CH₃-phenyl)-1H-pyrazol-3-yl |
| 4073. | 1-(m-CH₃-phenyl)-1H-pyrazol-3-yl |
| 4074. | 1-(p-CH₃-phenyl)-1H-pyrazol-3-yl |
| 4075. | 1-(o-CF₃-phenyl)-1H-pyrazol-3-yl |
| 4076. | 1-(m-CF₃-phenyl)-1H-pyrazol-3-yl |
| 4077. | 1-(p-CF₃-phenyl)-1H-pyrazol-3-yl |
| 4078. | 1-(o-CF₃-phenyl)-1H-pyrazol-3-yl |
| 4079. | 1-(m-CF₃-phenyl)-1H-pyrazol-3-yl |
| 4080. | 1-(p-CF₃-phenyl)-1H-pyrazol-3-yl |
| 4081. | 1-(o-OCH₃-phenyl)-1H-pyrazol-3-yl |
| 4082. | 1-(m-OCH₃-phenyl)-1H-pyrazol-3-yl |
| 4083. | 1-(p-OCH₃-phenyl)-1H-pyrazol-3-yl |
| 4084. | 1-(o-OCF₃-phenyl)-1H-pyrazol-3-yl |
| 4085. | 1-(m-OCF₃-phenyl)-1H-pyrazol-3-yl |

TABLE A-continued

| no. | R³-A- |
|---|---|
| 4086. | 1-(p-OCF₃-phenyl)-1H-pyrazol-3-yl |
| 4087. | 1-(o-COOCH₃-phenyl)-1H-pyrazol-3-yl |
| 4088. | 1-(m-COOCH₃-phenyl)-1H-pyrazol-3-yl |
| 4089. | 1-(p-COOCH₃-phenyl)-1H-pyrazol-3-yl |
| 4090. | 1-[o-N(CH₃)₂-phenyl]-1H-pyrazol-3-yl |
| 4091. | 1-[m-N(CH₃)₂-phenyl]-1H-pyrazol-3-yl |
| 4092. | 1-[p-N(CH₃)₂-phenyl]-1H-pyrazol-3-yl |
| 4093. | 1-(2,3-dicyanophenyl)-1H-pyrazol-3-yl |
| 4094. | 1-(2,4-dicyanophenyl)-1H-pyrazol-3-yl |
| 4095. | 1-(2,5-dicyanophenyl)-1H-pyrazol-3-yl |
| 4096. | 1-(2,6-dicyanophenyl)-1H-pyrazol-3-yl |
| 4097. | 1-(3,4-dicyanophenyl)-1H-pyrazol-3-yl |
| 4098. | 1-(3,5-dicyanophenyl)-1H-pyrazol-3-yl |
| 4099. | 1-(2,3-difluorophenyl)-1H-pyrazol-3-yl |
| 4100. | 1-(2,4-difluorophenyl)-1H-pyrazol-3-yl |
| 4101. | 1-(2,5-difluorophenyl)-1H-pyrazol-3-yl |
| 4102. | 1-(2,6-difluorophenyl)-1H-pyrazol-3-yl |
| 4103. | 1-(3,4-difluorophenyl)-1H-pyrazol-3-yl |
| 4104. | 1-(3,5-difluorophenyl)-1H-pyrazol-3-yl |
| 4105. | 1-(2,3-dichlorophenyl)-1H-pyrazol-3-yl |
| 4106. | 1-(2,4-dichlorophenyl)-1H-pyrazol-3-yl |
| 4107. | 1-(2,5-dichlorophenyl)-1H-pyrazol-3-yl |
| 4108. | 1-(2,6-dichlorophenyl)-1H-pyrazol-3-yl |
| 4109. | 1-(3,4-dichlorophenyl)-1H-pyrazol-3-yl |
| 4110. | 1-(3,5-dichlorophenyl)-1H-pyrazol-3-yl |
| 4111. | 1-(2,3-dibromophenyl)-1H-pyrazol-3-yl |
| 4112. | 1-(2,4-dibromophenyl)-1H-pyrazol-3-yl |
| 4113. | 1-(2,5-dibromophenyl)-1H-pyrazol-3-yl |
| 4114. | 1-(2,6-dibromophenyl)-1H-pyrazol-3-yl |
| 4115. | 1-(3,4-dibromophenyl)-1H-pyrazol-3-yl |
| 4116. | 1-(3,5-dibromophenyl)-1H-pyrazol-3-yl |
| 4117. | 1-(2,3-dimethylphenyl)-1H-pyrazol-3-yl |
| 4118. | 1-(2,4-dimethylphenyl)-1H-pyrazol-3-yl |
| 4119. | 1-(2,5-dimethylphenyl)-1H-pyrazol-3-yl |
| 4120. | 1-(2,6-dimethylphenyl)-1H-pyrazol-3-yl |
| 4121. | 1-(3,4-dimethylphenyl)-1H-pyrazol-3-yl |
| 4122. | 1-(3,5-dimethylphenyl)-1H-pyrazol-3-yl |
| 4123. | 1-[2,3-di(trifluoromethyl)phenyl]-1H-pyrazol-3-yl |
| 4124. | 1-[2,4-di(trifluoromethyl)phenyl]-1H-pyrazol-3-yl |
| 4125. | 1-[2,5-di(trifluoromethyl)phenyl]-1H-pyrazol-3-yl |
| 4126. | 1-[2,6-di(trifluoromethyl)phenyl]-1H-pyrazol-3-yl |
| 4127. | 1-[3,4-di(trifluoromethyl)phenyl]-1H-pyrazol-3-yl |
| 4128. | 1-[3,5-di(trifluoromethyl)phenyl]-1H-pyrazol-3-yl |
| 4129. | 1-(2,3-dimethoxyphenyl)-1H-pyrazol-3-yl |
| 4130. | 1-(2,4-dimethoxyphenyl)-1H-pyrazol-3-yl |
| 4131. | 1-(2,5-dimethoxyphenyl)-1H-pyrazol-3-yl |
| 4132. | 1-(2,6-dimethoxyphenyl)-1H-pyrazol-3-yl |
| 4133. | 1-(3,4-dimethoxyphenyl)-1H-pyrazol-3-yl |
| 4134. | 1-(3,5-dimethoxyphenyl)-1H-pyrazol-3-yl |
| 4135. | 1-(o-CN-phenoxy)-1H-pyrazol-3-yl |
| 4136. | 1-(m-CN-phenoxy)-1H-pyrazol-3-yl |
| 4137. | 1-(p-CN-phenoxy)-1H-pyrazol-3-yl |
| 4138. | 1-(o-NO₂-phenoxy)-1H-pyrazol-3-yl |
| 4139. | 1-(m-NO₂-phenoxy)-1H-pyrazol-3-yl |
| 4140. | 1-(p-NO₂-phenoxy)-1H-pyrazol-3-yl |
| 4141. | 1-(o-F-phenoxy)-1H-pyrazol-3-yl |
| 4142. | 1-(m-F-phenoxy)-1H-pyrazol-3-yl |
| 4143. | 1-(p-F-phenoxy)-1H-pyrazol-3-yl |
| 4144. | 1-(o-Cl-phenoxy)-1H-pyrazol-3-yl |
| 4145. | 1-(m-Cl-phenoxy)-1H-pyrazol-3-yl |
| 4146. | 1-(p-Cl-phenoxy)-1H-pyrazol-3-yl |
| 4147. | 1-(o-Br-phenoxy)-1H-pyrazol-3-yl |
| 4148. | 1-(m-Br-phenoxy)-1H-pyrazol-3-yl |
| 4149. | 1-(p-Br-phenoxy)-1H-pyrazol-3-yl |
| 4150. | 1-(o-CH₃-phenoxy)-1H-pyrazol-3-yl |
| 4151. | 1-(m-CH₃-phenoxy)-1H-pyrazol-3-yl |
| 4152. | 1-(p-CH₃-phenoxy)-1H-pyrazol-3-yl |
| 4153. | 1-(o-CF₃-phenoxy)-1H-pyrazol-3-yl |
| 4154. | 1-(m-CF₃-phenoxy)-1H-pyrazol-3-yl |
| 4155. | 1-(p-CF₃-phenoxy)-1H-pyrazol-3-yl |
| 4156. | 1-(o-CF₃-phenoxy)-1H-pyrazol-3-yl |
| 4157. | 1-(m-CF₃-phenoxy)-1H-pyrazol-3-yl |
| 4158. | 1-(p-CF₃-phenoxy)-1H-pyrazol-3-yl |
| 4159. | 1-(o-OCH₃-phenoxy)-1H-pyrazol-3-yl |
| 4160. | 1-(m-OCH₃-phenoxy)-1H-pyrazol-3-yl |
| 4161. | 1-(p-OCH₃-phenoxy)-1H-pyrazol-3-yl |
| 4162. | 1-(o-OCF₃-phenoxy)-1H-pyrazol-3-yl |
| 4163. | 1-(m-OCF₃-phenoxy)-1H-pyrazol-3-yl |
| 4164. | 1-(p-OCF₃-phenoxy)-1H-pyrazol-3-yl |
| 4165. | 1-(o-COOCH₃-phenoxy)-1H-pyrazol-3-yl |
| 4166. | 1-(m-COOCH₃-phenoxy)-1H-pyrazol-3-yl |
| 4167. | 1-(p-COOCH₃-phenoxy)-1H-pyrazol-3-yl |

TABLE A-continued

| no. | R³-A- |
|---|---|
| 4168. | 1-[o-N(CH₃)₂-phenoxy]-1H-pyrazol-3-yl |
| 4169. | 1-[m-N(CH₃)₂-phenoxy]-1H-pyrazol-3-yl |
| 4170. | 1-[p-N(CH₃)₂-phenoxy]-1H-pyrazol-3-yl |
| 4171. | 1-(2,3-dicyanophenoxy)-1H-pyrazol-3-yl |
| 4172. | 1-(2,4-dicyanophenoxy)-1H-pyrazol-3-yl |
| 4173. | 1-(2,5-dicyanophenoxy)-1H-pyrazol-3-yl |
| 4174. | 1-(2,6-dicyanophenoxy)-1H-pyrazol-3-yl |
| 4175. | 1-(3,4-dicyanophenoxy)-1H-pyrazol-3-yl |
| 4176. | 1-(3,5-dicyanophenoxy)-1H-pyrazol-3-yl |
| 4177. | 1-(2,3-difluorophenoxy)-1H-pyrazol-3-yl |
| 4178. | 1-(2,4-difluorophenoxy)-1H-pyrazol-3-yl |
| 4179. | 1-(2,5-difluorophenoxy)-1H-pyrazol-3-yl |
| 4180. | 1-(2,6-difluorophenoxy)-1H-pyrazol-3-yl |
| 4181. | 1-(3,4-difluorophenoxy)-1H-pyrazol-3-yl |
| 4182. | 1-(3,5-difluorophenoxy)-1H-pyrazol-3-yl |
| 4183. | 1-(2,3-dichlorophenoxy)-1H-pyrazol-3-yl |
| 4184. | 1-(2,4-dichlorophenoxy)-1H-pyrazol-3-yl |
| 4185. | 1-(2,5-dichlorophenoxy)-1H-pyrazol-3-yl |
| 4186. | 1-(2,6-dichlorophenoxy)-1H-pyrazol-3-yl |
| 4187. | 1-(3,4-dichlorophenoxy)-1H-pyrazol-3-yl |
| 4188. | 1-(3,5-dichlorophenoxy)-1H-pyrazol-3-yl |
| 4189. | 1-(2,3-dibromophenoxy)-1H-pyrazol-3-yl |
| 4190. | 1-(2,4-dibromophenoxy)-1H-pyrazol-3-yl |
| 4191. | 1-(2,5-dibromophenoxy)-1H-pyrazol-3-yl |
| 4192. | 1-(2,6-dibromophenoxy)-1H-pyrazol-3-yl |
| 4193. | 1-(3,4-dibromophenoxy)-1H-pyrazol-3-yl |
| 4194. | 1-(3,5-dibromophenoxy)-1H-pyrazol-3-yl |
| 4195. | 1-(2,3-dimethylphenoxy)-1H-pyrazol-3-yl |
| 4196. | 1-(2,4-dimethylphenoxy)-1H-pyrazol-3-yl |
| 4197. | 1-(2,5-dimethylphenoxy)-1H-pyrazol-3-yl |
| 4198. | 1-(2,6-dimethylphenoxy)-1H-pyrazol-3-yl |
| 4199. | 1-(3,4-dimethylphenoxy)-1H-pyrazol-3-yl |
| 4200. | 1-(3,5-dimethylphenoxy)-1H-pyrazol-3-yl |
| 4201. | 1-[2,3-di(trifluoromethyl)phenoxy]-1H-pyrazol-3-yl |
| 4202. | 1-[2,4-di(trifluoromethyl)phenoxy]-1H-pyrazol-3-yl |
| 4203. | 1-[2,5-di(trifluoromethyl)phenoxy]-1H-pyrazol-3-yl |
| 4204. | 1-[2,6-di(trifluoromethyl)phenoxy]-1H-pyrazol-3-yl |
| 4205. | 1-[3,4-di(trifluoromethyl)phenoxy]-1H-pyrazol-3-yl |
| 4206. | 1-[3,5-di(trifluoromethyl)phenoxy]-1H-pyrazol-3-yl |
| 4207. | 1-(2,3-dimethoxyphenoxy)-1H-pyrazol-3-yl |
| 4208. | 1-(2,4-dimethoxyphenoxy)-1H-pyrazol-3-yl |
| 4209. | 1-(2,5-dimethoxyphenoxy)-1H-pyrazol-3-yl |
| 4210. | 1-(2,6-dimethoxyphenoxy)-1H-pyrazol-3-yl |
| 4211. | 1-(3,4-dimethoxyphenoxy)-1H-pyrazol-3-yl |
| 4212. | 1-(3,5-dimethoxyphenoxy)-1H-pyrazol-3-yl |
| 4213. | 1-(o-CN-phenyl)-1H-pyrazol-4-yl |
| 4214. | 1-(m-CN-phenyl)-1H-pyrazol-4-yl |
| 4215. | 1-(p-CN-phenyl)-1H-pyrazol-4-yl |
| 4216. | 1-(o-NO₂-phenyl)-1H-pyrazol-4-yl |
| 4217. | 1-(m-NO₂-phenyl)-1H-pyrazol-4-yl |
| 4218. | 1-(p-NO₂-phenyl)-1H-pyrazol-4-yl |
| 4219. | 1-(o-F-phenyl)-1H-pyrazol-4-yl |
| 4220. | 1-(m-F-phenyl)-1H-pyrazol-4-yl |
| 4221. | 1-(p-F-phenyl)-1H-pyrazol-4-yl |
| 4222. | 1-(o-Cl-phenyl)-1H-pyrazol-4-yl |
| 4223. | 1-(m-Cl-phenyl)-1H-pyrazol-4-yl |
| 4224. | 1-(p-Cl-phenyl)-1H-pyrazol-4-yl |
| 4225. | 1-(o-Br-phenyl)-1H-pyrazol-4-yl |
| 4226. | 1-(m-Br-phenyl)-1H-pyrazol-4-yl |
| 4227. | 1-(p-Br-phenyl)-1H-pyrazol-4-yl |
| 4228. | 1-(o-CH₃-phenyl)-1H-pyrazol-4-yl |
| 4229. | 1-(m-CH₃-phenyl)-1H-pyrazol-4-yl |
| 4230. | 1-(p-CH₃-phenyl)-1H-pyrazol-4-yl |
| 4231. | 1-(o-CF₃-phenyl)-1H-pyrazol-4-yl |
| 4232. | 1-(m-CF₃-phenyl)-1H-pyrazol-4-yl |
| 4233. | 1-(p-CF₃-phenyl)-1H-pyrazol-4-yl |
| 4234. | 1-(o-CF₃-phenyl)-1H-pyrazol-4-yl |
| 4235. | 1-(m-CF₃-phenyl)-1H-pyrazol-4-yl |
| 4236. | 1-(p-CF₃-phenyl)-1H-pyrazol-4-yl |
| 4237. | 1-(o-OCH₃-phenyl)-1H-pyrazol-4-yl |
| 4238. | 1-(m-OCH₃-phenyl)-1H-pyrazol-4-yl |
| 4239. | 1-(p-OCH₃-phenyl)-1H-pyrazol-4-yl |
| 4240. | 1-(o-OCF₃-phenyl)-1H-pyrazol-4-yl |
| 4241. | 1-(m-OCF₃-phenyl)-1H-pyrazol-4-yl |
| 4242. | 1-(p-OCF₃-phenyl)-1H-pyrazol-4-yl |
| 4243. | 1-(o-COOCH₃-phenyl)-1H-pyrazol-4-yl |
| 4244. | 1-(m-COOCH₃-phenyl)-1H-pyrazol-4-yl |
| 4245. | 1-(p-COOCH₃-phenyl)-1H-pyrazol-4-yl |
| 4246. | 1-[o-N(CH₃)₂-phenyl]-1H-pyrazol-4-yl |
| 4247. | 1-[m-N(CH₃)₂-phenyl]-1H-pyrazol-4-yl |
| 4248. | 1-[p-N(CH₃)₂-phenyl]-1H-pyrazol-4-yl |
| 4249. | 1-(2,3-dicyanophenyl)-1H-pyrazol-4-yl |
| 4250. | 1-(2,4-dicyanophenyl)-1H-pyrazol-4-yl |
| 4251. | 1-(2,5-dicyanophenyl)-1H-pyrazol-4-yl |
| 4252. | 1-(2,6-dicyanophenyl)-1H-pyrazol-4-yl |
| 4253. | 1-(3,4-dioyanophenyl)-1H-pyrazol-4-yl |
| 4254. | 1-(3,5-dicyanophenyl)-1H-pyrazol-4-yl |
| 4255. | 1-(2,3-difluorophenyl)-1H-pyrazol-4-yl |
| 4256. | 1-(2,4-difluorophenyl)-1H-pyrazol-4-yl |

TABLE A-continued

| no. | R³-A- |
|---|---|
| 4257. | 1-(2,5-difluorophenyl)-1H-pyrazol-4-yl |
| 4258. | 1-(2,6-difluorophenyl)-1H-pyrazol-4-yl |
| 4259. | 1-(3,4-difluorophenyl)-1H-pyrazol-4-yl |
| 4260. | 1-(3,5-difluorophenyl)-1H-pyrazol-4-yl |
| 4261. | 1-(2,3-dichlorophenyl)-1H-pyrazol-4-yl |
| 4262. | 1-(2,4-dichlorophenyl)-1H-pyrazol-4-yl |
| 4263. | 1-(2,5-dichlorophenyl)-1H-pyrazol-4-yl |
| 4264. | 1-(2,6-dichlorophenyl)-1H-pyrazol-4-yl |
| 4265. | 1-(3,4-dichlorophenyl)-1H-pyrazol-4-yl |
| 4266. | 1-(3,5-dichlorophenyl)-1H-pyrazol-4-yl |
| 4267. | 1-(2,3-dibromophenyl)-1H-pyrazol-4-yl |
| 4268. | 1-(2,4-dibromophenyl)-1H-pyrazol-4-yl |
| 4269. | 1-(2,5-dibromophenyl)-1H-pyrazol-4-yl |
| 4270. | 1-(2,6-dibromophenyl)-1H-pyrazol-4-yl |
| 4271. | 1-(3,4-dibromophenyl)-1H-pyrazol-4-yl |
| 4272. | 1-(3,5-dibromophenyl)-1H-pyrazol-4-yl |
| 4273. | 1-(2,3-dimethylphenyl)-1H-pyrazol-4-yl |
| 4274. | 1-(2,4-dimethylphenyl)-1H-pyrazol-4-yl |
| 4275. | 1-(2,5-dimethylphenyl)-1H-pyrazol-4-yl |
| 4276. | 1-(2,6-dimethylphenyl)-1H-pyrazol-4-yl |
| 4277. | 1-(3,4-dimethylphenyl)-1H-pyrazol-4-yl |
| 4278. | 1-(3,5-dimethylphenyl)-1H-pyrazol-4-yl |
| 4279. | 1-[2,3-di(trifluoromethyl)phenyl]-1H-pyrazol-4-yl |
| 4280. | 1-[2,4-di(trifluoromethyl)phenyl]-1H-pyrazol-4-yl |
| 4281. | 1-[2,5-di(trifluoromethyl)phenyl]-1H-pyrazol-4-yl |
| 4282. | 1-[2,6-di(trifluoromethyl)phenyl]-1H-pyrazol-4-yl |
| 4283. | 1-[3,4-di(trifluoromethyl)phenyl]-1H-pyrazol-4-yl |
| 4284. | 1-[3,5-di(trifluoromethyl)phenyl]-1H-pyrazol-4-yl |
| 4285. | 1-(2,3-dimethoxyphenyl)-1H-pyrazol-4-yl |
| 4286. | 1-(2,4-dimethoxyphenyl)-1H-pyrazol-4-yl |
| 4287. | 1-(2,5-dimethoxyphenyl)-1H-pyrazol-4-yl |
| 4288. | 1-(2,6-dimethoxyphenyl)-1H-pyrazol-4-yl |
| 4289. | 1-(3,4-dimethoxyphenyl)-1H-pyrazol-4-yl |
| 4290. | 1-(3,5-dimethoxyphenyl)-1H-pyrazol-4-yl |
| 4291. | 1-(o-CN-phenoxy)-1H-pyrazol-4-yl |
| 4292. | 1-(m-CN-phenoxy)-1H-pyrazol-4-yl |
| 4293. | 1-(p-CN-phenoxy)-1H-pyrazol-4-yl |
| 4294. | 1-(o-NO$_2$-phenoxy)-1H-pyrazol-4-yl |
| 4295. | 1-(m-NO$_2$-phenoxy)-1H-pyrazol-4-yl |
| 4296. | 1-(p-NO$_2$-phenoxy)-1H-pyrazol-4-yl |
| 4297. | 1-(o-F-phenoxy)-1H-pyrazol-4-yl |
| 4298. | 1-(m-F-phenoxy)-1H-pyrazol-4-yl |
| 4299. | 1-(p-F-phenoxy)-1H-pyrazol-4-yl |
| 4300. | 1-(o-Cl-phenoxy)-1H-pyrazol-4-yl |
| 4301. | 1-(m-Cl-phenoxy)-1H-pyrazol-4-yl |
| 4302. | 1-(p-Cl-phenoxy)-1H-pyrazol-4-yl |
| 4303. | 1-(o-Br-phenoxy)-1H-pyrazol-4-yl |
| 4304. | 1-(m-Br-phenoxy)-1H-pyrazol-4-yl |
| 4305. | 1-(p-Br-phenoxy)-1H-pyrazol-4-yl |
| 4306. | 1-(o-CH$_3$-phenoxy)-1H-pyrazol-4-yl |
| 4307. | 1-(m-CH$_3$-phenoxy)-1H-pyrazol-4-yl |
| 4308. | 1-(p-CH$_3$-phenoxy)-1H-pyrazol-4-yl |
| 4309. | 1-(o-CF$_3$-phenoxy)-1H-pyrazol-4-yl |
| 4310. | 1-(m-CF$_3$-phenoxy)-1H-pyrazol-4-yl |
| 4311. | 1-(p-CF$_3$-phenoxy)-1H-pyrazol-4-yl |
| 4312. | 1-(o-CF$_3$-phenoxy)-1H-pyrazol-4-yl |
| 4313. | 1-(m-CF$_3$-phenoxy)-1H-pyrazol-4-yl |
| 4314. | 1-(p-CF$_3$-phenoxy)-1H-pyrazol-4-yl |
| 4315. | 1-(o-OCH$_3$-phenoxy)-1H-pyrazol-4-yl |
| 4316. | 1-(m-OCH$_3$-phenoxy)-1H-pyrazol-4-yl |
| 4317. | 1-(p-OCH$_3$-phenoxy)-1H-pyrazol-4-yl |
| 4318. | 1-(o-OCF$_3$-phenoxy)-1H-pyrazol-4-yl |
| 4319. | 1-(m-OCF$_3$-phenoxy)-1H-pyrazol-4-yl |
| 4320. | 1-(p-OCF$_3$-phenoxy)-1H-pyrazol-4-yl |
| 4321. | 1-(o-COOCH$_3$-phenoxy)-1H-pyrazol-4-yl |
| 4322. | 1-(m-COOCH$_3$-phenoxy)-1H-pyrazol-4-yl |
| 4323. | 1-(p-COOCH$_3$-phenoxy)-1H-pyrazol-4-yl |
| 4324. | 1-[o-N(CH$_3$)$_2$-phenoxy]-1H-pyrazol-4-yl |
| 4325. | 1-[m-N(CH$_3$)$_2$-phenoxy]-1H-pyrazol-4-yl |
| 4326. | 1-[p-N(CH$_3$)$_2$-phenoxy]-1H-pyrazol-4-yl |
| 4327. | 1-(2,3-dicyanophenoxy)-1H-pyrazol-4-yl |
| 4328. | 1-(2,4-dicyanophenoxy)-1H-pyrazol-4-yl |
| 4329. | 1-(2,5-dicyanophenoxy)-1H pyrazol-4-yl |
| 4330. | 1-(2,6-dicyanophenoxy)-1H-pyrazol-4-yl |
| 4331. | 1-(3,4-dicyanophenoxy)-1H-pyrazol-4-yl |
| 4332. | 1-(3,5-dicyanophenoxy)-1H-pyrazol-4-yl |
| 4333. | 1-(2,3-difluorophenoxy)-1H-pyrazol-4-yl |
| 4334. | 1-(2,4-difluorophenoxy)-1H-pyrazol-4-yl |
| 4335. | 1-(2,5-difluorophenoxy)-1H-pyrazol-4-yl |
| 4336. | 1-(2,6-difluorophenoxy)-1H-pyrazol-4-yl |
| 4337. | 1-(3,4-difluorophenoxy)-1H-pyrazol-4-yl |
| 4338. | 1-(3,5-difluorophenoxy)-1H-pyrazol-4-yl |

TABLE A-continued

| no. | R³-A- |
|---|---|
| 4339. | 1-(2,3-dichlorophenoxy)-1H-pyrazol-4-yl |
| 4340. | 1-(2,4-dichlorophenoxy)-1H-pyrazol-4-yl |
| 4341. | 1-(2,5-dichlorophenoxy)-1H-pyrazol-4-yl |
| 4342. | 1-(2,6-dichlorophenoxy)-1H-pyrazol-4-yl |
| 4343. | 1-(3,4-dichlorophenoxy)-1H-pyrazol-4-yl |
| 4344. | 1-(3,5-dichlorophenoxy)-1H-pyrazol-4-yl |
| 4345. | 1-(2,3-dibromophenoxy)-1H-pyrazol-4-yl |
| 4346. | 1-(2,4-dibromophenoxy)-1H-pyrazol-4-yl |
| 4347. | 1-(2,5-dibromophenoxy)-1H-pyrazol-4-yl |
| 4348. | 1-(2,6-dibromophenoxy)-1H-pyrazol-4-yl |
| 4349. | 1-(3,4-dibromophenoxy)-1H-pyrazol-4-yl |
| 4350. | 1-(3,5-dibromophenoxy)-1H-pyrazol-4-yl |
| 4351. | 1-(2,3-dimethylphenoxy)-1H-pyrazol-4-yl |
| 4352. | 1-(2,4-dimethylphenoxy)-1H-pyrazol-4-yl |
| 4353. | 1-(2,5-dimethylphenoxy)-1H-pyrazol-4-yl |
| 4354. | 1-(2,6-dimethylphenoxy)-1H-pyrazol-4-yl |
| 4355. | 1-(3,4-dimethylphenoxy)-1H-pyrazol-4-yl |
| 4356. | 1-(3,5-dimethylphenoxy)-1H-pyrazol-4-yl |
| 4357. | 1-[2,3-di(trifluoromethyl)phenoxy]-1H-pyrazol-4-yl |
| 4358. | 1-[2,4-di(trifluoromethyl)phenoxy]-1H-pyrazol-4-yl |
| 4359. | 1-[2,5-di(trifluoromethyl)phenoxy]-1H-pyrazol-4-yl |
| 4360. | 1-[2,6-di(trifluoromethyl)phenoxy]-1H-pyrazol-4-yl |
| 4361. | 1-[3,4-di(trifluoromethyl)phenoxy]-1H-pyrazol-4-yl |
| 4362. | 1-[3,5-di(trifluoromethyl)phenoxy]-1H-pyrazol-4-yl |
| 4363. | 1-(2,3-dimethoxyphenoxy)-1H-pyrazol-4-yl |
| 4364. | 1-(2,4-dimethoxyphenoxy)-1H-pyrazol-4-yl |
| 4365. | 1-(2,5-dimethoxyphenoxy)-1H-pyrazol-4-yl |
| 4366. | 1-(2,6-dimethoxyphenoxy)-1H-pyrazol-4-yl |
| 4367. | 1-(3,4-dimethoxyphenoxy)-1H-pyrazol-4-yl |
| 4368. | 1-(3,5-dimethoxyphenoxy)-1H-pyrazol-4-yl |

Table 2: Compounds 4369 to 8736:

Compounds of the formula (I.b.a) wherein $R^1$ means chlorine in position 2 of the pyrimidine ring and the combination of $R^3$-A for a compound corresponds in each case to one line of table A.

Table 3: Compounds 8737 to 13104:

Compounds of the formula (I.b.a), wherein $R^1$ means chlorine in position 2 of the pyrimidine ring and the combination of $R^3$-A for a compound corresponds in each case to one line of table A.

Table 4: Compounds 13105 to 17472:

Compounds of the formula (I.b.a) wherein $R^1$ means chlorine in position 6 of the pyrimidine ring and the combination of $R^3$-A for a compound corresponds in each case to one line of table A.

Table 5: Compounds 17473 to 21840:

Compounds of the formula (I.b.a) wherein $R^1$ means methyl in position 2 of the pyrimidine ring and the combination of $R^3$-A for a compound corresponds in each case to one line of table A.

Table 6: Compounds 21841 to 26208:

Compounds of the formula (I.b.a) wherein $R^1$ means methyl in position 5 of the pyrimidine ring and the combination of $R^3$-A for a compound corresponds in each case to one line of table A.

Table 7: Compounds 26209 to 30576:

Compounds of the formula (I.b.a) wherein $R^1$ means methyl in position 6 of the pyrimidine ring and the combination of $R^3$-A for a compound corresponds in each case to one line of table A.

Table 8: Compounds 30577 to 34944:

Compounds of the formula (I.b.a) wherein $R^1$ means methoxy in position 2 of the pyrimidine ring and the combination of $R^3$-A for a compound corresponds in each case to one line of table A.

Table 9: Compounds 34945 to 39312:

Compounds of the formula (I.b.a) wherein $R^1$ means methoxy in position 5 of the pyrimidine ring and the combination of $R^3$-A for a compound corresponds in each case to one line of table A.

Table 10: Compounds 39313 to 43680:

Compounds of the formula (I.b.a) wherein $R^1$ means methoxy in position 6 of the pyrimidine ring and the combination of $R^3$-A in each case corresponds to one line of table A.

Table 11: Compounds 43681 to 48048:

Compounds of the formula (I.b.a) wherein $R^1$ means methylthio in position 2 of the pyrimidine ring and the combination of $R^3$-A for a compound corresponds in each case to one line of table A.

Table 12: Compounds 48049 to 52416:

Compounds of the formula (I.b.a) wherein $R^1$ means methylthio in position 5 of the pyrimidine ring and the combination of $R^3$-A for a compound corresponds in each case to one line of table A.

Table 13: Compounds 52417 to 56784:

Compounds of the formula (I.b.a) wherein $R^1$ means methylthio in position 6 of the pyrimidine ring and the combination of $R^3$-A for a compound corresponds in each case to one line of table A.

Table 14: Compounds 56785 to 61152:

Compounds of the formula (I.c.a) wherein each $R^1$ means methyl, attached in positions 2 and 6 of the pyrimidine ring and the combination of $R^3$-A for a compound corresponds in each case to one line of table A.

Table 15: Compounds 61153 to 65520:

Compounds of the formula (I.c.a) wherein each $R^1$ means methyl, attached in positions 5 and 6 of the pyrimidine ring and the combination of $R^3$-A for a compound corresponds in each case to one line of table A.

Table 16: Compounds 65521 to 69888:

Compounds of the formula (I.c.a) wherein each $R^1$ means methoxy, attached in positions 2 and 6 of the pyrimidine ring and the combination of $R^3$-A for a compound corresponds in each case to one line of table A.

Table 17: Compounds 69889 to 74256:

Compounds of the formula (I.c.a), wherein each $R^1$ means methoxy, attached in positions 5 and 6 of the pyrimidine ring and the combination of $R^3$-A for a compound corresponds in each case to one line of table A.

Table 18: Compounds 74257 to 78624:
Compounds of the formula (I.b.a), wherein $R^1$ difluoromethoxy, attached in position 2 of the pyrimidine ring and the combination of $R^3$-A for a compound corresponds in each case to one line of table A.

Table 19: Compounds 78625 to 82992:
Compounds of the formula (I.b.a), wherein $R^1$ difluoromethoxy, attached in position 6 of the pyrimidine ring and the combination of $R^3$-A for a compound corresponds in each case to one line of table A.

Table 20: Compounds 82993 to 87360:
Compounds of the formula (I.b.a), wherein $R^1$ trifluoromethoxy, attached in position 2 of the pyrimidine ring and the combination of $R^3$-A for a compound corresponds in each case to one line of table A.

Table 21: Compounds 87361 to 91728:
Compounds of the formula (I.b.a), wherein $R^1$ trifluoromethoxy, attached in position 6 of the pyrimidine ring and the combination of $R^3$-A for a compound corresponds in each case to one line of table A.

Table 22: Compounds 91729 to 96096:
Compounds of the formula (I.b.a), wherein $R^1$ difluoromethylthio, attached in position 2 of the pyrimidine ring and the combination of $R^3$-A for a compound corresponds in each case to one line of table A.

Table 23: Compounds 96097 to 100464:
Compounds of the formula (I.b.a), wherein $R^1$ difluoromethylthio, attached in position 6 of the pyrimidine ring and the combination of $R^3$-A for a compound corresponds in each case to one line of table A.

Table 24: Compounds 100465 to 104832:
Compounds of the formula (I.b.a), wherein $R^1$ methylsulfonyl, attached in position 2 of the pyrimidine ring and the combination of $R^3$-A for a compound corresponds in each case to one line of table A.

Table 25: Compounds 104832 to 109200:
Compounds of the formula (I.b.a), wherein $R^1$ methylsulfinyl, attached in position 2 of the pyrimidine ring and the combination of $R^3$-A for a compound corresponds in each case to one line of table A.

Table 26: Compounds 109201 to 113568:
Compounds of the formula (I.b.a), wherein $R^1$ trifluoromethylthio, attached in position 2 of the pyrimidine ring and the combination of $R^3$-A for a compound corresponds in each case to one line of table A.

Table 27: Compounds 113569 to 117936:
Compounds of the formula (I.b.a), wherein $R^1$ trifluoromethylthio, attached in position 6 of the pyrimidine ring and the combination of $R^3$-A for a compound corresponds in each case to one line of table A.

Table 28: Compounds 117937 to 122304:
Compounds of the formula (I.b.a), wherein $R^1$ methylamino, attached in position 2 of the pyrimidine ring and the combination of $R^3$-A for a compound corresponds in each case to one line of table A.

Table 29: Compounds 122305 to 126672:
Compounds of the formula (I.b.a), wherein $R^1$ methylamino, attached in position 6 of the pyrimidine ring and the combination of $R^3$-A for a compound corresponds in each case to one line of table A.

Table 30: Compounds 126673 to 131040:
Compounds of the formula (I.b.a), wherein $R^1$ dimethylamino, attached in position 2 of the pyrimidine ring and the combination of $R^3$-A for a compound corresponds in each case to one line of table A.

Table 31: Compounds 131041 to 135408:
Compounds of the formula (I.b.a), wherein $R^1$ dimethylamino, attached in position 6 of the pyrimidine ring and the combination of $R^3$-A for a compound corresponds in each case to one line of table A.

Table 32: Compounds 135409 to 139776:
Compounds of the formula (I.b.a), wherein $R^1$ cyclopropyl, attached in position 2 of the pyrimidine ring and the combination of $R^3$-A for a compound corresponds in each case to one line of table A.

Table 33: Compounds 139777 to 144144:
Compounds of the formula (I.c.a), wherein one $R^1$ means methoxy, attached in position 2 of the pyrimidine ring, the other $R^1$ means methyl, attached in position 6 of the pyrimidine ring, and the combination of $R^3$-A for a compound corresponds in each case to one line of table A.

Table 34: Compounds 144144 to 148512:
Compounds of the formula (I.c.a), wherein one $R^1$ means methylthio, attached in position 2 of the pyrimidine ring, the other $R^1$ means methyl, attached in position 6 of the pyrimidine ring, and the combination of $R^3$-A for a compound corresponds in each case to one line of table A.

The inventive compounds of the formula (I) can be prepared by various routes in analogy to prior art processes known per se for preparing sulfonamide compounds and, advantageously, by the synthesis shown in the following schemes and in the experimental part of this application.

Scheme 1:

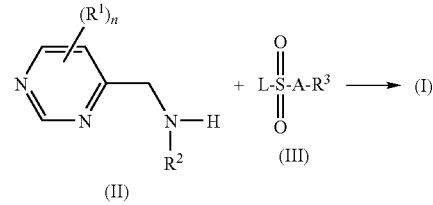

In scheme 1, $R^1$, $R^2$, $R^3$, A and n are as defined above, and L is a leaving group such as hydroxy or halogen, preferably chlorine.

According to the process depicted in scheme 1, a sulfonyl compound (III) is reacted with a pyrimidin-4-ylmethylamine compound (II) to obtain a compound of the formula (I) according to the present invention. The reaction of the sulfonyl compound (III) with compound (II) can be performed in accordance with standard methods of organic chemistry, see for example, Lieb. Ann. Chem. P. 641, 1990, or WO 2005/033081.

This reaction is usually carried out in an inert organic solvent. Suitable solvents are aliphatic hydrocarbons, such as pentane, hexane, cyclohexane and petroleum ether, aromatic hydrocarbons, such as toluene, o-, m- and p-xylene, halogenated hydrocarbons, such as dichloromethane, chloroform and chlorobenzene, ethers, such as diethyl ether, diisopropyl ether, tert.-butyl methyl ether, dioxane, anisole and tetrahydrofuran, nitriles, such as acetonitrile and propionitrile, ketones, such as acetone, methyl ethyl ketone, diethyl ketone and tert.-butyl methyl ketone, and also dimethyl sulfoxide, dimethylformamide and dimethylacetamide, preferably tetrahydrofuran, methyl tert-butylether, dichloromethane, chloroform, acetonitrile, toluene or dimethylformamide. It is also possible to use mixtures of the solvents mentioned.

The reaction is carried out in the presence of a base. Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to triethylamine, pyridine, triethylamine and potassium carbonate. The bases are generally employed in equimolar amounts, in excess or, if appropriate, as solvent. The excess of base is typically 0.5 to 5 molar equivalents relative to 1 mole of compounds (II).

Generally, the reaction is carried out at temperatures of from −30° C. to 120° C., preferably from −10° C. to 100° C.

The starting materials are generally reacted with one another in equimolar amounts.

Compounds of the formula (I), wherein $R^3$ is optionally substituted phenyl or heteroaryl and A is optionally substituted phenylene or 5- or 6-membered, optionally substituted heteroarenediyl can be prepared by reaction of a compound of formula (IV) with a boronic acid derivative of the formula (V) by a Suzuki coupling as shown in scheme 2.

Scheme 2:

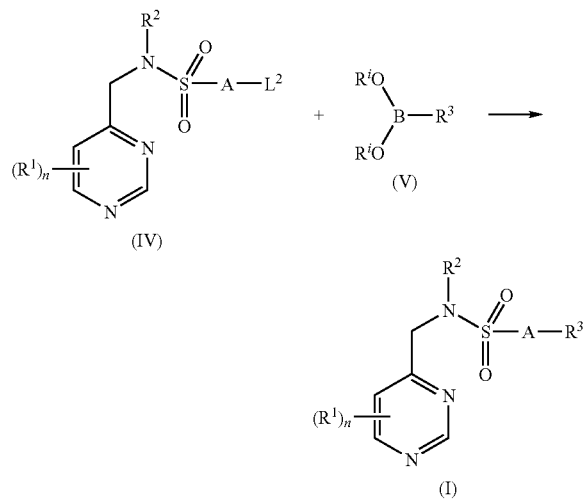

In scheme 2, $R^1$, $R^2$ and n are as defined above, $R^i$ and $R^j$ are each independently hydrogen or $C_1$-$C_4$-alkyl, or $R^i$ and $R^j$ together form an 1,2-ethylene or 1,2-propylene moiety the carbon atoms of which may be unsubstituted or may all or in part be substituted by methyl groups, and $L^2$ is a suitable leaving group.

Suitable leaving groups $L^2$ are halogen, preferably chlorine, bromine or iodine, alkylcarbonylate, benzoate, alkylsulfonate, haloalkylsulfonate or arylsulfonate, most preferably chlorine or bromine.

The reaction is usually carried out in the presence of a base and a catalyst, in particular a palladium catalyst, such as for example described in the following literature: Synth. Commun. Vol. 11, p. 513 (1981); Acc. Chem. Res. Vol. 15, pp. 178-184 (1982); Chem. Rev. Vol. 95, pp. 2457-2483 (1995); Organic Letters Vol. 6 (16), p. 2808 (2004); "Metal catalyzed cross coupling reactions", $2^{nd}$ Edition, Wiley, VCH 2005 (Eds. De Meijere, Diederich); "Handbook of organopalladium chemistry for organic synthesis" (Eds Negishi), Wiley, Interscience, New York, 2002; "Handbook of functionalized organometallics", (Ed. P. Knochel), Wiley, VCH, 2005.

Suitable catalysts are in tetrakis(triphenylphosphine)palladium(0); bis(triphenylphosphine)palladium(II) chloride; bis (acetonitrile)palladium(II) chloride; [1,1'-bis(diphenylphosphino)ferrocene]-palladium(II) chloride/methylene chloride (1:1) complex; bis[bis-(1,2-diphenylphosphino)ethane]palladium(0); bis(bis-(1,2-diphenylphosphino)butane]-palladium(II) chloride; palladium(II) acetate; palladium(II) chloride; and palladium(II) acetate/tri-o-tolylphosphine complex or mixtures of phosphines and Pd salts or phosphines and Pd-complexes e.g. dibenzylideneacetone-palladium and tritertbutylphosphine (or its tetrafluoroborate), tris cyclohexylphosphine; or a polymer-bound Pd-triphenylphosphine catalyst system.

Suitable bases are, in general, inorganic compounds, such as alkali metal and alkaline earth metal oxides, such as lithium oxide, sodium oxide, calcium oxide and magnesium oxide, alkali metal and alkaline earth metal carbonates, such as lithium carbonate, sodium carbonate, potassium carbonate, caesium carbonate and calcium carbonate, and also alkali metal bicarbonates, such as sodium bicarbonate, alkali metal and alkaline earth metal alkoxides, such as sodium methoxide, sodium ethoxide, potassium ethoxide and potassium tert.-butoxide, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to bases such as sodium carbonate, potassium carbonate, caesium carbonate, triethylamine and sodium bicarbonate.

The base is used in a 1:1 to 1:10, preferably a 1:1.5 to 5 molar ratio relative to 1 mole of compounds (IV), the boronic acid is used in a 1:1 to 1:5 ratio, preferably a 1:1 to 1:2.5 molar ratio relative to 1 mole of compounds (IV). In some cases it may be beneficial for easy purification to use the boronic acid in a substoichiometric amount of from 0.7:1 to 0.99:1, per 1 mole of compounds (IV).

The reaction is usually carried out in an inert organic organic solvent. Suitable solvents are aliphatic hydrocarbons, such as pentane, hexane, cyclohexane and petroleum ether, aromatic hydrocarbons, such as toluene, o-, m- and p-xylene, ethers, such as diisopropyl ether, tert.-butyl methyl ether, dioxane, anisole and tetrahydrofuran and dimethoxyethane, ketones, such as acetone, methyl ethyl ketone, diethyl ketone and tert.-butyl methyl ketone, and also dimethyl sulfoxide, dimethylformamide and dimethylacetamide, particularly preferably ethers, such as tetrahydrofuran, dioxane and dimethoxyethane. It is also possible to use mixtures of the solvents mentioned, or mixtures with water.

The reaction is usually carried out at temperatures of from 20° C. to 180° C., preferably from 40° C. to 120° C.

After completion of the reaction, the compounds of formula (I) can be isolated by employing conventional methods such as adding the reaction mixture to water, extracting with an organic solvent, concentrating the extract an the like. The isolated compounds (I) can be purified by a technique such as chromatography, recrystallization and the like, if necessary.

It is also possible to add a scavenger to the reaction mixtures to remove byproducts or unreacted starting materials by binding to those and simple filtration. For details see "Synthesis and purification catalog", Argonaut, 2003 and literature cited therein.

Boronic acids or esters (V) are commercially available or can be prepared according to "Science of Synthesis" Vol. 6, Thieme, 2005; WO 02/042275; Synlett 2003, (8) p. 1204; J. Org. Chem., 2003, 68, p. 3729, Synthesis, 2000, p. 442, J. Org. Chem., 1995, 60, p. 750; or "Handbook of functionalized organometallics", (Ed. P. Knochel), Wiley, VCH, 2005.

Pyrimidin-4-ylmethylamine compounds (II) are known from the literature or are commercially available or they can be prepared for example by reduction of the corresponding oxime VIa, nitrile VIb, or amide VIc as described below. Appropriate methods therefor are known to those skilled in the art:

Scheme 3:

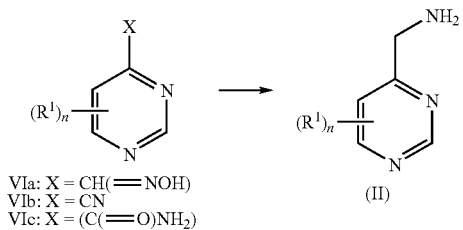

VIa: X = CH(═NOH)
VIb: X = CN
VIc: X = (C(═O)NH$_2$)

In scheme 3, $R^1$ and n are as defined.

Suitable methods for the reduction of an oxime compound (VIa) to the corresponding pyrimidin-4-ylmethylamine compound (II) have been described in the literature e.g. in Jerry March, reactions, mechanisms and structure, fourth edition, 1992, John Wiley and Sons, New York, pages 1218-1219.

Suitable methods for the reduction of a nitrile compound (VIb) to the corresponding pyrimidin-4-ylmethylamine compound (II) have been described in the literature, e.g. in Jerry March, reactions, mechanisms and structure, fourth edition, 1992, John Wiley and Sons, New York, pages 918-919.

Suitable methods for the reduction of an amide compound (VIc) to the corresponding pyrimidin-4-ylmethylamine compound (II) have been described in the literature, e.g. in Jerry March, reactions, mechanisms and structure, fourth edition, 1992, John Wiley and Sons, New York, pages 1212-1213.

The oxim compound (VIa) can be prepared for example from either the respective aldehyd compound (X═CHO; compound (VId)) or the methylderivative (X═CH$_3$; compound (VIe)), as described in Houben-Weyl, vol. 10/4, Thieme, Stuttgart, 1968; vol. 11/2, 1957; vol E5, 1985; J. Prakt. Chem-Chem. Ztg. 336(8), pp. 695-697, 1994; Tetrahedron Lett. 42(39), pp. 6815-6818, 2001; or Heterocycles, 29(9), pp. 1741-1760, 1989.

The aldehyd compound (VId) can be synthesized from a 4-methyl pyrimidine compound as outlined in J. Org. Chem. 51(4), pp. 536-537, 1986, or from a haloderivative (X=halogen, compound (VIf)) as shown in Eur. J. Org. Chem., 2003, (8), pp. 1576-1588; Tetrahedron Lett. 1999, 40 (19), pp. 3719-3722; Tetrahedron, 1999, 55 (41), pp. 12149-12156.

The nitrile compound (VIb) can be prepared for example from the corresponding 4-halogenepyrimidine compound (VIf) by reaction with cyanide. The 4-halogenepyrimidine compounds are either commercially available or can be synthesized according to standard methods.

The amide compound (VIc) can be prepared, for example, from the corresponding carboxylic acid chloride by reaction with ammonia.

A pyrimidin-4-ylmethylamine compound (II) carrying a substituent in the 2-position can be prepared for example as exemplified in schemes 4, 5 and 6.

Scheme 4:

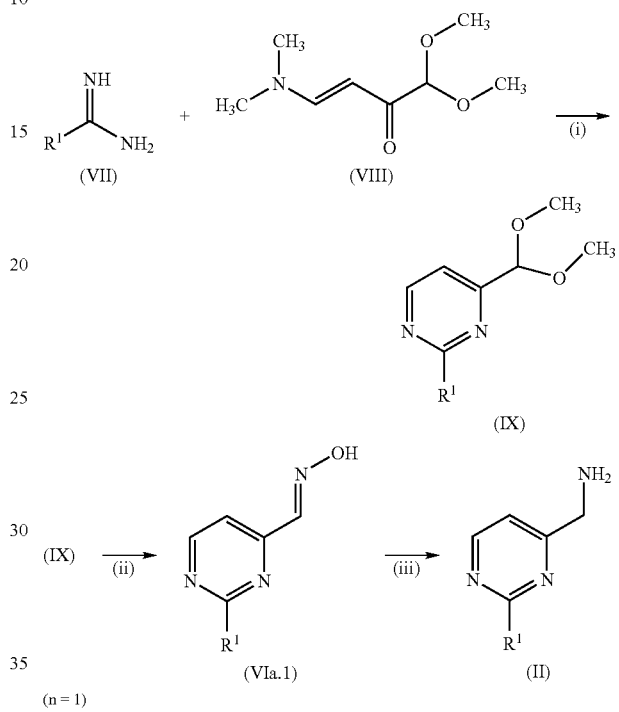

In scheme 4, $R^1$ is as defined above. In particular, $R^1$ is halogen, alkyl, amino, alkylamino or cycloalkyl.

According to the reaction sequence depicted in scheme 4, compounds of the formula (II) can be prepared analogously to methods described e.g. WO 2005/014572, Journal of Heterocyclic Chemistry (1978), 15(6), 1041-2 or Chemische Berichte (1964), 97(12), 3407-17. According to step (i), an enaminoketone (VIII) is reacted with an amidine compound (VII) or the hydrohalogenide thereof, as described e.g. in Journal of Heterocyclic Chemistry (1978), 15(6), 1041-2. Usually, the reaction (i) is carried out in the presence of a base. Suitable bases are $C_1$-$C_4$-alkoxide, especially methoxide. The reaction is generally carried out in the presence of a solvent. Suitable solvents are $C_1$-$C_4$-alkanoles, such as methanol, ethanol, n-propanol and mixtures thereof. Usually, the reaction is carried out at temperature of from room temperature to the boiling point of the solvent, preferably at refluxing temperature.

The compound (IX) is then treated with hydroxylamine to yield an oxime compound (VIa.1) (step ii). Hydrogenation of the resulting oxime compound (VIa.1) in the presence of a catalyst, e.g. palladium-on-carbon gives the pyrimidin-4-ylmethyl amine compound (II) (step iii).

A further method to build up pyrimidin-4-ylmethylamine compounds (II) carrying a substituent in the 2-position is shown in scheme 5.

Scheme 5:

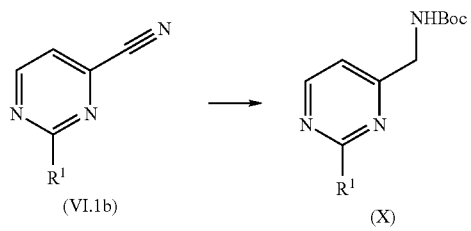

In scheme 5, $R^1$ is as defined above and Boc is tert-butyloxycarbonyl.

According to the process depicted in scheme 5, the hydrogenation of the nitrile (VIb.1) in the presence of a catalyst, such as Raney nickel or palladium-on-carbon and t-butyl dicarbonate gives the N-protected compound (X). On treating with hydrogen bromide/glacial acetic acid or with trifluoroacetic acid containing water, the compound (X) can be deprotected to yield a pyrimidin-4-ylmethyl amine compounds (II) carrying a substituent in the 2-position.

Compounds of the formula (II) wherein $R^1$ is alkoxy, haloalkoxy, alkylthio or haloalkylthio can be prepared in analogy to standard processes from a compound of the formula (X) wherein $R^1$ is halogen, especially chlorine, for example in analogy to methods described in Journal of Heterocyclic Chemistry (2005), 42(7), 1369-1379, Tetrahedron Letters, 47(26), 4415-4418, 2006 or Chemical & Pharmaceutical Bulletin 31(12), 4533-8, 1983. This synthesis route is shown in scheme 6.

typically preferred. Suitable solvents comprise ethers such as dioxane, diethyl ether, methyl tert-butyl ether and preferably tetrahydrofuran, halogenated hydrocarbons such as dichloromethane or dichloroethane, aromatic hydrocarbons such as toluene, and mixtures thereof. Deprotection of the amino group in formula (XII) to give the desired compound of the formula (II) can be accomplished as described in scheme 5 above.

Compounds of the formula (II) in which $R^1$ is alkyl, haloalkyl, alkenyl, alkynyl, cycloalkyl or alkyl-cycloalkyl can advantageously be prepared by reacting compounds X in which $R^1$ is halogen with organometallic compounds $R^{1a}$—Mt where $R^{1a}$ is alkyl, haloalkyl, alkenyl, alkynyl, cycloalkyl or alkyl-cycloalkyl and Mt is lithium, magnesium or zinc. The reaction is effected preferably in the presence of catalytic or, in particular, at least equimolar amounts of transition metal salts and/or compounds, in particular in the presence of Cu salts such as Cu(I) halides and especially Cu(I) iodide, or Pd-catalyzed. The reaction is effected generally in an inert organic solvent, for example one of the aforementioned ethers, in particular tetrahydrofuran, an aliphatic or cycloaliphatic hydrocarbon such as hexane, cyclohexane and the like, an aromatic hydrocarbon such as toluene, or in a mixture of these solvents. The temperatures required for this purpose are in the range of from −100 to +100° C. and especially in the range from −80° C. to +40° C.

Pyrimidin-4-ylmethylamine compounds (II) carrying a substituent in the 6-position can be prepared for example as exemplified in scheme 7.

Scheme 6:

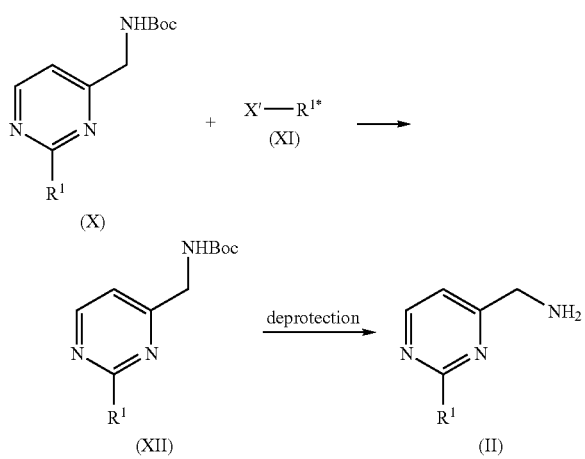

(X) $R^1$ = halogen
(XII) $R^1$ = $R^{1*}$ = alkoxy, haloalkoxy, alkylthio or haloalkylthio
(II) $R^1$ = alkoxy, haloalkoxy, alkylthio or haloalkylthio According to the process depicted in scheme 6, a compound of formula (XI) is reacted with a compound X'—$R^{1*}$ (also referred to hereinbelow as compounds of the formula (XI) to give a compound of formula (XII). Depending on the $R^{1*}$ group to be introduced, the compounds of the formula (XI) are inorganic alkoxides, haloalkoxides, thiolates or halothiolates. The reaction is effected advantageously in an inert solvent. The cation X' in formula (XI) is of little importance; for practical reasons, ammonium salts, tetraalkylammonium salts such as tetramethylammonium or tetraethylammonium salts, or alkali metal salts or alkaline earth metal salts are Scheme 7:

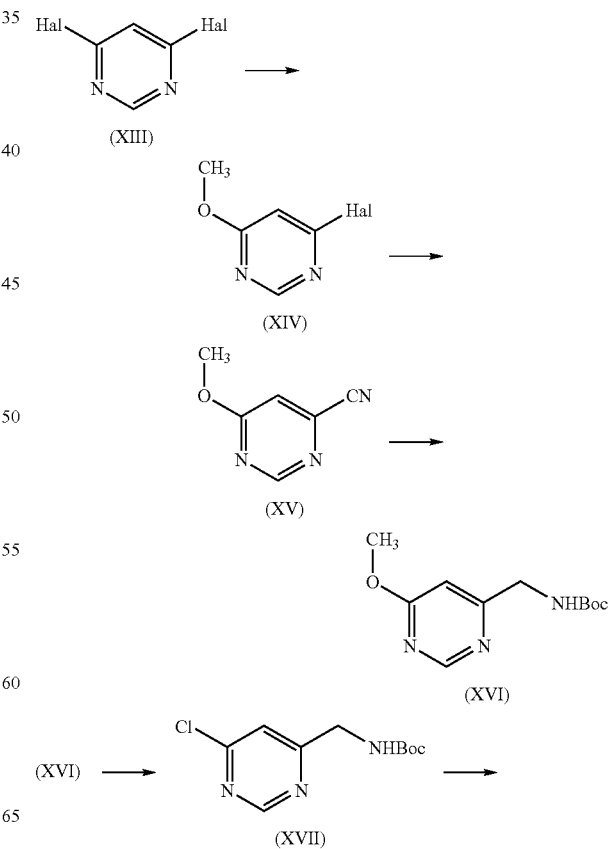

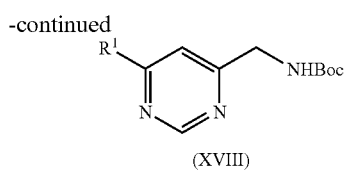

(XVIII)

In scheme 7, $R^1$ is as defined above, Hal means halogen, especially chlorine, Boc means tert-butyloxycarbonyl.

Treatment of 4,6-dihalosubstituted pyrimidines (XIII) with methoxide yields a 4-halopyrimidine compound (XIV). XIV is treated with 1,4-diazabicyclo[2.2.2]octane (DABCO) and then with sodium cyanide to yield a cyano compound (XV). The hydrogenation of (XV) in the presence of a catalyst such as nickel and in the presence of t-butyl dicarbonate gives the N-protected compound (XVI). Treatment of (XVI) with trimethylsilyl iodide followed by treatment with phosphoryl chloride affords a 6-chloropyrimidine compound (XVII). The nucleophilic attack of a nucleophil, such as alkoxide, haloalkoxide, alkylthiolate, occurs at the 6-position in compound XVII to yield the desired pyrimidin-4-ylmethylamine compound (XVIII) carrying a substituent $R^1$=alkoxide, haloalkoxide, alkylthiolate or halothiolates in the 6-position.

4,6-Dihalosubstituted pyrimidines are commercially available.

Pyrimidin-4-ylmethylamine compounds (II) carrying a substituent $R^1$ in the 6-position can also be prepared e.g. by the route outlined in scheme 8 below.

Scheme 8:

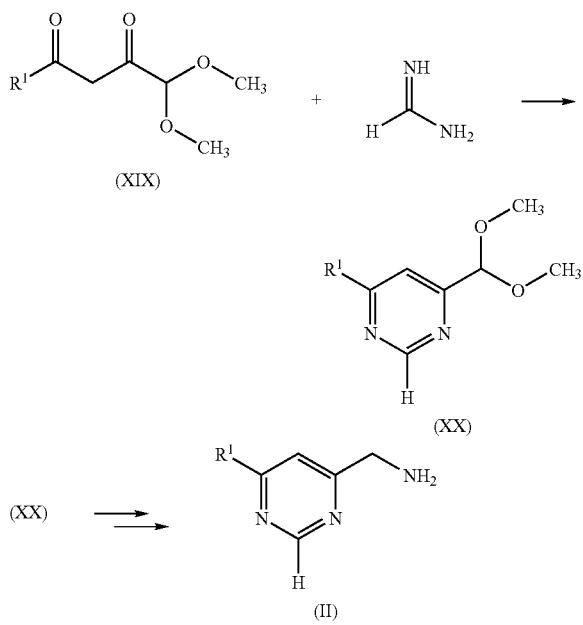

In scheme 8, $R^1$ is as defined above. According to the reaction depicted in scheme 8, compounds of the formula (II) can be prepared by reacting a carbonyl compound (XIX) with formamidine or a salt thereof, e.g. the hydrohalogenide such as the hydrochloride, giving a pyrimidine of the formula (XX), which can be converted to compounds of the formula (II) as described in scheme 4. The conversion of compounds of the formula (XIX) into compounds (XX) can be achieved by analogy to conventional methods as described, e.g., in Journal of Combinatorial Chemistry, 7(4), 517-519, 2005, Helvetica Chimica Acta 86(5), 1598-1624, 2003 or in scheme 4, step 1. The conversion of compounds (XX) into compounds (II) can be achieved as described in scheme 4, steps (ii) and (iii).

Acid addition salts of formamidine are commercially available.

Pyrimidin-4-ylmethylamine compounds (II) carrying a substituent $R^1$ in the 6-position and a substituent $R^1$ in the 2-position can also be prepared e.g. by the route outlined in scheme 9 below.

Scheme 9:

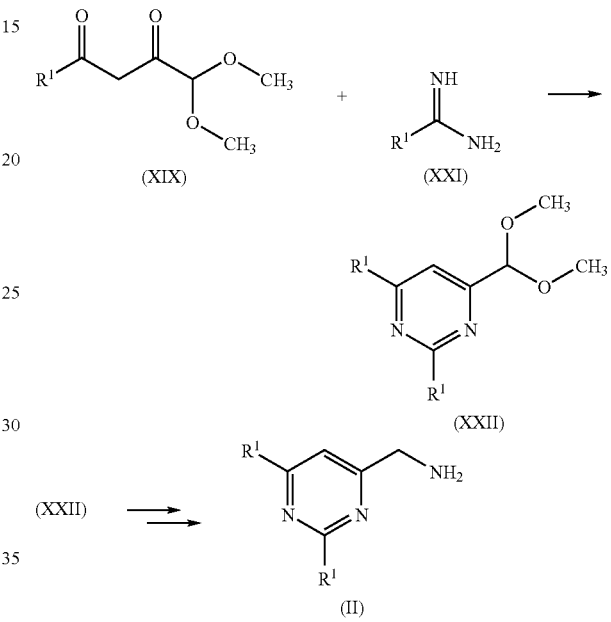

In scheme 9, $R^1$ is as defined above and each $R^1$ is selected independently of each other. According to the method of scheme 9, a carbonyl compound (XIX) is reacted with an amidine compound of the formula (XXI) giving a pyrimidine compound (XXII) which is converted into a compound of the formula (II) (for details, see scheme 8).

Sulfonyl compounds (III) are commercially available or can be obtained according to procedures known in the art.

The sulfonyl compound L-$SO_2$-A-$R^3$ of the formula (III) in which A is optionally substituted thiophenediyl and L is chlorine can be prepared according to the reaction scheme 10 below by treating a respective halide (XXIII) with alkylmagnesium halogenide such as $(CH_3)_2CH$—MgCl, $SO_2$ and $SO_2Cl_2$.

Scheme 10:

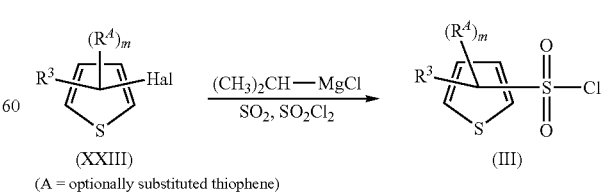

(A = optionally substituted thiophene)

In scheme 10, $R^4$ and $R^3$ are as defined above, m is 0, 1, or 2 and Hal means halogen.

Pyridine-SO$_3$ or dioxane-SO$_3$ complex converts optionally substituted furan into optionally substituted furan-2-sulfonic acid (III).

Sulfonation of optionally substituted pyrrole with sulfur trioxide-pyridine complex affords mainly the 3-sulfonated pyrroles of formula (III), in which A is an optionally substituted pyrrolediyl and L is OH [Mizuno, A. et. al., Tetrahedron Lett. 2000, 41, 6605.].

Sulfonation of optionally substituted imidazole and pyrazole, respectively, with oleum under heating yields optionally substituted imidazole-4-sulfonic acid and optionally substituted pyrrazole-4-sulfonic acid.

Sulfonation of optionally substituted isothiazole and isoxazole, respectively, with oleum takes usually place at the 4-position, provided that this position is unsubstituted to yield the corresponding sulfonated isothiazole and isoxazole, respectively. Sulfonation of optionally substituted thiazole with oleum at 250° C. in the presence of mercury(II)-acetate occurs usually at the 5-position to yield the corresponding sulfonated thiazole.

Pyridine-2-sulfonic acid, pyridine-3-sulfonic acid and pyridine-4-sulfonic acid are commerically available. For example, sulfonation of pyridine with oleum at 250° C. in the presence of Hg(II) as catalyst yields pyridine-3-sulfonic acid. Heating of pyridine-3-sulfonic acid at 360° C. or sulfonation of pyridine at 360° C. affords the pyridine-4-sulfonic acid. Pyridine-4-sulfonic acid can also be prepared starting from pyridine and thionyl chloride to afford N-(4-pyridyl)pyridinium chloride hydrochloride followed by the treatment of N-(4-pyridyl)pyridinium chloride hydrochloride with sodium sulfite heptahydrate to yield sodium 4-pyridine sulfonate. The treatment of sodium 4-pyridine sulfonate with an HCl affords pyridine-4-sulfonic acid [cf. Organic Syntheses, Coll. Vol. 5, p. 977 (1973); Vol. 43, p. 97 (1963).

Compounds of the formula (III), wherein A is optionally substituted phenylene are know from prior art cited in the introductory part.

Compounds of the formula (I) with R$^2$=H can be converted by conventional processes such as alkylation. Examples of suitable alkylating agents include alkyl halides, such as alkyl chloride, alkyl bromide or alkyl iodide, examples being methyl chloride, methyl bromide or methyl iodide, or dialkyl sulfates such as dimethyl sulfate or diethyl sulfate. The reaction with the alkylating agent is carried out advantageously in the presence of a solvent. Solvents used for these reactions are—depending on temperature range—aliphatic, cycloaliphatic or aromatic hydrocarbons such as hexane, cyclohexane, toluene, xylene, chlorinated aliphatic and aromatic hydrocarbons such as dichloromethane, chlorobenzene, open-chain dialkyl ethers such as diethyl ether, di-n-propyl ether, methyl tert-butyl ether, cyclic ethers such as tetrahydrofuran, 1,4-dioxane, glycol ethers such as dimethyl glycol ether, or mixtures of these solvents.

The N-oxides may be prepared from the compounds (I) according to conventional oxidation methods, for example by treating compounds (I) with an organic peracid such as metachloroperbenzoic acid [Journal of Medicinal Chemistry 38(11), 1892-903 (1995), WO 03/64572]; or with inorganic oxidizing agents such as hydrogen peroxide [cf. Journal of Heterocyclic Chemistry 18(7), 1305-8 (1981)] or oxone [cf. Journal of the American Chemical Society 123(25), 5962-5973 (2001)]. The oxidation may lead to pure mono-N-oxides or to a mixture of different N-oxides, which can be separated by conventional methods such as chromatography.

If individual compounds (I) cannot be obtained by the routes described above, they can be prepared by derivatization of other compounds I.

If the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the harmful fungus or pest to be controlled.

The compounds (I) are suitable as fungicides. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). Some are systemically effective and they can be used in crop protection as foliar fungicides, fungicides for seed dressing and soil fungicides.

They are particularly important in the control of a multitude of fungi on various cultivated plants, such as wheat, rye, barley, oats, rice, corn, lawns, bananas, cotton, soybeans, coffee, sugar cane, grapevines, fruit and ornamental plants, and vegetables, such as cucumbers, beans, tomatoes, potatoes and cucurbits, and on the seeds of these plants.

They are especially suitable for controlling the following plant diseases:

*Alternaria* species on vegetables, rape, sugar beets, fruit and rice (e.g. *A. solani* or *A. alternata* on potatoes and tomatoes),

*Aphanomyces* species on sugar beets and vegetables,

*Ascochyta* species on cereals and vegetables,

*Bipolaris* and *Drechslera* species on corn, cereals, rice and lawns (e.g. *D. maydis* on corn),

*Blumeria graminis* (powdery mildew) on cereals,

*Botrytis cinerea* (gray mold) on strawberries, vegetables, ornamental plants and grapevines,

*Bremia lactucae* on lettuce,

*Cerospora* species on corn, soybeans, rice and sugar beets,

*Cochliobolus* species on corn, cereals, rice (e.g. *Cochliobolus sativus* on cereals, *Cochliobolus miyabeanus* on rice),

*Colletotricum* species on soybeans and cotton,

*Drechslera* species, *Pyrenophora* species on corn, cereals, rice and lawns (e.g. *D. teres* on barley or *D. tritici-repentis* on wheat), Esca on grapevines, caused by *Phaeoacremonium chlamydosporium*, *Ph. Aleophilum* and *Formitipora punctata* (syn. *Phellinus punctatus*),

*Elsinoe ampelina* on grapevines,

*Exserohilum* species on corn,

*Erysiphe cichoracearum* and *Sphaerotheca fuliginea* on cucurbits,

*Fusarium* and *Verticillium* species on various plants (e.g. *F. graminearum* or *F. culmorum* on cereals or *F. oxysporum* on various plants, e.g. tomatoes),

*Gaeumanomyces graminis* on cereals,

*Gibberella* species on cereals and rice (e.g. *Gibberella fujikuroi* on rice),

*Glomerella cingulata* on grapevines and other plants,

Grainstaining complex on rice,

*Guignardia budwelli* on grapevines,

*Helminthosporium* species on corn and rice,

*Isariopsis clavispora* on grapevines,

*Michrodochium nivale* on cereals,

*Mycosphaerella* species on cereals, bananas and peanuts (e.g. *M. graminicola* on wheat or *M. fijiesis* on bananas),

*Peronospora* species on cabbage and onion plants (e.g. *P. brassicae* on cabbage or *P. destructor* on onions),

*Phakopsara pachyrhizi* and *Phakopsara meibomiae* on soybeans,

*Phomopsis* species on soybeans and sun flowers, *P. viticola* on grapevines,
*Phytophthora infestans* on potatoes and tomatoes,
*Phytophthora* species on various plants (e.g. *P. capsici* on paprika),
*Plasmopara viticola* on grapevines,
*Podosphaera leucotricha* on apples,
*Pseudocercosporella herpotrichoides* on cereals,
*Pseudoperonospora* on various plants (e.g. *P. cubensis* on cocumber or *P. humili* on hops),
*Pseudopezicula tracheiphilai* on grapevines,
*Puccinia* species on various plants (e.g. *P. triticina, P. striformins, P. hordei* or *P. graminis* on cereals or *P. asparagi* on asparagus),
*Pyricularia oryzae, Corticium sasakii, Sarocladium oryzae, S. attenuatum, Entyloma oryzae* on rice,
*Pyricularia grisea* on lawns and cereals,
*Pythium* spp. on lawns, rice, corn, cotton, rape, sun flowers, sugar beets, vegetables and other plants (e.g. *P. ultiumum* on various plants, *P. aphanidermatum* on lawns),
*Rhizoctonia* species on cotton, rice, potatoes, lawns, corn, rape, sugar beets, vegetables and on various plants (e.g. *R. solani* on beets and various plants),
*Rhynchosporium secalis* on barley, rye and triticale,
*Sclerotinia* species on rape and sun flowers,
*Septoria tritici* and *Stagonospora nodorum* on wheat,
*Erysiphe* (syn. *Uncinula*) *necator* on grapevines,
*Setospaeria* species on corn and lawns,
*Sphacelotheca reilinia* on corn,
*Sphaerotheca fuliginea* on cucumber,
*Thievaliopsis* species on soybeans and cotton,
*Tilletia* species on cereals,
*Ustilago* species on cereals, corn and sugar cane (e.g. *U. maydis* on corn),
*Venturia* species (scab) on apples and pears (e.g. *V. inaequalis* on apples).

The compounds (I) are also suitable for controlling harmful fungi in the protection of materials (e.g. wood, paper, paint dispersions, fiber or fabrics) and in the protection of stored products. As to the protection of wood, the following harmful fungi are worthy of note: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecilomyces* spp. and Zygomycetes such as *Mucor* spp., and in addition in the protection of stored products the following yeast fungi are worthy of note: *Candida* spp. and *Saccharomyces cerevisiae*.

The compounds (I) are employed by treating the fungi or the plants, seeds, materials or the soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound. The active compounds are employed in a purity of from 90% to 100%, preferably from 95% to 100% (according to NMR spectrum).

When employed in plant protection, the amounts applied are, depending on the kind of effect desired, between 0.01 and 2.0 kg of active compound per ha.

In seed treatment, for example by dusting, coating or drenching seed, amounts of active compound of from 0.1 g to 10 kg, frequently 1 to 1000 g, preferably from 5 to 100 g, per 100 kilogram of seed are generally required.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

In addition the compounds of the formula (I) may also be used in cultures which can tolerate insecticidal or fungal attack due to cultivation, including of genetic engineering.

The compounds of the formula (I) are furthermore suitable for controlling pests from the classes of the insects, arachnids and nematodes effectively. They can be used as pesticides in crop protection and in the sectors of hygiene and the protection of stored products and the veterinary sector.

They may act by contact or may be stomach-acting, or have systemic or residual action. Contact action means that the pest is killed by coming into contact with a compound I or with material that releases compound I. Stomach-acting means that the pest is killed if it ingests a pesticidially effective amount of the compound I or material containing a pesticidially effective amount of compound I. Systemic action means that the compound is absorbed into the plant tissues of treated plant and the pest is controlled, if it eats plant tissue or sucks plant-sap.

Compounds (I) are in particular suitable for controlling the following insect pests:

insects from the order of Lepidoptera, for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera eridania, Spodoptera frugiperda, Spodoptera littoralis, Spodoptera litura, Thaumatopoea pityocampa, Tortrix viridana, Trichoplusia ni* and *Zeiraphera canadensis*, from the order of Coleoptera (beetles), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna* varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria, from the order of Diptera, for example Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa, from the order of Thysanoptera (thrips), e.g. Dichromothrips spp., Frankliniella fusca, Frankliniella occidentalis, Frankliniella tritici, Scirtothrips citri, Thrips oryzae, Thrips palmi and Thrips tabaci, ants, bees, wasps, sawflies from the order of (Hymenoptera) e.g. Athalia rosae, Atta cephalotes, Atta cephalotes, Atta laevigata, Atta robusta, Atta capiguara, Atta sexdens, Atta texana, Crematogaster spp., Hoplocampa minuta, Hoplocampa testudinea, Monomorium pharaonis, Solenopsis geminata, and Solenopsis invicta, Solenopsis richteri, Solenopsis xyloni, Pogonomyrmex barbatus, Pogonomyrmex californicus, Pheidole megacephala, Dasymutilla occidentalis, Bombus spp. Vespula squamosa, Paravespula vulgaris, Paravespula pennsylvanica, Paravespula germanica, Dolichovespula maculata, Vespa crabro, Polistes rubiginosa, Camponotus floridanus, and Linepithema humile, from the order of Homoptera, e.g. Acyrthosiphon onobrychis, Adelges laricis, Aphidula nasturtii, Aphis craccivora, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisa tabaci, Bemisa argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, and Viteus vitifolii, from the order of Isoptera (termites), e.g. Calotermes flavicollis, Heterotermes aureus, Leucotermes flavipes, Reticulitermes flavipes, Reticulitermes virginicus, Reticulitermes lucifugus, aund Termes natalensis, and Coptotermes formosanus, cockroaches (Blattaria-Blattodea), e.g. Blattella germanica, Blattella asahinae, Periplaneta americana, Periplaneta japonica, Periplaneta brunnea, Periplaneta fuligginosa, Periplaneta australasiae, and Blatta orientalis, true bugs (Hemiptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma spp., and Arilus critatus, crickets, grasshoppers, locusts from the order of (Orthoptera), e.g. Acheta domestica, Blatta orientalis, Blattella germanica, Calliptamus italicus, Chortoicetes terminifera, Dociostaurus maroccanus, Forficula auricularia, Gryllotalpa gryllotalpa, Hieroglyphus daganensis, Kraussaria angulifera, Locusta migratoria, Locustana pardalina, Melanoplus bivittatus, Melanoplus femur-rubrum, Melanoplus mexicanus, Melanoplus sanguinipes, Melanoplus spretus, Nomadacris septemfasciata, Oedaleus senegalensis, Periplaneta americana, Schistocerca americana, Schistocerca peregrina, Schistocerca gregaria, Stauronotus maroccanus and, Tachycines asynamorus, Tachycines asynamorus, Zonozerus variegatus.

The compounds of the formula (I) and their salts are also useful for controlling arachnids (Arachnoidea), such as acarians (Acarina), e.g. of the families Argasidae, Ixodidae and Sarcoptidae, such as Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus hermsi, Ornithodorus turicata, Ornithonyssus bacoti, Ornithodorus moubata, Otobius megnini, Dermanyssus gallinae, Psoroptes ovis, Rhipicephalus sanguineus, Rhipicephalus appendiculatus, Rhipicephalus evertsi, Sarcoptes scabiei, and Eriophyidae spp. such as Aculus schlechtendali, Phyllocoptrata oleivora and Eriophyes sheldoni; Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetrany-

*chus pacificus, Tetranychus telarius* and *Tetranychus urticae, Panonychus ulmi, Panonychus citri,* and *oligonychus pratensis* and *Oligonychus pratensis; Araneida,* e.g. *Latrodectus mactans,* and *Loxosceles reclusa,* fleas (*Siphonaptera*), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp., earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

The compounds of the formula (I), their N-oxides and their salts are also useful for controlling nematodes, for example, root gall nematodes, e.g. *Meloidogyne hapla, Meloidogyne incognita, Meloidogyne javanica,* cyst-forming nematodes, e.g. *Globodera rostochiensis, Heterodera avenae, Heterodera glycines, Heterodera schachtii, Heterodera trifolii,* stem and leaf nematodes, e.g. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

Compounds of the formula (I) are particularly useful for controlling insects of the order *Lepidoptera.*

In general, the insecticidal compositions comprise from 0.01 to 95% by weight, preferably from 0.1 to 90% by weight, of the active compound. The active compounds are employed in a purity of from 90% to 100%, preferably from 95% to 100% (according to NMR spectrum).

Under outdoor conditions, the active compound application rate for controlling pests is from 0.1 to 2.0, preferably from 0.2 to 1.0, kg/ha.

The compounds (I), their N-oxides and salts can be converted into customary formulations (agricultural formulations), e.g. solutions, emulsions, suspensions, dusts, powders, pastes and granules. The application form depends on the particular intended purpose; in each case, it should ensure a fine and uniform distribution of the compound according to the invention.

The formulations are prepared in a known manner, e.g. by extending the active ingredient with solvents and/or carriers, if desired using emulsifiers and dispersants. Solvents/auxiliaries, which are suitable, are essentially:

water, aromatic solvents (for example Solvesso® products, xylene), paraffins (for example mineral fractions), alcohols (for example methanol, butanol, pentanol, benzyl alcohol), ketones (for example cyclohexanone, gamma-butyrolactone), pyrrolidones (N-methylpyrrolidone, N-octylpyrrolidone), acetates (glycol diacetate), glycols, fatty acid dimethylamides, fatty acids and fatty acid esters. In principle, solvent mixtures may also be used.

carriers such as ground natural minerals (e.g. kaolins, clays, talc, chalk) and ground synthetic minerals (e.g. highly disperse silica, silicates); emulsifiers such as nonionic and anionic emulsifiers (e.g. polyoxyethylene fatty alcohol ethers, alkyl-sulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalene-sulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Also anti-freezing agents such as glycerin, ethylene glycol and propylene glycol can be added to the formulation.

Suitable antifoaming agents are, for example, those based on silicone or magnesium stearate.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

Formulations for the treatment of seed may additionally comprise binders and/or gelling agents and, if appropriate, colorants.

Binders may be added to increase the adhesion of the active compounds on the seed after the treatment. Suitable binders are, for example, EO/PO block copolymer surfactants, but also polyvinyl alcohols, polyvinylpyrrolidones, polyacrylates, polymethacrylates, polybutenes, polyisobutylenes, polystyrenes, polyethylenamines, polyethylenamides, polyethylenimines (Lupasol®, Polymin®), polyethers, polyurethanes, polyvinyl acetates, tylose and copolymers of these polymers.

A suitable gelling agent is, for example, carrageen (Satiagel®).

In general, the formulations comprise from 0.01 to 95% by weight, preferably from 0.1 to 90% by weight, of the active compound. The active compounds are employed in a purity of from 90% to 100%, preferably from 95% to 100% (according to NMR spectrum).

The concentrations of active compound in the ready-for-use preparations can be varied within relatively wide ranges. In general, they are between 0.0001 and 10%, preferably between 0.01 and 1%.

The active compounds can also be used with great success in the ultra-low volume (ULV) process, it being possible to apply formulations with more than 95% by weight of active compound or even the active compound without additives.

For the treatment of seed, the formulations in question give, after two-to-tenfold dilution, active compound concentrations of from 0.01 to 60% by weight, preferably from 0.1 to 40% by weight, in the ready-to-use preparations.

The following are examples of formulations: 1. Products for dilution with water

A) Water-Soluble Concentrates (SL, LS)

10 parts by weight of a compound I according to the invention are dissolved in 90 parts by weight of water or in a water-soluble solvent. As an alternative, wetting agents or other auxiliaries are added. The active compound dissolves upon dilution with water. In this way, a formulation having a content of 10% by weight of active compound is obtained.

B) Dispersible Concentrates (DC)

20 parts by weight of a compound I according to the invention are dissolved in 70 parts by weight of cyclohexanone with addition of 10 parts by weight of a dispersant, for example polyvinylpyrrolidone. Dilution with water gives a dispersion. The active compound content is 20% by weight.

C) Emulsifiable Concentrates (EC)

15 parts by weight of a compound I according to the invention are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D) Emulsions (EW, EO, ES)

25 parts by weight of a compound I according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The formulation has an active compound content of 25% by weight.

E) Suspensions (SC, OD, FS)

In an agitated ball mill, 20 parts by weight of a compound I according to the invention are comminuted with addition of 10 parts by weight of dispersants and wetting agents and 70 parts by weight of water or an organic solvent to give a fine active compound suspension. Dilution with water gives a stable suspension of the active compound. The active compound content in the formulation is 20% by weight.

F) Water-Dispersible Granules and Water-Soluble Granules (WG, SG)

50 parts by weight of a compound I according to the invention are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

G) Water-Dispersible Powders and Water-Soluble Powders (WP, SP, SS, WS)

75 parts by weight of a compound I according to the invention are ground in a rotor-stator mill with addition of 25 parts by weight of dispersants, wetting agents and silica gel. Dilution with water gives a stable dispersion or solution of the active compound. The active compound content of the formulation is 75% by weight.

H) Gel (GF)

In an agitated ball mill, 20 parts by weight of a compound I according to the invention are comminuted with addition of 10 parts by weight of dispersants, 1 part by weight of a gelling agent welters and 70 parts by weight of water or of an organic solvent to give a fine suspension of the active compound. Dilution with water gives a stable suspension of the active compound, whereby a formulation with 20% (w/w) of active compound is obtained.

2. Products to be Applied Undiluted

J) Dustable Powders (DP, DS)

5 parts by weight of a compound I according to the invention are ground finely and mixed intimately with 95 parts by weight of finely divided kaolin. This gives a dustable product having an active compound content of 5% by weight.

K) Granules (GR, FG, GG, MG)

0.5 parts by weight of a compound I according to the invention is ground finely and associated with 99.5 parts by weight of carriers. Current methods are extrusion, spray-drying or the fluidized bed. This gives granules to be applied undiluted having an active compound content of 0.5% by weight.

L) ULV solutions (UL)

10 parts by weight of a compound I according to the invention are dissolved in 90 parts by weight of an organic solvent, for example xylene. This gives a product to be applied undiluted having an active compound content of 10% by weight.

The active ingredients can be used as such, in the form of their formulations or the use forms prepared therefrom, e.g. in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; it is intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.001 to 1%.

The active ingredients may also be used successfully in the ultra-low-volume process (ULV), it being possible to apply formulations comprising over 95% by weight of active ingredient, or even to apply the active ingredient without additives.

Various types of oils, wetters, adjuvants, herbicides, fungicides, other pesticides, or bactericides may be added to the active compounds, if appropriate not until immediately prior to use (tank mix). These agents can be admixed with the agents according to the invention in a weight ratio of 1:10 to 10:1.

The compositions according to the invention can, in the use form as fungicides, also be present together with other active compounds, e.g. with herbicides, insecticides, growth regulators, fungicides or else with fertilizers. Mixing the compounds (I) or the compositions comprising them in the use form as fungicides with other fungicides results in many cases in an expansion of the fungicidal spectrum of activity being obtained.

The following list of fungicides, in conjunction with which the compounds according to the invention can be used, is intended to illustrate the possible combinations but does not limit them:

acylalanines, such as benalaxyl, metalaxyl, ofurace or oxadixyl,
amine derivatives, such as aldimorph, dodine, dodemorph, fenpropimorph, fenpropidin, guazatine, iminoctadine, spiroxamine or tridemorph,
anilinopyrimidines, such as pyrimethanil, mepanipyrim or cyprodinil,
antibiotics, such as cycloheximide, griseofulvin, kasugamycin, natamycin, polyoxin or streptomycin,
azoles, such as bitertanol, bromoconazole, cyproconazole, difenoconazole, dinitroconazole, enilconazole, epoxiconazole, fenbuconazole, fluquinconazole, flusilazole, flutriafol, hexaconazole, imazalil, ipconazole, metconazole, myclobutanil, penconazole, propiconazole, prochloraz, prothioconazole, simeconazole, tebuconazole,
tetraconazole, triadimefon, triadimenol, triflumizole or triticonazole,
dicarboximides, such as iprodione, myclozolin, procymidone or vinclozolin,
dithiocarbamates, such as ferbam, nabam, maneb, mancozeb, metam, metiram, propineb, polycarbamate, thiram, ziram or zineb,
heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, picobenzamide, probenazole, proquinazid, pyrifenox, pyroquilon, quinoxyfen, silthiofam, thiabendazole, thifluzamide, thiophanate-methyl, tiadinil, tricyclazole or triforine,
copper fungicides, such as Bordeaux mixture, copper acetate, copper oxychloride or basic copper sulfate,
nitrophenyl derivatives, such as binapacryl, dinocap, dinobuton or nitrophthal-isopropyl,
phenylpyrroles, such as fenpiclonil or fludioxonil,
sulfur,
other fungicides, such as acibenzolar-5-methyl, benthiavalicarb, carpropamid, chlorothalonil, cyflufenamid, cymoxanil, diclomezine, diclocymet, diethofencarb, edifenphos, ethaboxam, fenhexamid, fentin acetate, fenoxanil, ferimzone, fluazinam, fosetyl, fosetyl-aluminum, phosphorous acid, iprovalicarb, hexachlorobenzene, metrafenone, pencycuron, penthropyrad, propamocarb, phthalide, toloclofos-methyl, quintozene or zoxamide,
strobilurins, such as azoxystrobin, dimoxystrobin, enestroburin, fluoxastrobin, kresoxim-methyl, metominostrobin, orysastrobin, picoxystrobin, pyraclostrobin or trifloxystrobin,
sulfenic acid derivatives, such as captafol, captan, dichlofluanid, folpet or tolylfluanid,
cinnamides and analogous compounds, such as dimethomorph, flumetover or flumorph.

Compositions of this invention may also contain other active ingredients, for example other pesticides such as insecticides and herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents usually are admixed with the agents according to the invention in a weight ratio of 1:100 to 100:1.

The following list of pesticides together with which the compounds according to the invention can be used, is intended to illustrate the possible combinations, but not to impose any limitation:

A.1. Organo(thio)phosphates: e.g. acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: e.g. alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: e.g. allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. Growth regulators: a) chitin synthesis inhibitors: e.g. benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: e.g. halofenozide, methoxyfenozide, tebufenozide, azadirachtin; c) juvenoids: e.g. pyriproxyfen, methoprene, fenoxycarb; d) lipid biosynthesis inhibitors: e.g. spirodiclofen, spiromesifen or spirotetramat;

A.5. Nicotinic receptor agonists/antagonists compounds (nicotinoid insecticides or neonicotinoids): e.g. clothianidin, dinotefuran, imidacloprid, thiamethoxam, nitenpyram, acetamiprid, thiacloprid or the thiazol compound of formula P1

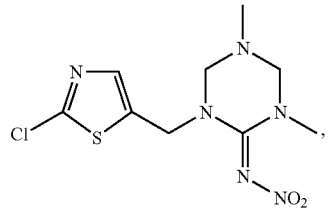

(P1)

A.6. GABA antagonist compounds: e.g. acetoprole, endosulfan, ethiprole, fipronil, vaniliprole, pyrafluprole, pyriprole, 5-amino-3-(aminothiocarbonyl)-1-(2,6-dichloro-4-trifluoromethylphenyl)-4-(trifluoromethylsulfinyl)-pyrazole;

A.7. Macrocyclic lactone insecticides: abamectin, emamectin, milbemectin, lepimectin, spinosad, A.8. Mitochondrial complex I electron transport inhibitors (METI I compounds): e.g. fenazaquin, pyridaben, tebufenpyrad, tolfenpyrad, flufenerim;

A.9. Mitochondrial complex II and/or complex III electron transport inhibitors (METI II and III compounds): e.g. acequinocyl, fluacyprim, hydramethylnon;

A.10. Uncoupler compounds: e.g. chlorfenapyr;

A.11. Oxidative phosphorylation inhibitor compounds: cyhexatin, diafenthiuron, fenbutatin oxide, propargite;

A.12. Moulting disruptor compounds: e.g. cyromazine;

A.13. Mixed function oxidase inhibitor compounds: e.g. piperonyl butoxide;

A.14. Sodium channel blocker compounds: e.g. indoxacarb, metaflumizone,

A.15. Various: benclothiaz, bifenazate, cartap, flonicamid, pyridalyl, pymetrozine, sulfur, thiocyclam, flubendiamide, cyenopyrafen, flupyrazofos, cyflumetofen, amidoflumet, compounds of the formula P2:

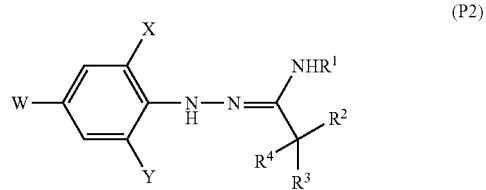

(P2)

wherein X and Y are each independently halogen, in particular chlorine;

W is halogen or $C_1$-$C_2$-haloalkyl, in particular trifluoromethyl;

$R^1$ is $C_1$-$C_6$-alkyl, $C_2$-$C_6$-alkenyl, $C_2$-$C_6$-alkynyl, $C_1$-$C_4$-alkoxy-$C_1$-$C_4$-alkyl or $C_3$-$C_6$-cycloalkyl each of which may be substituted with 1, 2, 3, 4 or 5 halogen atoms; in particular $R^1$ is methyl or ethyl;

$R^2$ and $R^3$ are $C_1$-$C_6$-alkyl, in particular methyl, or may form together with the adjacent carbon atom a $C_3$-$C_6$-cycloalkyl moiety, in particular a cyclopropyl moiety, which may carry 1, 2 or 3 halogen atoms, examples including 2,2-dichlorocyclopropyl and 2,2-dibromocyclopropyl; and $R^4$ is hydrogen or $C_1$-$C_6$-alkyl, in particular hydrogen methyl or ethyl;

anthranilamide compounds of formula P3

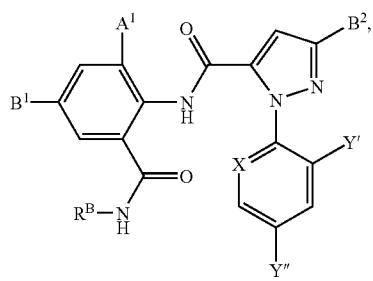

P3 wherein $A^1$ is $CH_3$, Cl, Br, I, X is C—H, C—Cl, C—F or N, Y' is F, Cl, or Br, Y" is F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$;

and malononitrile compounds as described in JP 2002/284608, WO 02/89579, WO 02/90320, WO 02/90321, WO 04/06677, WO 04/20399 or JP 2004/99597.

Suitable pesticides compounds also include microorganisms such as *Bacillus thuringiensis, Bacillus tenebrionis* and *Bacillus subtilis.*

The aforementioned compositions are particularly useful for protecting plants against infestation of said pests and also for protecting plants against infections of phytopathogenic fungi or to combat these pests/fungi in infested/infected plants.

However, the compounds of formula (I) are also suitable for the treatment of seeds. Application to the seeds is carried out before sowing, either directly on the seeds or after having pregerminated the latter.

Compositions which are useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Dustable powders (DP, DS)

Preferred FS formulations of compounds of formula (I) for seed treatment usually comprise from 0.5 to 80% of the active ingredient, from 0.05 to 5% of a wetter, from 0.5 to 15% of a dispersing agent, from 0.1 to 5% of a thickener, from 5 to 20% of an anti-freeze agent, from 0.1 to 2% of an anti-foam agent, from 1 to 20% of a pigment and/or a dye, from 0 to 15% of a sticker/adhesion agent, from 0 to 75% of a filler/vehicle, and from 0.01 to 1% of a preservative.

Suitable pigments or dyes for seed treatment formulations are pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Stickers/adhesion agents are added to improve the adhesion of the active materials on the seeds after treatment. Suitable adhesives are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymine), polyethers and copolymers derived from these polymers.

For use against ants, termites, wasps, flies, mosquitos, crickets, or cockroaches, compounds of formula (I) are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula (I) as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula (I) and its respective compositions can also be used in mosquito and fumigating coils, smoke cartridges, vaporizer plates or long-term vaporizers and also in moth papers, moth pads or other heat-independent vaporizer systems.

The compounds of formula (I) and its compositions can be used for protecting non-living material, in particular cellulose-based materials such as wooden materials e.g. trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula (I) are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

In the methods according to the invention the pests are controlled by contacting the target parasite/pest, its food supply, habitat, breeding ground or its locus with a pesticidally effective amount of at least one compounds (I), or the N-oxide or salt thereof, or with a composition, containing a pesticidally effective amount of at least one compound I, or the N-oxide or salt thereof.

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds (I) of the invention can also be applied preventively to places at which occurrence of the pests is expected.

The compounds of formula (I) may be also used to protect growing plants from attack or infestation by pests by contacting the plant with a pesticidally effective amount of compounds of formula (I). As such, "contacting" includes both direct contact (applying the compounds/compositions directly on the pest and/or plant—typically to the foliage, stem or roots of the plant) and indirect contact (applying the compounds/compositions to the locus of the pest and/or plant).

The compounds (I) are employed by treating the fungi, pests or the plants, seeds, materials or the soil to be protected from fungal attack or pesticidal attack with a fungicidally or pesticidally effective amount of at least one active compound I, its N-oxide or salt. The application can be carried out both before and after the infection/infestation of the materials, plants or seeds by the fungi or pest.

When employed in plant protection, the amounts applied are, depending on the kind of effect desired, in the range of 0.1 g to 4000 g per hectare, desirably from 25 g to 600 g per hectare, more desirably from 50 g to 500 g per hectare.

In the treatment of seed, the application rates of the active compounds are generally from 0.001 g to 100 g per kg of seed, preferably from 0.01 g to 50 g per kg of seed, in particular from 0.01 g to 2 g per kg of seed.

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.001 weight % to 15 weight %, desirably from 0.001 weight % to 5% weight % of active compound.

For use in spray compositions, the content of active ingredient is from 0.001 to 80 weights %, preferably from 0.01 to 50 weight % and most preferably from 0.01 to 15 weight %.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

Under outdoor conditions, the active compound application rate for controlling pests is from 0.1 to 2.0, preferably from 0.2 to 1.0, kg/ha.

Various types of oils, wetters, adjuvants, herbicides, fungicides, other pesticides, or bactericides may be added to the active compounds, if appropriate not until immediately prior to use (tank mix). These agents can be admixed with the agents according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, z. B. Pluronic RPE 2035® and Genapol B®; alcohol ethoxylates such as Lutensol XP 80®; and dioctyl sulfosuccinate sodium such as Leophen RA®.

Compounds of formula (I), their N-oxides and veterinarily acceptable salts as well as the compositions comprising them can also be used for controlling and preventing infestations and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula (I) and compositions comprising them are suitable for systemic and/or non-systemic control of ecto- and/or endoparasites. They are active against all or some stages of development.

Administration can be carried out both prophylactically and therapeutically. Administration of the active compounds (I)s carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds, their N-oxides and salts may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Generally it is favorable to apply solid formulations which release compounds of formula (I) in total amounts of 10 mg/kg to 300 mg/kg, preferably 20 mg/kg to 200 mg/kg.

The active compounds can also be used as a mixture with synergists or with other active compounds which act against pathogenic endo- and ectoparasites.

In general, the compounds of formula (I) are applied in parasiticidally effective amount-meaning the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

SYNTHESIS EXAMPLES

Preparation of Intermediates

I. Preparation of pyrimidinyl-4-yl methylamine compounds

I.1 Preparation of (2-methyl-pyrimidin-4-yl)-methylamine

I.1.1 4-Dimethoxymethyl-2-methyl-pyrimidine

Acetamidine hydrochloride (3 mol) and 4-dimethylamino-1,1-dimethoxy-but-3-en-2-one (2 mol) were mixed in methanol (500 ml) and the reaction mixture was warmed to 40° C. A solution of sodium methoxide in methanol (558 g, 30%) was added quickly and a brown suspension was formed. The reaction mixture was heated under reflux for 2 h, cooled to room temperature overnight followed by evaporation of methanol under reduced pressure. The resulting residue was taken up in dichloromethane (500 ml) and washed several times with water (100 mL). The solvent was removed to give 307 g of black oil. The distillation of this oil gave a colourless liquid of boiling point 55-58° C. (0.5 mbar).

I.1.2 2-Methyl-pyrimidine-4-carbaldehyde oxime

To a solution of 4-dimethoxymethyl-2-methyl-pyrimidine (10 g) from I.1.1 in methanol (100 mL) was added 8.2 g of hydroxylamine hydrochloride and 10% HCl and the reaction mixture was heated under reflux for 2 h. After cooling to room temperature, the pH was adjusted to 8 using solid sodium carbonate. The mixture was stirred for 30 minutes. The solid was sucked off, dried at 50° C. under reduced pressure to yield 6.0 g (73%) of the title compound as white solid.

I.1.3 (2-Methyl-pyrimidin-4-yl)-methylamine

An autoclave was charged with 2-methyl-pyrimidine-4-carbaldehyde oxime (13 g) from I.1.2, 150 ml of methanol and 70 ml of triethylamine. The autoclave was purged with nitrogen. To this mixture was added 3 g of a 10% palladium-on-carbon catalyst. The autoclave was sealed and purged twice with hydrogen gas. The hydrogenation was run for 2 h. In doing this, the reaction mixture was warmed up to 40° C. in the meantime. The precipitate was filtered off, washed with methanol to yield the title compound as light red solid (11 g, 94%).

I.2 (2-Chloro-pyrimidin-4-ylmethyl)carbamic acid tert-butylester

2-Chloropyrimidine-4-carbonitrile (24 g), 40.8 g of t-butyl dicarbonate ($Boc_2O$) in 1.2 L of methanol and 5 g of Raney nickel (Raney 2400) were charged in an autoclave. The autoclave was sealed and purged with hydrogen. The hydrogenation was run at 30 psi hydrogen gas. The reduction was carried out to completion and the reactor was vented and purged with nitrogen. The reaction mixture was filtered over diatomaceous earth and the filtrate was concentrated. The residue was purified by chromatography to yield the title compound (35 g, 84%) as white solid of melting point of 86-88° C.

II. Preparation of Sulfonic Acid Amides (I)

Example 1

4'-Chlorobiphenyl-4-sulfonic acid (pyrimidin-4-ylmethyl)-amide

Pyrimidin-4-yl-methylamine dihydrochloride (1.0 eq) and triethylamine (3.0 eq) were dissolved in acetonitrile (5 mL/mmol) and the solution was cooled to 0° C. Chlorobiphenylsulfochloride (1.0 eq) was added in portions and the reaction mixture was warmed to room temperature overnight. The solvent was evaporated under reduced pressure and the residue was washed with cold water and diisopropyl ether.

The title compound was obtained as beige solid.

Example 2

4-Iodo-N-pyrimidin-4-ylmethylbenzenesulfonamide

Pyrimidin-4-yl-methylamine dihydrochloride (1.0 eq) and triethylamine (3.0 eq) were dissolved in acetonitrile (5 mL/mmol) and the solution was cooled to 0° C. 4-Iodobenzenesulfonic acid chloride (1.0 eq) was added in portions and the reaction mixture was warmed to room temperature. The solvent was evaporated under reduced pressure and the residue was washed with cold water and cold diisopropyl ether to yield the title compound as beige solid.

Example 3

4'-Fluorobiphenyl-4-sulfonic acid (pyrimidin-4-ylmethyl) amide

The sulphonamide from example 2 (1.0 eq), 4-fluorophenylboronic acid and $Pd(PPh_3)_4$ were dissolved in dioxane (3 mL/mmol) and an aqueous solution of sodium carbonate (2 mL/mmol) was added. The reaction mixture was heated under reflux overnight and after completion of the reaction the solvent was removed under reduced pressure. The residue was purified by chromatography to yield the title compound as beige solid.

The compounds listed in table I can be prepared in an analogous manner.

TABLE I

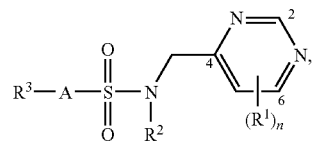

(I)

| ex. no | $(R^1)_n$ | $R^2$ | A—$R^3$ | m.p. [° C.] RT[min] |
|---|---|---|---|---|
| 1 | -- | H | 4-(4-Cl-phenyl)-phenyl | 177 |
| 2 | -- | H | 4-iodophenyl | 133 |
| 3 | -- | H | 4-(4-F-phenyl)-phenyl | 128 |
| 4 | 2-NH($CH_3$) | H | 4-(4-F-phenyl)-phenyl | 140 |
| 5 | 2-NH($CH_3$) | H | 4-(4-Cl-phenyl)-phenyl | 177 |
| 6 | 2-N($CH_3$)$_2$ | H | 4-(4-Cl-phenyl)-phenyl | 122 |
| 7 | 2-N($CH_3$)$_2$ | H | 4-(4-F-phenyl)-phenyl | 146 |
| 8 | 2-S$CH_3$ | H | 4-(4-Cl-phenyl)-phenyl | 148 |
| 9 | 2-S$CH_3$ | H | 4-(4-F-phenyl)-phenyl | 168 |
| 10 | -- | H | 6-(3-chloro-4-methoxy-phenyl)-pyridin-3-yl | 154 |
| 11 | 2-NH($CH_3$) | H | 5-(4-Cl-phenyl)-thiophen-3-yl | 141 |
| 12 | 2-N($CH_3$)$_2$ | H | 5-(4-Cl-phenyl)-thiophen-3-yl | 2.84 |
| 13 | 2-S$CH_3$ | H | 5-(4-Cl-phenyl)-thiophen-3-yl | 3.53 |
| 14 | 2-NH($CH_3$) | H | 4-(4-$CF_3$-phenyl)-thiophen-2-yl | 172 |
| 15 | 2-NH($CH_3$) | H | 4-(3-CN-phenyl)-thiophen-2-yl | 201 |
| 16 | 2-N($CH_3$)$_2$ | H | 4-(4-$CF_3$-phenyl)-thiophen-2-yl | 2.94 |
| 17 | 2-N($CH_3$)$_2$ | H | 4-(3-CN-phenyl)-thiophen-2-yl | 2.49 |
| 18 | 2-S$CH_3$ | H | 4-(4-$CF_3$-phenyl)-thiophen-2-yl | 3, 61 |
| 19 | 2-S$CH_3$ | H | 4-(3-CN-phenyl)-thiophen-2-yl | 3.09 |
| 20 | 2-S$CH_3$ | H | 6-(3-chloro-4-methoxy-phenyl)-pyridin-3-yl | 178 |
| 21 | 2-NH($CH_3$) | H | 6-(3-chloro-4-methoxy-phenyl)-pyridin-3-yl | 189 |
| 22 | 2-NH($CH_3$) | H | 6-(4-chloro-phenyl)-pyridin-3-yl | 197 |
| 23 | 2-N($CH_3$)$_2$ | H | 6-(4-chloro-phenyl)-pyridin-3-yl | 152 |
| 24 | 2-S$CH_3$ | H | 6-(4-chloro-phenyl)-pyridin-3-yl | 145 |
| 25 | 2-S$CH_3$ | H | 5-(3-chloro-4-methoxy-phenyl)-pyridin-2-yl | 154 |
| 26 | 2-$CH_3$ | H | 4-(4-F-phenyl)-phenyl | 118 |

TABLE I-continued (I)

$R^3-A-\underset{\underset{O}{\overset{O}{\|}}}{\overset{\overset{O}{\|}}{S}}-\underset{R^2}{N}-CH_2-\underset{(R^1)_n}{\text{pyrimidine}}$

| ex. no | $(R^1)_n$ | $R^2$ | A—$R^3$ | m.p. [° C.] RT[min] |
|---|---|---|---|---|
| 27 | 2-cyclopropyl | H | 4-(4-F-phenyl)-phenyl | 110 |
| 28 | 2-CH$_3$ | H | 4-(4-Cl-phenyl)-phenyl | 153 |
| 29 | 2-cyclopropyl | H | 4-(4-Cl-phenyl)-phenyl | 171 |
| 30 | 2-CH$_3$ | H | 5-(4-Cl-phenyl)-thiophen-2-yl | 135 |
| 31 | 2-CH$_3$ | H | 5-(4-CF$_3$-phenyl)-thiophen-2-yl | 121 |
| 32 | 2-cyclopropyl | H | 5-(4-Cl-phenyl)-thiophen-2-yl | 149 |
| 33 | 2-cyclopropyl | H | 5-(4-CF$_3$-phenyl)-thiophen-2-yl | 155 |
| 34 | -- | H | 4-(phenyl)-phenyl | 3.13 |
| 35 | -- | H | 4-(2-Cl-phenyl)-phenyl | 2.98 |
| 36 | -- | H | 4-(3-Cl-phenyl)-phenyl | 3.11 |
| 37 | -- | H | 4-(4-Cl-phenyl)-phenyl | 3.13 |
| 38 | -- | H | 4-(2-F-phenyl)-phenyl | 2.85 |
| 39 | -- | H | 4-(3-F-phenyl)-phenyl | 2.89 |
| 40 | -- | H | 4-(4-F-phenyl)-phenyl | 2.88 |
| 41 | -- | H | 4-(2-CH$_3$-phenyl)-phenyl | 2.99 |
| 42 | -- | H | 4-(3-CH$_3$-phenyl)-phenyl | 3.06 |
| 43 | -- | H | 4-(4-CH$_3$-phenyl)-phenyl | 3.07 |
| 44 | -- | H | 4-(2-OCH$_3$-phenyl)-phenyl | 2.85 |
| 45 | -- | H | 4-(3-OCH$_3$-phenyl)-phenyl | 2.84 |
| 46 | -- | H | 4-(4-OCH$_3$-phenyl)-phenyl | 2.82 |
| 47 | -- | H | 4-(2-CF$_3$-phenyl)-phenyl | 3.08 |
| 48 | -- | H | 4-(3-CF$_3$-phenyl)-phenyl | 3.21 |
| 49 | -- | H | 4-(4-CF$_3$-phenyl)-phenyl | 3.24 |
| 50 | -- | H | 4-(3-CN-phenyl)-phenyl | 2.64 |
| 51 | -- | H | 4-(4-CN-phenyl)-phenyl | 2.64 |
| 52 | -- | H | 4-(2,4-difluoro-phenyl)-phenyl | 2.93 |
| 53 | -- | H | 4-(3,4-difluoro-phenyl)-phenyl | 2.97 |
| 54 | -- | H | 4-(2,4-dichloro-phenyl)-phenyl | 3.32 |
| 55 | -- | H | 4-(3,4-dichloro-phenyl)-phenyl | 3.36 |
| 56 | 2-CH$_3$ | H | 4-phenoxy-phenyl | 104 |
| 57 | 2-cyclopropyl | H | 4-phenoxy-phenyl | 118 |
| 58 | 2-SCH$_3$ | H | 4-phenoxy-phenyl | 3.37 |
| 59 | 2-CH$_3$ | H | 4-(4-Cl-phenoxy)-phenyl | 112 |
| 60 | 2-cyclopropyl | H | 4-(4-Cl-phenoxy)-phenyl | 144 |
| 61 | 2-SCH$_3$ | H | 4-(4-Cl-phenoxy)-phenyl | 124 |
| 62 | 2-CH$_3$ | H | 4-(4-CF$_3$-phenyl)-thiophen-2-yl | 121 |
| 63 | 2-CH$_3$ | H | 4-(3-CN-phenyl)-thiophen-2-yl | 155 |
| 64 | 2-cyclopropyl | H | 4-(4-CF$_3$-phenyl)-thiophen-2-yl | 120 |
| 65 | 2-cyclopropyl | H | 4-(3-CN-phenyl)-thiophen-2-yl | 118 |
| 66 | 2-N(CH$_3$)$_2$ | CH$_3$ | 4-(4-F-phenyl)-phenyl | 2.94 |
| 67 | 2-N(CH$_3$)$_2$ | CH$_3$ | 4-(4-Cl-phenyl)-phenyl | 118 |
| 68 | 2-CH$_3$ | H | benzo[b]furan-2-yl | 129 |
| 69 | 2-cyclopropyl | H | benzo[b]furan-2-yl | 161 |
| 70 | 2-CH$_3$ | H | benzo[b]thiophen-3-yl | 206 |
| 71 | 2-cyclopropyl | H | benzo[b]thiophen-3-yl | 143 |
| 72 | 2-CH$_3$ | H | 5-chloro-3-methyl-benzo[b]thiophen-2-yl | 162 |
| 73 | 2-cyclopropyl | H | 5-chloro-3-methyl-benzo[b]thiophen-2-yl | 121 |
| 74 | -- | H | 4-(4-F-phenyl)-5-methyl-thiophen-2-yl | 3.13 |
| 75 | 2-CH$_3$ | H | 4-(4-F-phenyl)-5-methyl-thiophen-2-yl | 3.21 |
| 76 | 2-cyclopropyl | H | 4-(4-F-phenyl)-5-methyl-thiophen-2-yl | 3.24 |
| 77 | 2-SCH$_3$ | H | 4-(4-F-phenyl)-5-methyl-thiophen-2-yl | 3.45 |
| 78 | 2-CH$_3$ | H | 3-(4-Cl-phenoxy)-phenyl | 3.11 |
| 79 | 2-cyclopropyl | H | 3-(4-Cl-phenoxy)-phenyl | 3.40 |
| 80 | 2,6-dimethyl | H | 3-(4-Cl-phenoxy)-phenyl | 3.01 |
| 81 | 2-CH$_3$ | H | 3-phenoxy-phenyl | 3.82 |
| 82 | 2,6-dimethyl | H | 3-phenoxy-phenyl | 2.73 |
| 83 | 2-cyclopropyl | H | 3-phenoxy-phenyl | 126 |
| 84 | 2-CH$_3$ | H | 4-(4-F-phenyl)-5-CF$_3$-thiophen-2-yl | 83 |
| 85 | 2-cyclopropyl | H | 4-(4-F-phenyl)-5-CF$_3$-thiophen-2-yl | 110 |
| 86 | 2-SCH$_3$ | H | 4-(4-F-phenyl)-5-CF$_3$-thiophen-2-yl | 92 |
| 87 | 2,6-dimethyl | H | 4-(4-Cl-phenyl)-phenyl | 124 |
| 88 | 2-OCH$_3$ | H | 4-(4-Cl-phenyl)-phenyl | 134 |
| 89 | 6-OCH$_3$ | H | 4-(4-Cl-phenyl)-phenyl | 183 |
| 90 | 2,6-dimethyl | H | 5-(4-CF$_3$-phenyl)-thiophen-2-yl | 157 |
| 91 | 2-OCH$_3$ | H | 5-(4-CF$_3$-phenyl)-thiophen-2-yl | 107 |
| 92 | 6-OCH$_3$ | H | 5-(4-CF$_3$-phenyl)-thiophen-2-yl | 157 |
| 93 | 2-OCH$_3$ | H | 6-(3-chloro-4-methoxy-phenyl)-pyridin-3-yl | 182 |
| 94 | 2-OCH$_3$ | H | 4-(4-CF$_3$-phenyl)-thiophen-2-yl | 117 |

TABLE I-continued (I)

$$R^3-A-\underset{\underset{O}{\overset{O}{\|}}}{\overset{\overset{O}{\|}}{S}}-\underset{R^2}{N}-CH_2-\text{pyrimidinyl}(R^1)_n$$

| ex. no | $(R^1)_n$ | $R^2$ | A—$R^3$ | m.p. [° C.] RT[min] |
|---|---|---|---|---|
| 95 | 2-OCH$_3$ | H | 4-(3-CN-phenyl)-thiophen-2-yl | 147 |
| 96 | 6-OCH$_3$ | H | 4-(3-CN-phenyl)-thiophen-2-yl | 146 |
| 97 | 6-OCH$_3$ | H | 6-(3-chloro-4-methoxy-phenyl)-pyridin-3-yl | 172 |
| 98 | -- | H | 1-(4-fluoro-phenyl)-1H-pyrazol-4-yl | 157 |
| 99 | 2-CH$_3$ | H | 1-(4-fluoro-phenyl)-1H-pyrazol-4-yl | 142 |
| 100 | 2,6-dimethyl | H | 1-(4-fluoro-phenyl)-1H-pyrazol-4-yl | 180 |
| 101 | 2-cyclopropyl | H | 1-(4-fluoro-phenyl)-1H-pyrazol-4-yl | 101 |
| 102 | 2-SCH$_3$ | H | 1-(4-fluoro-phenyl)-1H-pyrazol-4-yl | 2.63 |
| 103 | -- | H | 1-(4-F-phenyl)-1H-pyrrol-3-yl | 114 |
| 104 | 2-CH$_3$ | H | 1-(4-F-phenyl)-1H-pyrrol-3-yl | 109 |
| 105 | 2,6-dimethyl | H | 1-(4-F-phenyl)-1H-pyrrol-3-yl | 2.33 |
| 106 | 2-cyclopropyl | H | 1-(4-F-phenyl)-1H-pyrrol-3-yl | 2.72 |
| 107 | 2-SCH$_3$ | H | 1-(4-F-phenyl)-1H-pyrrol-3-yl | 2.98 |
| 108 | -- | H | 1-(4-F-phenyl)-1H-imidazol-4-yl | 2.08 |
| 109 | 2-CH$_3$ | H | 1-(4-F-phenyl)-1H-imidazol-4-yl | 2.07 |
| 110 | 2-cyclopropyl | H | 1-(4-F-phenyl)-1H-imidazol-4-yl | 148 |
| 111 | 2-SCH$_3$ | H | 1-(4-F-phenyl)-1H-imidazol-4-yl | 2.59 |
| 112 | 2-cyclopropyl | H | 2-(4-F-phenyl)-thiazol-5-yl | 131 |
| 113 | 2-cyclopropyl | H | 4-(4-F-phenyl)-thiazol-2-yl | 167 |
| 114 | 2-SCH$_3$ | H | 4-(4-F-phenyl)-thiazol-2-yl | 136 |
| 115 | -- | H | 2-(4-F-phenyl)-thiazol-5-yl | 153 |
| 116 | 2-CH$_3$ | H | 2-(4-F-phenyl)-thiazol-5-yl | 171 |
| 117 | -- | H | 4-(4-F-phenyl)-thiazol-2-yl | 117 |
| 118 | 2-CH$_3$ | H | 4-(4-F-phenyl)-thiazol-2-yl | 164 |
| 119 | -- | H | 4-(3-CN-phenyl)-thiophen-2-yl | 2.63 |
| 120 | -- | H | 4-(4-Cl-phenyl)-thiophen-2-yl | 3.05 |
| 121 | -- | H | 4-(3,4-Cl$_2$-phenyl)-thiophen-2-yl | 3.28 |
| 122 | -- | H | 4-(2,4-Cl$_2$-phenyl)-thiophen-2-yl | 2.91 |
| 123 | -- | H | 4-(3,4-F$_2$-phenyl)-thiophen-2-yl | 2.88 |
| 124 | -- | H | 4-(2,4-F$_2$-phenyl)-thiophen-2-yl | 2.59 |
| 125 | -- | H | 4-(4-CN-phenyl)-thiophen-2-yl | 2.47 |
| 126 | -- | H | 6-phenyl-pyridin-3-yl | 2.63 |
| 127 | -- | H | 6-(3-F-phenyl)-pyridin-3-yl | 2.59 |
| 128 | -- | H | 6-(4-F-phenyl)-pyridin-3-yl | 2.39 |
| 129 | -- | H | 6-(2-methoxy-phenyl)-pyridin-3-yl | 3.05 |
| 130 | -- | H | 6-(3-CF$_3$-phenyl)-pyridin-3-yl | 3.02 |
| 131 | -- | H | 6-(4-CF$_3$-phenyl)-pyridin-3-yl | 3.04 |
| 132 | -- | H | 5-(4-methyl-phenyl)-thiophen-2-yl | 3.05 |
| 133 | -- | H | 5-(4-Cl-phenyl)-thiophen-2-yl | 3, 12 |
| 134 | -- | H | 5-(2-methoxy-phenyl)-thiophen-2-yl | 2.83 |
| 135 | -- | H | 4-(2-F-phenyl)-thiophen-2-yl | 2.79 |
| 136 | -- | H | 4-(3-CF$_3$-phenyl)-thiophen-4-yl | 3.14 |
| 137 | -- | H | 6-(2-Cl-phenyl)-pyridin-3-yl | 2.55 |
| 138 | -- | H | 4-(2-Cl-phenyl)-thiophen-2-yl | 2.91 |
| 139 | -- | H | 6-(3-Cl-phenyl)-pyridin-3-yl | 2.87 |
| 140 | -- | H | 6-(2-F-phenyl)-pyridin-3-yl | 2.51 |
| 141 | -- | H | 6-(2-CH$_3$-phenyl)-pyridin-3-yl | 2.51 |
| 142 | -- | H | 6-(3-CH$_3$-phenyl)-pyridin-3-yl | 2.72 |
| 143 | -- | H | 6-(4-CH$_3$-phenyl)-pyridin-3-yl | 2.72 |
| 144 | -- | H | 6-(3-OCH$_3$-phenyl)-pyridin-3-yl | 2.56 |
| 145 | -- | H | 6-(4-OCH$_3$-phenyl)-pyridin-3-yl | 2.51 |
| 146 | -- | H | 6-(3-CN-phenyl)-pyridin-3-yl | 2.45 |
| 147 | -- | H | 6-(4-CN-phenyl)-pyridin-3-yl | 2.45 |
| 148 | -- | H | 6-(2,4-difluoro-phenyl)-pyridin-3-yl | 2.63 |
| 149 | -- | H | 6-(3,4-difluoro-phenyl)-pyridin-3-yl | 2.76 |
| 150 | -- | H | 6-(2,4-dichloro-phenyl)-pyridin-3-yl | 2.94 |
| 151 | -- | H | 6-(4-chloro-phenyl)-pyridin-3-yl | 2.97 |
| 152 | -- | H | 5-(2-CH$_3$-phenyl)-thiophen-2-yl | 2.96 |
| 153 | -- | H | 5-(3-CH$_3$-phenyl)-thiophen-2-yl | 3.09 |
| 154 | -- | H | 5-(2-Cl-phenyl)-thiophen-2-yl | 2.95 |
| 155 | -- | H | 5-(3-Cl-phenyl)-thiophen-2-yl | 3.09 |
| 156 | -- | H | 5-(4-OCH$_3$-phenyl)-thiophen-2-yl | 2.83 |
| 157 | -- | H | 5-(3-OCH$_3$-phenyl)-thiophen-2-yl | 2.86 |
| 158 | -- | H | 5-(3,4-difluoro-phenyl)-thiophen-2-yl | 2.97 |
| 159 | -- | H | 5-(2-CF$_3$-phenyl)-thiophen-2-yl | 3.06 |
| 160 | -- | H | 5-(3-F-phenyl)-thiophen-2-yl | 2.88 |
| 161 | -- | H | 5-(4-F-phenyl)-thiophen-2-yl | 2.86 |
| 162 | -- | H | 5-(3-CN-phenyl)-thiophen-2-yl | 2.66 |

TABLE I-continued (I)

$R^3-A-\underset{\underset{O}{\overset{O}{\|}}}{\overset{\overset{O}{\|}}{S}}-\underset{R^2}{N}-CH_2-\text{pyrimidine}(R^1)_n$

| ex. no | $(R^1)_n$ | $R^2$ | A—$R^3$ | m.p. [° C.] RT[min] |
|---|---|---|---|---|
| 163 | -- | H | 5-(4-CN-phenyl)-thiophen-2-yl | 2.65 |
| 164 | -- | H | 5-(3-CF$_3$-phenyl)-thiophen-2-yl | 3.19 |
| 165 | -- | H | 5-(4-CF$_3$-phenyl)-thiophen-2-yl | 3.24 |
| 166 | -- | H | 5-(2,4-dichloro-phenyl)-thiophen-2-yl | 3.39 |
| 167 | -- | H | 5-(3,4-dichloro-phenyl)-thiophen-2-yl | 3.36 |
| 168 | -- | H | 4-phenyl-thiophen-2-yl | 2.73 |
| 169 | -- | H | 4-(3-Cl-phenyl)-thiophen-2-yl | 3.03 |
| 170 | -- | H | 4-(3-F-phenyl)-thiophen-2-yl | 2.82 |
| 171 | -- | H | 4-(4-F-phenyl)-thiophen-2-yl | 2.80 |
| 172 | -- | H | 4-(3-CH$_3$-phenyl)-thiophen-2-yl | 2.97 |
| 173 | -- | H | 4-(4-CH$_3$-phenyl)-thiophen-2-yl | 2.98 |
| 174 | -- | H | 4-(2-OCH$_3$-phenyl)-thiophen-2-yl | 2.81 |
| 175 | -- | H | 4-(3-OCH$_3$-phenyl)-thiophen-2-yl | 2.78 |
| 176 | -- | H | 4-(4-OCH$_3$-phenyl)-thiophen-2-yl | 2.75 |
| 177 | -- | H | 4-(4-CF$_3$-phenyl)-thiophen-2-yl | 3.17 |
| 178 | -- | H | 5-phenyl-thiophen-2-yl | 2.80 |
| 179 | -- | H | 5-(2,4-difluoro-phenyl)-thiophen-2-yl | 2.92 |
| 180 | -- | H | 4-(2-methyl-phenyl)-thiophen-2-yl | 2.91 |
| 181 | -- | H | 4-(2-CF$_3$-phenyl)-thiophen-2-yl | 3.01 |
| 182 | -- | H | 6-(2-CF$_3$-phenyl)-pyridin-3-yl | 2.67 |
| 183 | 5,6-dimethyl | H | 5-(4-Cl-phenyl)-thiophen-2-yl | 100 |
| 184 | 6-CH$_3$ | H | 5-(4-Cl-phenyl)-thiophen-2-yl | 139 |
| 185 | 2-SCH$_3$, 6-CH$_3$ | H | 4-(4-Cl-phenoxy)-phenyl | 171 |
| 186 | 2-Cl | H | 4-(4-Cl-phenyl)-phenyl | 155 |
| 187 | 2-OCH$_3$, 6-CH$_3$ | H | 4-(4-Cl-phenoxy)-phenyl | 154 |
| 188 | 2,6-dimethyl | H | 1-(4-F-phenyl)-1H-imidazol-4-yl | 165 |
| 189 | 5,6-dimethyl | H | 4-(4-Cl-phenoxy)-phenyl | 121 |
| 190 | 2,6-dimethyl | H | 5-(4-Cl-phenyl)-thiophen-2-yl | 151 |
| 191 | 2-OCH$_3$, 6-CH$_3$ | H | 5-(4-Cl-phenyl)-thiophen-2-yl | 163 |
| 192 | 2,5,6-trimethyl | H | 5-(4-Cl-phenyl)-thiophen-2-yl | 168 |
| 193 | 2-SCH$_3$, 6-CH$_3$ | H | 5-(4-Cl-phenyl)-thiophen-2-yl | 146 |
| 194 | 6-N(CH$_3$)$_2$ | H | 4-(4-Cl-phenoxy)-phenyl | 161 |
| 195 | 2,6-dimethyl | H | 4-(4-F-phenyl)-thiazol-2-yl | 164 |
| 196 | 6-CH$_3$ | H | 4-(4-Cl-phenyl)-phenyl | 143 |
| 197 | 2,5,6-trimethyl | H | 4-(4-Cl-phenyl)-phenyl | 155 |
| 198 | 2-OCH$_3$ | H | 4-(2,4-difluorophenoxy)-phenyl | 3.14 |
| 199 | -- | H | 4-(4-Cl-phenoxy)-phenyl | 121 |
| 200 | 2-CH$_3$ | H | 4-phenoxyphenyl | 104 |
| 201 | 2-cyclopropyl | H | 4-phenoxyphenyl | 118 |
| 202 | 2-SCH$_3$ | H | 4-phenoxyphenyl | 3.14 |
| 203 | 2-CH$_3$ | H | 4-(4-Cl-phenoxy)-phenyl | 112 |
| 204 | 2-cyclopropyl | H | 4-(4-Cl-phenoxy)-phenyl | 144 |
| 205 | 2-SCH$_3$ | H | 4-(4-Cl-phenoxy)-phenyl | 124 |
| 206 | 6-CH$_3$ | H | 4-(4-Cl-phenoxy)-phenyl | 126 |
| 207 | 2,6-(CH$_3$)$_2$ | H | 4-(4-Cl-phenoxy)-phenyl | 107 |
| 208 | 5,6-(CH$_3$)$_2$ | H | 4-(4-Cl-phenoxy)-phenyl | 121 |
| 209 | 2-OCH$_3$, 6-CH$_3$ | H | 4-(4-Cl-phenoxy)-phenyl | 154 |
| 210 | 2-OCH$_3$ | H | 4-(2,4-F$_2$-phenoxy)-phenyl | 3.09 |
| 211 | 2-S(O)CH$_3$ | H | 4-(4-Cl-phenoxy)-phenyl | 70 |
| 212 | 2-S(O)$_2$CH$_3$ | H | 4-(4-Cl-phenoxy)-phenyl | 3.16 |
| 213 | 2-SCH$_3$ | H | 4-(2,4-F$_2$-phenoxy)-phenyl | 2.91* |
| 214 | 6-SCHF$_2$ | H | 4-(2,4-F$_2$-phenoxy)-phenyl | 3.29* |
| 215 | 6-SCF$_3$ | H | 4-(2,4-F$_2$-phenoxy)-phenyl | 3.40* |
| 216 | 2-SCF$_3$ | H | 4-(2,4-F$_2$-phenoxy)-phenyl | 3.65* |
| 217 | 2-SCF$_3$ | H | 4-(4-Cl-phenoxy)-phenyl | 3.53* |
| 218 | 2-SCHF$_2$ | H | 4-(2,4-F$_2$-phenoxy)-phenyl | 3.38* |
| 219 | 2-SCHF$_2$ | H | 4-(4-Cl-phenoxy)-phenyl | 3.52* |
| 220 | 2-OCHF$_2$ | H | 4-(4-Cl-phenoxy)-phenyl | 3.42* |
| 221 | 2-OCHF$_2$ | H | 4-(2,4-F$_2$-phenoxy)-phenyl | 3.26* |
| 222 | -- | H | 4-(4-Cl-phenoxy)-phenyl | 121 |
| 223 | -- | H | 4-(2,4-F$_2$-phenoxy)-phenyl | 93 |
| 224 | 6-N(CH$_3$)$_2$ | H | 4-(4-Cl-phenoxy)-phenyl | 161 |
| 225 | 6-NHCH$_3$ | H | 4-(4-Cl-phenoxy)-phenyl | 173 |

TABLE I-continued (I)

$$R^3-A-\underset{\underset{O}{\parallel}}{\overset{\overset{O}{\parallel}}{S}}-\underset{R^2}{N}-\underset{4}{\diagup}\underset{6}{\overset{N}{\diagdown}}\underset{(R^1)_n}{\overset{2}{\diagup}}N,$$

| ex. no | $(R^1)_n$ | $R^2$ | $A-R^3$ | m.p. [° C.] RT[min] |
|---|---|---|---|---|
| 226 | 2-SCH$_3$, 6-CH$_3$ | H | 4-(4-Cl-phenoxy)-phenyl | 171 |
| 227 | 6-SCHF$_2$ | H | 4-(4-Cl-phenoxy)-phenyl | 3.42* |
| 228 | 6-SCF$_3$ | H | 4-(4-Cl-phenoxy)-phenyl | 3.53* |

-- when referring to $(R^1)_n$ means that n is zero;
m.p. melting point
RT retention time, determined by HPLC; HPLC column: RP-18 column (Chromolith Speed ROD from Merck KgaA, Germany 50*4.6 mm). Elution: acetonitrile + 0.1% trifluoroacetic acid (TFA)/water in a ratio of from 5:95 to 95:5 in 5 minutes at 40° C., flow rate 1.6 ml/min; the RT values indicated with an asterisk were determined by using a HPLC column Waters X-BridgeTM C18 502.1 mm. Elution: gradient of 0.1% formic acid in acetonitrile and 0.1% formic acid in water in a ration from 2:98 to 98:2 in 4 minutes at 35° C., flow rate 0.8 ml/min.

Examples of the Action Against Harmful Fungi

The fungicidal action of the compounds of the formula I was demonstrated by the following experiments:

Greenhouse Tests:

The active compounds were formulated separately or together as a stock solution comprising 25 mg of active compound which was made up to 10 ml using a mixture of acetone and/or dimethyl sulfoxide (DMSO) and the emulsifier Wettol (wetting agent having emulsifying and dispersing action based on ethoxylated alkylphenols) in a volume ratio of solvent/emulsifier of 99 to 1. This solution was then made up to 100 ml using water. This stock solution was diluted with the solvent/emulsifier/water mixture described to the active compound concentration given below.

Use Example 1

Activity Against Early Blight on Tomatoes Caused by *Alternaria solani*

Young seedlings of tomato plants were grown in pots. These plants were sprayed to run-off with an aqueous suspension, containing the concentration of active ingredient stated below. The next day, the treated plants were inoculated with an aqueous spore suspension of *Alternaria solani* containing $0.17 \times 10^6$ spores per ml. Then the trial plants were immediately transferred to a humid chamber. After 5 days at 20 and 22° C. and a relative humidity close to 100%, the extent of fungal attack on the leaves was visually assessed as % diseased leaf area.

In this test, the plants which had been treated with 250 ppm of the active compound from examples 8, 11, 18, 25, 29, 30, 31, 32, 33, 34, 36, 40, 44, 45 or 61, showed an infection of less than or equal to 15% whereas the untreated plants were 90% infected.

Use Example 2

Activity Against Early Blight of Tomato Caused by *Alternaria solani*

Leaves of potted tomato plants were sprayed to runoff point with an aqueous suspension having the active compound concentration stated below. The next day, the treated plants were inoculated with a spore suspension of *Alternaria solani* which contained $0.17 \times 10^6$ spores/ml in a 2% aqueous biomalt solution. The test plants were then placed in a water vapor-saturated chamber at temperatures of from 20 to 22° C. After 5 days the disease on the untreated infected control plants had developed to such an extent that the infection of all plants could be determined visually in %.

In this test, the plants which had been treated with 250 ppm of the active compound from examples 200, 201, 202, 203, 204, 205, 209, 210, 213, 220 or 222 showed an infection of less than or equal to 15% whereas the untreated plants were 90% infected.

In this test, the plants which had been treated with 250 ppm of the active compound from example 199

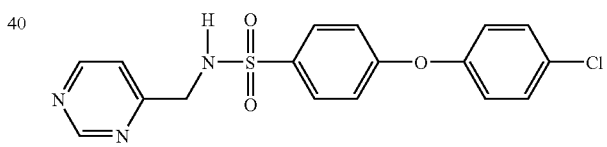

Example 199 showed an infection of less than or equal to 5% whereas the untreated plants were 90% infected.

In contrast thereto, the plants which had been treated with 250 ppm of the compound of formula (RC 1), prepared by analogy to WO 2006/097488, showed an infection of 40%.

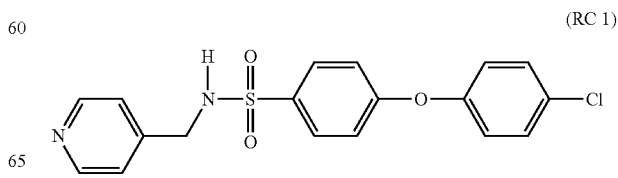

(RC 1)

Use Example 3

Activity Against Gray Mold on Bell Pepper Leaves Caused by *Botrytis cinerea* with Protective Application for 1 Day Bell pepper leaves of the cultiva "Neusiedler Ideal Elite" were, after 2 to 3 leaves had become well developed, sprayed to runoff point with an aqueous suspension having the concentration of active compounds stated below. The next day, the treated plants were inoculated with an aqueous spore suspension of *Botrytis cinerea* in a 2% aqueous biomalt solution having a density of $1.7 \times 10^6$ spores/ml. The plants were then placed in a climatized chamber at temperatures between 22 and 24° C., darkness and at high atmospheric humidity. After 5 days, the extent of the fungal infection was determined visually by the infected leaf area.

In this test, the plants which had been treated with 250 ppm of the active compound from examples 25, 35, 94, or 102 showed an infection of less than or equal to 20%, whereas the untreated plants were 100% infected.

Use Example 4

Activity Against Late Blight on Tomatoes Caused by *Phytophthora infestans*, Protective Treatment Young seedlings of tomato plants were grown in pots. The plants were sprayed to runoff with an aqueous suspension containing the concentration of active ingredient stated below. The next day, the treated plants were inoculated with an aqueous suspension of sporangia of *Phytophthora infestans*. After inoculation, the trial plants were immediately transferred to a humid chamber. After six days at 18 to 20° C. and a relative humidity close to 100%, the extent of fungal attack on the leaves was visually assessed as % diseased leaf area.

In this test, the plants which had been treated with 250 ppm of the active compound from examples 1, 4, 7, 10, 11, 12, 19, 27, 28, 29, 30, 40, 45, 49, 50, 51, 53, 76, 87, 88, 98, 101, 102, 103, 107, 110, 115, 143, 145, 151, 161, 197, 198, 206, 207, 208, 211, 212, 221, 222 or 223 showed an infection of less than or equal to 20%, whereas the untreated plants were 90% infected.

In this test, the plants which had been treated with 250 ppm of the compound of formula (RC 2), prepared by analogy to WO 2006/097488 showed an infection of 90%.

(RC 2)

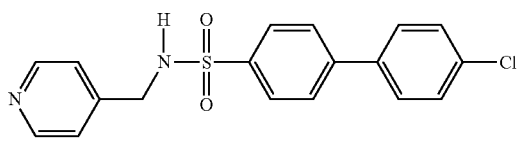

In contrast thereto, the compound of example 1 showed an infection of 0%.

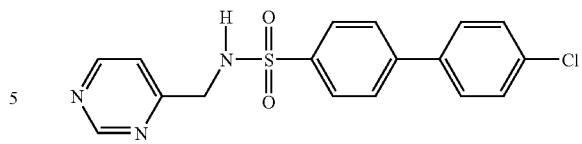

Use Example 5

Curative Activity Against Brown Rust of Wheat Caused by *Puccinia* Recondite

Leaves of potted wheat seedlings of the cultivar "Kanzler" were inoculated with a spore suspension of brown rust (*Puccinia recondita*). The pots were then placed in a chamber at high atmospheric humidity (90 to 95%) and 20 to 22° C. for 24 hours. During this time, the spores germinated and the germ tubes penetrated into the leaf tissue. The next day, the infected plants were sprayed to runoff point with an aqueous solution having the active compound concentration stated below. The solution had been prepared as described above. After the spray coating had dried, the test plants were cultivated in a greenhouse at temperatures between 20 and 22° C. and at 65 to 70% relative atmospheric humidity for 7 days. The extent of the rust fungus development on the leaves was then determined.

In this test, the plants which had been treated with 250 ppm of the active compound from examples 19, 27, 31, 33, 47, 49, 52, 61, 81, 85, 87, 88, 200, 201, 202, 203, 204, 205, 206, 207, 208, 209, 211, 212, 213, 216, 217, 219, 220 or 221 showed an infection of less than or equal to 15%, whereas the untreated plants were 90% infected.

Use Example 6

Protective Action Against *Puccinia recondita* on Wheat (Brown Rust of Wheat)

Leaves of potted wheat seedlings of the cultivar "Kanzler" were sprayed to runoff point with an aqueous suspension having the concentration of active compound stated below. The next day, the treated plants were dusted with spores of brown rust of wheat (*Puccinia recondita*). The plants were then placed in a chamber with high atmospheric humidity (90 to 95%), at 20-22° C., for 24 hours. During this time, the spores germinated and the germinal tubes penetrated into the leaf tissue. The next day, the test plants were returned into the greenhouse and cultivated at temperatures between 20 and 22° C. and at 65 to 70% relative atmospheric humidity for a further 7 days. The extent of the rust development on the leaves was then determined visually.

In this test, the plants which had been treated with 250 ppm of the active compound from examples 8, 18, 52, 53, 74, 76, 77, 79, 80, 81, 85, 94, 107, 131, 151, 159, 165, or 198 showed an infection of less than or equal to 20%, whereas the untreated plants were 90% infected.

Use Example 7

Activity Against Soyabean Rust Caused by *Phakospora pachyrhizi*

Leaves of potted soyabean seedlings of the cultivar "Oxford" were inoculated with a spore suspension of soyabean rust (*Phakospora pachyrhizi*). The pots were then placed in a chamber at high atmospheric humidity (90 to 95%) and 23 to 27° C. for 24 hours. During this time, the spores germinated and the germ tubes penetrated into the leaf tissue. The next day, the infected plants were sprayed to runoff point with an aqueous solution having the active compound concentration stated below. The solution had been prepared as described above. After the spray coating had dried, the test plants were cultivated in a greenhouse at temperatures between 23 and 27° C. and at 60 to 80% relative atmospheric humidity for 14 days. The extent of the rust fungus development on the leaves was then determined.

In this test, the plants which had been treated with 250 ppm of the active compound from examples 1, 20, 24, 100, 214, 215 or 218 showed an infection of less than or equal to 20%, whereas the untreated plants were 90% infected.

Use Example 8

Protective Action Against Blight of Cucumber Leaves Caused by *Sphaerotheca fuliginea*

Leaves of potted cucumber seedlings in the cotyledon stage were sprayed to runoff with an aqueous suspension containing the concentration of active ingredient stated below. The next day the treated plants were inoculated with an aqueous suspension of sporangia of *Sphaerotheca fuliginea*. After inoculation, the trial plants were transferred to a green house. After seven days at 20 to 24° C. and a relative humidity close at 60 to 80%, the extent of fungal attack on the leaves was visually assessed as % diseased leaf area.

In this test, the compound of example 88

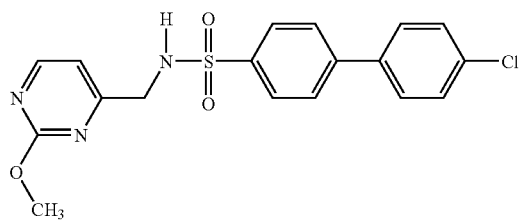

Example 88 showed no infection whereas the untreated plants were 90% infected.

In contrast thereto, the plants which had been treated with 250 ppm of the compound of formula (RC 3), prepared by analogy to WO 2006/097488 showed an infection of 90%.

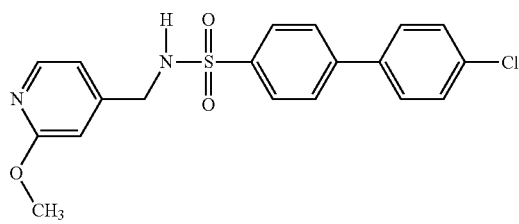

(RC 3)

Microtiter Tests

The active compounds were formulated separately as a stock solution in dimethyl sulfoxide (DMSO) at a concentration of 10 000 ppm.

Use Example 9

Activity Against the Late Blight Pathogen *Phytophthora infestans* in the Microtiter Test The stock solution was pipetted into a microtiter plate (MTP) and diluted to the stated active compound concentration using a pea juice-based aqueous nutrient medium for fungi. An aqueous zoospore suspension of *Phytophthora infestans* was then added. The plates were placed in a water vapor-saturated chamber at temperatures of 18° C. Using an absorption photometer, the MTPs were measured at 405 nm on day 7 after the inoculation. The measured parameters were compared to the growth of the active compound-free control variant (=100%) and the fungus- and active compound-free blank value to determine the relative growth in % of the pathogens in the individual active compounds.

In this test, the sample which had been treated with 125 ppm of the active compound from examples 3, 5, 9, 22, 26, 34, 37, 38, 42, 43, 50, 56, 59, 60, 62, 64, 66, 68, 73, 75, 84, 84, 99, 103, 104, 108, 109, 154, 157, 161, 168, 170, 171, 171, 175, 183, 184, 185, 186, 187, 188, 189, 189, 190, 191, 192, 193, 194, 195 196, 224, 225, 226 or 227, respectively showed up to at most 25% growth of the pathogen.

Use Example 10

Activity Against the Rice Blast Pathogen Caused by *Pyricularia oryzae* in the Microtiter Test The stock solution was pipetted into a microtiter plate (MTP) and diluted to the stated active compound concentration using a malt-based aqueous nutrient medium for fungi. An aqueous spore suspension of *Pyricularia oryzae* was then added. The plates were placed in a water vapor-saturated chamber at temperatures of 18° C. Using an absorption photometer, the microtiter plates were measured at 405 nm on day 7 after the inoculation. The measured parameters were compared to the growth of the active compound-free control variant (=100%) and the fungus- and active compound-free blank value to determine the relative growth in % of the pathogens in the individual active compounds.

In this test, the sample which had been treated with 125 ppm of the active compound from examples 3, 4, 5, 6, 7, 9, 12, 13, 16, 26, 32, 39, 41, 42, 44, 48, 54, 56, 57, 58, 59, 60, 62, 64, 66, 67, 73, 75, 78, 79, 80, 84, 86, 89, 99, 109, 120, 122, 138, 158, 159, 166, 167, 169, 171, 172, 175, 177, 180, 181, 183, 186, 187, 190, 192, 195 or 224, respectively, showed up to at most 25% relative growth of the pathogen Use Example 11

Activity Against the *Septoria blotch* Pathogen Caused by *Septoria tritici* in the Microtiter Test The stock solution was pipetted into a microtiter plate (MTP) and diluted to the stated active compound concentration using a malt-based aqueous nutrient medium for fungi. An aqueous spore suspension of *Septoria tritici* was then added. The plates were placed in a water vapor-saturated chamber at temperatures of 18° C. Using an absorption photometer, the microtiter plates were measured at 405 nm on day 7 after the inoculation. The measured parameters were compared to the growth of the active compound-free control variant (=100%) and the fungus- and active compound-free blank value to determine the relative growth in % of the pathogens in the individual active compounds.

In this test, the sample which had been treated with 125 ppm of the active compound from examples 13, 38, 39, 41, 43, 54, 55, 57, 58, 67, 78, 104, 120, 157, 158, 166, 167, 177 or 228, respectively, showed up to at most 25% relative growth of the pathogen.

The action of the compounds of the formula (I) against harmful pests was demonstrated by the following experiments:

Use Example 12

Activity Against Boll Weevil (*Anthonomus grandis*)

The active compounds were formulated in 1:3 dimethylsulfoxide/water. 10 to 15 eggs were placed into microtiterplates filled with 2% agar-agar in water and 300 ppm formaline. The eggs were sprayed with 20 μl of the test solution, the plates were sealed with pierced foils and kept at 24-26° C. and 75-85% humidity with a day/night cycle for 3 to 5 days. Mortality was assessed on the basis of the remaining unhatched eggs or larvae on the agar surface and/or quantity and depth of the digging channels caused by the hatched larvae. Tests were replicated 2 times.

In this test the eggs which have been treated with 2500 ppm of the active compounds of examples 4, 9 and 54, respectively, showed a mortality of at least 75%.

Use Example 13

Activity Against Mediterranean Fruitfly (*Ceratitis capitata*)

The active compounds were formulated in 1:3 Dimethylsulfoxide/water. 50 to 80 eggs were placed into microtiterplates filled with 0.5% agar-agar and 14% diet in water. The eggs were sprayed with 5 μl of the test solution; the plates were sealed with pierced foils and kept at 27-29° C. and 75-85% humidity under fluorescent light for 6 days. Mortality was assessed on the basis of the agility of the hatched larvae. Tests were replicated 2 times.

Use Example 14

Activity Against Tobacco Budworm (*Heliothis virescens*)

The active compounds were formulated in 1:3 dimethylsulfoxide/water. 15 to 25 eggs were placed into microtiterplates filled with diet. The eggs were sprayed with 10 μl of the test solution, the plates were sealed with pierced foils and kept at 27-29° C. and 75-85% humidity under fluorescent light for 6 days. Mortality was assessed on the basis of the agility and of comparative feeding of the hatched larvae. Tests were replicated 2 times. In this test the eggs which have been treated with 2500 ppm of the active compounds from example 54 showed a mortality of at least 75%.

Use Example 15

Activity Against Vetch Aphid (*Megoura viciae*)

The active compounds were formulated in 1:3 dimethylsulfoxide/water. Bean leaf disks were placed into microtiterplates filled with 0.8% agar-agar and 2.5 ppm OPUS®. The leaf disks were sprayed with 2.5 μl of the test solution and 5 to 8 adult aphids were placed into the microtiterplates which were then closed and kept at 22-24° C. and 35-45% under fluorescent light for 6 days. Mortality was assessed on the basis of vital, reproduced aphids. Tests were replicated 2 times.

We claim:
1. A compound of formula (I)

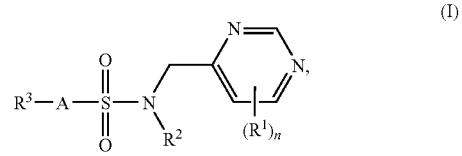

wherein:
n is zero, one, two or three;
$R^1$ is halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, amino, $C_1$-$C_4$-alkylamino, di($C_1$-$C_4$-alkyl)amino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_8$-cycloalkyl or $C_1$-$C_4$-alkyl-$C_3$-$C_8$-cycloalkyl;
$R^2$ is hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylamino, di($C_1$-$C_4$-alkyl)amino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_3$-$C_8$-cycloalkyl, $C_1$-$C_4$-alkyl-$C_3$-$C_8$-cycloalkyl or benzyl wherein the phenyl moiety of benzyl is unsubstituted or carries 1, 2, 3, 4, or 5 substituents selected from the group consisting of cyano, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl;
A is 1,3- or 1,4-phenylene or heteroarenediyl selected from the group consisting of thiophene-2,5-diyl, thiophene-2,4-diyl, thiophene-3,5-diyl, thiazole-2,5-diyl, thiazole-2,4-diyl, oxazole-2,5-diyl, oxazole-2,4-diyl, pyrazole-3,5-diyl, pyrazole-1,3-diyl, pyrazole-1,4-diyl, pyridine-2,5-diyl, pyridine-2,6-diyl, pyridine-2,4-diyl, and pyridine-3,5-diyl, wherein said 1,3- or 1,4-phenylene or heteroarenediyl is unsubstituted or carries one, two or three substituents $R^4$ selected from the group consisting of cyano, halogen, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, ($C_1$-$C_4$-alkoxy)carbonyl and di($C_1$-$C_4$-alkyl)aminocarbonyl;
$R^3$ is hydrogen, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino, di($C_1$-$C_4$-alkyl)amino, ($C_1$-$C_4$-alkyl)carbonyl, ($C_1$-$C_4$-alkoxy)iminomethyl, acryloyl(vinylcarbonyl), $C_3$-$C_8$-cycloalkyl, $C_1$-$C_4$-alkyl-$C_3$-$C_8$-cycloalkyl, $C_5$-$C_8$-cycloalkenyl,
phenyl, benzyl, phenoxy, phenylthio, a 5- or 6-membered heteroaryl radical, wherein the heteroaryl ring has 1, 2, 3 or 4 heteroatoms selected from the group consisting of 1, 2, 3 or 4 nitrogen atoms, 1 oxygen atom and 1 sulfur atom, as ring members, it being possible for the heteroaryl ring and the phenyl ring of phenyl, benzyl, phenoxy and phenylthio to be unsubstituted or substituted by one, two or three substituents $R^B$, each selected from the group consisting of cyano, nitro, amino, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl, di($C_1$-$C_4$-alkyl)aminocarbonyl, $C_1$-$C_4$-alkylthio, $C_1$-$C_4$-alkylsulfinyl and $C_1$-$C_4$-alkylsulfonyl; or a 5- or 6-membered heteroaryloxy radical or a 5- or 6-membered heteroarylthio radical, wherein the heteroaryl ring in the two aforementioned radicals has 1, 2, 3 or 4 heteroatoms selected from the group consisting of 1, 2, 3, or 4 nitrogen atoms, 1 oxygen atom and 1 sulfur atom, as ring members, it being possible for said heteroaromatic ring to carry one, two or three substituents $R^B$;

the radical $R^3$ together with a radical $R^A$ may form together with the carbon atoms to which they are bound a fused benzene ring, wherein the fused benzene ring may be unsubstituted or may carry 1, 2 or 3 substituents selected, independently from one another, from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl, or the radical $R^3$ can also be $C_1$-$C_4$-alkyl, $C_2$-$C_4$-alkenyl or $C_2$-$C_4$-alkynyl;

and the N-oxides, the agriculturally acceptable salts and the veterinarily acceptable salts of the compounds of the formula (I).

2. The compound of claim 1, wherein $R^3$ is phenyl or phenoxy, wherein the two last-mentioned radicals are unsubstituted or carry one, two, or three substituents $R^B$.

3. The compound of claim 1, wherein $R^2$ is hydrogen.

4. The compound of claim 1, wherein n is 1, 2 or 3.

5. The compound of claim 4, wherein $R^1$ is selected from the group consisting of methyl, methylthio, methoxy, difluoromethylthio, trifluoromethylthio, difluoromethoxy, trifluoromethoxy, methylamino, methylsulfonyl, dimethylamino, fluorine, bromine and chlorine.

6. A process for preparing compounds of formula (I) of claim 1, which comprises reacting an aminomethylpyrimidine compound of the formula (II)

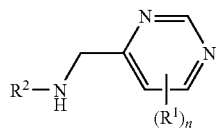
(II)

under basic conditions with a sulfonic acid derivative of the wherein n, $R^1$ and $R^2$ are as defined in claim 1, formula (III)

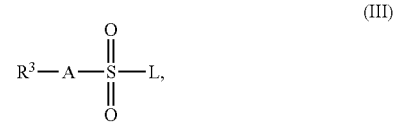
(III)

wherein A and $R^3$ are as defined in claim 1 and L is hydroxy or halogen.

7. An agricultural composition which comprises a solid or liquid carrier and at least one compound of the formula (I) or an N-oxide or an agriculturally acceptable salt thereof, according to claim 1.

8. A method for the treatment of phytopathogenic harmful fungi, which process comprises treating the fungi or the materials, plants, the soil or seeds to be protected against fungal attack, with an effective amount of at least one compound of the formula (I) or an or an N-oxide or an agriculturally acceptable salt thereof, according to claim 1.

9. A method for combating arthropod pests, which comprises contacting said pests, their habitat, breeding ground, food supply, plant, seed, soil, area, material or environment in which the arthropod pests are growing or may grow, or the materials, plants, seeds, soils, surfaces or spaces to be protected from an attack of or infestation by said pests, with a pesticidally effective amount of at least one compound of the formula (I), an N-oxide, an agriculturally acceptable salt or a veterinarily acceptable salt thereof, according to claim 1, or with a composition comprising at least one compound of the formula (I), an N-oxide, an agriculturally acceptable salt or a veterinarily acceptable salt thereof.

10. A seed treated with a compound of the formula (I), or an N-oxide or an agriculturally acceptable salt thereof, as defined in claim 1, in an amount of from 0.1 g to 10 kg per 100 kg of seed.

* * * * *